(12) United States Patent
Fukushima et al.

(10) Patent No.: US 7,638,281 B2
(45) Date of Patent: Dec. 29, 2009

(54) POLYPEPTIDE, CDNA ENCODING THE SAME AND USE OF THEM

(75) Inventors: Daikichi Fukushima, Osaka (JP); Shiro Shibayama, Osaka (JP); Hideaki Tada, Osaka (JP)

(73) Assignee: ONO Pharmaceutical Co., Ltd., Osaka (JP)

( * ) Notice: Subject to any disclaimer, the term of this patent is extended or adjusted under 35 U.S.C. 154(b) by 149 days.

(21) Appl. No.: 11/703,200

(22) Filed: Feb. 7, 2007

(65) Prior Publication Data

US 2008/0009056 A1    Jan. 10, 2008

Related U.S. Application Data

(60) Division of application No. 10/414,378, filed on Apr. 16, 2003, now Pat. No. 7,189,546, which is a continuation of application No. 09/529,063, filed as application No. PCT/JP98/04514 on Oct. 6, 1998, now abandoned.

(30) Foreign Application Priority Data

Oct. 7, 1997    (JP)    ............... P. 9-274674

(51) Int. Cl.
C07H 21/04    (2006.01)
C12N 15/00    (2006.01)
C12N 5/06    (2006.01)

(52) U.S. Cl. .................. 435/6; 435/320.1; 435/325; 536/23.2

(58) Field of Classification Search ............... None
See application file for complete search history.

(56) References Cited

U.S. PATENT DOCUMENTS 5,424,398 A    6/1995    Middeldorp et al.
5,501,969 A    3/1996    Hastings et al.

FOREIGN PATENT DOCUMENTS

| EP | 0 594 879 | 5/1994 |
|---|---|---|
| WO | WO 95/19570 | 7/1995 |
| WO | WO 98/07855 | 2/1998 |
| WO | WO 98 39448 | 9/1998 |
| WO | WO 98/45435 | 10/1998 |
| WO | WO 98/45437 | 10/1998 |
| WO | WO 99 00508 | 1/1999 |
| WO | WO 99 06439 | 2/1999 |
| WO | WO 99/06554 | 2/1999 |
| WO | WO 99/27079 | 6/1999 |
| WO | WO 00 00610 | 1/2000 |

OTHER PUBLICATIONS

Perry et al. (Current Opinion in Chemical Biology, 1998, vol. 2, p. 472-481).*
Livi et al. (Molecular and Cellular Biology, 1990, vol. 10, No. 6, p. 2678-2686).*
Van Driel et al. (JBC 1987, vol. 262, No. 10, p. 4882-4887).*
Okumura et al, Biochimica et Biophysica Acta, 1245(2):221-226 (1995).
Russell et al, J. of Mol. Biol., 224(3):332-350 (1994).
Gal et al, Biochem. J., 253(3):303-306 (1988).
Fujiwara et al, Database Accession No. D78812.
Bouchon et al, Nature, 410:1103-1106(2001).
Dolenc et al, Biological Chemistry Hoppe-Seyler, 373(7):407-412 (1992).
Database Accession No. X91755, XP002217252 (Sep. 12, 1996).
Database Accession No. P25975, XP002217253 (May 1, 1992).
Database Accession No. D78812, XP002259607, Abstract (Feb. 7, 1996).
Database Accession No. AA494171, XP002259608, Abstract (Jun. 28, 1997).
Database Accession No. H04128, XP002259609, Abstract (Jun. 22, 1995).
Database Accession No. AA099228, XP002259610, Abstract (Oct. 29, 1996).
Database Accession No. AA101983, XP002259611, Abstract (Oct. 29, 1996).
Buckley et al, JBC, 265(29):17506-17511 (1990).
van Driel et al, JBC, 262(10):4882-4887 (1987).
Sequence Search Results, pp. 2-3, Result 5, Accession #A39216.
Calculation of Protein Molecular Weight, Obtained Using ProtParam Program at ExPaSy.
Grodzova et al, Biochemistry and Molecular Biology International, 40(6):1159-1166 (1996).
Rost et al, J. Mol. Biol., 318(2):595-608 (2002).
Deissler et al, J. Biol. Chem., 270(17):9849-9855 (1995).
Belli et al, Eur. J. Biochem., 226(2):433-443 (1994).
Nagase et al, DNA Research, 5(6):355-364 (1998).
Lazar et al, Mol. Cell Biol., 8:1247-1252 (1988).
Hill et al, Biochem. Biophys. Res. Comm., 244:573-577 (1998).
Guo et al, Proc. Natl. Acad. Sci. USA, 101:9205-9210 (2004).

* cited by examiner

Primary Examiner—Gary Benzion
Assistant Examiner—Stephanie K Mummert
(74) Attorney, Agent, or Firm—Sughrue Mion, PLLC

(57) ABSTRACT

A new polypeptide prepared from human library by the SST method and a process for preparation of it; a cDNA encoding the polypeptide; a fragment selectively hybridizing with the sequence of the cDNA; a replication or expression plasmid containing the cDNA integrated thereinto; a host cell transformed with plasmid; an antibody against the polypeptide; and a pharmaceutical composition containing the polypeptide or the antibody.

9 Claims, 1 Drawing Sheet

POLYPEPTIDE, CDNA ENCODING THE SAME AND USE OF THEM

CROSS-REFERENCE TO RELATED APPLICATIONS

This application is a Divisional of U.S. application Ser. No. 10/414,378 filed Apr. 16, 2003 now U.S. Pat. No. 7,189,546 (now allowed), which is a Continuation of U.S. application Ser. No. 09/529,063, filed Apr. 7, 2000 (now abandoned), which was a national stage entry under 35 U.S.C. §371 of PCT/JP98/04514, filed Oct. 6, 1998. The entire disclosures of the prior applications are incorporated herein by reference.

TECHNICAL FIELD

The present invention relates to novel polypeptides, a method for preparation of them, a cDNA encoding it, a vector containing it, a host cell transformed with the vector, an antibody against the peptide, and a pharmaceutical composition containing the polypeptide or the antibody.

TECHNICAL BACKGROUND

Until now, when a man skilled in the art intends to obtain a particular polypeptide or a cDNA encoding it, he generally utilizes methods by confirming an aimed biological activity in a tissue or in a cell medium, isolating and purifying the polypeptide and then cloning a gene or methods by "expression-cloning" with the guidance of the said biological activity. However, physiologically active polypeptides in living body have often many kinds of activities. Therefore, it happens increasingly that after cloning a gene, the isolated gene is found to be identical to that encoding a polypeptide already known. In addition, some factors could be generated in only a very slight amount and/or under specific conditions and it makes difficult to isolate and to purify the factor and to confirm its biological activity.

Recent rapid developments in techniques for constructing cDNAs and sequencing techniques have made it possible to quickly sequence a large amount of cDNAs. By utilizing these techniques, a process, which comprises constructing cDNAs library using various cells or tissues, cloning the cDNA at random, identifying the nucleotide sequences thereof, expressing novel polypeptides encoded by them, is now in progress. Although this process is advantageous in that a gene can be cloned and information regarding its nucleotide sequence can be obtained without any biochemical or genetic analysis, the target gene can be discovered thereby only accidentally in many cases.

The present inventors have studied cloning method to isolate genes encoding proliferation and/or differentiation factors functioning in hematopoietic systems and immune systems. Focusing their attention on the fact that most of the secretory proteins such as proliferation and/or differentiation factors (for example various cytokines) and membrane proteins such as receptors thereof (hereafter these proteins will be referred to generally as secretory proteins and the like) have sequences called signal peptides in the N-termini, the inventors have conducted extensive studies on a process for efficiently and selectively cloning a gene encoding for a signal peptide. Finally, we have successfully developed a screening method for the signal peptides (signal sequence trap (SST)) by using mammalian cells (See Japanese Patent Application No. Hei 6-13951). We also developed yeast SST method on the same concept. By the method based on the same conception using yeast, (yeast SST method), genes including sequence encoding signal peptide can be identified more easily and efficiently (See U.S. Pat. No. 5,536,637).

DISCLOSURE OF THE PRESENT INVENTION

The present inventors et al. have diligently performed certain investigation in order to isolate novel factors (polypeptides) useful for treatment, diagnosis and/or study, particularly, secretory proteins containing secretory signal and membrane protein.

From the result, the present inventors achieved to find novel secretory proteins and membrane proteins produced from cell lines and tissue, for example, human placenta, human adult brain tissue, cell lines derived from human brain tissue, human bone, cell line derived from human bone marrow, and endothelial cell line of vein derived from human umbilical cord and cDNAs encoding them, and then completed the present invention.

The present invention provides the cDNA sequences identified as clone ON056, ON034, OX003 which were isolated by the said yeast SST method using cDNA libraries prepared from human placenta tissue. Clone ON056, ON034, OX003 were full-length cDNA including full cDNA sequences encoding secretory proteins (Each protein is represented as ON056, ON034, OX003 protein, respectively).

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of ON056, ON034, OX003 of the present invention. From the above, it was proved that polypeptides of the present invention were new secretory proteins.

The present invention provides the cDNA sequences identified as clone OA052, OC004, OM017, OM101, OM126, OM160, OMA016a, OMA016b, OMB130, OMB142, OVB100 which were isolated by the said yeast SST method using cDNA libraries prepared from human adult brain tissue and cell lines derived from human brain tissue (T98G, IMR-32, and CCF-STTG1). Clone OA052, OC004, OM017, OM101, OM126, OM160, OMA016a, OMA016b, OMB130, OMB142, OVB100003 were full-length cDNA including full cDNA sequences encoding secretory protein (Each protein is represented as OA052, OC004, OM017, OM101, OM126, OM160, OMA016a, OMA016b, OMB130, OMB142, OVB100 protein, respectively).

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OA052, OC004, OM017, OM101, OM126, OM160, OMA016a, OMA016b, OMB130, OMB142, OVB100 of the present invention. From these results, it was proved that polypeptides of the present invention were new secretary proteins.

The present invention provides the cDNA sequences identified as clone OAF062, OAF075, OAG119 which were isolated by the said yeast SST method using cDNA libraries prepared from human bone and bone marrow cell line (HAS303, LP101. Clone OAF062, OAF075, OAG119003 were full-length cDNA including full cDNA sequences encoding secretory protein (Each protein is represented as OAF062, OAF075, OAG119 protein, respectively).

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAF062, OAF075, OAG119 of the present invention. From these results, it was proved that polypeptides of the present invention were new secretary proteins.

The present invention provides the cDNA sequences identified as clone OAH040, OAH058 which were isolated by the said yeast SST method using cDNA libraries prepared from epithelial cell line of human umbilical vein (HUV-EC-C). Clone OAH040, OAH058003 were full-length cDNA including full cDNA sequences encoding secretory protein (Each protein is represented as OAH040, OAH058 protein, respectively).

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAH040, OAH058 of the present invention. From these results, it was proved that polypeptides of the present invention were new secretary proteins.

The present invention provides the cDNA sequences identified as clone OM011, OM028, OMB092, OMB108, OT007 which were isolated by the said yeast SST method using cDNA libraries prepared from human adult brain tissue and cell lines derived from human brain tissue (IMR-32). Clone OM011, OM028, OMB092, OMB108, OT007 membrane protein (Each protein is represented as OM011, OM028, OMB092, OMB108, OT007 protein, respectively).

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OM011, OM028, OMB092, OMB108, OT007 of the present invention. From these results, it was proved that polypeptides of the present invention were new secretary proteins.

The present invention provides the cDNA sequences identified as clone OAG051, OUB068 which were isolated by the said yeast SST method using cDNA libraries prepared from human bone and bone marrow cell line (LP101 and U-20S). Clone OAGO51, OUB068 membrane protein (Each protein is represented as OAG051, OUB068 protein, respectively).

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAG051, OUB068 of the present invention. From these results, it was proved that polypeptides of the present invention were new secretary proteins.

That is to say, the present invention relates to
(1) a polypeptide comprising an amino acid sequence of SEQ ID NOS. 1, 4, 7, 10, 13,16, 19, 22, 25, 28, 31, 34, 37, 40, 43, 46, 49, 52, 55, 58, 61, 64, 67, 70, 73, 76 or 79,
(2) a cDNA encoding the polypeptide described in (1),
(3) a cDNA comprising a nucleotide sequence of SEQ ID NOS. 2, 5, 8, 11, 14, 17, 20, 23, 26, 29, 32, 35, 38, 41, 44, 47, 50, 53, 56, 59, 62, 65, 68, 71, 74, 77 or 80, and
(4) a cDNA comprising a nucleotide sequence of SEQ ID NOS. 3, 6, 9, 12, 15, 18, 21, 24, 27, 30, 33, 36, 39, 42, 45, 48, 51, 54, 57, 60, 63, 66, 69, 72, 75, 78 or 81.

DETAILED DESCRIPTION OF THE PRESENT INVENTION

Figure 1:
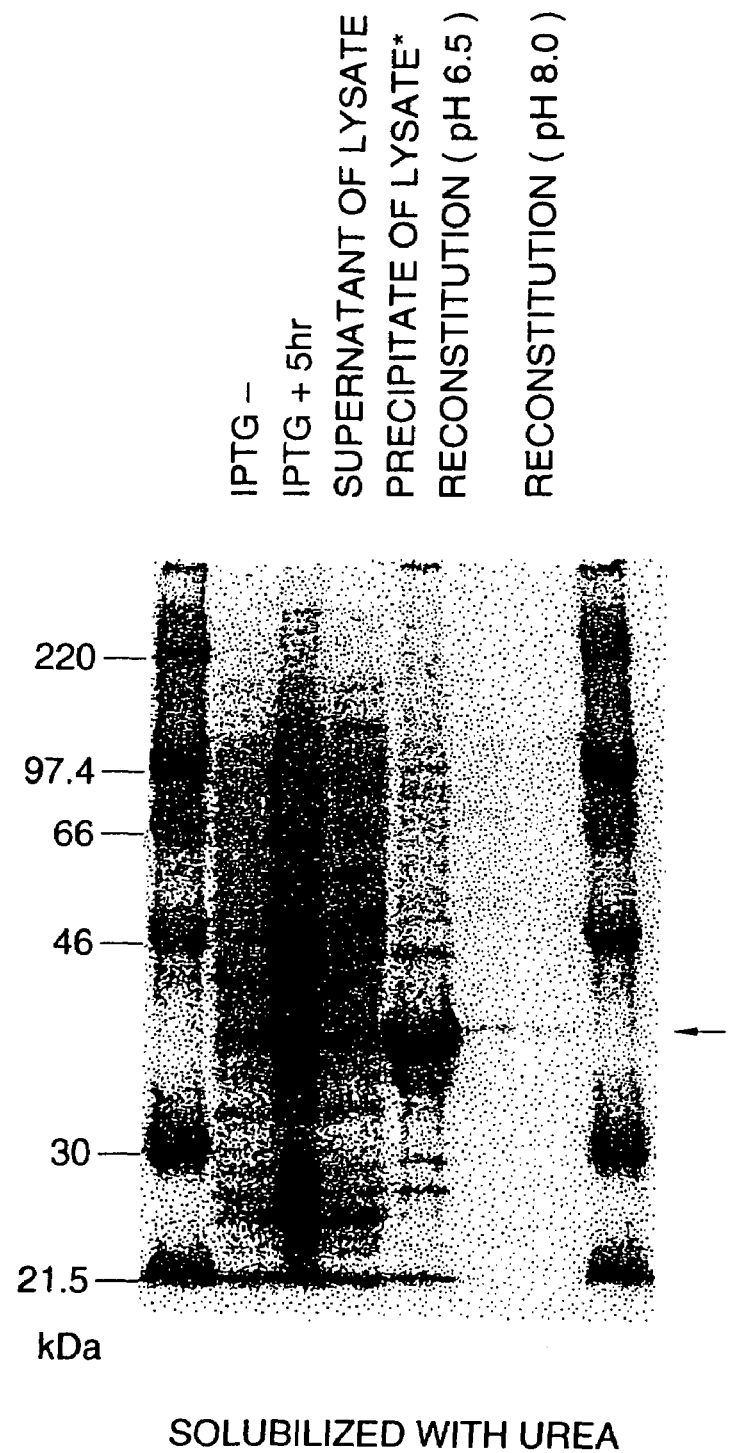
FIG. 1 is a printed data of electrophoresis (SDS-PAGE). Each prepared fraction and the solubilized fraction obtained from insolble fraction by urea described in Example 1 were subjected to SDS-PAGE. The proteins on the gel were detected by image analyzer (BAS2000) as shown in the FIG. 1. The expression of ON056 in *E. coli* is shown at the arrowhead in the FIGURE.

The present invention relates to a substantially purified form of the polypeptide comprising the amino acid sequence shown in SEQ ID NOS. 1, 4, 7, 10, 13, 16, 19, 22, 25, 28, 31, 34, 37, 40, 43, 46, 49, 52, 55, 58, 61, 64, 67, 70, 73, 76 or 79, homologue thereof, fragment thereof or homologue of the fragment.

Further, the present invention relates to cDNAs encoding the above peptides. More particularly the invention is provided cDNAs comprising nucleotide sequence shown in SEQ ID NOS. 2, 5, 8, 11, 14, 17, 20, 23, 26, 29, 32, 35, 38, 41, 44, 47, 50, 53, 56, 59, 62, 65, 68, 71, 74, 77, 80, 3, 6, 9, 12, 15, 18, 21, 24, 27, 30, 33, 36, 39, 42, 45, 48, 51, 54, 57, 60, 63, 66, 69, 72, 75, 78 or 81, and cDNA containing a fragment which is selectively hybridizing to the cDNA comprising nucleotide sequence shown in SEQ ID NOS. 2, 5, 8, 11, 14, 17, 20, 23, 26, 29, 32, 35, 38, 41, 44, 47, 50, 53, 56, 59, 62, 65, 68, 71, 74, 77, 80, 3, 6, 9, 12, 15, 18, 21, 24, 27, 30, 33, 36, 39, 42, 45, 48, 51, 54, 57, 60, 63, 66, 69, 72, 75, 78 or 81. A said cDNA capable for hybridizing to the cDNA includes the contemporary sequence of the above sequence.

A polypeptide comprising amino acid sequence shown in SEQ ID NOS. 1, 4, 7, 10, 13, 16, 19, 22, 25, 28, 31, 34, 37, 40, 43, 46, 49, 52, 55, 58, 61, 64, 67, 70, 73, 76 or 79 in substantially purified form will generally comprise the polypeptide in a preparation in which more than 90%, e.g. 95%, 98% or 99% of the polypeptide in the preparation is that of the SEQ ID NOS. 1, 4, 7, 10, 13, 16, 19, 22, 25, 28, 31, 34, 37, 40, 43, 46, 49, 52, 55, 58, 61, 64, 67, 70, 73, 76 or 79.

A homologue of polypeptide comprising amino acid sequence shown in SEQ ID NOS. 1, 4, 7, 10, 13, 16, 19, 22, 25, 28, 31, 34, 37, 40, 43, 46, 49, 52, 55, 58, 61, 64, 67, 70, 73, 76 or 79 will be generally at least 70%, preferably at least 80 or 90% and more preferably at least 95% homologous to the polypeptide comprising the said amino acid sequence over a region of at least 20, preferably at least 30, for instance 40, 60 or 100 more contiguous amino acids. Such a polypeptide homologue will be referred to a polypeptide of the present invention.

Generally, a fragment of polypeptide comprising amino acid sequence shown in SEQ ID NOS. 1, 4, 7, 10, 13, 16, 19, 22, 25, 28, 31, 34, 37, 40, 43, 46, 49, 52, 55, 58, 61, 64, 67, 70, 73, 76 or 79 or its homologues will be at least 10, preferably at least 15, for example 20, 25, 30, 40, 50 or 60 amino acids in length.

A cDNA capable of selectively hybridizing to the cDNA comprising nucleotide sequence shown in SEQ ID NOS. 2, 5, 8, 11, 14, 17, 20, 23, 26, 29, 32, 35, 38, 41, 44, 47, 50, 53, 56, 59, 62, 65, 68, 71, 74, 77, 80, 3, 6, 9, 12, 15, 18, 21, 24, 27, 30, 33, 36, 39, 42, 45, 48, 51, 54, 57, 60, 63, 66, 69, 72, 75, 78 or 81 will be generally at least 70%, preferably at least 80 or 90% and more preferably at least 95% homologous to the cDNA comprising the said nucleotide sequence over a region of at least 20, preferably at least 30, for instance 40, 60 or 100 or more contiguous nucleotides. Such a cDNA will be referred to "a cDNA of the present invention".

Fragments of the cDNA comprising nucleotide sequence shown in SEQ ID NOS. 2, 5, 8, 11, 14, 17, 20, 23, 26, 29, 32, 35, 38, 41, 44, 47, 50, 53, 56, 59, 62, 65, 68, 71, 74, 77, 80, 3, 6, 9, 12, 15, 18, 21, 24, 27, 30, 33, 36, 39, 42, 45, 48, 51, 54, 57, 60, 63, 66, 69, 72, 75, 78 or 81 will be at least 10, preferably at least 15, for example 20, 25, 30 or 40 nucleotides in length, and will be also referred to "a cDNA of the present invention" as used herein.

A further embodiment of the present invention provides replication and expression vectors carrying cDNA of the present invention. The vectors may be, for example, plasmid, virus or phage vectors provided with an origin of replication, optionally a promoter for the expression of the said cDNA and optionally a regulator of the promoter. The vector may contain one or more selectable marker genes, for example ampicillin resistance gene. The vector may be used in vitro, for example of the production of RNA corresponding to the cDNA, or used to transfect a host cell.

A further embodiment of the present invention provides host cells transformed with the vectors for the replication and expression of the cDNA of the present invention, including the cDNA comprising nucleotide sequence shown in SEQ ID NOS. 2, 5, 8, 11, 14, 17, 20, 23, 26, 29, 32, 35, 38, 41, 44, 47, 50, 53, 56, 59, 62, 65, 68, 71, 74, 77, 80, 3, 6, 9, 12, 15, 18, 21, 24, 27, 30, 33, 36, 39, 42, 45, 48, 51, 54, 57, 60, 63, 66, 69, 72, 75, 78 or 81 or the open reading frame thereof. The cells will be chosen to be compatible with the vector and may for example be bacterial, yeast, insect cells or mammalian cells.

A further embodiment of the present invention provides a method of producing a polypeptide which comprises culturing host cells of the present invention under conditions effective to express a polypeptide of the present invention. Preferably, in addition, such a method is carried out under conditions in which the polypeptide of the present invention is expressed and then produced from the host cells.

cDNA of the present invention may also be inserted into the vectors described above in an antisense orientation in order to prove for the production of antisense RNA. Such antisense RNA may be used in a method of controlling the levels of a polypeptide of the present invention in a cell.

The invention also provides monoclonal or polyclonal antibodies against a polypeptide of the present invention. The invention further provides a process for the production of monoclonal or polyclonal antibodies to the polypeptides of the present invention. Monoclonal antibodies may be prepared by common hybridoma technology using polypeptides of the present invention or fragments thereof, as an immunogen. Polyclonal antibodies may also be prepared by common means which comprise inoculating host animals, (for example a rat or a rabbit etc.), with polypeptides of the present invention and recovering immune serum.

The present invention also provides pharmaceutical compositions containing a polypeptide of the present invention, or an antibody thereof, in association with a pharmaceutically acceptable diluent and/or carrier.

The polypeptide of the present invention specified in (1) includes that which a part of their amino acid sequence is lacking (e.g., a polypeptide comprised of the only essential sequence for revealing a biological activity in an amino acid sequence shown in SEQ ID NO. 1), that which a part of their amino acid sequence is replaced by other amino acids (e.g., those replaced by an amino acid having a similar property) and that which other amino acids are added or inserted into a part of their amino acid sequence, as well as those comprising the amino acid sequence shown in SEQ ID NOS. 1, 4, 7, 10, 13, 16, 19, 22, 25, 28, 31, 34, 37, 40, 43, 46, 49, 52, 55, 58, 61, 64, 67, 70, 73, 76 or 79.

As known well, there are one to six kinds of codon as that encoding one amino acid (for example, one kind of codon for Methionine (Met), and six kinds of codon for Leucine (Leu) are known). Accordingly, the nucleotide sequence of cDNA can be changed in order to encode the polypeptide having the same amino acid sequence.

The cDNA of the present invention, specified in (2) includes a group of every nucleotide sequence encoding polypeptides (1) shown in SEQ ID NOS. 1, 4, 7, 10, 13, 16, 19, 22, 25, 28, 31, 34, 37, 40, 43, 46, 49, 52, 55, 58, 61, 64, 67, 70, 73, 76 or 79. There is a probability that yield of a polypeptide is improved by changing a nucleotide sequence.

The cDNA specified in (3) is the embodiment of the cDNA shown in (2), and indicate the sequence of natural form.

The cDNA shown in (4) indicates the sequence of the cDNA specified in (3) with natural non-translational region.

cDNA carrying nucleotide sequence shown in SEQ ID NOS. 3 is prepared by the following method:

Brief description of Yeast SST method (see U.S. Pat. No. 5,536,637) is as follows.

Yeast such as *Saccharomyces cerevisiae* should secrete invertase into the medium in order to take sucrose or raffinose as a source of energy or carbon. (Invertase is an enzyme to cleave raffinose into sucrose and melibiose, sucrose into fructose and glucose.). It is known that many known mammalian signal sequence make yeast secrete its invertase. From these knowledge, SST method was developed as a screening method to find novel signal peptide which make it possible can to secrete yeast invertase from mammalian cDNA library. SST method uses yeast growth on raffinose medium as a marker. Non-secretory type invertase gene SUC2 (GENBANK Accession No. V 01311) lacking initiation codon ATG was inserted to yeast expression vector to prepare yeast SST vector pSUC2. In this expression vector, ADH promoter, ADH terminator (both were derived from AAH5 plasmid (Gammerer, Methods in Enzymol. 101, 192-201, 1983)), 2 m ori (as a yeast replication origin), TRP1 (as a yeast selective marker), ColE1 ori (as a *E. Coli* replication origin) and ampicillin resistance gene (as a drug resistance marker) were inserted. Mammalian cDNA was inserted into the upstream of SUC2 gene to prepare yeast SST cDNA library. Yeast lacking secretory type invertase, was transformed with this library. If inserted mammalian cDNA encodes a signal peptide, yeast could survive in raffinose medium as a result of restoring secretion of invertase. Only to culture yeast colonies, prepare plasmids and determine the nucleotide sequence of the insert cDNAs, it is possible to identify novel signal peptide rapidly and easily.

Preparation of yeast SST cDNA library is as follows:
(1) mRNA is isolated from the targeted cells, double-strand synthesis is performed by using random primer with certain restriction enzyme (enzyme I) recognition site,
(2) obtained double-strand cDNA is ligated to adapter containing certain restriction endonuclease (enzyme II) recognition site, differ from enzyme I, digested with enzyme I and fractionated in a appropriate size,
(3) obtained cDNA fragment is inserted into yeast expression vector on the upstream region of invertase gene which signal peptide is deleted and the library was transformed.

Detailed Description of Each Step is as Follows:
(1) mRNA is isolated from mammalian organs and cell lines stimulate them with appropriate stimulator if necessary) by known methods (Molecular Cloning (Sambrook, J., Fritsch, E. F. and Maniats, T., Cold Spring Harbor Laboratory Press, 1989) or Current Protocol in Molecular Biology (F. M. Ausubel et al, John Wiley & Sons, Inc.) if not remark especially).

TG98G (human glioblastoma cell line: ATCC No. CRL-1690), IMR-32 (human neuroblastoma cell line: ATCC No. CCL-127), U-2OS (human osteosarcoma cell line: ATCC No. HTB-96), CCF-STTG1 (human astrocytoma cell line: ATCC No. CRL-1718), HAS303 (human bone marrow stroma cell line: provide from Professor Keisuke Sotoyama, Dr. Makoto Aizawa of First Medicine, Tokyo Medical College; see J. Cell. Physiol., 148, 245-251, 1991 and Experimental Hematol., 22, 482-487, 1994), LP101 (human bone marrow stroma cell line: provide from Professor Keisuke Sotoyama, Dr. Makoto Aizawa of First Medicine, Tokyo Medical College; see J. Cell. Physiol., 148, 245-251, 1991 and Experimental Hematol., 22, 482-487, 1994) and HUV-EC-C (endothelial cell of vein derived from human umbilical cord: ATCC No. CRL-1730) are chosen as a cell line. Human placenta and human adult brain are chosen as a tissue source. Double-strand cDNA synthesis using random primer is performed by known methods.

Any sites may be used as restriction endonuclease recognition site I which is linked to adapter and restriction endonuclease recognition site II which is used in step (2), if both sites are different each other. Preferably, XhoI is used as enzyme I and EcoRI as enzyme II.

In step (2), cDNA is created blunt-ends with T4 DNA polymerase, ligated enzyme II adapter and digested with enzyme I. Fragment cDNA is analyzed with agarose-gel electrophoresis (AGE) and is selected cDNA fraction ranging in size from 300 to 800 bp. As mentioned above, any enzyme may be used as enzyme II if it is not same the enzyme I.

In step (3), cDNA fragment obtained in step (2) is inserted into yeast expression vector on the upstream region of invertase gene which signal peptide is deleted. *E. Coli* was transformed with the expression vector. Many vectors are known as yeast expression plasmid vector. For example, YEp24 is also functioned in *E. Coli*. Preferably pSUC2 as described above is used.

Many host *E. Coli* strains are known for transformation, preferably DH10B competent cell is used. Any known transformation method is available, preferably it is performed by electropolation method. Transformant is cultured by conventional methods to obtain cDNA library for yeast SST method.

However not every all of the clones do not contain cDNA fragment. Further all of the gene fragments do not encode unknown signal peptides. It is therefore necessary to screen a gene fragment encoding for an unknown signal peptide from the library.

Therefore, screening of fragments containing a sequence encoding an appropriate signal peptide is performed by transformation of the cDNA library into Saccharomyces cerevisiae (e.g. YT455 strain) which lack invertase (it may be prepared by known methods.). Transformation of yeast is performed by known methods, e.g. lithium acetate method. Transformant is cultured in a selective medium, then transferred to a medium containing raffinose as a carbon source. Survival colonies are selected and then prepared plasmid. Survival colonies on a raffinose-medium indicates that some signal peptide of secretory protein was inserted to this clone.

As for isolated positive clones, the nucleotide sequence is determined. As to a cDNA encodes unknown protein, full-length clone may be isolated by using cDNA fragment as a probe and then determined to obtain full-length nucleotide sequence. These manipulation is performed by known methods.

Once the nucleotide sequences shown in SEQ ID NO. 2, 5, 8, 11, 14, 17, 20, 23, 26, 29, 32, 35, 38, 41, 44, 47, 50, 53, 56, 59, 62, 65, 68, 71, 74, 77, 80, 3, 6, 9, 12, 15, 18, 21, 24, 27, 30, 33, 36, 39, 42, 45, 48, 51, 54, 57, 60, 63, 66, 69, 72, 75, 78 or 81 are determined partially or preferably fully, it is possible to obtain DNA encode mammalian protein itself, homologue or subset. cDNA library or mRNA derived from mammals was screened by PCR with any synthesized oligonucleotide primers or by hybridization with any fragment as a probe. It is possible to obtain DNA encodes other mammalian homologue protein from other mammalian cDNA or genome library.

If a cDNA obtained above contains a nucleotide sequence of cDNA fragment obtained by SST (or consensus sequence thereof), it will be thought that the cDNA encodes signal peptide. So it is clear that the cDNA will be full-length or almost full. (All signal peptides exist at N-termini of a protein and are encoded at 5'-temini of open reading frame of cDNA.)

The confirmation may be carried out by Northern analysis with the said cDNA as a probe. It is thought that the cDNA is almost complete length, if length of the cDNA is almost the same length of the mRNA obtained in the hybridizing band.

Once the nucleotide sequences shown in SEQ ID NOS. 2, 5, 8, 11, 14, 17, 20, 23, 26, 29, 32, 35, 38, 41, 44, 47, 50, 53, 56, 59, 62, 65, 68, 71, 74, 77, 80, 3, 6, 9, 12, 15, 18, 21, 24, 27, 30, 33, 36, 39, 42, 45, 48, 51, 54, 57, 60, 63, 66, 69, 72, 75, 78 or 81 are determined, DNAs of the invention are obtained by chemical synthesis, or by hybridization making use of nucleotide fragments which are chemically synthesized as a probe. Furthermore, DNAs of the invention are obtained in desired amount by transforming a vector that contains the DNA into a proper host, and culturing the transformant.

The polypeptides of the present invention may be prepared by:
(1) isolating and purifying from an organism or a cultured cell,
(2) chemically synthesizing, or
(3) using recombinant cDNA technology, preferably, by the method described in (3) in an industrial production.

Examples of expression system (host-vector system) for producing a polypeptide by using recombinant cDNA technology are the expression systems of bacteria, yeast, insect cells and mammalian cells.

In the expression of the polypeptide, for example, in *E. Coli*, the expression vector is prepared by adding the initiation codon (ATG) to 5' end of a cDNA encoding mature peptide, connecting the cDNA thus obtained to the downstream of a proper promoter (e.g., trp promoter, lac promoter, λ PL promoter, T7 promoter etc.), and then inserting it into a vector (e.g., pBR322, pUC18, pUC19 etc.) which functions in an *E. coli* strain.

Then, an *E. coli* strain (e.g., *E. coli* DH1 strain, *E. coli* JM109 strain, *E. coli* HB101 strain, etc.) which is transformed with the expression vector described above may be cultured in a appropriate medium to obtain the desired polypeptide. When a signal sequence of bacteria (e.g., signal sequence of pel B) is utilized, the desired polypeptide may be also released in periplasm. Furthermore, a fusion protein with other polypeptide may be also produced readily.

In the expression of the polypeptide, for example, in a mammalian cells, for example, the expression vector is prepared by inserting the cDNA encoding nucleotide shown in SEQ ID NOS. 3, 6, 9, 12, 15, 18, 21, 24, 27, 30, 33, 36, 39, 42, 45, 48, 51, 54, 57, 60, 63, 66, 69, 72, 75, 78 or 81 into the downstream of a proper promoter (e.g., SV40 promoter, LTR promoter, metallothionein promoter etc.) in a proper vector (e.g., retrovirus vector, papilloma virus vector, vaccinia virus vector, SV40 vector, etc.). A proper mammalian cell (e.g., monkey COS-7 cell, Chinese hamster CHO cell, mouse L cell etc.) is transformed with the expression vector thus obtained, and then the transformant is cultured in a proper medium to express the aimed secretory protein and membrane protein of the present invention by the following method.

In case of secretory protein as for the present invention, the aimed polypeptide was expressed in the supernatant of the cells. In addition, fusion protein may be prepared by conjugating cDNA fragment encoding the other polypeptide, for example, Fc portion of antibody.

On the other hand, in case of membrane protein as for the present invention, the aimed polypeptide was expressed on the cell membrane. A cDNA encoding the nucleotide sequence of SEQ ID NOS. 3, 6, 9, 12, 15, 18, 21, 24, 27, 30, 33, 36, 39, 42, 45, 48, 51, 54, 57, 60, 63, 66, 69, 72, 75, 78 or 81 with deletion of extracellular region was inserted into the said vector, transfected into the an adequate mammalian cells to secret the aimed soluble polypeptide in the culture medium. In addition, fusion protein may be prepared by conjugating cDNA fragment encoding the said mutant with deletion of extracellular region and other polypeptide, for example, Fc portion of antibody.

The polypeptide available by the way described above can be isolated and purified by conventional biochemical method.

INDUSTRIAL APPLICABILITY

It is considered that the polypeptide of the present invention and a cDNA which encodes the polypeptide will show one or more of the effects or biological activities (including those which relates to the assays cited below) The effects or biological activities described in relation to the polypeptide of the present invention are provided by administration or use of the polypeptide or by administration or use of a cDNA molecule which encodes the polypeptide (e.g., vector suitable for gene therapy or cDNA introduction).

[Cytokine Activity and Cell Proliferation/Differentiation Activity]

The protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a polypeptide of the present invention is evidenced by any one of a number of routine factor dependent cell proliferation assays for cell lines.

[Immune Stimulating/Suppressing Activity]

The protein of the present invention may also exhibit immune stimulating or immune suppressing activity. The protein of the present invention may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral infection such as HIV as well as bacterial or fungal infections, or may result from autoimmune disorders. More specifically, infectious diseases causes by viral, bacterial, fungal or other infection may be treatable using the polypeptide of the present invention, including infections by HIV, hepatitis viruses, herpes viruses, mycobacteria, leshmania, malaria and various fungal infections such as candida. Of course, in this regard, the protein of the present invention may also be useful where a boost to the immune system generally would be indicated, i.e., in the treatment of cancer.

The protein of the present invention may be useful in the treatment of allergic reactions and conditions, such as asthma or other respiratory problems. The protein of the present invention may also be useful in the treatment of the other conditions required to suppress the immuno system (for example, asthma or respiratory disease.)

The protein of the present invention may also suppress chronic or acute inflammation, such as, for example, that associated with infection such as septic shock or systemic inflammatory response syndrome (SIRS), inflammatory bowel disease, Crohn's disease or resulting from over production of cytokines such as TNF or IL-I wherein the effect was demonstrated by IL-11.

[Hematopoiesis Regulating Activity]

The protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis. The said biological activities are concerned with the following all or some example(s). e.g. in supporting the growth and proliferation of erythroid progenitor cells alone or in combination with other cytokines, thereby indicating utility, for example, in treating various anemia or for use in conjunction with irradiation/chemotherapy to stimulate the production of erythroid precursors and/or erythroid cells; in supporting the growth and proliferation of myeloid cells such as, granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vitro or ex-vivo (i.e. in conjunction with bone marrow transplantation) as normal cells or genetically manipulated for gene therapy.

The activity of the protein of the present invention may, among other means, be measured by the following methods:

[Tissue Generation/Regeneration Activity]

The protein of the present invention also may have utility in compositions used for bone, cartilage, tendon, Ligament and/or nerve tissue growth or regeneration, as well as for wound healing and tissue repair, and in the treatment of burns, incisions and ulcers.

The protein of the present invention, which induces cartilage and/or bone growth in circumstances where bone is not normally formed, may be applied to the healing of bone fractures and cartilage damage or defects in humans and other animals. Such a preparation employing the protein of the present invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

The protein of the present invention may also be used in the treatment of periodontal disease, and in other tooth repair processes. Such agents may provide an environment to attract bone-forming cells, stimulate growth of bone-forming cells or induce differentiation of progenitors of bone-forming cells. The protein of the present invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. The protein of the present invention, which induces tendon/ligament-like tissue or other tissue formation in circumstances where such tissue is not normally formed, may be applied to the healing of tendon or ligament tears, deformities and other tendon or ligament defects in humans and other animals. Such a preparation employing the protein inducing a tendon/Ligament-like tissue may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon Ligament cells or progenitors ex vivo for return in vivo to effect tissue repair. The compositions of the present invention may also be useful in the treatment of tendinitis, Carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue. i.e. for the treatment of central and peripheral nervous system diseases and neuropathies as well as mechanical and traumatic disorders, which involve degeneration, death or trauma to neural cells or nerve tissue. More specifically, the protein of the present invention may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the invention include mechanical and traumatic disorders, such as spinal cord disorders, head trauma and cerebrovascular diseases such as stroke. Peripheral neuropathies resulting from chemotherapy or other medical therapies may also be treatable using the polypeptide of the present invention.

It is expected that the protein of the present invention may also exhibit activity for generation of other tissues, such as organs (including, for example, pancreas, liver, intestine, kidney, skin, endothelium), muscle (smooth, skeletal or cardiac) and vascular (including vascular endothelium) tissue, or for promoting the proliferation of cells comprising such tissues. Part of the desired effects may be by inhibition of fibrotic scarring to allow normal tissue to regenerate.

The protein of the present invention may also be useful for gut protection or regeneration and treatment of lung or liver fibrosis, reperfusion injury in various tissues, and conditions resulting from systemic cytokine damage.

[Activin/Inhibin Activity]

The protein of the present invention may also exhibit activin- or inhibin-related activities. Inhibins are characterized by their ability to inhibit the release of follicle stimulating hormone (FSH), while activins are characterized by their ability to stimulate the release of follicle stimulating hormone (FSH). Thus, the protein of the present invention alone or in heterodimers with a member of the inhibin *a family, may be useful as a contraceptive based on the ability of inhibins to decrease fertility in female mammals and decrease spermatogenesis in male mammals. Administration of sufficient amounts of other inhibins can induce infertility in these mammals.

Alternatively, the protein of the present invention, as a homodimer or as a heterodimer with other protein subunits of the inhibin-*b group, may be useful as a fertility inducing therapeutic, based upon the ability of activin molecules in stimulating FSH release from cells of the anterior pituitary (See U.S. Pat. No. 4,798,885). The protein of the present invention may also be useful for advancement of the onset of fertility in sexually immature mammals, so as to increase the lifetime reproductive performance of domestic animals such as cows, sheep and pigs.

[Chemotactic/Chemokinetic Activity]

The protein of the present invention may have chemotactic or chemokinetic activity e.g., functioning as a chemokine, for mammalian cells, including, for example, monocytes, neutrophils, T-cells, mast cells, eosinophils and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

If a protein or peptide can stimulate, directly or indirectly, the directed orientation or movement of such cell population, it has chemotactic activity for a particular cell population. Preferably, the protein or peptide has the ability to directly stimulate directed movement of cells. Whether a particular protein has chemotactic activity for a population of cells can be readily determined by employing such protein or peptide in any known assay for cell chemotaxis.

[Hemostatic and Thrombolytic Activity]

The protein of the present invention may also exhibit hemostatic or thrombolyic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the present invention may also be useful for dissolving or inhibiting formation of thromboses and for treatment and prevention of conditions resulting therefrom such as, for example, infarction or stroke.

[Receptor/Ligand Activity]

The protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including cellular adhesion molecules such as Selectins, Integrins and their ligands) and receptor/ligand pairs involved in antigen presentation, antigen recognition and development of cellular and humoral immune responses. Receptors and ligands are also useful for screening of potential peptide or small molecule inhibitors of the relevant receptor/ligand interaction. The protein of the present invention (including, without limitation, fragments of receptors and ligands) may themselves be useful as inhibitors of receptor/ligand interactions.

[Other Activity]

The protein of the present invention may also exhibit one or more of the following additional activities or effects: inhibiting growth of or killing the infecting agents including bacteria, viruses, fungi and other parasites; effecting (suppressing or enhancing) body characteristics including height, weight, hair color, eye color, skin, other tissue pigmentation, or organ or body part size or shape such as, for example, breast augmentation or diminution etc.; effecting elimination of dietary fat, protein, carbohydrate; effecting behavioral characteristics including appetite, libido, stress, cognition (including cognitive disorders), depression and violent behaviors; providing analgesic effects or other pain reducing effects; promoting differentiation and growth of embryonic stem cells in lineages other than hematopoietic lineages; in the case of enzymes, correcting deficiencies of the enzyme and treating deficiency-related diseases.

The protein with above activities, is suspected to have following functions by itself or interaction with its ligands or receptors or association with other molecules. For example, proliferation or cell death of B cells, T cells and/or mast cells; specific induction by promotion of class switch of immunoglobulin genes; differentiation of B cells to antibody-forming cells; proliferation, differentiation, or cell death of precursors of granulocytes; proliferation, differentiation, or cell death of precursors of monocytes-macrophages; proliferation, of up regulation or cell death of neutrophils, monocytes-macrophages, eosinophils and/or basophils; proliferation, or cell death of precursors of megakaryocytes; proliferation, differentiation, or cell death of precursors of neutrophils; proliferation, differentiation, or cell death of precursors of T cells and B cells; promotion of production of erythrocytes; sustainment of proliferation of erythrocytes, neutrophils, eosinophils, basophils, monocytes-macrophages, mast cells, precursors of megakaryocyte; promotion of migration of neutrophils, monocytes-macrophages, B cells and/or T cells; proliferation or cell death of thymocytes; suppression of differentiation of adipocytes; proliferation or cell death of natural killer cells; proliferation or cell death of hematopoietic stem cells; suppression of proliferation of stem cells and each hematopoietic precursor cells; promotion of differentiation from mesenchymal stem cells to osteoblasts or chondrocytes, proliferation or cell death of mesenchymal stem cells, osteoblasts or chondrocytes and promotion of bone absorption by activation of osteoclasts and promotion of differentiation from monocytes to osteoclasts.

The polypeptide of the present invention is also suspected to function to nervous system, so expected to have functions below; differentiation to kinds of neurotransmitter-responsive neurons, survival or cell death of these cells; promotion of proliferation or cell death of glial cells; spread of neural dendrites; survival or cell death of gangriocytes; proliferation, promotion of differentiation, or cell death of astrocytes; proliferation, survival or cell death of peripheral neurons; proliferation or cell death of Schwann cells; proliferation, survival or cell death of motoneurons.

Furthermore, in the process of development of early embryonic, the polypeptide of the present invention is expected to promote or inhibit the organogenesis of epidermis, brain, backbone, and nervous system by induction of ectoderm, that of notochord connective tissues (bone, muscle, tendon), hemocytes, heart, kidney, and genital organs by induction of mesoderm, and that of digestive apparatus (stomach, intestine, liver, pancreas), respiratory apparatus (lung, trachea) by induction of endoderm. In adult, also, this polypeptide is thought to proliferate or inhibit the above organs.

Therefore, the polypeptide of the present invention itself is expected to be used as an agent for the prevention or treatment of disease of progression or suppression of immune, nervous, or bone metabolic function, hypoplasia or overgrowth of hematopoietic cells: for example, inflammatory disease (rheumatism, ulcerative colitis, etc.), decrease of hematopoietic stem cells after bone marrow transplantation, decrease of leukocytes, platelets, B-cells, or T-cells after radiation exposure or chemotherapeutic dosage against cancer or leukemia, anemia, infectious disease, cancer, leukemia, AIDS, bone metabolic disease (osteoporosis etc.), various degenerative disease (Alzheimer's disease, multiple sclerosis, etc.), or nervous lesion.

In addition, since the polypeptide of the present invention is thought to induce the differentiation or growth of organs derived from ectoderm, mesoderm, and endoderm, this polypeptide is expected to be an agent for tissue repair (epidermis, bone, muscle, tendon, heart, kidney, stomach, intestine, liver, pancreas, lung, and trachea, etc.).

By using polyclonal or monoclonal antibodies against the polypeptide of the present invention, quantitation of the said polypeptide in the body can be performed. It can be used in the study of relationship between this polypeptide and disease or diagnosis of disease, and so on. Polyclonal and monoclonal antibodies can be prepared using this polypeptide or its fragment as an antigen by conventional methods.

Identification, purification or molecular cloning of known or unknown proteins which bind the polypeptide of the present invention (preferably polypeptide of extracellular domain) can be performed using the polypeptide of the present invention by, for example, preparation of the affinity-column.

Identification of the downstream signal transmission molecules which interact with the polypeptide of the present invention in cytoplasma and molecular cloning of the gene can be performed by west-western method using the polypeptide of the present invention (preferably polypeptide of transmembrane region or intracellular domain), or by yeast two-hybrid system using the cDNA (preferably cDNA encoding transmembrane region or cytoplasmic domain of the polypeptide).

Agonists/antagonists of this receptor polypeptide and inhibitors between receptor and signal transduction molecules can be screened using the polypeptide of the present invention.

cDNAs of the present invention are useful not only the important and essential template for the production of the polypeptide of the present invention which is expected to be largely useful, but also be useful for diagnosis or therapy (for example, treatment of gene lacking, treatment to stop the expression of the polypeptide by antsense cDNA (mRNA)). Genomic cDNA may be isolated with the cDNA of the present invention, as a probe. As the same manner, a human gene encoding which can be highly homologous to the cDNA of the present invention, that is, which encodes a polypeptide highly homologous to the polypeptide of the present invention and a gene of animals excluding mouse which can be highly homologous to the cDNA of the present invention, also may be isolated.

[Application to Medicaments]

The polypeptide of the present invention or the antibody specific for the polypeptide of the present invention is administered systemically or topically and in general orally or parenterally, preferably parenterally, intravenously and intraventricularly, for preventing or treating the said diseases.

The doses to be administered depend upon age, body weight, symptom, desired therapeutic effect, route of administration, and duration of the treatment etc. In human adults, one dose per person is generally between 100 μg and 100 mg, by oral administration, up to several times per day, and between 10 μg and 100 mg, by parental administration up to several times per day.

As mentioned above, the doses to be used depend upon various conditions. Therefore, there are cases in which doses lower than or greater than the ranges specified above may be used.

The compounds of the present invention, may be administered as solid compositions, liquid compositions or other compositions for oral administration, as injections, liniments or suppositories etc. for parental administration.

Solid compositions for oral administration include compressed tablets, pills, capsules, dispersible powders, and granules. Capsules include soft or hard capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid etc.).

The tablets or pills may, if desired, be coated with a film of gastric or enteric materials (such as sugar, gelatin, hydroxypropyl cellulose or hydroxypropylmethyl cellulose phthalate, etc.), or be coated with more than two films. And then, coating may include containment within capsules of absorbable materials such as gelatin.

Liquid compositions for oral administration include pharmaceutically-acceptable emulsions, solutions, syrups and elixirs. In such compositions, one or more of the active compound(s) is or are contained in inert diluent(s) commonly used (purified water, ethanol etc.). Besides inert diluents, such compositions may also comprise adjuvants (such as wetting agents, suspending agents, etc.), sweetening agents, flavoring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfite etc.), isotonic buffer (sodium chloride, sodium citrate, citric acid, etc.). For preparation of such spray compositions, for example, the method described in the U.S. Pat. Nos. 2,868,691 or 3,095,355 (herein incorporated in their entireties by reference) may be used.

Injections for parental administration include sterile aqueous or non-aqueous solutions, suspensions and emulsions. In such compositions, one or more active compound(s) is or are admixed with at least one inert aqueous diluent(s) (distilled water for injection, physiological salt solution, etc.) or inert non-aqueous diluents(s)(propylene glycol, polyethylene glycol, olive oil, ethanol, POLYSOLBATE 80 (Trade mark) etc.).

Injections may comprise additional compound other than inert diluents: e.g. preserving agents, wetting agents, emulsifying agents, dispersing agents, stabilizing agent (such as human serum albumin, lactose, etc.), and assisting agents such as assisting agents for dissolving (arginine, asparaginic acid, etc.).

BEST MODE CARRYING OUT THE INVENTION

The invention is illustrated by the following examples, but not limit the invention.

EXAMPLE 1

Clone ON056

(1) Preparation of Poly(A)+RNA Total RNA was prepared from human placenta tissue by TRIzol reagent (Trade Mark, marketed by GIBCO BRL Co.). Poly(A)+RNA was purified from the total RNA by mRNA Purification Kit (Trade name, marketed by Pharmacia Co.).

(2) Preparation of Yeast SST cDNA Library

Double strand cDNA was synthesized by Super Script Plasmid System for cDNA Synthesis and Plasmid Cloning (Trade name, marketed by GIBCO BRL Co.) with above poly(A)+RNA as template and random 9 mer as primer which was containing XhoI site:

```
                                          (SEQ ID NO. 82)
5'-CGA TTG AAT TCT AGA CCT GCC TCG AGN NNN NNN NN-
3'.
``` cDNA was ligated EcoRI adapter by DNA ligation kit ver. 2 (Trade name, marketed by Takara Shuzo Co.; this kit was used in all ligating steps hereafter.) and digested by XhoI. cDNAs were separated by agarose-gel electrophoresis. 300~800 bp cDNAs were isolated and were ligated to EcoRI/NotI site of pSUC2 (see U.S. Pat. No. 5,536,637). *E. Coli* DH10B strains were transformed by pSUC2 with electropolation to obtain yeast SST cDNA library.

(3) Screening by SST Method and Determination of Nucleotide Sequence of SST Positive Clone Plasmids of the said cDNA library were prepared. Yeast YTK12 strains were transformed by the plasmids with lithium acetate method (Current Protocols In Molecular Biology 13.7.1). The transformed yeast were plated on triptphan-free medium (CMD-Trp medium) for selection. The plate was incubated for 48 hour at 30° C. Replica of the colony (transformant) which was obtained by Accutran Replica Plater (Trade name, marketed by Schleicher & Schuell) were placed onto YPR plate containing raffinose for carbon source, and the plate was incubated for 14 days at 30° C. After 3 days, each colony appeared was streaked on YPR plate again. The plates were incubated for 48 hours at 30° C. Single colony was inoculated to YPD medium and was incubated for 48 hours at 30° C. Then plasmids were prepared. Insert cDNA was amplified by PCR with two kind primers which exist end side of cloning site on pSUC2 (sense strand primers were biotinylated). Biotinylated single strand of cDNAs were purified with Dynabeads (Trade name, marketed by DYNAL Co.) and the nucleotide sequences were determined. Sequencing was performed by Dye Terminator Cycle Sequencing Ready Reaction with DNA Sequencing kit (Trade name, marketed by Applied Biosystems Inc.) and sequence was determined by DNA sequencer 373 (Applied Biosystems Inc.) (All sequencing hereafter was carried out with this method.).

We tried to carry out cloning of full-length cDNA which was proved to be new one according to the homology search for the obtained nucleotide sequences and deduced amino acid sequences in data base. We also confirmed that each cDNA contains signal peptide in view of function and structure, by comparison with known peptide which has signal peptide and deduced amino acid sequence.

(4) Cloning of a Full-Length cDNA and Determination of Nucleotide Sequence

A full-length cDNA was cloned using GENETRAPPER cDNA Positive Selection System (marketed by GIBCO BRL Co.). First, dt-primed cDNA library was prepared from poly (A)+RNA in human placenta tissue using pSPORT1 plasmid (marketed by GIBCO BRL Co.), as a vector, by Super Script Plasmid System for cDNA Synthesis and Plasmid Cloning. Next, after preparing biotinylated primer ON056-F1 (27 mer):

```
                                        (SEQ ID NO. 83)
      5' biotin-AACATGAATCTTTCGCTCGTCCTGGCT-3'
``` based on the information of nucleotide sequence obtained by SST, plasmid hybridized specifically with the biotinylated primer were recovered from the cDNA library according to the method of Gene Trapper Kit and then transfected into *E. Coli* DH10B. Colony hybridization with ON056 SST cDNA which was labeled with $^{32}$P-dCTP, as a probe, was performed by using Random Primer DNA Labeling kit (Trade name, marketed by Takara Shuzo Co.) according to known method to isolate the positive clone and to prepare the plasmid. Nucleotide sequences of 5'-end were determined, and the existence of nucleotide sequence ON056 SST cDNA was confirmed. Nucleotide sequence of full-length ON056 SST cDNA was determined and then sequence shown in SEQ ID NO. 3 was obtained. An open reading frame was determined and deduced amino acid sequence and nucleotide sequence shown in SEQ ID NOS. 1 and 2, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of ON056 of the present invention. From these results, it was proved that polypeptide of the present invention was new secretary protein.

However, the search using BLASTX, BLASTP and FASTA revealed a significant homology between clone ON056 (region of 1st~334th amino acid in SEQ ID NO. 1) and Human Cathepsin L (Swiss Prot Accession P07711) (region of 1st~334th amino acid) or between clone ON056 (region of 22nd~334th amino acid in SEQ ID NO. 1) and Human Cathepsin K (Swiss Prot Accession P43235) (region of 19th~329th amino acid). Based on these homologies, clone ON0566 and Human Cathepsin L family were expected to share at least some activity.

(5) Expression of Protein Using *E. Coli*

The coding region cDNA fragments without sequence encoding signal peptide were amplified by PCR and inserted into the downstream of initiation codon ATG in pET expression vector (marketed by Novagen Co.) for *E. Coli* inframe to construct the plasmid for expression. The obtained plasmids were transfected into *E. Coli* BL21 (DE3) and the transformant was cultured with IPTG to induce the expression of protein. The obtained *E. Coli* was harvested and lysed with ultra-sonication or detergent. The insoluble fraction was solubilized with urea and subjected to SDS-PAGE. The expression of ON056 protein was confirmed by Coomassie staining (arrow in FIG. 1).

(6) Expression of the Protein Using Mammalian Cell

Thus obtained full-length cDNA was conjugated into XhoI (or EcoRI)-NotI site of the pED6 expression vector of mammalian cells (See Kaufman et al., Nucleic Acids Res. 19, 4485-4490 (1991)) to construct plasmid to express the secretory protein or membrane protein. The obtained plasmids were transfected into Cos 7 cells using Lypofectine (Trade name, marketed by GIBCO BRL Co.). After 24 hours, the transfection mixture was removed. The cells were cultured in the Met and Cys-free medium with $^{35}$S-labeled Met and $^{35}$S-labeled Cys for 5 hours. The supernatants were harvested and 10-fold concentrated with Centricon-10 (Trade name, marketed by Amicon Co.). The samples were separated on SDS-PAGE gels. After drying the acrylamidogel, the expression of $^{35}$S-labeled protein was detected using BAS2000 (marketed by Fuji Film Co.).

EXAMPLE 2

Clone ON034

In Example relating to clone ON034 of the present invention, the same procedure as in Example of ON056 was used except for the following points.

(1) Preparation of Poly(A)+RNA

Total RNA was prepared from human placenta tissue by TRIzol reagent. Poly(A)+RNA was purified from the total RNA by mRNA Purification Kit.

(2) Cloning of a Full-Length cDNA and Determination of Nucleotide Sequence

A full-length cDNA was cloned using GENETRAPPER cDNA Positive Selection System. First, dT-primed cDNA library was prepared from poly (A)+RNA in human placenta tissue using pSPORT1 plasmid, as a vector, by Super Script Plasmid System for cDNA Synthesis and Plasmid Cloning. Next, after preparing biotinylated primer ON034-F1 (28 mer):

```
                                       (SEQ ID NO.: 84)
      5' biotin-TGAAGCCCATCACTACATCGCCATTACG-3'
``` based on the information of nucleotide sequence obtained by SST, plasmid hybridized specifically with the biotinylated primer were recovered from the cDNA library according to the method of Gene Trapper Kit and then transfected into *E. Coli* DH10B. Colony hybridization with ON034 SST cDNA which was labeled with 32P-dCTP, as a probe, was performed by using Random Primer DNA Labeling kit according to known method to isolate the positive clone and to prepare the plasmid. Nucleotide sequence of full-length ON034 SST cDNA was determined by the same procedure as ON056 and then sequence shown in SEQ ID NO. 6 was obtained. An open reading frame was determined and deduced amino acid sequence and nucleotide sequence shown in SEQ ID NOS. 4 and 5, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of ON034 of the present invention. From these results, it was proved that polypeptide of the present invention was new secretary protein.

EXAMPLE 3

Clone OX003

In Example relating to clone OX003 of the present invention, the same procedure as in Example of ON056 was used except for the following points.

(1) Preparation of Poly(A)$^+$RNA

Total RNA was prepared from human placenta tissue by TRIzol reagent. Poly(A)$^+$RNA was purified from the total RNA by mRNA Purification Kit.

(2) Cloning of a Full-Length cDNA and Determination of Nucleotide Sequence

A full-length cDNA was cloned using Marathon cDNA Amplification Kit (Trade name, marketed by Clontech Co.) according to 3' RACE (Rapid Amplification of cDNA End) method. Double strand cDNA was prepared from the origin of each clone, i.e., poly (A)$^+$RNA in human placenta tissue. 27 mer primer OX003-F1:

5'-CAAAACCCACAAGAAATTCACCAAGGC-3' (SEQ ID NOS. 85)

containing the deduced initiation ATG codon region based on the information of nucleotide sequence obtained by SST, was prepared. PCR was performed with the said primer and adapter primer attached in the kit. Due to insufficient amplification of cDNA by only one-time PCR, 23 mer primer OX003-F2:

5'-TCACCAAGGCTAACATGGTGGCC-3' (SEQ ID NOS. 86)

was prepared additionally at 3' end of OX003-F1 primer and then nested PCR was performed. cDNA which was amplified with clone OX003 specifically was separated with agarosegel electrophoresis, ligated to pT7 Blue-2 T-Vector (Trade name, marketed by Novagen Co.) and transfected into *E. Coli* DH5a to prepare the plasmid. First, Nucleotide sequences of 5'-end were determined, and the existence of nucleotide sequence OX003 SST cDNA was confirmed. Nucleotide sequence of full-length OX003 SST cDNA was determined and then sequence shown in SEQ ID NO. 9 was obtained. An open reading frame was determined and deduced amino acid sequence and nucleotide sequence shown in SEQ ID NOS. 7 and 8, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OX003 of the present invention. From these results, it was proved that polypeptide of the present invention was new secretary protein.

EXAMPLE 4

Clone OA052

In Example relating to clone OA052 of the present invention, the same procedure as in Example of ON056 was used except for the following points.

(1) Preparation of Poly(A)$^+$RNA

Total RNA was prepared from human glioblastoma cell line T98G (ATCC No. CRL-1690) by TRIzol reagent. Poly (A)$^+$RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA conjugating adapter was prepared from the origin of each clone, i.e., poly (A)$^+$RNA in human glioblastoma cell line T98G according to the method of the said kit. 27 mer primer OA052-F1:

5'-ATGCCTAGAAGAGGACTGATTCTTCAC-3' (SEQ ID NO. 87)

containing the deduced initiation ATG codon region based on the information of nucleotide sequence obtained by SST, was prepared. PCR was performed with the said primer and adapter primer attached in the kit. cDNA which was amplified with clone OA052 specifically was separated with recloning by the same method as Example of OX003. Full nucleotide sequence was determined and then sequence shown in SEQ ID NO. 12 was obtained. An open reading frame was determined and deduced amino acid sequence and nucleotide sequence shown in SEQ ID NOS. 10 and 11, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OA052 of the present invention. From these results, it was proved that polypeptide of the present invention was new secretary protein.

EXAMPLE 5

Clone OC004

In Example relating to clone OC004 of the present invention, the same procedure as in Example of ON056 was used except for the following points.

(1) Preparation of Poly(A)$^+$RNA

Total RNA was prepared from human adult brain tissue by TRIzol reagent. Poly(A)$^+$RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)⁺RNA in human adult brain tissue. 27 mer primer OC004-F1:

5'-ATGAGGAAAGGGAACCTTCTGCTGAGC-3' (SEQ ID NOS. 88)

containing the deduced initiation ATG codon region based on the information of nucleotide sequence obtained by SST, was prepared. PCR was performed with the said primer and adapter primer attached in the kit. Due to insufficient amplification of cDNA by only one-time PCR, 18 mer primer OC004-F2:

5'-TGAGCTTCCAGAGCTGTC-3' (SEQ ID NOS. 89)

was prepared additionally at 3' end of OC004-F1 primer and then nested PCR was performed. cDNA which was amplified with clone OC004 specifically was separated with recloning by the same method as Example of OX003. Full nucleotide sequence was determined and then sequence shown in SEQ ID NO. 15 was obtained. An open reading frame was determined and deduced amino acid sequence and nucleotide sequence shown in SEQ ID NOS. 13 and 14, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OC004 of the present invention. From these results, it was proved that polypeptide of the present invention was new secretary protein.

EXAMPLE 6

Clone OM017

In Example relating to clone OM017 of the present invention, the same procedure as in Example of ON056 was used except for the following points.

(1) Preparation of Poly(A)⁺RNA

Total RNA was prepared from human adult brain tissue by TRIzol reagent. Poly(A)⁺RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)⁺RNA in human adult brain tissue. 27 mer primer OM017-F3:

5'-GGGAAATGAAACATTTCTGTAACCTGC-3' (SEQ ID NOS. 90)

containing the deduced initiation ATG codon region based on the information of nucleotide sequence obtained by SST, was prepared. PCR was performed with the said primer and adapter primer attached in the kit. Due to insufficient amplification of cDNA by only one-time PCR, 27 mer primer OM017-F1:

5'-ATGAAACATTTCTGTAACCTGCTTTGT-3' (SEQ ID NOS. 91)

was prepared additionally at 3' end of OM017-F3 primer and then nested PCR was performed. cDNA which was amplified with clone OM017 specifically was separated with recloning by the same method as Example of OX003. Full nucleotide sequence was determined and then sequence shown in SEQ ID NO. 18 was obtained. An open reading frame was determined and deduced amino acid sequence and nucleotide sequence shown in SEQ ID NOS. 16 and 17, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OM017 of the present invention. From these results, it was proved that polypeptide of the present invention was new secretary protein.

However, the search using BLASTX, BLASTP and FASTA revealed a significant homology between clone OM017 (region of 433th~709th, 42nd~225th, 170th~399th and 1st~224th amino acid in SEQ ID NO. 16) and Human DXS6673E (Candidate gene for Mental Retardation) (PRF Code 2218282A (Genbank Accession X95808) ) (region of 1083rd~1358th, 758th~932nd, 850th~1081st and 739th~965th amino acid) Based on these homologies, clone OM017 and Human DXS6673E were expected to share at least some activity.

EXAMPLE 7

Clone OM101

In Example relating to clone OM101 of the present invention, the same procedure as in Example of ON056 was used except for the following points.

(1) Preparation of Poly(A)⁺RNA

Total RNA was prepared from human adult brain tissue by TRIzol reagent. Poly(A)⁺RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)⁺RNA in human adult brain tissue. 27 mer primer OM101-F3:

(SEQ ID NOS. 92)
5'-TGAAGTTGCAGATAATGAGGACTTACC-3' containing the deduced initiation ATG codon region based on the information of nucleotide sequence obtained by SST, was prepared. PCR was performed with the said primer and adapter primer attached in the kit. Due to insufficient amplification of cDNA by only one-time PCR, 27 mer primer OM101-F1:

(SEQ ID NOS. 93)
5'-ATGAGGACTTACCATTATATACCATTA-3' was prepared additionally at 3' end of OM0101-F3 primer and then nested PCR was performed. cDNA which was amplified with clone OM101 specifically was separated with recloning by the same method as Example of OX003. Full nucleotide sequence was determined and then sequence shown in SEQ ID NO. 21 was obtained. An open reading frame was determined and deduced amino acid sequence and nucleotide sequence shown in SEQ ID NOS. 19 and 20, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OM101 of the present invention. From these results, it was proved that polypeptide of the present invention was new secretary protein.

However, the search using BLASTX, BLASTP and FASTA revealed a significant homology between clone OM101 (region of 1st~77th amino acid in SEQ ID NO. 19), and a lot of Cadherin family such as Human Cadherin-6 (Swiss Prot Accession P55285) (region of 1st~77th amino acid) and Human Brain-Cadherin (Swiss Prot Accession P55289) (region of 1st~78th amino acid). Based on these homologies, clone OM101 and Human Cadherin-6 and the other Cadherin family were expected to share at least some activity.

EXAMPLE 8

Clone OM126

In Example relating to clone OM126 of the present invention, the same procedure as in Example of ON056 was used except for the following points.

(1) Preparation of Poly(A)$^+$RNA

Total RNA was prepared from human adult brain tissue by TRIzol reagent. Poly(A)$^+$RNA was purified from the total RNA by mRNA Purification Kit.

(2) Cloning of a Full-Length cDNA and Determination of Nucleotide Sequence

Double strand cDNA was prepared from the origin of each clone, i.e., poly (A)$^+$RNA in human adult brain tissue. 27 mer primer OM126-F3:

(SEQ ID NOS. 94)
5'-AGGAAGGATGAGGAAGACCAGGCTCTG-3' containing the deduced initiation ATG codon region based on the information of nucleotide sequence obtained by SST, was prepared. cDNA which was amplified with clone OM126 specifically was separated with reckoning by the same method as Example of OX003. Full nucleotide sequence was determined and then sequence shown in SEQ ID NO. 24 was obtained. An open reading frame was determined and deduced amino acid sequence and nucleotide sequence shown in SEQ ID NOS. 22 and 23, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OM126 of the present invention. From these results, it was proved that polypeptide of the present invention was new secretary protein.

However, the search using BLASTX, BLASTP and FASTA revealed a significant homology between clone OM126 (region of 25th~115th amino acid in SEQ ID NO. 22), and immunoglobulin domain. Based on these homologies, clone OM126 and immunoglobulin superfamily were expected to share at least some activity.

EXAMPLE 9

Clone OM160

In Example relating to clone OM160 of the present invention, the same procedure as in Example of ON056 was used except for the following points.

(1) Preparation of Poly(A)$^+$RNA

Total RNA was prepared from human adult brain tissue by TRIzol reagent. Poly(A)$^+$RNA was purified from the total RNA by mRNA Purification Kit.

(2) Cloning of a Full-Length cDNA and Determination of Nucleotide Sequence

A full-length cDNA was cloned using GENETRAPPER cDNA Positive Selection System. First, dT-primed cDNA library was prepared from poly (A)+RNA in human adult brain tissue using pSPORT1 plasmid, as a vector, by Super Script Plasmid System for cDNA Synthesis and Plasmid Cloning. Next, after preparing biotinylated primer ON160-F1 (27 mer):

(SEQ ID NO. 95)
5' biotin-ATGCTTCAGTGGAGGAGAAGACACTGC-3' based on the information of nucleotide sequence obtained by SST, plasmid hybridized specifically with the biotinylated primer were recovered from the cDNA library according to the method of Gene Trapper Kit and then transfected into *E. Coli* DH10B. Colony hybridization with OM160 SST cDNA which was labeled with 32P-dCTP, as a probe, was performed by using Random Primer DNA Labeling kit according to known method to isolate the positive clone and to prepare the plasmid. Nucleotide sequence of full-length OM160 SST cDNA was determined by the same procedure as ON056 and then sequence shown in SEQ ID NO. 27 was obtained. An open reading frame was determined and deduced amino acid sequence and nucleotide sequence shown in SEQ ID NOS. 25 and 26, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OM160 of the present invention. From these results, it was proved that polypeptide of the present invention was new secretary protein.

However, the search using BLASTX, BLASTP and FASTA revealed a significant homology between clone OM160 (region of 153rd~395th amino acid in SEQ ID NO. 25) and Drosophila neurogenic secreted signaling protein (Genepept Accession U41449) (region of 80th~317th amino acid). Based on these homologies, clone OM160 and Drosophila neurogenic secreted signaling protein were expected to share at least some activity.

EXAMPLE 10

Clone OMA016

In Example relating to clone OMA016 of the present invention, the same procedure as in Example of ON056 was used except for the following points.

(1) Preparation of Poly(A)+RNA

Total RNA was prepared from human adult brain tissue by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA in human adult brain tissue. 27 mer primer OMA016-F1:

(SEQ ID NOS. 96)
5'-AGAAATGGTGAATGCCTGCTGGTGTGG-3' containing the deduced initiation ATG codon region based on the information of nucleotide sequence obtained by SST, was prepared. PCR was performed with the said primer and adapter primer attached in the kit. There existed two kinds of cDNAs which were amplified with clone OMA016 specifically and which were named OMA016a and OMA016b. These two were separated with recloning by the same method as Example of OX003. Full nucleotide sequences were determined and then sequences shown in SEQ ID NOS. 30 and 33 were obtained. Each open reading frame was determined and reduced amino acid sequences and nucleotide sequences shown in SEQ ID NOS. 28, 31 and SEQ ID NOS. 29, 32, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OMA016a and OMA016b of the present invention. From these results, it was proved that polypeptide of the present invention was new secretary protein.

EXAMPLE 11

Clone OMB130

In Example relating to clone OMB130 of the present invention, the same procedure as in Example of ON056 was used except for the following points.

(1) Preparation of Poly(A)+RNA

Total RNA was prepared from human adult brain tissue by TRIzol reagent. Poly(A)+RNA was purified from the total RNA by mRNA Purification Kit.

(2) Cloning of a Full-Length cDNA and Determination of Nucleotide Sequence

Double strand cDNA was prepared from the origin of each clone, i.e., poly (A)+RNA in human adult brain tissue. 27 mer primer OMB130-F1:

(SEQ ID NOS. 97)
5'-TCCTCTGACTTTTCTTCTGCAAGCTCC-3' containing the deduced initiation ATG codon region based on the information of nucleotide sequence obtained by SST, was prepared. cDNA which was amplified with clone OMB130 specifically was separated with recloning by the same method as Example of OX003. Full nucleotide sequence was determined and then sequence shown in SEQ ID NO. 36 was obtained. An open reading frame was determined and deduced amino acid sequence and nucleotide sequence shown in SEQ ID NOS. 34 and 35, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OMB130 of the present invention. From these results, it was proved that polypeptide of the present invention was new secretary protein.

However, the search using BLASTX, BLASTP and FASTA revealed a significant homology between clone OMB130 (region of 10th~177th amino acid in SEQ ID NO. 34), and Monkey Hepatitis A virus receptor (PRF Code 2220266A (Genbank Accession X98252) (region of 6th~173rd amino acid. Based on these homologies, clone OMB130 and Monkey Hepatitis A virus receptor were expected to share at least some activity.

EXAMPLE 12

Clone OMB142

In Example relating to clone OMB142 of the present invention, the same procedure as in Example of ON056 was used except for the following points.

(1) Preparation of Poly(A)+RNA

Total RNA was prepared from human adult brain tissue by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA in human adult brain tissue. 27 mer primer OMB142-F2:

(SEQ ID NOS. 98)
5'-GCCCAAGGTCAAGGAGATGGTACGGAT-3' containing the deduced initiation ATG codon region based on the information of nucleotide sequence obtained by SST, was prepared. PCR was performed with the said primer and adapter primer attached in the kit. Due to insufficient amplification of cDNA by only one-time PCR, 28 mer primer OMB142-F1:

```
                                                (SEQ ID NOS. 99)
        5'-GGAGATGGTACGGATCTTAAGGACTGTG-3'
``` was prepared additionally at 3' end of OMB142-F2 primer and then nested PCR was performed. cDNA which was amplified with clone OMB142 specifically was separated with recloning by the same method as Example of OX003. Full nucleotide sequence was determined and then sequence shown in SEQ ID NO. 39 was obtained. An open reading frame was determined and deduced amino acid sequence and nucleotide sequence shown in SEQ ID NOS. 37 and 38, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OMB142 of the present invention. From these results, it was proved that polypeptide of the present invention was new secretary protein.

EXAMPLE 13

Clone OTB033

In Example relating to clone OTB033 of the present invention, the same procedure as in Example of ON056 was used except for the following points.

(1) Preparation of Poly(A)+RNA

Total RNA was prepared from human neuroblastoma cell line IMR-32 (ATCC No. CCL-127) by TRIzol reagent. Poly (A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA of IMR-32. 27 mer primer OTB033-F1:

```
                                               (SEQ ID NOS. 100)
        5'-TGCACTATCCAAAAGCTCCATGTACAC-3'
``` containing the deduced initiation ATG codon region based on the information of nucleotide sequence obtained by SST, was prepared. PCR was performed with the said primer and adapter primer attached in the kit. Due to insufficient amplification of cDNA by only one-time PCR, 19 mer primer OTB003-F2:

```
        5'-CCATGTACACAGTGGGGGC-3'   (SEQ ID NOS. 101)
``` was prepared additionally at 3' end of OTB033-F1 primer and then nested PCR was performed. cDNA which was amplified with clone OTB033 specifically was separated with recloning by the same method as Example of OX003. Full nucleotide sequence was determined and then sequence shown in SEQ ID NO. 42 was obtained. An open reading frame was determined and deduced amino acid sequence and nucleotide sequence shown in SEQ ID NOS. 40 and 41, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OTB033 of the present invention. From these results, it was proved that polypeptide of the present invention was new secretary protein.

EXAMPLE 14

Clone OVB100

In Example relating to clone OVB100 of the present invention, the same procedure as in Example of ON056 was used except for the following points.

(1) Preparation of Poly(A)+RNA

Total RNA was prepared from human astrocytoma cell line CCF-STTG1 (ATCC No. CRL-1718) by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA of CCF-STTG1. 27 mer primer OVB100-F1:

```
                                               (SEQ ID NOS. 102)
        5'-CACTTGGTGTTTGATTTACCTAAGCAC-3'
``` containing the deduced initiation ATG codon region based on the information of nucleotide sequence obtained by SST, was prepared. cDNA which was amplified with clone OVB100 specifically was separated with recloning by the same method as Example of OX003. Full nucleotide sequence was determined and then sequence shown in SEQ ID NO. 45 was obtained. An open reading frame was determined and deduced amino acid sequence and nucleotide sequence shown in SEQ ID NOS. 43 and 44, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OVB100 of the present invention. From these results, it was proved that polypeptide of the present invention was new secretary protein.

EXAMPLE 15

Clone OAF062

In Example relating to clone OAF062 of the present invention, the same procedure as in Example of ON056 was used except for the following points.

(1) Preparation of Poly(A)+RNA

Total RNA was prepared from human bone marrow stroma cell line HAS303 (provided from Prof. Keisuke Sotoyama, Dr. Makoto Aizawa, First Medicine, Tokyo Medical College)

by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. A full-length cDNA was cloned using Marathon cDNA Amplification Kit according to 3' RACE method as described in Example of OX003. Double strand cDNA was prepared from the origin of each clone, i.e., poly (A)+RNA of HAS303. 27 mer primer OAF062-F2:

(SEQ ID NOS. 103)
5'-GAGTTTCGTAAGCAAAATAGAGGACAG-3' containing the deduced initiation ATG codon region based on the information of nucleotide sequence obtained by SST, was prepared. PCR was performed with the said primer and adapter primer attached in the kit. Due to insufficient amplification of cDNA by only one-time PCR, 27 mer primer OAF062-F3:

(SEQ ID NOS. 104)
5'-TAGAGGACAGAAATGCAGTTCATGAAC-3' was prepared additionally at 3' end of OAF062-F2 primer and then nested PCR was performed. cDNA which was amplified with clone OAF062 specifically was separated with recloning by the same method as Example of OX003. Full nucleotide sequence was determined and then sequence shown in SEQ ID NO. 48 was obtained. An open reading frame was determined and deduced amino acid sequence and nucleotide sequence shown in SEQ ID NOS. 46 and 47, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAF062 of the present invention. From these results, it was proved that polypeptide of the present invention was new secretary protein.

EXAMPLE 16

Clone OAF075

In Example relating to clone OAF075 of the present invention, the same procedure as in Example of ON056 was used except for the following points.

(1) Preparation of Poly(A)+RNA

Total RNA was prepared from human bone marrow stroma cell line HAS303 (provided from Prof. Keisuke Sotoyama, Dr. Makoto Aizawa, First Medicine, Tokyo Medical College) by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA of HAS303. 28 mer primer OAF075-F1:

(SEQ ID NOS. 105)
5'-GACATGAGGTGGATACTGTTCATTGGGG-3' containing the deduced initiation ATG codon region based on the information of nucleotide sequence obtained by SST, was prepared. cDNA which was amplified with clone OAF075 specifically was separated with recloning by the same method as Example of OX003. Full nucleotide sequence was determined and then sequence shown in SEQ ID NO. 51 was obtained. An open reading frame was determined and deduced amino acid sequence and nucleotide sequence shown in SEQ ID NOS. 49 and 50, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAF075 of the present invention. From these results, it was proved that polypeptide of the present invention was new secretary protein.

However, the search using BLASTX, BLASTP and FASTA revealed a significant homology between clone OAF075 (region of 1st~421st amino acid in SEQ ID NO. 49), and Human Carboxypeptidase A2 (Swiss Prot Accession P48052) (region of 1st~417th amino acid), Human Carboxypeptidase A1 (Swiss Prot Accession P15085) (region of 1st~417th amino acid), Human Carboxypeptidase B (Swiss Prot Accession P15086) (region of 5th~416th amino acid) and Human Mast Cell Carboxypeptidase A (Swiss Prot Accession P15088) (region of 1st~412th amino acid) . Based on these homologies, clone OAF075 and Carboxypeptidase family were expected to share at least some activity.

EXAMPLE 17

Clone OAG 119

In Example relating to clone OAG119 of the present invention, the same procedure as in Example of ON056 was used except for the following points.

(1) Preparation of Poly(A)+RNA

Total RNA was prepared from human bone marrow stroma cell line LP101 (provided from Prof. Keisuke Sotoyama, Dr. Makoto Aizawa, First Medicine, Tokyo Medical College) by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA of LP101. 28 mer primer OAG119-F1:

(SEQ ID NOS. 106)
5'-TGGCGTGTAACTATGCTCATCATTGTTC-3' containing the deduced initiation ATG codon region based on the information of nucleotide sequence obtained by SST, was prepared. cDNA which was amplified with clone OAG119 specifically was separated with recloning by the same method as Example of OX003. Full nucleotide sequence was determined and then sequence shown in SEQ ID NO. 54 was obtained. An open reading frame was determined and deduced amino acid sequence and nucleotide sequence shown in SEQ ID NOS. 52 and 53, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAG119 of the present invention. From these results, it was proved that polypeptide of the present invention was new secretary protein.

EXAMPLE 18

Clone OAH040

In Example relating to clone OAH040 of the present invention, the same procedure as in Example of ON056 was used except for the following points.

(1) Preparation of Poly(A)+RNA

Total RNA was prepared from endothelial cell line of vein derived from human umbilical cord UV-EC-C (ATCC No. CRL-1730) by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA of HUV-EC-C. 28 mer primer OAH040-F1:

(SEQ ID NOS. 107)
5'-TTAGCCCACCCATGTTGATAGAACACCC-3' containing the deduced initiation ATG codon region based on the information of nucleotide sequence obtained by SST, was prepared. cDNA which was amplified with clone OAH040 specifically was separated with recloning by the same method as Example of OX003. Full nucleotide sequence was determined and then sequence shown in SEQ ID NO. 57 was obtained. An open reading frame was determined and deduced amino acid sequence and nucleotide sequence shown in SEQ ID NOS. 55 and 56, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAH040 of the present invention. From these results, it was proved that polypeptide of the present invention was new secretary protein.

EXAMPLE 19

Clone OAH058

In Example relating to clone OAH058 of the present invention, the same procedure as in Example of OAH056 was used except for the following points.

(1) Preparation of Poly(A)+RNA

Total RNA was prepared from endothelial cell line of vein derived from human umbilical cord HUV-EC-C (ATCC No. CRL-1730) by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA of HUV-EC-C. 28 mer primer OAH058-F1:

(SEQ ID NOS. 108)
5'-ACAATGTTGGCCTGTC TGCAAGCTTGTG-3' containing the deduced initiation ATG codon region based on the information of nucleotide sequence obtained by SST, was prepared. cDNA which was amplified with clone OAH058 specifically was separated with recloning by the same method as Example of OX003. Full nucleotide sequence was determined and then sequence shown in SEQ ID NO. 60 was obtained. An open reading frame was determined and deduced amino acid sequence and nucleotide sequence shown in SEQ ID NOS. 58 and 59, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAH058 of the present invention. From these results, it was proved that polypeptide of the present invention was new secretary protein.

EXAMPLE 20

Clone OM011

In Example relating to clone OM011 of the present invention, the same procedure as in Example of ON056 was used except for the following points.

(1) Preparation of Poly(A)+RNA

Total RNA was prepared from human adult brain tissue by TRIzol reagent. Poly(A)+RNA was purified from the total RNA by mRNA Purification Kit.

(2) Cloning of a Full-Length cDNA and Determination of Nucleotide Sequence

A full-length cDNA was cloned using GENETRAPPER cDNA Positive Selection System. First, dT-primed cDNA library was prepared from poly (A)+RNA in human adult brain tissue using pSPORT1 plasmid, as a vector, by Super Script Plasmid System for cDNA Synthesis and Plasmid Cloning. Next, after preparing biotinylated primer OM011-F1 (27 mer):

(SEQ ID NOS. 109)
5' biotin-GAAGTGACTCTTCCTCTAGTTTGCCAC-3' based on the information of nucleotide sequence obtained by SST, plasmid hybridized specifically with the biotinylated primer were recovered from the cDNA library according to the method of Gene Trapper Kit and then transfected into *E.*

Coli DH10B. Colony hybridization with OM011 SST cDNA which was labeled with 32P-dCTP, as a probe, was performed by using Random Primer DNA Labeling kit according to known method to isolate the positive clone and to prepare the plasmid. Nucleotide sequence of full-length OM011 SST cDNA was determined by the same procedure as ON056 and then sequence shown in SEQ ID NO. 63 was obtained. An open reading frame was determined and deduced amino acid sequence and nucleotide sequence shown in SEQ ID NOS. 61 and 62, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OM011 of the present invention. From these results, it was proved that polypeptide of the present invention was new secretary protein.

However, the search using BLASTX, BLASTP and FASTA revealed a significant homology between clone OM011 (region of 26th~396th amino acid in SEQ ID NO. 61) and Human Plasma-cell Glycoprotein PC-1 (Alkaline Phosphodiesterase I) (Swiss Prot Accession P22413) (region of 158th~543rd amino acid). Based on these homologies, clone OM011 and Human Plasma-cell Glycoprotein PC-1 were expected to share at least some activity.

EXAMPLE 21

Clone OM028

In Example relating to clone OM028 of the present invention, the same procedure as in Example of ON056 was used except for the following points.

(1) Preparation of Poly(A)$^+$RNA

Total RNA was prepared from human adult brain tissue by TRIzol reagent. Poly(A)$^+$RNA was purified from the total RNA by mRNA Purification Kit.

(2) Cloning of a Full-Length cDNA and Determination of Nucleotide Sequence

A full-length cDNA was cloned using GENETRAPPER cDNA Positive Selection System. First, dT-primed cDNA library was prepared from poly (A)+RNA in human adult brain tissue using pSPORT1 plasmid, as a vector, by Super Script Plasmid System for cDNA Synthesis and Plasmid Cloning. Next, after preparing biotinylated primer OM028-F1 (27 mer):

```
                                    (SEQ ID NOS. 110)
    5' biotin-ATGAAGGACATGCCACTCCGAATTCAT-3'
``` based on the information of nucleotide sequence obtained by SST, plasmid hybridized specifically with the biotinylated primer were recovered from the cDNA library according to the method of Gene Trapper Kit and then transfected into *E. Coli* DH10B. Colony hybridization with OM028 SST cDNA which was labeled with 32P-dCTP, as a probe, was performed by using Random Primer DNA Labeling kit according to known method to isolate the positive clone and to prepare the plasmid. Nucleotide sequence of full-length OM028 SST cDNA was determined by the same procedure as ON056 and then sequence shown in SEQ ID NO. 66 was obtained. An open reading frame was determined and deduced amino acid sequence and nucleotide sequence shown in SEQ ID NOS. 64 and 65, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OM028 of the present invention. From these results, it was proved that polypeptide of the present invention was new secretary protein.

However, the search using BLASTX, BLASTP and FASTA revealed a significant homology between clone OM028 (region of 1st~708th amino acid in SEQ ID NO. 64) and many proteins containing Leu-rich repeat such as Mouse Leu-rich repeat protein (PRF Code 2212307A (GENBANK Accession D49802) (region of 1st~707th amino acid). Based on these homologies, clone OM028 and certain proteins containing Leu-rich repeat were expected to share at least some activity.

EXAMPLE 22

Clone OMB092

In Example relating to clone OMB092 of the present invention, the same procedure as in Example of ON056 was used except for the following points.

(1) Preparation of Poly(A)$^+$RNA

Total RNA was prepared from human adult brain tissue by TRIzol reagent. Poly(A)$^+$RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)$^+$RNA in human adult brain tissue. 27 mer primer OMB092-F1:

```
                                    (SEQ ID NOS. 111)
        5'-ACTCACCTGGATCCCTAAGGGCACAGC-3'
``` containing the deduced initiation ATG codon region based on the information of nucleotide sequence obtained by SST, was prepared. PCR was performed with the said primer and adapter primer attached in the kit. Due to insufficient amplification of cDNA by only one-time PCR, 28 mer primer OMB092-F2:

```
                                    (SEQ ID NOS. 112)
        5'-AGAATGAGCTATTACGGCAGCAGCTATC-3'
``` was prepared additionally at 3' end of OMB092-F1 primer and then nested PCR was performed. cDNA which was amplified with clone OMB092 specifically was separated with recloning by the same method as Example of OX003. Full nucleotide sequence was determined and then sequence shown in SEQ ID NO. 69 was obtained. An open reading frame was determined and deduced amino acid sequence and nucleotide sequence shown in SEQ ID NOS. 67 and 68, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OMB092 of the present invention. From these results, it was proved that polypeptide of the present invention was new secretary protein.

However, the search using BLASTX, BLASTP and FASTA revealed a significant homology between clone OMB092 (region of 1st~254th amino acid in SEQ ID NO. 67) and many Potassium Channels family such as Rat Inward Rectifier Potassium Channel BIR9 (Swiss Prot Accession P52191) (region of 1st~254th amino acid). Based on these homologies, clone OMB092 and Potassium Channel were expected to share at least some activity.

EXAMPLE 23

Clone OMB108

In Example relating to clone OMB108 of the present invention, the same procedure as in Example of ON056 was used except for the following points.

(1) Preparation of Poly(A)+RNA

Total RNA was prepared from human adult brain tissue by TRIzol reagent. Poly(A)+RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)+RNA in human adult brain tissue. 27 mer primer OMB108-F1:

(SEQ ID NOS. 113)
5'-CTCTCTCCATCTGCTGTGGTTATGGCC-3' containing, the deduced initiation ATG codon region based on the information of nucleotide sequence obtained by SST, was prepared. PCR was performed with the said primer and adapter primer attached in the kit. Due to insufficient amplification of cDNA by only one-time PCR, 22 mer primer OMB108-F2:

5'-TGGTTATGGCCTGTCGCTGGAG-3' (SEQ ID NOS. 114)

was prepared additionally at 3' end of OMB108-F1 primer and then nested PCR was performed. cDNA which was amplified with clone OMB108 specifically was separated with recloning by the same method as Example of OX003. Full nucleotide sequence was determined and then sequence shown in SEQ ID NO. 72 was obtained. An open reading frame was determined and deduced amino acid sequence and nucleotide sequence shown in SEQ ID NOS. 70 and 71, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OMB108 of the present invention. From these results, it was proved that polypeptide of the present invention was new secretary protein.

However, the search using BLASTX, BLASTP and FASTA revealed a significant homology between clone OMB108 (region of 164th~256th and 374th~487th amino acid in SEQ ID NO. 70) and LDL-repeat region of many LDL receptors family such as Human Low-Density Lipoprotein Receptor Related Protein 10 (Swiss Prot Accession Q07954) or OMB108 (region of 47th~158th and 259th~370th amino acid in SEQ ID NO. 70) and CUB domain included in Human Bone Morphogenetic Protein 1 (Swiss Prot Accession P13497). That is to say, clone OMB108 proved to possess the common sequences of two parts of CUB domain and five parts of LDL-repeat at the extracell domain. Based on these homologies, clone OMB108, protein including LDL-repeat and protein including CUB domain were expected to share at least some activity.

EXAMPLE 24

Clone OT007

In Example relating to clone OT007 of the present invention, the same procedure as in Example of ON056 was used except for the following points.

(1) Preparation of Poly(A)+RNA

Total RNA was prepared from human neuroblastoma cell line IMR-32 (ATCC No. CCL-127) by TRIzol reagent. Poly (A)+RNA was purified from the total RNA by mRNA Purification Kit.

(2) Cloning of a Full-Length cDNA and Determination of Nucleotide Sequence

A full-length cDNA was cloned using GENETRAPPER cDNA Positive Selection System. First, dT-primed cDNA library was prepared from poly (A)+RNA in IMR-32 using pSPORT1 plasmid, as a vector, by Super Script Plasmid System for cDNA Synthesis and Plasmid Cloning. Next, after preparing biotinylated primer OT007-F1 (27 mer):

(SEQ ID NOS. 115)
5' biotin-AAAATGACTCCCCAGTCGCTGCTGCAG-3' based on the information of nucleotide sequence obtained by SST, plasmid hybridized specifically with the biotinylated primer were recovered from the cDNA library according to the method of Gene Trapper Kit and then transfected into *E. Coli* DH10B. Colony hybridization with OT007 SST cDNA which was labeled with 32P-dCTP, as a probe, was performed by using Random Primer DNA Labeling kit according to known method to isolate the positive clone and to prepare the plasmid. Nucleotide sequence of full-length OT007 SST cDNA was determined by the same procedure as ON056 and then sequence shown in SEQ ID NO. 75 was obtained. An open reading frame was determined and deduced amino acid sequence and nucleotide sequence shown in SEQ ID NOS. 73 and 74, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OT007 of the present invention. From these results, it was proved that polypeptide of the present invention was new secretary protein.

However, the search using BLASTX, BLASTP and FASTA revealed a significant homology between clone OT007 (region of 217th~660th amino acid in SEQ ID NO. 73) and transmembrane region of Secretin/Vasoactive Intestinal Peptide receptor superfamily such as Human Seven Transmembrane-domain receptor (Genepept Accession X82892), Rat Latrophilin-related protein 1 (Genepept Accession U78105), Human CD97 (Swiss Prot Accession P48960) etc. Based on these homologies, clone OT007 and certain proteins containing seven transmembrane region type of Secretin/Vasoactive Intestinal Peptide were expected to share at least some activity.

EXAMPLE 25

Clone OAG051

In Example relating to clone OAG051 of the present invention, the same procedure as in Example of ON056 was used except for the following points.

(1) Preparation of Poly(A)$^+$RNA

Total RNA was prepared from human bone marrow stroma cell line LP101 (provided from Prof. Keisuke Sotoyama, Dr. Makoto Aizawa, First Medicine, Tokyo Medical College) by TRIzol reagent. Poly(A)$^+$RNA was purified from the total RNA by mRNA Purification Kit.

(2) Cloning of a Full-Length cDNA and Determination of Nucleotide Sequence

A full-length cDNA was cloned using Marathon cDNA Amplification Kit according to 3' RACE method as described in Example of OX003. Double strand cDNA was prepared from the origin of each clone, i.e., poly (A)$^+$RNA of LP101. 27 mer primer OAG051-F1:

(SEQ ID NOS. 116)
5'-GGAAATGTTTACATTTTT GTTGACGTG-3' containing the deduced initiation ATG codon region based on the information of nucleotide sequence obtained by SST, was prepared. cDNA which was amplified with clone OAG051 specifically was separated with recloning by the same method as Example of OX003. Full nucleotide sequence was determined and then sequence shown in SEQ ID NO. 78 was obtained. An open reading frame was determined and deduced amino acid sequence and nucleotide sequence shown in SEQ ID NOS. 76 and 77, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OAG051 of the present invention. From these results, it was proved that polypeptide of the present invention was new secretary protein.

However, the search using BLASTX, BLASTP and FASTA revealed a significant homology between clone OAG051 and many Frizzled family, for example, clone OAG051 (region of 4th~703rd amino acid in SEQ ID NO. 76) and Mouse Frizzled-6 (PRF Code2208383E (Genebank Accession U43319) (region of 6th~708th amino acid) or clone OAG051 (region of 1st~627th amino acid in SEQ ID NO. 76) and Mouse Frizzled-3 (PRF Code 2208383E (Genebank Accession U43205) (region of 7th~618th amino acid). Based on these homologies, clone clone OAG051 and Frizzled family were expected to share at least some activity.

EXAMPLE 26

Clone OUB068

In Example relating to clone OUB068 of the present invention, the same procedure as in Example of ON056 was used except for the following points.

(1) Preparation of Poly(A)$^+$RNA

Total RNA was prepared from human osteosarcoma cell line U-20S (ATCC No. HTB-96) by TRIzol reagent. Poly(A)$^+$RNA was purified from the total RNA by mRNA Purification Kit.

(2) Cloning of a Full-Length cDNA and Determination of Nucleotide Sequence

A full-length cDNA was cloned using GENETRAPPER cDNA Positive Selection System. First, dT-primed cDNA library was prepared from poly (A)+RNA in U-20S using pSPORT1 plasmid, as a vector, by Super Script Plasmid System for cDNA Synthesis and Plasmid Cloning. Next, after preparing biotinylated primer OUB068-F1 (27 mer):

(SEQ ID NOS. 117)
5' biotin-CACTCATGAAGGAAATTCCAGCGCTGC-3' based on the information of nucleotide sequence obtained by SST, plasmid hybridized specifically with the biotinylated primer were recovered from the cDNA library according to the method of Gene Trapper Kit and then transfected into E. Coli DH10B. Colony hybridization with OUB068 SST cDNA which was labeled with 32P-dCTP, as a probe, was performed by using Random Primer DNA Labeling kit according to known method to isolate the positive clone and to prepare the plasmid. Nucleotide sequence of full-length OUB068 SST cDNA was determined by the same procedure as ON056 and then sequence shown in SEQ ID NO. 81 was obtained. An open reading frame was determined and deduced amino acid sequence and nucleotide sequence shown in SEQ ID NOS. 79 and 80, respectively, were obtained.

It was indicated from the results of homology search for the public database of the nucleic acid sequences by using BLASTN and FASTA, and for the public database of the amino acid sequences by using BLASTX, BLASTP and FASTA, that there was no sequence identical to the polypeptide sequence and the nucleotide sequence of OUB068 of the present invention. From these results, it was proved that polypeptide of the present invention was new secretary protein.

However, the search using BLASTX, BLASTP and FASTA revealed a significant homology between clone OUB068 (region of 5th~386th amino acid in SEQ ID NO. 79) and Xenopus Unknown Transmembrane Protein (Genepept Accession X92871) (region of 3rd~407th amino acid). Based on these homologies, clone OUB068 and Xenopus Unknown Transmembrane Protein were expected to share at least some activity.

The invention claimed is:

1. A cDNA encoding a polypeptide comprising the amino acid sequence shown in SEQ ID NO: 61.
2. A cDNA comprising the nucleotide sequence shown in SEQ ID NO: 62.
3. A cDNA comprising the nucleotide sequence shown in SEQ ID NO: 63.
4. A replication or expression vector carrying the cDNA according to claim 1.
5. A replication or expression vector carrying the cDNA according to claim 2.
6. A replication or expression vector carrying the cDNA according to claim 3.
7. An isolated host cell transformed with the replication or expression vector according to claim 4.
8. An isolated host cell transformed with the replication or expression vector according to claim 5.
9. An isolated host cell transformed with the replication or expression vector according to claim 6.

* * * * *

SEQUENCE LISTING

<160> NUMBER OF SEQ ID NOS: 117

<210> SEQ ID NO 1
<211> LENGTH: 334
<212> TYPE: PRT
<213> ORGANISM: Homo sapiens

<400> SEQUENCE: 1

Met Asn Leu Ser Leu Val Leu Ala Ala Phe Cys Leu Gly Ile Ala Ser
    -15                 -10                 -5

Ala Val Pro Lys Phe Asp Gln Asn Leu Asp Thr Lys Trp Tyr Gln Trp
-1   1               5                  10                  15

Lys Ala Thr His Arg Arg Leu Tyr Gly Ala Asn Glu Glu Gly Trp Arg
                 20                  25                  30

Arg Ala Val Trp Glu Lys Asn Met Lys Met Ile Glu Leu His Asn Gly
                35                  40                  45

Glu Tyr Ser Gln Gly Lys His Gly Phe Thr Met Ala Met Asn Ala Phe
            50                  55                  60

Gly Asp Met Thr Asn Glu Glu Phe Arg Gln Met Met Gly Cys Phe Arg
65                  70                  75

Asn Gln Lys Phe Arg Lys Gly Lys Val Phe Arg Glu Pro Leu Phe Leu
80                  85                  90                  95

Asp Leu Pro Lys Ser Val Asp Trp Arg Lys Lys Gly Tyr Val Thr Pro
                100                 105                 110

Val Lys Asn Gln Lys Gln Cys Gly Ser Cys Trp Ala Phe Ser Ala Thr
                115                 120                 125

Gly Ala Leu Glu Gly Gln Met Phe Arg Lys Thr Gly Lys Leu Val Ser
            130                 135                 140

Leu Ser Glu Gln Asn Leu Val Asp Cys Ser Arg Pro Gln Gly Asn Gln
145                 150                 155

Gly Cys Asn Gly Gly Phe Met Ala Arg Ala Phe Gln Tyr Val Lys Glu
160                 165                 170                 175

Asn Gly Gly Leu Asp Ser Glu Glu Ser Tyr Pro Tyr Val Ala Val Asp
                180                 185                 190

Glu Ile Cys Lys Tyr Arg Pro Glu Asn Ser Val Ala Asn Asp Thr Gly
                195                 200                 205

Phe Thr Val Val Ala Pro Gly Lys Glu Lys Ala Leu Met Lys Ala Val
            210                 215                 220

Ala Thr Val Gly Pro Ile Ser Val Ala Met Asp Ala Gly His Ser Ser
225                 230                 235

Phe Gln Phe Tyr Lys Ser Gly Ile Tyr Phe Glu Pro Asp Cys Ser Ser
240                 245                 250                 255

Lys Asn Leu Asp His Gly Val Leu Val Val Gly Tyr Gly Phe Glu Gly
                260                 265                 270

Ala Asn Ser Asn Asn Ser Lys Tyr Trp Leu Val Lys Asn Ser Trp Gly
                275                 280                 285

Pro Glu Trp Gly Ser Asn Gly Tyr Val Lys Ile Ala Lys Asp Lys Asn
            290                 295                 300

Asn His Cys Gly Ile Ala Thr Ala Ala Ser Tyr Pro Asn Val
305                 310                 315

<210> SEQ ID NO 2
<211> LENGTH: 1002
<212> TYPE: DNA

<213> ORGANISM: Homo sapiens

<400> SEQUENCE: 2

```
atgaatcttt cgctcgtcct ggctgccttt tgcttgggaa tagcctccgc tgttccaaaa      60
tttgaccaaa atttggatac aaagtggtac cagtggaagg caacacacag aagattatat     120
ggcgcgaatg aagaaggatg gaggagagca gtgtgggaaa agaatatgaa atgattgaa      180
ctgcacaatg ggaatacag ccaagggaaa catggcttca caatggccat gaatgctttt     240
ggtgacatga ccaatgaaga attcaggcag atgatgggtt gctttcgaaa ccagaaattc     300
aggaagggga aagtgttccg tgagcctctg tttcttgatc ttcccaaatc tgtggattgg     360
agaaagaaag gctacgtgac gccagtgaag aatcagaaac agtgtggttc ttgtttgggct    420
tttagtgcga ctggtgctct tgaaggacag atgttccgga aaactgggaa acttgtctca     480
ctgagcgagc agaatctggt ggactgttcg cgtcctcaag caatcaggg ctgcaatggt      540
ggcttcatgg ctagggcctt ccagtatgtc aaggagaacg gaggcctgga ctctgaggaa     600
tcctatccat atgtagcagt ggatgaaatc tgtaagtaca gacctgagaa ttctgttgct     660
aatgacactg gcttcacagt ggtcgcacct ggaaaggaga aggccctgat gaaagcagtc     720
gcaactgtgg ggcccatctc cgttgctatg gatgcaggcc attcgtcctt ccagttctac     780
aaatcaggca tttattttga accagactgc agcagcaaaa acctggatca tggtgttctg     840
gtggttggct acggctttga aggagcaaat tcgaataaca gcaagtattg gctcgtcaaa     900
aacagctggg gtccagaatg gggctcgaat ggctatgtaa aaatagccaa agacaagaac     960
aaccactgtg gaatcgccac agcagccagc taccccaatg tg                       1002
```

<210> SEQ ID NO 3
<211> LENGTH: 1370
<212> TYPE: DNA
<213> ORGANISM: Homo sapiens
<220> FEATURE:
<221> NAME/KEY: sig_peptide
<222> LOCATION: (60)..(110)
<220> FEATURE:
<221> NAME/KEY: mat_peptide
<222> LOCATION: (111)..(1061)
<220> FEATURE:
<221> NAME/KEY: CDS
<222> LOCATION: (60)..(1061)

<400> SEQUENCE: 3

```
ctcagaggct tgtttgctga gggtgcctgc gcagctgcga cggctgctgg ttttgaaac       59 atg aat ctt tcg ctc gtc ctg gct gcc ttt tgc ttg gga ata gcc tcc      107
Met Asn Leu Ser Leu Val Leu Ala Ala Phe Cys Leu Gly Ile Ala Ser
        -15             -10                 -5 gct gtt cca aaa ttt gac caa aat ttg gat aca aag tgg tac cag tgg      155
Ala Val Pro Lys Phe Asp Gln Asn Leu Asp Thr Lys Trp Tyr Gln Trp
-1   1               5                  10                  15 aag gca aca cac aga aga tta tat ggc gcg aat gaa gaa gga tgg agg      203
Lys Ala Thr His Arg Arg Leu Tyr Gly Ala Asn Glu Glu Gly Trp Arg
                 20                  25                  30 aga gca gtg tgg gaa aag aat atg aaa atg att gaa ctg cac aat ggg      251
Arg Ala Val Trp Glu Lys Asn Met Lys Met Ile Glu Leu His Asn Gly
             35                  40                  45 gaa tac agc caa ggg aaa cat ggc ttc aca atg gcc atg aat gct ttt      299
Glu Tyr Ser Gln Gly Lys His Gly Phe Thr Met Ala Met Asn Ala Phe
         50                  55                  60 ggt gac atg acc aat gaa gaa ttc agg cag atg atg ggt tgc ttt cga      347
Gly Asp Met Thr Asn Glu Glu Phe Arg Gln Met Met Gly Cys Phe Arg
```

```
                       65                  70                   75
aac cag aaa ttc agg aag ggg aaa gtg ttc cgt gag cct ctg ttt ctt        395
Asn Gln Lys Phe Arg Lys Gly Lys Val Phe Arg Glu Pro Leu Phe Leu
 80                  85                  90                  95 gat ctt ccc aaa tct gtg gat tgg aga aag aaa ggc tac gtg acg cca        443
Asp Leu Pro Lys Ser Val Asp Trp Arg Lys Lys Gly Tyr Val Thr Pro
                    100                 105                 110 gtg aag aat cag aaa cag tgt ggt tct tgt tgg gct ttt agt gcg act        491
Val Lys Asn Gln Lys Gln Cys Gly Ser Cys Trp Ala Phe Ser Ala Thr
                115                 120                 125 ggt gct ctt gaa gga cag atg ttc cgg aaa act ggg aaa ctt gtc tca        539
Gly Ala Leu Glu Gly Gln Met Phe Arg Lys Thr Gly Lys Leu Val Ser
        130                 135                 140 ctg agc gag cag aat ctg gtg gac tgt tcg cgt cct caa ggc aat cag        587
Leu Ser Glu Gln Asn Leu Val Asp Cys Ser Arg Pro Gln Gly Asn Gln
    145                 150                 155 ggc tgc aat ggt ggc ttc atg gct agg gcc ttc cag tat gtc aag gag        635
Gly Cys Asn Gly Gly Phe Met Ala Arg Ala Phe Gln Tyr Val Lys Glu
160                 165                 170                 175 aac gga ggc ctg gac tct gag gaa tcc tat cca tat gta gca gtg gat        683
Asn Gly Gly Leu Asp Ser Glu Glu Ser Tyr Pro Tyr Val Ala Val Asp
                    180                 185                 190 gaa atc tgt aag tac aga cct gag aat tct gtt gct aat gac act ggc        731
Glu Ile Cys Lys Tyr Arg Pro Glu Asn Ser Val Ala Asn Asp Thr Gly
                195                 200                 205 ttc aca gtg gtc gca cct gga aag gag aag gcc ctg atg aaa gca gtc        779
Phe Thr Val Val Ala Pro Gly Lys Glu Lys Ala Leu Met Lys Ala Val
        210                 215                 220 gca act gtg ggg ccc atc tcc gtt gct atg gat gca ggc cat tcg tcc        827
Ala Thr Val Gly Pro Ile Ser Val Ala Met Asp Ala Gly His Ser Ser
    225                 230                 235 ttc cag ttc tac aaa tca ggc att tat ttt gaa cca gac tgc agc agc        875
Phe Gln Phe Tyr Lys Ser Gly Ile Tyr Phe Glu Pro Asp Cys Ser Ser
240                 245                 250                 255 aaa aac ctg gat cat ggt gtt ctg gtg gtt ggc tac ggc ttt gaa gga        923
Lys Asn Leu Asp His Gly Val Leu Val Val Gly Tyr Gly Phe Glu Gly
                    260                 265                 270 gca aat tcg aat aac agc aag tat tgg ctc gtc aaa aac agc tgg ggt        971
Ala Asn Ser Asn Asn Ser Lys Tyr Trp Leu Val Lys Asn Ser Trp Gly
                275                 280                 285 cca gaa tgg ggc tcg aat ggc tat gta aaa ata gcc aaa gac aag aac       1019
Pro Glu Trp Gly Ser Asn Gly Tyr Val Lys Ile Ala Lys Asp Lys Asn
        290                 295                 300 aac cac tgt gga atc gcc aca gca gcc agc tac ccc aat gtg              1061
Asn His Cys Gly Ile Ala Thr Ala Ala Ser Tyr Pro Asn Val
    305                 310                 315 tgagctgatg gatggtgagg aggaaggact taaggacagc atgtctgggg aaattttatc     1121
ttgaaactga ccaaacgctt attgtgtaag ataaccagt tgaatcatgg aggatccaag      1181
ttgagatttt aattctgtga cattttaca agggtaaaat gttaccacta ctttaattat     1241
tgttatacac agcttatga tatcaaagac tcattgctta attctaagac ttttgaattt     1301
tcatttttta aaagatgta caaaacagtt tgaataaat tttaattcgt atataaaaaa      1361
aaaaaaaaa                                                             1370

<210> SEQ ID NO 4
<211> LENGTH: 111
<212> TYPE: PRT
<213> ORGANISM: Homo sapiens
```

<400> SEQUENCE: 4

```
Met Leu Pro Leu Cys Ser Leu Phe Leu Phe Gly Ser Ser Val Gly
            -10                 -5                  -1  1
Val Lys Gln Tyr Gln Ala Leu Glu Leu Pro Leu Val Val Phe Val Thr
             5                  10                  15
Tyr Leu Lys Met Ala Ala Cys Phe Leu Arg Ile Ser Gly Ser Ala Leu
         20                  25                  30
Pro Val Phe Ile Cys Thr Phe Phe Ser His Cys Ala Ser Cys Thr His
 35                  40                  45                  50
Thr Pro Leu Pro His His Leu Pro Asn Leu Arg Leu Phe Gln Gln Phe
                     55                  60                  65
Leu Phe Arg Ala Gly Pro Cys Trp Asp Met Ile Ser Ile Lys Ser Glu
             70                  75                  80
Gly Pro Asn Cys Ser Cys Pro Cys Ser Pro Tyr His Arg Pro Leu
             85                  90                  95
```

<210> SEQ ID NO 5
<211> LENGTH: 333
<212> TYPE: DNA
<213> ORGANISM: Homo sapiens

<400> SEQUENCE: 5

```
atgttaccac tttgttcttt attccttttt ggatcatctt cagtgggggt aaaacagtat    60
caagctctag agctccctct ggtggttttt gtgacatatt tgaagatggc agcttgcttt   120
ttgagaattt ctggctctgc tctccctgtt tttatctgta ctttttttc tcattgtgcc   180
tcttgcacac acacccct tccccaccat ctacccaatt tgcgcctgtt ccagcagttt   240
ctcttcaggg cagggccgtg ttgggacatg atttctatta agagtgaggg cccaaattgc   300
tcttgcccct gcagcccta tcacagaccc ctg                                 333
```

<210> SEQ ID NO 6
<211> LENGTH: 1086
<212> TYPE: DNA
<213> ORGANISM: Homo sapiens
<220> FEATURE:
<221> NAME/KEY: sig_peptide
<222> LOCATION: (151)..(192)
<220> FEATURE:
<221> NAME/KEY: mat_peptide
<222> LOCATION: (193)..(483)
<220> FEATURE:
<221> NAME/KEY: CDS
<222> LOCATION: (151)..(483)

<400> SEQUENCE: 6

```
ttaattttaa actttgacac ctttaccctg ctaaacaata cagtacagtg accttcaaac    60
atttcagcag ccttcgggtt gttacatatt tattcttttt tgaagcccat cactacatcg   120
ccattacgtt ttacactgtg tatgtaacaa atg tta cca ctt tgt tct tta ttc   174
                                 Met Leu Pro Leu Cys Ser Leu Phe
                                                             -10 ctt ttt gga tca tct tca gtg ggg gta aaa cag tat caa gct cta gag   222
Leu Phe Gly Ser Ser Ser Val Gly Val Lys Gln Tyr Gln Ala Leu Glu
    -5                  -1  1                   5                  10 ctc cct ctg gtg gtt ttt gtg aca tat ttg aag atg gca gct tgc ttt   270
Leu Pro Leu Val Val Phe Val Thr Tyr Leu Lys Met Ala Ala Cys Phe
                 15                  20                  25 ttg aga att tct ggc tct gct ctc cct gtt ttt atc tgt act ttt ttt   318
Leu Arg Ile Ser Gly Ser Ala Leu Pro Val Phe Ile Cys Thr Phe Phe
             30                  35                  40
```

```
tct cat tgt gcc tct tgc aca cac aca ccc ctt ccc cac cat cta ccc    366
Ser His Cys Ala Ser Cys Thr His Thr Pro Leu Pro His His Leu Pro
        45                  50                  55 aat ttg cgc ctg ttc cag cag ttt ctc ttc agg gca ggg ccg tgt tgg    414
Asn Leu Arg Leu Phe Gln Gln Phe Leu Phe Arg Ala Gly Pro Cys Trp
60                  65                  70 gac atg att tct att aag agt gag ggc cca aat tgc tct tgc ccc tgc    462
Asp Met Ile Ser Ile Lys Ser Glu Gly Pro Asn Cys Ser Cys Pro Cys
75                  80                  85                  90 agc cct tat cac aga ccc ctg tagtcattat tggaacatgc tggtcttggg       513
Ser Pro Tyr His Arg Pro Leu
                95 cctgcttttc tcagtcactg gagttctcca gtttgtaaga cggctcctcg cctcccctct    573 gcttcttcct gtacaaaggc cgtcaccctg caagccttgt tgctctcaac atgggttgtc    633 tctacttgtt cctatttag agttactgca gaatgcttg ccatctagct tggttgtagc     693 tggtaaccat aggttttgt ttttttgcta tccttattgc actatgtttt atggaacaat    753 tggagaagat taaaaattca ccctgcccac tgggcgtggt ggctcacgcc tgtaatccca    813 gctctttggg aggccgaggc aggcagatca cgaggtcagg agatcgagac catcgtggct    873 aatacagtga aacccgtctc tactaaaaa tgcaaaaaa attagccggg catggtggtg     933 ggcgcctgta gtcccagcta cttgggaggc tgaggcagga gaatggcatg aattcgggag    993 gcggagcttg cagtgagcca agatcacgcc actgtactcc agcctgggca acagagcgag   1053 actccgtctc aaaaaaaaaa aaaaaaaaaa aaa                                1086

<210> SEQ ID NO 7
<211> LENGTH: 111
<212> TYPE: PRT
<213> ORGANISM: Homo sapiens

<400> SEQUENCE: 7

Met Val Ala Thr Ser Thr Ala Val Ile Ser Gly Val Met Ser Leu Leu
        -25                 -20                 -15

Gly Leu Ala Leu Ala Pro Ala Thr Gly Gly Gly Ser Leu Leu Leu Ser
-10                 -5                  -1  1                   5

Thr Ala Gly Gln Gly Leu Ala Thr Ala Ala Gly Val Thr Ser Ile Val
                10                  15                  20

Ser Gly Thr Leu Glu Arg Ser Lys Asn Lys Glu Ala Gln Ala Arg Ala
                25                  30                  35

Glu Asp Ile Leu Pro Thr Tyr Asp Gln Glu Asp Arg Glu Asp Glu Glu
40                  45                  50

Glu Lys Ala Asp Tyr Val Thr Ala Ala Gly Lys Ile Ile Tyr Asn Leu
55                  60                  65                  70

Arg Asn Thr Leu Lys Tyr Ala Lys Lys Asn Val Arg Ala Phe Trp
                75                  80                  85

<210> SEQ ID NO 8
<211> LENGTH: 333
<212> TYPE: DNA
<213> ORGANISM: Homo sapiens

<400> SEQUENCE: 8
atggtggcca cctctactgc tgtcatctct ggagtgatga gcctcctggg tttagccctt      60
gccccagcaa caggaggagg aagcctgctg ctctccaccg ctggtcaagg tttggcaaca     120
gcagctgggg tcaccagcat cgtgagtggt acgttggaac gctccaaaaa taagaagcc     180
```

| | |
|---|---|
| caagcacggg cggaagacat actgcccacc tacgaccaag aggacaggga ggatgaggaa | 240 |
| gagaaggcag actatgtcac agctgctgga aagattatct ataatcttag aaacaccttg | 300 |
| aagtatgcca agaaaaacgt ccgtgcattt tgg | 333 |

<210> SEQ ID NO 9
<211> LENGTH: 2604
<212> TYPE: DNA
<213> ORGANISM: Homo sapiens
<220> FEATURE:
<221> NAME/KEY: sig_peptide
<222> LOCATION: (173)..(250)
<220> FEATURE:
<221> NAME/KEY: mat_peptide
<222> LOCATION: (251)..(505)
<220> FEATURE:
<221> NAME/KEY: CDS
<222> LOCATION: (173)..(505)

<400> SEQUENCE: 9

| | |
|---|---|
| cgctcctctg tgtgaagacg tggagctaca agacggagat ctgtcccccg aagaaaaaat | 60 |
| atttttgaga gaatttccca gattgaaaga agatctgaaa gggaacattg acaagctccg | 120 |
| tgccctcgca gacgatattg acaaaaccca agaaattc accaaggcta ac atg gtg | 178 |
|                                                                                                                   Met Val<br>                                                                                                                   -25 | |
| gcc acc tct act gct gtc atc tct gga gtg atg agc ctc ctg ggt tta<br>Ala Thr Ser Thr Ala Val Ile Ser Gly Val Met Ser Leu Leu Gly Leu<br>        -20                      -15                    -10 | 226 |
| gcc ctt gcc cca gca aca gga gga gga agc ctg ctg ctc tcc acc gct<br>Ala Leu Ala Pro Ala Thr Gly Gly Gly Ser Leu Leu Leu Ser Thr Ala<br> -5                       -1  1                         5 | 274 |
| ggt caa ggt ttg gca aca gca gct ggg gtc acc agc atc gtg agt ggt<br>Gly Gln Gly Leu Ala Thr Ala Ala Gly Val Thr Ser Ile Val Ser Gly<br>    10                  15                   20 | 322 |
| acg ttg gaa cgc tcc aaa aat aaa gaa gcc caa gca cgg gcg gaa gac<br>Thr Leu Glu Arg Ser Lys Asn Lys Glu Ala Gln Ala Arg Ala Glu Asp<br>25                30                   35                   40 | 370 |
| ata ctg ccc acc tac gac caa gag gac agg gag gat gag gaa gag aag<br>Ile Leu Pro Thr Tyr Asp Gln Glu Asp Arg Glu Asp Glu Glu Glu Lys<br>                45                   50                   55 | 418 |
| gca gac tat gtc aca gct gct gga aag att atc tat aat ctt aga aac<br>Ala Asp Tyr Val Thr Ala Ala Gly Lys Ile Ile Tyr Asn Leu Arg Asn<br>        60                  65                   70 | 466 |
| acc ttg aag tat gcc aag aaa aac gtc cgt gca ttt tgg taactcagag<br>Thr Leu Lys Tyr Ala Lys Lys Asn Val Arg Ala Phe Trp<br>75                80                   85 | 515 |
| ccaacccacg ctcggccaat gctaccaagc gtcttctgac cactggccaa gtctcctccc | 575 |
| ggagccgcgt gcaggtgcaa aaggcctttg cgggaacaac actggcgatg accaaaaatg | 635 |
| ctcgcgtgct gggaggtgtg atgtccgcct tctcccttgg ctatgacttg ccactctct | 695 |
| caaaggaatg gaagcacctg aaggaaggag caaggacaaa gtttgcggaa gagttgagag | 755 |
| ccaaggcctt ggagctggag aggaaactca cagaactcac ccagctctac aagagcttgc | 815 |
| agcagaaagt gaggtcaagg gccagagggg tggggaagga tttaactggg acctgcgaaa | 875 |
| ccgaggctta ctggaaggag ttaagggagc atgtgtggat gtggctgtgg ctgtgtgtgt | 935 |
| gtctgtgtgt ctgtgtgtat gtacagttta catgaatgtt cctcaggaca tggcatacaa | 995 |
| tggccttgga ggtccaaata atatcaagta catcttggag atgagggtgc ctgtcctgga | 1055 |
| cagacctcgg catgccttct gtttctcctt caatgctcct taaggcctat gtgctgggaa | 1115 |

```
aagggtcttc cctgtttgtt tgtttgtttg tttgtttgtt tgtttgaga cggggtctct    1175
gttgcactcc agtctgggtg tcagaatgag accccatctc aaaaaaaaaa aaaaaaaaaa    1235
aaaagaagaa gaatacagtc atgtatctct tggtgacagg gacgcattct gataaatgtg    1295
tcattaggca attgcattgt agtgtgatta tcacagattg tacttataca aaacttagat    1355
ggcatagcct actgcatacc taggctatat gggagagcct attgctccca ggctacgcac    1415
ctgtacagca tgtgactact gaatactata ggcaattgca gcacaatggg aaatatttgt    1475
gtatctaaac atatgtaaac agagaaaaag gaaagtaaaa atatggcata aaagataaga    1535
attggctctc ctgtacaggg cacttactac gaatggagct tgcagggctg agagttgctc    1595
cagatgagtc agtgagtggt gaatgaatgt gaaggcctag ggcattactg tatactactg    1655
taggctttat aaacacagca cacttagggt acacaaaatg catattaaaa catttt cttc    1715
cttcagtata ttaggcaata ggaattttc aagtccacta taaatcttat caaaccatgg    1775
ttgtatatgc agttgaccga acattgtta ttggacacat aactatagtt gaaagaataa    1835
gcaaaaagtc tatctaggtg tgctgtcttg agcaacttttt aattattctc ccgtcctgca    1895
atatgagtta atcttctctg atcgatgtag attccaggaa ggggtgtcca ggacaattac    1955
cttccttctg gagaaacttc ccttaatcaa ataagagaac ttcaaagaaa atccctccct    2015
gtgctttgga agggaaggga ggtgggcagc agtgggtcag agatagacct ttgttctctt    2075
atttctgagg cccttcagtc tcctttattc aaagcactca gcatgccaaa gcacccta tt    2135
ttagggtatc ttttttctgag ccctaaacac tgtgttgggg atgtcaactg tgacaggaaa    2195
atatcttggg gccccagaat cactaaggaa aactcaagct tagggaaact tcttagggca    2255
aacccacctc ccactctatt caaagttatc tctctgctca ctgagataga tacatatctg    2315
attgcctcct ttggaaaggc taatcagaaa ctcaaaagaa tgcaactgtt tgtgtctcac    2375
ctatctgtga cctggaagct ccctccccac tgaaccaatg ttcttcttac atatattgat    2435
taatgtctta tgtctcccta aaatgtataa aaccaaggta tgccccaacc atcttggtca    2495
catgtcatca ggacttcctg agtctgtgtc acagtgtgtc ctcaaccttg gcaaaataaa    2555
ctttctaaat taacaaaaaa aaaaaaaaaa aaaaaaaaa aaaaaaaa                  2604
```

```
<210> SEQ ID NO 10
<211> LENGTH: 542
<212> TYPE: PRT
<213> ORGANISM: Homo sapiens

<400> SEQUENCE: 10

Met Pro Arg Arg Gly Leu Ile Leu His Thr Arg Thr His Trp Leu Leu
            -30                 -25                 -20

Leu Gly Leu Ala Leu Leu Cys Ser Leu Val Leu Phe Met Tyr Leu Leu
            -15                 -10                  -5

Glu Cys Ala Pro Gln Thr Asp Gly Asn Ala Ser Leu Pro Gly Val Val
     -1  1                   5                  10

Gly Glu Asn Tyr Gly Lys Glu Tyr Tyr Gln Ala Leu Leu Gln Glu Gln
 15                  20                  25                  30

Glu Glu His Tyr Gln Thr Arg Ala Thr Ser Leu Lys Arg Gln Ile Ala
                 35                  40                  45

Gln Leu Lys Gln Glu Leu Gln Glu Met Ser Glu Lys Met Arg Ser Leu
             50                  55                  60

Gln Glu Arg Arg Asn Val Gly Ala Asn Gly Ile Gly Tyr Gln Ser Asn
 65                  70                  75
```

-continued

```
Lys Glu Gln Ala Pro Ser Asp Leu Leu Glu Phe Leu His Ser Gln Ile
    80              85                  90

Asp Lys Ala Glu Val Ser Ile Gly Ala Lys Leu Pro Ser Glu Tyr Gly
95              100                 105                 110

Val Ile Pro Phe Glu Ser Phe Thr Leu Met Lys Val Phe Gln Leu Glu
            115                 120                 125

Met Gly Leu Thr Arg His Pro Glu Glu Lys Pro Val Arg Lys Asp Lys
            130                 135                 140

Arg Asp Glu Leu Val Glu Val Ile Glu Ala Gly Leu Glu Val Ile Asn
        145                 150                 155

Asn Pro Asp Glu Asp Glu Gln Glu Asp Glu Gly Pro Leu Gly
        160                 165                 170

Glu Lys Leu Ile Phe Asn Glu Asn Asp Phe Val Glu Gly Tyr Tyr Arg
175                 180                 185                 190

Thr Glu Arg Asp Lys Gly Thr Gln Tyr Glu Leu Phe Phe Lys Lys Ala
                195                 200                 205

Asp Leu Thr Glu Tyr Arg His Val Thr Leu Phe Arg Pro Phe Gly Pro
            210                 215                 220

Leu Met Lys Val Lys Ser Glu Met Ile Asp Ile Thr Arg Ser Ile Ile
            225                 230                 235

Asn Ile Ile Val Pro Leu Ala Glu Arg Thr Glu Ala Phe Val Gln Phe
            240                 245                 250

Met Gln Asn Phe Arg Asp Val Cys Ile His Gln Asp Lys Lys Ile His
255                 260                 265                 270

Leu Thr Val Val Tyr Phe Gly Lys Glu Gly Leu Ser Lys Val Lys Ser
                275                 280                 285

Ile Leu Glu Ser Val Thr Ser Glu Ser Asn Phe His Asn Tyr Thr Leu
            290                 295                 300

Val Ser Leu Asn Glu Glu Phe Asn Arg Gly Arg Gly Leu Asn Val Gly
            305                 310                 315

Ala Arg Ala Trp Asp Lys Gly Glu Val Leu Met Phe Phe Cys Asp Val
        320                 325                 330

Asp Ile Tyr Phe Ser Ala Glu Phe Leu Asn Ser Cys Arg Leu Asn Ala
335                 340                 345                 350

Glu Pro Gly Lys Lys Val Phe Tyr Pro Val Val Phe Ser Leu Tyr Asn
                355                 360                 365

Pro Ala Ile Val Tyr Ala Asn Gln Glu Val Pro Pro Val Glu Gln
            370                 375                 380

Gln Leu Val His Lys Lys Asp Ser Gly Phe Trp Arg Asp Phe Gly Phe
            385                 390                 395

Gly Met Thr Cys Gln Tyr Arg Ser Asp Phe Leu Thr Ile Gly Gly Phe
            400                 405                 410

Asp Met Glu Val Arg Gly Trp Gly Gly Glu Asp Val His Leu Tyr Arg
415                 420                 425                 430

Lys Tyr Leu His Gly Asp Leu Ile Val Ile Arg Thr Pro Val Pro Gly
                435                 440                 445

Pro Phe His Leu Trp His Glu Lys Arg Cys Ala Asp Glu Leu Thr Pro
            450                 455                 460

Glu Gln Tyr Arg Met Cys Ile Gln Ser Lys Ala Met Asn Glu Ala Ser
            465                 470                 475

His Ser His Leu Gly Met Leu Val Phe Arg Glu Glu Ile Glu Thr His
    480                 485                 490
```

```
Leu His Lys Gln Ala Tyr Arg Thr Asn Ser Glu Ala Val Gly
495             500             505

<210> SEQ ID NO 11
<211> LENGTH: 1626
<212> TYPE: DNA
<213> ORGANISM: Homo sapiens

<400> SEQUENCE: 11
atgcctagaa gaggactgat tcttcacacc cggacccact ggttgctgtt gggccttgct      60
ttgctctgca gtttggtatt atttatgtac ctcctggaat gtgcccccca gactgatgga     120
aatgcatctc ttcctggtgt tgttggggaa aattatggta agagtatta tcaagccctc      180 ctacaggaac aagaagaaca ttatcagacc agggcaacca gtctgaaacg ccaaattgcc     240
caactaaaac aagaattaca agaaatgagt gagaagatgc ggtcactgca agaaagaagg     300
aatgtagggg ctaatggcat aggctatcag agcaacaaag agcaagcacc tagtgatctt     360
ttagagtttc ttcattccca aattgacaaa gctgaagtta gcatagggc caaactaccc      420 agtgagtatg gggtcattcc ctttgaaagt tttaccttaa tgaaagtatt tcaattggaa     480
atgggtctca ctcgccatcc tgaagaaaag ccagttagaa aagacaaacg agatgaattg     540
gtggaagtta ttgaagcggg cttggaggtc attaataatc ctgatgaaga tgatgaacaa     600
gaagatgagg agggtcccct tggagagaaa ctgatattta tgaaaatga cttcgtagaa     660 ggttattatc gcactgagag agataagggc acacagtatg aactcttttt taagaaagca     720
gaccttacgg aatatagaca tgtgaccctc ttccgccctt tggacctct catgaaagtg       780 aagagtgaga tgattgacat cactagatca attattaata tcattgtgcc acttgctgaa     840
agaactgaag catttgtaca atttatgcag aacttcaggg atgtttgtat tcatcaagac     900
aagaagattc atctcacagt ggtgtatttt ggtaaagaag gactgtctaa ggtcaagtct     960
atcctagaat ctgtcaccag tgagtctaat tttcacaatt acaccttggt ctcattgaat    1020 gaagaatta atcgtggacg aggactaaat gtgggtgccc gagcttggga caagggagag    1080
gtcttgatgt ttttctgtga tgttgatatc tatttctcag ccgaattcct taacagctgc    1140
cggttaaatg ctgagccagg taagaaggtg ttttaccctg tggtgttcag tctttacaat    1200
cctgccattg tttatgccaa ccaggaagtg ccaccacctg tggagcagca gctggttcac    1260
aaaaaggatt ctggcttttg gcgagatttt ggctttggaa tgacttgtca gtatcgttca    1320
gatttcctga ccattggtgg atttgacatg aagtgagag gttggggtgg agaagatgtt    1380
catctttatc gaaatactt acatggtgac ctcattgtga ttcggactcc ggttcctggt     1440
cctttccacc tctggcatga aaagcgctgt gctgatgagc tgaccccga gcagtaccgc     1500 atgtgcatcc agtctaaagc catgaatgag gcctctcact cccacctggg aatgctggtc    1560
ttcagggagg aaatagagac gcatcttcat aaacaggcat acaggacaaa cagtgaagct    1620
gttggt                                                              1626

<210> SEQ ID NO 12
<211> LENGTH: 3451
<212> TYPE: DNA
<213> ORGANISM: Homo sapiens
<220> FEATURE:
<221> NAME/KEY: sig_peptide
<222> LOCATION: (41)..(142)
<220> FEATURE:
<221> NAME/KEY: mat_peptide
<222> LOCATION: (143)..(1666)
<220> FEATURE:
```

```
<221> NAME/KEY: CDS
<222> LOCATION: (41)..(1666)

<400> SEQUENCE: 12
aggcctagcg attttgttag gcaaatacac attaataaga atg cct aga aga gga        55
                                              Met Pro Arg Arg Gly
                                                             -30 ctg att ctt cac acc cgg acc cac tgg ttg ctg ttg ggc ctt gct ttg       103
Leu Ile Leu His Thr Arg Thr His Trp Leu Leu Leu Gly Leu Ala Leu
            -25                 -20                 -15 ctc tgc agt ttg gta tta ttt atg tac ctc ctg gaa tgt gcc ccc cag       151
Leu Cys Ser Leu Val Leu Phe Met Tyr Leu Leu Glu Cys Ala Pro Gln
        -10                  -5                  -1   1 act gat gga aat gca tct ctt cct ggt gtt gtt ggg gaa aat tat ggt       199
Thr Asp Gly Asn Ala Ser Leu Pro Gly Val Val Gly Glu Asn Tyr Gly
      5                  10                  15 aaa gag tat tat caa gcc ctc cta cag gaa caa gaa gaa cat tat cag       247
Lys Glu Tyr Tyr Gln Ala Leu Leu Gln Glu Gln Glu Glu His Tyr Gln
 20                  25                  30                  35 acc agg gca acc agt ctg aaa cgc caa att gcc caa cta aaa caa gaa       295
Thr Arg Ala Thr Ser Leu Lys Arg Gln Ile Ala Gln Leu Lys Gln Glu
                 40                  45                  50 tta caa gaa atg agt gag aag atg cgg tca ctg caa gaa aga agg aat       343
Leu Gln Glu Met Ser Glu Lys Met Arg Ser Leu Gln Glu Arg Arg Asn
             55                  60                  65 gta ggg gct aat ggc ata ggc tat cag agc aac aaa gag caa gca cct       391
Val Gly Ala Asn Gly Ile Gly Tyr Gln Ser Asn Lys Glu Gln Ala Pro
         70                  75                  80 agt gat ctt tta gag ttt ctt cat tcc caa att gac aaa gct gaa gtt       439
Ser Asp Leu Leu Glu Phe Leu His Ser Gln Ile Asp Lys Ala Glu Val
     85                  90                  95 agc ata ggg gcc aaa cta ccc agt gag tat ggg gtc att ccc ttt gaa       487
Ser Ile Gly Ala Lys Leu Pro Ser Glu Tyr Gly Val Ile Pro Phe Glu
100                 105                 110                 115 agt ttt acc tta atg aaa gta ttt caa ttg gaa atg ggt ctc act cgc       535
Ser Phe Thr Leu Met Lys Val Phe Gln Leu Glu Met Gly Leu Thr Arg
                120                 125                 130 cat cct gaa gaa aag cca gtt aga aaa gac aaa cga gat gaa ttg gtg       583
His Pro Glu Glu Lys Pro Val Arg Lys Asp Lys Arg Asp Glu Leu Val
            135                 140                 145 gaa gtt att gaa gcg ggc ttg gag gtc att aat aat cct gat gaa gat       631
Glu Val Ile Glu Ala Gly Leu Glu Val Ile Asn Asn Pro Asp Glu Asp
        150                 155                 160 gat gaa caa gaa gat gag gag ggt ccc ctt gga gag aaa ctg ata ttt       679
Asp Glu Gln Glu Asp Glu Glu Gly Pro Leu Gly Glu Lys Leu Ile Phe
    165                 170                 175 aat gaa aat gac ttc gta gaa ggt tat tat cgc act gag aga gat aag       727
Asn Glu Asn Asp Phe Val Glu Gly Tyr Tyr Arg Thr Glu Arg Asp Lys
180                 185                 190                 195 ggc aca cag tat gaa ctc ttt ttt aag aaa gca gac ctt acg gaa tat       775
Gly Thr Gln Tyr Glu Leu Phe Phe Lys Lys Ala Asp Leu Thr Glu Tyr
                200                 205                 210 aga cat gtg acc ctc ttc cgc cct ttt gga cct ctc atg aaa gtg aag       823
Arg His Val Thr Leu Phe Arg Pro Phe Gly Pro Leu Met Lys Val Lys
            215                 220                 225 agt gag atg att gac atc act aga tca att att aat atc att gtg cca       871
Ser Glu Met Ile Asp Ile Thr Arg Ser Ile Ile Asn Ile Ile Val Pro
        230                 235                 240 ctt gct gaa aga act gaa gca ttt gta caa ttt atg cag aac ttc agg       919
Leu Ala Glu Arg Thr Glu Ala Phe Val Gln Phe Met Gln Asn Phe Arg
```

```
                245                 250                 255
gat gtt tgt att cat caa gac aag aag att cat ctc aca gtg gtg tat      967
Asp Val Cys Ile His Gln Asp Lys Lys Ile His Leu Thr Val Val Tyr
260                 265                 270                 275 ttt ggt aaa gaa gga ctg tct aag gtc aag tct atc cta gaa tct gtc     1015
Phe Gly Lys Glu Gly Leu Ser Lys Val Lys Ser Ile Leu Glu Ser Val
                280                 285                 290 acc agt gag tct aat ttt cac aat tac acc ttg gtc tca ttg aat gaa     1063
Thr Ser Glu Ser Asn Phe His Asn Tyr Thr Leu Val Ser Leu Asn Glu
            295                 300                 305 gaa ttt aat cgt gga cga gga cta aat gtg ggt gcc cga gct tgg gac     1111
Glu Phe Asn Arg Gly Arg Gly Leu Asn Val Gly Ala Arg Ala Trp Asp
        310                 315                 320 aag gga gag gtc ttg atg ttt ttc tgt gat gtt gat atc tat ttc tca     1159
Lys Gly Glu Val Leu Met Phe Phe Cys Asp Val Asp Ile Tyr Phe Ser
    325                 330                 335 gcc gaa ttc ctt aac agc tgc cgg tta aat gct gag cca ggt aag aag     1207
Ala Glu Phe Leu Asn Ser Cys Arg Leu Asn Ala Glu Pro Gly Lys Lys
340                 345                 350                 355 gtg ttt tac cct gtg gtg ttc agt ctt tac aat cct gcc att gtt tat     1255
Val Phe Tyr Pro Val Val Phe Ser Leu Tyr Asn Pro Ala Ile Val Tyr
                360                 365                 370 gcc aac cag gaa gtg cca cca cct gtg gag cag cag ctg gtt cac aaa     1303
Ala Asn Gln Glu Val Pro Pro Pro Val Glu Gln Gln Leu Val His Lys
            375                 380                 385 aag gat tct ggc ttt tgg cga gat ttt ggc ttt gga atg act tgt cag     1351
Lys Asp Ser Gly Phe Trp Arg Asp Phe Gly Phe Gly Met Thr Cys Gln
        390                 395                 400 tat cgt tca gat ttc ctg acc att ggt gga ttt gac atg gaa gtg aga     1399
Tyr Arg Ser Asp Phe Leu Thr Ile Gly Gly Phe Asp Met Glu Val Arg
    405                 410                 415 ggt tgg ggt gga gaa gat gtt cat ctt tat cga aaa tac tta cat ggt     1447
Gly Trp Gly Gly Glu Asp Val His Leu Tyr Arg Lys Tyr Leu His Gly
420                 425                 430                 435 gac ctc att gtg att cgg act ccg gtt cct ggt cct ttc cac ctc tgg     1495
Asp Leu Ile Val Ile Arg Thr Pro Val Pro Gly Pro Phe His Leu Trp
                440                 445                 450 cat gaa aag cgc tgt gct gat gag ctg acc ccc gag cag tac cgc atg     1543
His Glu Lys Arg Cys Ala Asp Glu Leu Thr Pro Glu Gln Tyr Arg Met
            455                 460                 465 tgc atc cag tct aaa gcc atg aat gag gcc tct cac tcc cac ctg gga     1591
Cys Ile Gln Ser Lys Ala Met Asn Glu Ala Ser His Ser His Leu Gly
        470                 475                 480 atg ctg gtc ttc agg gag gaa ata gag acg cat ctt cat aaa cag gca     1639
Met Leu Val Phe Arg Glu Glu Ile Glu Thr His Leu His Lys Gln Ala
    485                 490                 495 tac agg aca aac agt gaa gct gtt ggt tgaaatcata attaatgcgt           1686
Tyr Arg Thr Asn Ser Glu Ala Val Gly
500                 505 tactgtatga accacaaaac agcactattt atttagcctt acttctactt ccagatgcag   1746
tgcctctttt ggagaagaca tgtttatttt tcatgttctt tctgacatta ctttagcaat   1806
tcaacttgat gtgagaagaa aaaacaaatg tttcaacaca aaatctctgt tttgtgagaa   1866
tactgcacta tggaataatt gacaaattga aatctcatat ttgtcccaaa agttgttttg   1926
agttagttct acctggtgcc catgttctga ttgtgtgtgg gattgcatgg tgtcctgatt   1986
gcatctaggt ggagcggatg gaatgtgctg ggcactgttt gggtggagag cagcacattc   2046
ttacagagga gatggagcgt tatgagcata gtatgtggat aggtatcttc acctgcccgc   2106
```

```
ccctgagtca gcctccttga cttgatagct tgaagaatcc ttttccactg aaatagagga   2166
taattaattg acacatctga aatccccaat caatcaatca agagaaaggt agaactaaaa   2226
actccttaac ttactgttgc ttacacccct gaaagtctgt ttttaagcaa atgggtaata   2286
gtagaaaata ggttagaatc tatggcttga ttaaaaatat gttattacat tatcatgttc   2346
aggattagga ttagtagtca gttgctgtaa actattttga acaaacagaa aagaacacgg   2406
aaacattttt aacagagcat ttaattatgt tggaatacag gatcctagct ctgtctggga   2466
acattagctt atgtgagcca gctctatcag ggtcttccca tggtggttca gaatagatga   2526
gcatagcatg gttttgtttg tttttgcttt caattttcta atttggcatg gatccatatg   2586
tatttactat cctttttcta atatattaat atatgctaca tttgtatttg cattactata   2646
atactttgag ttgaaaaaga gtttcattgt ggagagaaaa agcaaatggt atgccacaag   2706
atcactctga tttgagaaaa gggaggaggg gaagatagtc tgaatggaaa tctgaaatac   2766
ggaatgtttt agagaaatat gtcacttgca tagaatgt tttaattgag gtataaatta   2826
atgagacaaa gtgaaaaaga aattatattc agataggact gcactacatt atttgtcaca   2886
catggatctg ttaccatcag gtcaattcct agtatgcata aatttttaa ccctttaaa    2946
agagacctat gttgaaaaacc cctgaaaatt cactgaagaa aaatcattac tcttttctc   3006
agtaaatcat atcatctgaa atattacaaa tttcaaattt ctaggtgcta tattaattca   3066
atattacaat aactcttacc taattattct tacaagtttt aagttgtggt agtttagtga   3126
ttttttttaaa agatgtgtga aatgttctct gcaaataat tcaggccact gtctccttt   3186
atatattatt ataattattt attatgaaga ccagtgaatt acgatattta aagtgagaga   3246
acttaattat ttgcaaaggt aagttacagc ttgtttttg agagaatcaa atgagtttac   3306
ttttgttcct gttgttttta actagcttta agtttaaaga tggaagctaa gcaatggaaa   3366
tgctatacgt ttttgacatt tattaaatgg taccaataaa gtatttatt accaaaaaaa   3426
aaaaaaaaaa aaaaaaaaaa aaaaa                                         3451
```

<210> SEQ ID NO 13
<211> LENGTH: 119
<212> TYPE: PRT
<213> ORGANISM: Homo sapiens

<400> SEQUENCE: 13

Met Arg Lys Gly Asn Leu Leu Leu Ser Trp Leu Leu Gly Pro Glu Leu
        -15                 -10                  -5

Pro Glu Leu Ser Pro Arg Ala Arg Lys Ala Asp Leu Lys Asp Glu Asn
 -1   1               5                  10                  15

Leu Lys Phe Ser Cys Trp Trp Glu Pro Arg Lys Thr Ala Gly Val Leu
                 20                  25                  30

Thr Trp Pro Phe Leu Ala Glu Leu Ala Glu Val Gly Val Leu Ala Asp
             35                  40                  45

Gly Met Tyr Leu Gly Ala Val Ser Val Ala Gln Gln Arg Cys Arg Ala
         50                  55                  60

Asp Trp Leu Ser His Trp Val Leu Pro Ala Gly Ser Pro Leu His Trp
 65                  70                  75

Ala Phe Thr Gln Pro Cys Ser Trp Val Ser Leu Pro Cys Lys Gln Ser
 80                  85                  90                  95

His Asn Asn Thr Arg Ile Val
                 100

<210> SEQ ID NO 14
<211> LENGTH: 357
<212> TYPE: DNA
<213> ORGANISM: Homo sapiens

<400> SEQUENCE: 14

```
atgaggaaag ggaaccttct gctgagctgg cttctggggc ctgagcttcc agagctgtcc      60
ccaagggcta ggaaggccga cctgaaggat gagaaccctca aattcagttg ctggtgggag     120
ccaaggaaga cggcgggtgt tctaacgtgg cccttcttgg ctgagctggc ggaagtgggc     180
gttttggccg atgggatgta tctcggcgct gtgtctgtgg cccagcaaag gtgcagggct     240
gactggctga gccactgggt ctacccgca ggctccccac tgcactgggc tttcacacag     300
ccatgctctt gggtttccct cccttgtaag cagagtcata taacacacg aatagtc         357
```

<210> SEQ ID NO 15
<211> LENGTH: 814
<212> TYPE: DNA
<213> ORGANISM: Homo sapiens
<220> FEATURE:
<221> NAME/KEY: sig_peptide
<222> LOCATION: (62)..(112)
<220> FEATURE:
<221> NAME/KEY: mat_peptide
<222> LOCATION: (113)..(418)
<220> FEATURE:
<221> NAME/KEY: CDS
<222> LOCATION: (62)..(418)

<400> SEQUENCE: 15

```
caaaaatata agcatcagct gaggtgatat tagttcagtc acctaacaac tcctagaaga      60 g atg agg aaa ggg aac ctt ctg ctg agc tgg ctt ctg ggg cct gag ctt     109
  Met Arg Lys Gly Asn Leu Leu Leu Ser Trp Leu Leu Gly Pro Glu Leu
      -15                 -10                 -5 cca gag ctg tcc cca agg gct agg aag gcc gac ctg aag gat gag aac       157
Pro Glu Leu Ser Pro Arg Ala Arg Lys Ala Asp Leu Lys Asp Glu Asn
-1  1               5                   10                  15 ctc aaa ttc agt tgc tgg tgg gag cca agg aag acg gcg ggt gtt cta       205
Leu Lys Phe Ser Cys Trp Trp Glu Pro Arg Lys Thr Ala Gly Val Leu
                20                  25                  30 acg tgg ccc ttt ctg gct gag ctg gcg gaa gtg ggc gtt ttg gcc gat       253
Thr Trp Pro Phe Leu Ala Glu Leu Ala Glu Val Gly Val Leu Ala Asp
            35                  40                  45 ggg atg tat ctc ggc gct gtg tct gtg gcc cag caa agg tgc agg gct       301
Gly Met Tyr Leu Gly Ala Val Ser Val Ala Gln Gln Arg Cys Arg Ala
        50                  55                  60 gac tgg ctg agc cac tgg gtt cta ccc gca ggc tcc cca ctg cac tgg       349
Asp Trp Leu Ser His Trp Val Leu Pro Ala Gly Ser Pro Leu His Trp
    65                  70                  75 gct ttc aca cag cca tgc tct tgg gtt tcc ctc cct tgt aag cag agt       397
Ala Phe Thr Gln Pro Cys Ser Trp Val Ser Leu Pro Cys Lys Gln Ser
80                  85                  90                  95 cat aat aac aca cga ata gtc taacgctggg tattctggtc agcagaggtc         448
His Asn Asn Thr Arg Ile Val
                100 cttgagtcac agtgttactg aaatggttct gagcctgaga atctctttgg cctctgaaag    508 ggcagggcag gtgggcaccg acttcctgcc agtcctttca ggtttcctgt tcaaagccag    568 tcctgttggt ggagggatc accgagagtg tctgtatcat tttgtagccc ttttctctga     628 cgttttctgg tagaaaatgt cccttgtcaa aatgctaata attatcataa taatctgctt    688
```

-continued

```
tccaaccaac ttccacaagt gacaacctgt gtagaactgt gataaaggtt tgcataatgt    748
agggtttgta ccaagtgtgt gtaagtttct gttaaataaa agtctgtttt ccaaaaaaaa    808
aaaaaa                                                               814
```

<210> SEQ ID NO 16
<211> LENGTH: 714
<212> TYPE: PRT
<213> ORGANISM: Homo sapiens

<400> SEQUENCE: 16

```
Met Lys His Phe Cys Asn Leu Leu Cys Ile Leu Met Phe Cys Asn Gln
    -15                 -10                  -5                  -1

Gln Ser Val Cys Asp Pro Pro Ser Gln Asn Asn Ala Ala Asn Ile Ser
  1               5                  10                  15

Met Val Gln Ala Ala Ser Ala Gly Pro Pro Ser Leu Arg Lys Asp Ser
                 20                  25                  30

Thr Pro Val Ile Ala Asn Val Val Ser Leu Ala Ser Ala Pro Ala Ala
             35                  40                  45

Gln Pro Thr Val Asn Ser Asn Ser Val Leu Gln Gly Ala Val Pro Thr
         50                  55                  60

Val Thr Ala Lys Ile Ile Gly Asp Ala Ser Thr Gln Thr Asp Ala Leu
 65                  70                  75                  80

Lys Leu Pro Pro Ser Gln Pro Pro Arg Leu Leu Lys Asn Lys Ala Leu
                 85                  90                  95

Leu Cys Lys Pro Ile Thr Gln Thr Lys Ala Thr Ser Cys Lys Pro His
                100                 105                 110

Thr Gln Asn Lys Glu Cys Gln Thr Glu Asp Thr Pro Ser Gln Pro Gln
            115                 120                 125

Ile Ile Val Val Pro Val Pro Val Phe Val Pro Ile Pro Leu
        130                 135                 140

His Leu Tyr Thr Gln Tyr Ala Pro Val Pro Phe Gly Ile Pro Val Pro
145                 150                 155                 160

Met Pro Val Pro Met Leu Ile Pro Ser Ser Met Asp Ser Glu Asp Lys
                165                 170                 175

Val Thr Glu Ser Ile Glu Asp Ile Lys Glu Lys Leu Pro Thr His Pro
            180                 185                 190

Phe Glu Ala Asp Leu Leu Glu Met Ala Glu Met Ile Ala Glu Asp Glu
        195                 200                 205

Glu Lys Lys Thr Leu Ser Gln Gly Glu Ser Gln Thr Ser Glu His Glu
    210                 215                 220

Leu Phe Leu Asp Thr Lys Ile Phe Glu Lys Asp Gln Gly Ser Thr Tyr
225                 230                 235                 240

Ser Gly Asp Leu Glu Ser Glu Ala Val Ser Thr Leu His Ser Trp Glu
                245                 250                 255

Glu Glu Leu Asn His Tyr Ala Leu Lys Ser Asn Ala Val Gln Glu Ala
            260                 265                 270

Asp Ser Glu Leu Lys Gln Phe Ser Lys Gly Glu Thr Glu Gln Asp Leu
        275                 280                 285

Glu Ala Asp Phe Pro Ser Asp Ser Phe Asp Pro Leu Asn Lys Gly Gln
    290                 295                 300

Gly Ile Gln Ala Arg Ser Arg Thr Arg Arg His Arg Asp Gly Phe
305                 310                 315                 320

Pro Gln Pro Arg Arg Arg Gly Lys Lys Ser Ile Val Ala Val Glu
                325                 330                 335
```

| | | | | | | | | | | | |
|---|---|---|---|---|---|---|---|---|---|---|---|
|Pro|Arg|Ser|Leu|Ile|Gln|Gly|Ala|Phe|Gln|Gly|Cys|Ser|Val|Ser|Gly|
| |  |  |340|   |   |   |   |345|   |   |   |350|   |   |   |

```
            Pro Arg Ser Leu Ile Gln Gly Ala Phe Gln Gly Cys Ser Val Ser Gly
                        340                 345                 350

Met Thr Leu Lys Tyr Met Tyr Gly Val Asn Ala Trp Lys Asn Trp Val
                        355                 360                 365

Gln Trp Lys Asn Ala Lys Glu Gln Gly Asp Leu Lys Cys Gly Gly
                        370                 375             380

Val Glu Gln Ala Ser Ser Pro Arg Ser Asp Pro Leu Gly Ser Thr
            385                 390                 395                 400

Gln Asp His Ala Leu Ser Gln Glu Ser Glu Pro Gly Cys Arg Val
                            405                 410                 415

Arg Ser Ile Lys Leu Lys Glu Asp Ile Leu Ser Cys Thr Phe Ala Glu
                        420                 425                 430

Leu Ser Leu Gly Leu Cys Gln Phe Ile Gln Glu Val Arg Arg Pro Asn
                        435                 440                 445

Gly Glu Lys Tyr Asp Pro Asp Ser Ile Leu Tyr Leu Cys Leu Gly Ile
                        450                 455                 460

Gln Gln Tyr Leu Phe Glu Asn Gly Arg Ile Asp Asn Ile Phe Thr Glu
            465                 470                 475                 480

Pro Tyr Ser Arg Phe Met Ile Glu Leu Thr Lys Leu Leu Lys Ile Trp
                            485                 490                 495

Glu Pro Thr Ile Leu Pro Asn Gly Tyr Met Phe Ser Arg Ile Glu Glu
                        500                 505                 510

Glu His Leu Trp Glu Cys Lys Gln Leu Gly Ala Tyr Ser Pro Ile Val
                        515                 520                 525

Leu Leu Asn Thr Leu Leu Phe Phe Asn Thr Lys Tyr Phe Gln Leu Lys
                        530                 535                 540

Asn Val Thr Glu His Leu Lys Leu Ser Phe Ala His Val Met Arg Arg
            545                 550                 555                 560

Thr Arg Thr Leu Lys Tyr Ser Thr Lys Met Thr Tyr Leu Arg Phe Phe
                            565                 570                 575

Pro Pro Leu Gln Lys Gln Glu Ser Glu Pro Asp Lys Leu Thr Val Gly
                        580                 585                 590

Lys Arg Lys Arg Asn Glu Asp Asp Glu Val Pro Val Gly Val Glu Met
                        595                 600                 605

Ala Glu Asn Thr Asp Asn Pro Leu Arg Cys Pro Val Arg Leu Tyr Glu
                        610                 615                 620

Phe Tyr Leu Ser Lys Cys Ser Glu Ser Val Lys Gln Arg Asn Asp Val
            625                 630                 635                 640

Phe Tyr Leu Gln Pro Glu Arg Ser Cys Val Pro Asn Ser Pro Met Trp
                            645                 650                 655

Tyr Ser Ala Phe Pro Ile Asp Pro Gly Thr Leu Asp Thr Met Leu Thr
                        660                 665                 670

Arg Ile Leu Met Val Arg Glu Val His Glu Glu Leu Ala Lys Ala Lys
                        675                 680                 685

Ser Glu Asp Ser Asp Val Glu Leu Ser Asp
                690                 695

<210> SEQ ID NO 17
<211> LENGTH: 2142
<212> TYPE: DNA
<213> ORGANISM: Homo sapiens

<400> SEQUENCE: 17
atgaaacatt tctgtaacct gctttgtatc ttgatgttct gtaatcagca aagtgtatgt    60
```

```
gacccgcctt cacaaaataa tgcagcaaat atttccatgg ttcaagctgc ttcagcagga      120
cccccatctc tgagaaaaga ttcgactcca gttatagcca atgtagtatc attggcaagt      180
gcccctgctg ctcagcctac agtgaattct aacagtgtct tacaaggtgc agttccaaca      240
gtaacagcga aaatcatcgg tgatgcaagt actcaaacag atgccctgaa actgccacct      300
tcccaacctc caaggctttt gaagaacaaa gctttattat gcaaacccat cacacagact      360
aaagccacct cttgcaaacc atacccaa acaaagaat gccagacaga agacactcca      420
agtcagcccc agattattgt ggtgccagtt cccgtaccag tgtttgttcc catacctctt      480
cacctttata ctcaatatgc tccagtccca tttggaattc cagttccaat gcctgtccct      540
atgcttattc catcttcaat ggatagtgaa ataaagtca cagagagtat tgaagacatt      600
aaagaaaagc ttcccacaca tccatttgaa gctgatctcc ttgagatggc agaaatgatt      660
gcagaagatg aagagaagaa gactctatct cagggagagt cccaaacttc tgaacacgaa      720
ctctttctag acaccaagat atttgaaaaa gaccaaggaa gtacatacag tggtgatctt      780
gaatcagagg cagtatctac tctacatagc tgggaggaag agctgaatca ctatgcctta      840
aagtcaaatg ctgtgcaaga ggctgattca gaattgaagc agttctcaaa aggggaaact      900
gaacaggacc tggaagcaga ttttccatca gactcctttg acccacttaa taaaggacag      960
ggaatccagg cacgttcccg aacaagacga cgacacagag atggcttccc ccaacccaga      1020
cgaagaggac ggaagaagtc tatagtggct gtggagccca ggagtcttat tcaaggagcc      1080
tttcaaggct gctcagtgtc cggatgacaa ctgaaatacaa tgtatgggt aaatgcttgg      1140 aagaactggg ttcagtggaa aaatgccaag gaagagcagg gggatctaaa atgtggaggg      1200
gttgaacagg cctcatctag cccacgttct gacccccttag gaagtactca agaccatgca      1260
ctctctcaag aatcctcaga gccaggctgt agagtccgct ctatcaagct gaaggaagac      1320
attctgtcct gcacttttgc tgagttgagt ttgggcttat gccagtttat ccaagaggtg      1380
cggagaccaa atggtgaaaa atatgatcca gacagtatct tatacttgtg ccttggaatt      1440
caacagtacc tgtttgaaaa tggtagaata gataacattt ttactgagcc ctattccaga      1500
tttatgattg aacttaccaa actcttgaaa atatgggaac ctacaatact tcctaatggt      1560
tacatgttct ctcgcattga ggaagagcat ttgtgggagt gcaaacagct gggcgcttac      1620
tcaccaatcg tccttttaaa caccctcctt ttcttcaata ccaaatactt ccaactaaag      1680
aatgttactg agcacttgaa gctttccttt gccatgtga tgagacggac caggactctg      1740
aagtacagta ccaagatgac atatctgagg ttcttccac ctttacagaa gcaggagtca      1800
gaaccagata aactgactgt tggcaagagg aaacgaaatg aagatgatga ggttccagtg      1860
ggggtggaga tggcagagaa tactgacaat ccactaagat gcccagtccg actttatgag      1920
ttttacctgt caaaatgttc tgaaagtgtg aagcaaagga atgatgtgtt ttaccttcaa      1980
cctgagcgct cctgtgtccc gaatagcccc atgtggtact ccgcattccc gatagaccct      2040
ggaaccctgg acaccatgtt aacacgtatt ctcatggtga gggaggtaca tgaagaactt      2100
gccaaagcca aatctgaaga ctctgatgtt gaattatcag at      2142
```

<210> SEQ ID NO 18
<211> LENGTH: 2662
<212> TYPE: DNA
<213> ORGANISM: Homo sapiens
<220> FEATURE:
<221> NAME/KEY: sig_peptide
<222> LOCATION: (6)..(53)

```
<220> FEATURE:
<221> NAME/KEY: mat_peptide
<222> LOCATION: (54)..(2147)
<220> FEATURE:
<221> NAME/KEY: CDS
<222> LOCATION: (6)..(2147)

<400> SEQUENCE: 18 gggaa atg aaa cat ttc tgt aac ctg ctt tgt atc ttg atg ttc tgt aat       50
      Met Lys His Phe Cys Asn Leu Leu Cys Ile Leu Met Phe Cys Asn
          -15                 -10                 -5 cag caa agt gta tgt gac ccg cct tca caa aat aat gca gca aat att         98
Gln Gln Ser Val Cys Asp Pro Pro Ser Gln Asn Asn Ala Ala Asn Ile
-1  1               5                   10                  15 tcc atg gtt caa gct gct tca gca gga ccc cca tct ctg aga aaa gat        146
Ser Met Val Gln Ala Ala Ser Ala Gly Pro Pro Ser Leu Arg Lys Asp
                20                  25                  30 tcg act cca gtt ata gcc aat gta gta tca ttg gca agt gcc cct gct        194
Ser Thr Pro Val Ile Ala Asn Val Val Ser Leu Ala Ser Ala Pro Ala
                35                  40                  45 gct cag cct aca gtg aat tct aac agt gtc tta caa ggt gca gtt cca        242
Ala Gln Pro Thr Val Asn Ser Asn Ser Val Leu Gln Gly Ala Val Pro
        50                  55                  60 aca gta aca gcg aaa atc atc ggt gat gca agt act caa aca gat gcc        290
Thr Val Thr Ala Lys Ile Ile Gly Asp Ala Ser Thr Gln Thr Asp Ala
65                  70                  75 ctg aaa ctg cca cct tcc caa cct cca agg ctt ttg aag aac aaa gct        338
Leu Lys Leu Pro Pro Ser Gln Pro Pro Arg Leu Leu Lys Asn Lys Ala
80                  85                  90                  95 tta tta tgc aaa ccc atc aca cag act aaa gcc acc tct tgc aaa cca        386
Leu Leu Cys Lys Pro Ile Thr Gln Thr Lys Ala Thr Ser Cys Lys Pro
                100                 105                 110 cat acc caa aac aaa gaa tgc cag aca gaa gac act cca agt cag ccc        434
His Thr Gln Asn Lys Glu Cys Gln Thr Glu Asp Thr Pro Ser Gln Pro
                115                 120                 125 cag att att gtg gtg cca gtt ccc gta cca gtg ttt gtt ccc ata cct        482
Gln Ile Ile Val Val Pro Val Pro Val Pro Val Phe Val Pro Ile Pro
            130                 135                 140 ctt cac ctt tat act caa tat gct cca gtc cca ttt gga att cca gtt        530
Leu His Leu Tyr Thr Gln Tyr Ala Pro Val Pro Phe Gly Ile Pro Val
145                 150                 155 cca atg cct gtc cct atg ctt att cca tct tca atg gat agt gaa gat        578
Pro Met Pro Val Pro Met Leu Ile Pro Ser Ser Met Asp Ser Glu Asp
160                 165                 170                 175 aaa gtc aca gag agt att gaa gac att aaa gaa aag ctt ccc aca cat        626
Lys Val Thr Glu Ser Ile Glu Asp Ile Lys Glu Lys Leu Pro Thr His
                180                 185                 190 cca ttt gaa gct gat ctc ctt gag atg gca gaa atg att gca gaa gat        674
Pro Phe Glu Ala Asp Leu Leu Glu Met Ala Glu Met Ile Ala Glu Asp
                195                 200                 205 gaa gag aag aag act cta tct cag gga gag tcc caa act tct gaa cac        722
Glu Glu Lys Lys Thr Leu Ser Gln Gly Glu Ser Gln Thr Ser Glu His
            210                 215                 220 gaa ctc ttt cta gac acc aag ata ttt gaa aaa gac caa gga agt aca        770
Glu Leu Phe Leu Asp Thr Lys Ile Phe Glu Lys Asp Gln Gly Ser Thr
225                 230                 235 tac agt ggt gat ctt gaa tca gag gca gta tct act cta cat agc tgg        818
Tyr Ser Gly Asp Leu Glu Ser Glu Ala Val Ser Thr Leu His Ser Trp
240                 245                 250                 255 gag gaa gag ctg aat cac tat gcc tta aag tca aat gct gtg caa gag        866
Glu Glu Glu Leu Asn His Tyr Ala Leu Lys Ser Asn Ala Val Gln Glu
```

-continued

|     | 260 | | | | 265 | | | | 270 | | | | |
|---|---|---|---|---|---|---|---|---|---|---|---|---|---|

```
gct gat tca gaa ttg aag cag ttc tca aaa ggg gaa act gaa cag gac      914
Ala Asp Ser Glu Leu Lys Gln Phe Ser Lys Gly Glu Thr Glu Gln Asp
            275                 280                 285 ctg gaa gca gat ttt cca tca gac tcc ttt gac cca ctt aat aaa gga      962
Leu Glu Ala Asp Phe Pro Ser Asp Ser Phe Asp Pro Leu Asn Lys Gly
            290                 295                 300 cag gga atc cag gca cgt tcc cga aca aga cga cga cac aga gat ggc     1010
Gln Gly Ile Gln Ala Arg Ser Arg Thr Arg Arg Arg His Arg Asp Gly
            305                 310                 315 ttc ccc caa ccc aga cga aga gga cgg aag aag tct ata gtg gct gtg     1058
Phe Pro Gln Pro Arg Arg Arg Gly Arg Lys Lys Ser Ile Val Ala Val
320                 325                 330                 335 gag ccc agg agt ctt att caa gga gcc ttt caa ggc tgc tca gtg tcc     1106
Glu Pro Arg Ser Leu Ile Gln Gly Ala Phe Gln Gly Cys Ser Val Ser
                340                 345                 350 ggg atg aca ctg aaa tac atg tat ggg gta aat gct tgg aag aac tgg     1154
Gly Met Thr Leu Lys Tyr Met Tyr Gly Val Asn Ala Trp Lys Asn Trp
                355                 360                 365 gtt cag tgg aaa aat gcc aag gaa gag cag ggg gat cta aaa tgt gga     1202
Val Gln Trp Lys Asn Ala Lys Glu Glu Gln Gly Asp Leu Lys Cys Gly
                370                 375                 380 ggg gtt gaa cag gcc tca tct agc cca cgt tct gac ccc tta gga agt     1250
Gly Val Glu Gln Ala Ser Ser Ser Pro Arg Ser Asp Pro Leu Gly Ser
385                 390                 395 act caa gac cat gca ctc tct caa gaa tcc tca gag cca ggc tgt aga     1298
Thr Gln Asp His Ala Leu Ser Gln Glu Ser Ser Glu Pro Gly Cys Arg
400                 405                 410                 415 gtc cgc tct atc aag ctg aag gaa gac att ctg tcc tgc act ttt gct     1346
Val Arg Ser Ile Lys Leu Lys Glu Asp Ile Leu Ser Cys Thr Phe Ala
                420                 425                 430 gag ttg agt ttg ggc tta tgc cag ttt atc caa gag gtg cgg aga cca     1394
Glu Leu Ser Leu Gly Leu Cys Gln Phe Ile Gln Glu Val Arg Arg Pro
                435                 440                 445 aat ggt gaa aaa tat gat cca gac agt atc tta tac ttg tgc ctt gga     1442
Asn Gly Glu Lys Tyr Asp Pro Asp Ser Ile Leu Tyr Leu Cys Leu Gly
                450                 455                 460 att caa cag tac ctg ttt gaa aat ggt aga ata gat aac att ttt act     1490
Ile Gln Gln Tyr Leu Phe Glu Asn Gly Arg Ile Asp Asn Ile Phe Thr
465                 470                 475 gag ccc tat tcc aga ttt atg att gaa ctt acc aaa ctc ttg aaa ata     1538
Glu Pro Tyr Ser Arg Phe Met Ile Glu Leu Thr Lys Leu Leu Lys Ile
480                 485                 490                 495 tgg gaa cct aca ata ctt cct aat ggt tac atg ttc tct cgc att gag     1586
Trp Glu Pro Thr Ile Leu Pro Asn Gly Tyr Met Phe Ser Arg Ile Glu
                500                 505                 510 gaa gag cat ttg tgg gag tgc aaa cag ctg ggc gct tac tca cca atc     1634
Glu Glu His Leu Trp Glu Cys Lys Gln Leu Gly Ala Tyr Ser Pro Ile
                515                 520                 525 gtc ctt tta aac acc ctc ctt ttc ttt aat acc aaa tac ttc caa cta     1682
Val Leu Leu Asn Thr Leu Leu Phe Phe Asn Thr Lys Tyr Phe Gln Leu
                530                 535                 540 aag aat gtt act gag cac ttg aag ctt tcc ttt gcc cat gtg atg aga     1730
Lys Asn Val Thr Glu His Leu Lys Leu Ser Phe Ala His Val Met Arg
545                 550                 555 cgg acc agg act ctg aag tac agt acc aag atg aca tat ctg agg ttc     1778
Arg Thr Arg Thr Leu Lys Tyr Ser Thr Lys Met Thr Tyr Leu Arg Phe
560                 565                 570                 575 ttc cca cct tta cag aag cag gag tca gaa cca gat aaa ctg act gtt     1826
```

```
Phe Pro Pro Leu Gln Lys Gln Glu Ser Glu Pro Asp Lys Leu Thr Val
            580                 585                 590 ggc aag agg aaa cga aat gaa gat gat gag gtt cca gtg ggg gtg gag    1874
Gly Lys Arg Lys Arg Asn Glu Asp Asp Glu Val Pro Val Gly Val Glu
            595                 600                 605 atg gca gag aat act gac aat cca cta aga tgc cca gtc cga ctt tat    1922
Met Ala Glu Asn Thr Asp Asn Pro Leu Arg Cys Pro Val Arg Leu Tyr
            610                 615                 620 gag ttt tac ctg tca aaa tgt tct gaa agt gtg aag caa agg aat gat    1970
Glu Phe Tyr Leu Ser Lys Cys Ser Glu Ser Val Lys Gln Arg Asn Asp
            625                 630                 635 gtg ttt tac ctt caa cct gag cgc tcc tgt gtc ccg aat agc ccc atg    2018
Val Phe Tyr Leu Gln Pro Glu Arg Ser Cys Val Pro Asn Ser Pro Met
640                 645                 650                 655 tgg tac tcc gca ttc ccg ata gac cct gga acc ctg gac acc atg tta    2066
Trp Tyr Ser Ala Phe Pro Ile Asp Pro Gly Thr Leu Asp Thr Met Leu
                660                 665                 670 aca cgt att ctc atg gtg agg gag gta cat gaa gaa ctt gcc aaa gcc    2114
Thr Arg Ile Leu Met Val Arg Glu Val His Glu Glu Leu Ala Lys Ala
            675                 680                 685 aaa tct gaa gac tct gat gtt gaa tta tca gat taaaacgaa gtgaggttct   2167
Lys Ser Glu Asp Ser Asp Val Glu Leu Ser Asp
            690                 695 tattttcata catattggta tgcaccaaac tgtgaatgca tccagctgtt ggaaaatgat   2227
gtataagtct aagtcctctt gacttgacca taagatcatg gaaaacagat gacttgtgaa   2287
ccccacagtg tggatgtgca aatgaaaatt gaaggaaaga atatgaactg agaaatgttc   2347
tttggcagtg atatagttct tagacatctt cagaatgact aatttctccg agtggtgcat   2407
aatcttattt tgtttgggag taacaaatcg tggaatattt ttaaggaaaa ctgttgtata   2467
aaactttacc atagtaacct tagaccttag agaggtagct ttggagtgaa actttggctg   2527
caataggcta ctttggcaag ccctccgtaa aagtcagagg agagatcagt acagagctaa   2587
gagtgacatc aaatgaggac tgtgggaccc agatttgaag acccaataaa aatactcaac   2647
tttttaaaaa aaaaa                                                   2662

<210> SEQ ID NO 19
<211> LENGTH: 81
<212> TYPE: PRT
<213> ORGANISM: Homo sapiens

<400> SEQUENCE: 19

Met Arg Thr Tyr His Tyr Ile Pro Leu Phe Ile Trp Thr Tyr Met Phe
                -20                 -15                 -10

His Thr Val Asp Thr Ile Leu Leu Gln Glu Lys Pro Asn Ser Tyr Leu
        -5                  -1   1                   5

Ser Ser Lys Lys Ile Ala Gly Leu Thr Lys Asp Asp Gly Lys Met Leu
    10                  15                  20

Arg Arg Thr Lys Arg Gly Trp Met Trp Asn Gln Phe Phe Leu Leu Glu
25                  30                  35                  40

Glu Tyr Thr Gly Thr Asp Thr Gln Tyr Val Gly Lys Val Arg Ile Phe
                45                  50                  55

Val

<210> SEQ ID NO 20
<211> LENGTH: 243
<212> TYPE: DNA
<213> ORGANISM: Homo sapiens
```

<400> SEQUENCE: 20

```
atgaggactt accattatat accattattc atctggacct atatgttcca tacagttgac     60
accatcctat tacaagaaaa acctaacagt tatttatcaa gcaaaaagat agcgggtctg    120
acaaaagatg acggtaaaat gctacgtcgc accaagcgtg gctggatgtg aatcagttc    180
ttcttattgg aagagtacac aggtactgac acacaatatg taggcaaggt aagaattttt    240
gta                                                                  243
```

<210> SEQ ID NO 21
<211> LENGTH: 630
<212> TYPE: DNA
<213> ORGANISM: Homo sapiens
<220> FEATURE:
<221> NAME/KEY: sig_peptide
<222> LOCATION: (160)..(231)
<220> FEATURE:
<221> NAME/KEY: mat_peptide
<222> LOCATION: (232)..(402)
<220> FEATURE:
<221> NAME/KEY: CDS
<222> LOCATION: (160)..(402)

<400> SEQUENCE: 21

```
aagatcagct gtgaagatac tataaaaagg gaagagaagg accgagacag aagcaacaac     60
ggaactgtca gtgcggagta gggctaaact cagttccatt gttaagcaag gaaaaacaaa    120
caatacattg aatttgacaa cccactgaag ttgcagata atg agg act tac cat       174
                                            Met Arg Thr Tyr His
                                                            -20
``` tat ata cca tta ttc atc tgg acc tat atg ttc cat aca gtt gac acc     222
Tyr Ile Pro Leu Phe Ile Trp Thr Tyr Met Phe His Thr Val Asp Thr
            -15                 -10                  -5 atc cta tta caa gaa aaa cct aac agt tat tta tca agc aaa aag ata     270
Ile Leu Leu Gln Glu Lys Pro Asn Ser Tyr Leu Ser Ser Lys Lys Ile
 -1  1               5                  10 gcg ggt ctg aca aaa gat gac ggt aaa atg cta cgt cgc acc aag cgt     318
Ala Gly Leu Thr Lys Asp Asp Gly Lys Met Leu Arg Arg Thr Lys Arg
 15                  20                  25 ggc tgg atg tgg aat cag ttc ttc tta ttg gaa gag tac aca ggt act     366
Gly Trp Met Trp Asn Gln Phe Phe Leu Leu Glu Glu Tyr Thr Gly Thr
 30                  35                  40                  45 gac aca caa tat gta ggc aag gta aga att ttt gta tgagaaatct          412
Asp Thr Gln Tyr Val Gly Lys Val Arg Ile Phe Val
                 50                  55

```
aaaagctgaa agtgacagct atttattttt ttccagcaac ttttcttttc actagtgatt    472
attaaaaaat atttaactaa ttatgttctg aaggtgtgat attgcaaact attttagtgg    532
ggaagaacaa ggaaccatat ttgggttcta aatgtaaatc aatgtcaata taagcgtaa    592
gctactaagt catatgtgga tggatgtgat cattatta                            630
```

<210> SEQ ID NO 22
<211> LENGTH: 150
<212> TYPE: PRT
<213> ORGANISM: Homo sapiens

<400> SEQUENCE: 22

Met Arg Lys Thr Arg Leu Trp Gly Leu Leu Trp Met Leu Phe Val Ser
-20                 -15                 -10                  -5

Glu Leu Arg Ala Ala Thr Lys Leu Thr Glu Glu Lys Tyr Glu Leu Lys
        -1  1                   5                  10

Glu Gly Gln Thr Leu Asp Val Lys Cys Asp Tyr Thr Leu Glu Lys Phe
       15                  20                  25

Ala Ser Ser Gln Lys Ala Trp Gln Ile Ile Arg Asp Gly Glu Met Pro
        30                  35                  40

Lys Thr Leu Ala Cys Thr Glu Arg Pro Ser Lys Asn Ser His Pro Val
45                  50                  55                  60

Gln Val Gly Arg Ile Ile Leu Glu Asp Tyr His Asp His Gly Leu Leu
                65                  70                  75

Arg Val Arg Met Val Asn Leu Val Glu Asp Ser Gly Leu Tyr Gln
                80                  85                  90

Cys Val Ile Tyr Gln Pro Pro Lys Glu Pro His Met Leu Phe Asp Arg
            95                 100                 105

Ile Arg Leu Val Val Thr Lys Gly Phe Arg Cys Ser Thr Leu Ser Phe
        110                 115                 120

Ser Trp Leu Val Asp Ser
125             130

<210> SEQ ID NO 23
<211> LENGTH: 450
<212> TYPE: DNA
<213> ORGANISM: Homo sapiens

<400> SEQUENCE: 23
atgaggaaga ccaggctctg ggggctgctg tggatgctct ttgtctcaga actccgagct      60
gcaactaaat taactgagga aaagtatgaa ctgaaagagg ggcagaccct ggatgtgaaa     120
tgtgactaca cgctagagaa gtttgccagc agccagaaag cttggcagat aataagggac     180
ggagagatgc ccaagaccct ggcatgcaca gagaggcctt caaagaattc ccatccagtc     240
caagtgggga ggatcatact agaagactac catgatcatg gtttactgcg cgtccgaatg     300
gtcaaccttc aagtggaaga ttctggactg tatcagtgtg tgatctacca gcctcccaag     360
gagcctcaca tgctgttcga tcgcatccgc ttggtggtga ccaaggggtt ccggtgttca     420
acattgtcat tctcctggct ggtggattcc                                     450

<210> SEQ ID NO 24
<211> LENGTH: 701
<212> TYPE: DNA
<213> ORGANISM: Homo sapiens
<220> FEATURE:
<221> NAME/KEY: sig_peptide
<222> LOCATION: (19)..(78)
<220> FEATURE:
<221> NAME/KEY: mat_peptide
<222> LOCATION: (79)..(468)
<220> FEATURE:
<221> NAME/KEY: CDS
<222> LOCATION: (19)..(468)

<400> SEQUENCE: 24
agctggtgca caggaagg atg agg aag acc agg ctc tgg ggg ctg ctg tgg     51
                   Met Arg Lys Thr Arg Leu Trp Gly Leu Leu Trp
                   -20              -15                  -10 atg ctc ttt gtc tca gaa ctc cga gct gca act aaa tta act gag gaa      99
Met Leu Phe Val Ser Glu Leu Arg Ala Ala Thr Lys Leu Thr Glu Glu
             -5                  -1 1                   5 aag tat gaa ctg aaa gag ggg cag acc ctg gat gtg aaa tgt gac tac     147
Lys Tyr Glu Leu Lys Glu Gly Gln Thr Leu Asp Val Lys Cys Asp Tyr
         10                  15                  20 acg cta gag aag ttt gcc agc agc cag aaa gct tgg cag ata ata agg     195

-continued

| | | | | | | | | | | | | | | |
|---|---|---|---|---|---|---|---|---|---|---|---|---|---|---|
|Thr|Leu|Glu|Lys|Phe|Ala|Ser|Ser|Gln|Lys|Ala|Trp|Gln|Ile|Ile|Arg|
| |25| | | | |30| | | | |35| | | |

```
gac gga gag atg ccc aag acc ctg gca tgc aca gag agg cct tca aag      243
Asp Gly Glu Met Pro Lys Thr Leu Ala Cys Thr Glu Arg Pro Ser Lys
 40              45                  50                  55 aat tcc cat cca gtc caa gtg ggg agg atc ata cta gaa gac tac cat      291
Asn Ser His Pro Val Gln Val Gly Arg Ile Ile Leu Glu Asp Tyr His
                 60                  65                  70 gat cat ggt tta ctg cgc gtc cga atg gtc aac ctt caa gtg gaa gat      339
Asp His Gly Leu Leu Arg Val Arg Met Val Asn Leu Gln Val Glu Asp
             75                  80                  85 tct gga ctg tat cag tgt gtg atc tac cag cct ccc aag gag cct cac      387
Ser Gly Leu Tyr Gln Cys Val Ile Tyr Gln Pro Pro Lys Glu Pro His
         90                  95                  100 atg ctg ttc gat cgc atc cgc ttg gtg gtg acc aag ggg ttc cgg tgt      435
Met Leu Phe Asp Arg Ile Arg Leu Val Val Thr Lys Gly Phe Arg Cys
    105                 110                 115 tca aca ttg tca ttc tcc tgg ctg gtg gat tcc tgagtaagag cctggtcttc    488
Ser Thr Leu Ser Phe Ser Trp Leu Val Asp Ser
120             125                 130 tctgtcctgt tgctgtcac gctgaggtca tttgtaccct aggcccacga acccacgaga     548
atgtcctctg acttccagcc acatccatct ggcagttgtg ccaagggagg agggaggagg    608
taaaaggcag ggagttaata acatgaatta aatctgtaat caccagctaa agaaaaaaaa    668
aaaaaaaaaa aaaaaaaaaa aaaaaaaaaa aaa                                 701

<210> SEQ ID NO 25
<211> LENGTH: 422
<212> TYPE: PRT
<213> ORGANISM: Homo sapiens

<400> SEQUENCE: 25

Met Leu Gln Trp Arg Arg Arg His Cys Cys Phe Ala Lys Met Thr Trp
            -35                 -30                 -25

Asn Ala Lys Arg Ser Leu Phe Arg Thr His Leu Ile Gly Val Leu Ser
        -20                 -15                 -10

Leu Val Phe Leu Phe Ala Met Phe Leu Phe Phe Asn His His Asp Trp
    -5                  -1  1               5                   10

Leu Pro Gly Arg Ala Gly Phe Lys Glu Asn Pro Val Thr Tyr Thr Phe
                15                  20                  25

Arg Gly Phe Arg Ser Thr Lys Ser Glu Thr Asn His Ser Ser Leu Arg
            30                  35                  40

Asn Ile Trp Lys Glu Thr Val Pro Gln Thr Leu Arg Pro Gln Thr Ala
        45                  50                  55

Thr Asn Ser Asn Asn Thr Asp Leu Ser Pro Gln Gly Val Thr Gly Leu
    60                  65                  70

Glu Asn Thr Leu Ser Ala Asn Gly Ser Ile Tyr Asn Glu Lys Gly Thr
75                  80                  85                  90

Gly His Pro Asn Ser Tyr His Phe Lys Tyr Ile Ile Asn Glu Pro Glu
                95                  100                 105

Lys Cys Gln Glu Lys Ser Pro Phe Leu Ile Leu Ile Ala Ala Glu
            110                 115                 120

Pro Gly Gln Ile Glu Ala Arg Arg Ala Ile Arg Gln Thr Trp Gly Asn
        125                 130                 135

Glu Ser Leu Ala Pro Gly Ile Gln Ile Thr Arg Ile Phe Leu Leu Gly
    140                 145                 150
```

```
Leu Ser Ile Lys Leu Asn Gly Tyr Leu Gln Arg Ala Ile Leu Glu Glu
155                 160                 165                 170

Ser Arg Gln Tyr His Asp Ile Ile Gln Gln Glu Tyr Leu Asp Thr Tyr
                175                 180                 185

Tyr Asn Leu Thr Ile Lys Thr Leu Met Gly Met Asn Trp Val Ala Thr
            190                 195                 200

Tyr Cys Pro His Ile Pro Tyr Val Met Lys Thr Asp Ser Asp Met Phe
        205                 210                 215

Val Asn Thr Glu Tyr Leu Ile Asn Lys Leu Leu Lys Pro Asp Leu Pro
    220                 225                 230

Pro Arg His Asn Tyr Phe Thr Gly Tyr Leu Met Arg Gly Tyr Ala Pro
235                 240                 245                 250

Asn Arg Asn Lys Asp Ser Lys Trp Tyr Met Pro Pro Asp Leu Tyr Pro
                255                 260                 265

Ser Glu Arg Tyr Pro Val Phe Cys Ser Gly Thr Gly Tyr Val Phe Ser
                270                 275                 280

Gly Asp Leu Ala Glu Lys Ile Phe Lys Val Ser Leu Gly Ile Arg Arg
            285                 290                 295

Leu His Leu Glu Asp Val Tyr Val Gly Ile Cys Leu Ala Lys Leu Arg
        300                 305                 310

Ile Asp Pro Val Pro Pro Asn Glu Phe Val Phe Asn His Trp Arg
315                 320                 325                 330

Val Ser Tyr Ser Ser Cys Lys Tyr Ser His Leu Ile Thr Ser His Gln
                335                 340                 345

Phe Gln Pro Ser Glu Leu Ile Lys Tyr Trp Asn His Leu Gln Gln Asn
                350                 355                 360

Lys His Asn Ala Cys Ala Asn Ala Ala Lys Glu Lys Ala Gly Arg Tyr
                365                 370                 375

Arg His Arg Lys Leu His
    380

<210> SEQ ID NO 26
<211> LENGTH: 1266
<212> TYPE: DNA
<213> ORGANISM: Homo sapiens

<400> SEQUENCE: 26
atgcttcagt ggaggagaag acactgctgc tttgcaaaga tgacctggaa tgccaaaagg     60
tctctgttcc gcactcatct tattggagta ctttctctag tgtttctttt tgctatgttt    120 ttgttttca atcatcatga ctggctgcca ggcagagctg gattcaaaga aaaccctgtg    180
acatacactt tccgaggatt tcggtcaaca aaaagtgaga caaaccacag ctcccttcgg    240
aacatttgga agaaacagt ccctcaaacc ctgaggcctc aaacagcaac taactctaat    300
aacacagacc tgtcaccaca aggagttaca ggcctggaga atacttag tgccaatgga    360 agtatttaca atgaaaaagg tactggacat ccaaattctt accatttcaa atatattatt    420
aatgagcctg aaaatgcca agagaaaagt cctttttta tactactaat agctgcagag    480
cctggacaaa tagaagctag aagagctatt cggcaaactt ggggcaatga agtctagca    540 cctggtattc aaatcacaag aatatttttg ttgggcttaa gtattaagct aaatggctac    600
cttcaacgtg caatactgga agaaagcaga caatatcatg atataattca acaggaatac    660
ttagatacgt actataattt gaccattaaa cactaatgg gcatgaactg ggttgcaaca    720
tactgtccac atattccata tgttatgaaa actgacagtg acatgtttgt caacactgaa    780
```

-continued

| | |
|---|---|
| tatttaatca ataagttact gaagccagat ctgcctccca gacataacta tttcactggt | 840 |
| tacctaatgc gaggatatgc acccaatcga aacaaagata gcaagtggta catgccacca | 900 |
| gacctctacc caagtgagcg ttatcctgtc ttctgttctg aactggtta tgttttttct | 960 |
| ggagatctgg cagaaaagat ttttaaagtt tctttaggta tccgccgttt gcacttggaa | 1020 |
| gatgtatatg tagggatctg tcttgccaag ttgagaattg atcctgtacc ccctcccaat | 1080 |
| gagtttgtgt tcaatcactg gcgagtctct tattcgagct gtaaatacag ccacctaatt | 1140 |
| acctctcatc agttccagcc tagtgaactg ataaaatact ggaaccattt acaacaaaat | 1200 |
| aagcacaatg cctgtgccaa cgcagcaaaa gaaaaggcag gcaggtatcg ccaccgtaaa | 1260 |
| ctacat | 1266 |

<210> SEQ ID NO 27
<211> LENGTH: 2420
<212> TYPE: DNA
<213> ORGANISM: Homo sapiens
<220> FEATURE:
<221> NAME/KEY: sig_peptide
<222> LOCATION: (698)..(811)
<220> FEATURE:
<221> NAME/KEY: mat_peptide
<222> LOCATION: (812)..(1963)
<220> FEATURE:
<221> NAME/KEY: CDS
<222> LOCATION: (698)..(1963)

<400> SEQUENCE: 27

| | |
|---|---|
| gcctgtgcag cagctgagga accgtggatt tcatattata gactaaaacc ccattaaaac | 60 |
| tgctcaaaat ccttcctgca gctgccaggc aacaacgaaa gaagagaggt aaatcctatt | 120 |
| cttttccaat acaactgaag cactacattt tagctctggc tgctttacat tgcagctcag | 180 |
| tgttattagt agaaatatgg atactgagac gagaacacag cactgcattg tccagccagg | 240 |
| aaaatagcag atgtaaaaag cttcaatgca tcaactgtcg ggaagagtca acagtgctac | 300 |
| aagcagaacg ggcaactaca gctcttttgt ttaacgaaag agagaaaatg aaagaaaggg | 360 |
| aaaatttcag aagactagga cccatatgaa caaggagggt aactcgaaga caagcagaca | 420 |
| gatggacact ttggatactg tgaaaagcaa tcgcaggagg cagactgttg ggggatgtgc | 480 |
| gcatgttcga tagcatcttt tttgctgaag tgatggcgtg ccaaaagtat ttcagtggg | 540 |
| cataatcctc ttcacataaa tggcctgacc aaggaagaat gactacaaga gagacaatgt | 600 |
| gactgaatta gaaaatgatt gccaaagaat agtattaagg agaagaaaac atttttggtc | 660 |
| accaatctct catataccac tactggatat ttacaac atg ctt cag tgg agg aga | 715 |
|   Met Leu Gln Trp Arg Arg   −35 | |
| aga cac tgc tgc ttt gca aag atg acc tgg aat gcc aaa agg tct ctg | 763 |
| Arg His Cys Cys Phe Ala Lys Met Thr Trp Asn Ala Lys Arg Ser Leu   −30            −25                −20 | |
| ttc cgc act cat ctt att gga gta ctt tct cta gtg ttt ctt ttt gct | 811 |
| Phe Arg Thr His Leu Ile Gly Val Leu Ser Leu Val Phe Leu Phe Ala   −15            −10               −5                −1 | |
| atg ttt ttg ttt ttc aat cat cat gac tgg ctg cca ggc aga gct gga | 859 |
| Met Phe Leu Phe Phe Asn His His Asp Trp Leu Pro Gly Arg Ala Gly   1                5                   10                  15 | |
| ttc aaa gaa aac cct gtg aca tac act ttc cga gga ttt cgg tca aca | 907 |
| Phe Lys Glu Asn Pro Val Thr Tyr Thr Phe Arg Gly Phe Arg Ser Thr   20                  25                  30 | |
| aaa agt gag aca aac cac agc tcc ctt cgg aac att tgg aaa gaa aca | 955 |
| Lys Ser Glu Thr Asn His Ser Ser Leu Arg Asn Ile Trp Lys Glu Thr | |

```
                 35                  40                  45
gtc cct caa acc ctg agg cct caa aca gca act aac tct aat aac aca        1003
Val Pro Gln Thr Leu Arg Pro Gln Thr Ala Thr Asn Ser Asn Asn Thr
 50                  55                  60 gac ctg tca cca caa gga gtt aca ggc ctg gag aat aca ctt agt gcc        1051
Asp Leu Ser Pro Gln Gly Val Thr Gly Leu Glu Asn Thr Leu Ser Ala
 65                  70                  75                  80 aat gga agt att tac aat gaa aaa ggt act gga cat cca aat tct tac        1099
Asn Gly Ser Ile Tyr Asn Glu Lys Gly Thr Gly His Pro Asn Ser Tyr
                 85                  90                  95 cat ttc aaa tat att att aat gag cct gaa aaa tgc caa gag aaa agt        1147
His Phe Lys Tyr Ile Ile Asn Glu Pro Glu Lys Cys Gln Glu Lys Ser
            100                 105                 110 cct ttt tta ata cta cta ata gct gca gag cct gga caa ata gaa gct        1195
Pro Phe Leu Ile Leu Leu Ile Ala Ala Glu Pro Gly Gln Ile Glu Ala
            115                 120                 125 aga aga gct att cgg caa act tgg ggc aat gaa agt cta gca cct ggt        1243
Arg Arg Ala Ile Arg Gln Thr Trp Gly Asn Glu Ser Leu Ala Pro Gly
        130                 135                 140 att caa atc aca aga ata ttt ttg ttg ggc tta agt att aag cta aat        1291
Ile Gln Ile Thr Arg Ile Phe Leu Leu Gly Leu Ser Ile Lys Leu Asn
145                 150                 155                 160 ggc tac ctt caa cgt gca ata ctg gaa gaa agc aga caa tat cat gat        1339
Gly Tyr Leu Gln Arg Ala Ile Leu Glu Glu Ser Arg Gln Tyr His Asp
                165                 170                 175 ata att caa cag gaa tac tta gat acg tac tat aat ttg acc att aaa        1387
Ile Ile Gln Gln Glu Tyr Leu Asp Thr Tyr Tyr Asn Leu Thr Ile Lys
            180                 185                 190 aca cta atg ggc atg aac tgg gtt gca aca tac tgt cca cat att cca        1435
Thr Leu Met Gly Met Asn Trp Val Ala Thr Tyr Cys Pro His Ile Pro
        195                 200                 205 tat gtt atg aaa act gac agt gac atg ttt gtc aac act gaa tat tta        1483
Tyr Val Met Lys Thr Asp Ser Asp Met Phe Val Asn Thr Glu Tyr Leu
    210                 215                 220 atc aat aag tta ctg aag cca gat ctg cct ccc aga cat aac tat ttc        1531
Ile Asn Lys Leu Leu Lys Pro Asp Leu Pro Pro Arg His Asn Tyr Phe
225                 230                 235                 240 act ggt tac cta atg cga gga tat gca ccc aat cga aac aaa gat agc        1579
Thr Gly Tyr Leu Met Arg Gly Tyr Ala Pro Asn Arg Asn Lys Asp Ser
                245                 250                 255 aag tgg tac atg cca cca gac ctc tac cca agt gag cgt tat cct gtc        1627
Lys Trp Tyr Met Pro Pro Asp Leu Tyr Pro Ser Glu Arg Tyr Pro Val
            260                 265                 270 ttc tgt tct gga act ggt tat gtt ttt tct gga gat ctg gca gaa aag        1675
Phe Cys Ser Gly Thr Gly Tyr Val Phe Ser Gly Asp Leu Ala Glu Lys
        275                 280                 285 att ttt aaa gtt tct tta ggt atc cgc cgt ttg cac ttg gaa gat gta        1723
Ile Phe Lys Val Ser Leu Gly Ile Arg Arg Leu His Leu Glu Asp Val
    290                 295                 300 tat gta ggg atc tgt ctt gcc aag ttg aga att gat cct gta ccc cct        1771
Tyr Val Gly Ile Cys Leu Ala Lys Leu Arg Ile Asp Pro Val Pro Pro
305                 310                 315                 320 ccc aat gag ttt gtg ttc aat cac tgg cga gtc tct tat tcg agc tgt        1819
Pro Asn Glu Phe Val Phe Asn His Trp Arg Val Ser Tyr Ser Ser Cys
                325                 330                 335 aaa tac agc cac cta att acc tct cat cag ttc cag cct agt gaa ctg        1867
Lys Tyr Ser His Leu Ile Thr Ser His Gln Phe Gln Pro Ser Glu Leu
            340                 345                 350 ata aaa tac tgg aac cat tta caa caa aat aag cac aat gcc tgt gcc        1915
```

```
                Ile Lys Tyr Trp Asn His Leu Gln Gln Asn Lys His Asn Ala Cys Ala
                        355                 360                 365 aac gca gca aaa gaa aag gca ggc agg tat cgc cac cgt aaa cta cat        1963
Asn Ala Ala Lys Glu Lys Ala Gly Arg Tyr Arg His Arg Lys Leu His
        370                 375                 380 tagaaaagac aatttttttt caaatgtgca atttgtaaat attgctaaaa gcatgtatag      2023
ttagaactga ttcatccgt  aggacaagtt ttagttaaaa ctcatcacat aaagaaattc      2083
aagaagtatt ttttaattt  ctgaagaagt taattcttaa aactataaca ttatataaca      2143
aaaaaggttt cccaaaacaa tctatttaaa aaactgtata aggagattct gtgtattaac      2203
atgcaataac aagcatgcat aaatcaatgg ttcaagtctt ctgttagggg ccaataaaat      2263
gtatctgcat atgttttcca cataaatttt aattcaagaa atgacagtca aaagatcctt      2323
cattttagat taagcttttc attttaatat ataatttaat gtaaataaaa catcactatc      2383
aattttaagg aaaaaaaaaa aaaaaaaaaa aaaaaaa                               2420

<210> SEQ ID NO 28
<211> LENGTH: 521
<212> TYPE: PRT
<213> ORGANISM: Homo sapiens

<400> SEQUENCE: 28

Met Val Asn Ala Cys Trp Cys Gly Leu Leu Ala Ala Leu Ser Leu Leu
        -20                 -15                 -10

Leu Asp Ala Ser Thr Asp Glu Val Ala Thr Glu Asn Ile Leu Lys Ala
-5                   -1  1               5                   10

Glu Leu Thr Met Ala Ala Leu Cys Gly Arg Leu Gly Leu Val Thr Ser
                15                  20                  25

Arg Asp Ala Phe Ile Thr Ala Ile Cys Lys Gly Ser Leu Pro Pro His
            30                  35                  40

Tyr Ala Leu Thr Val Leu Asn Thr Thr Ala Ala Thr Leu Ser Asn
        45                  50                  55

Lys Ser Tyr Ser Val Gln Gly Gln Ser Val Met Met Ile Ser Pro Ser
60                  65                  70                  75

Ser Glu Ser His Gln Gln Val Val Ala Val Gly Gln Pro Leu Ala Val
                80                  85                  90

Gln Pro Gln Gly Thr Val Met Leu Thr Ser Lys Asn Ile Gln Cys Met
            95                  100                 105

Arg Thr Leu Leu Asn Leu Ala His Cys His Gly Ala Val Leu Gly Thr
        110                 115                 120

Ser Trp Gln Leu Val Leu Ala Thr Leu Gln His Leu Val Trp Ile Leu
    125                 130                 135

Gly Leu Lys Pro Ser Ser Gly Gly Ala Leu Lys Pro Gly Arg Ala Val
140                 145                 150                 155

Glu Gly Pro Ser Thr Val Leu Thr Ala Val Met Thr Asp Leu Pro
                160                 165                 170

Val Ile Ser Asn Ile Leu Ser Arg Leu Phe Glu Ser Ser Gln Tyr Leu
            175                 180                 185

Asp Asp Val Ser Leu His His Leu Ile Asn Ala Leu Cys Ser Leu Ser
        190                 195                 200

Leu Glu Ala Met Asp Met Ala Tyr Gly Asn Asn Lys Glu Pro Ser Leu
    205                 210                 215

Phe Ala Val Ala Lys Leu Leu Glu Thr Gly Leu Val Asn Met His Arg
220                 225                 230                 235
```

Ile Glu Ile Leu Trp Arg Pro Leu Thr Gly His Leu Glu Lys Val
            240                 245                 250

Cys Gln His Pro Asn Ser Arg Met Gly Glu Trp Gly Ala Glu Ala Leu
            255                 260                 265

Thr Ser Leu Ile Lys Ala Gly Leu Thr Phe Asn His Asp Pro Pro Leu
            270                 275                 280

Ser Gln Asn Gln Arg Leu Gln Leu Leu Leu Asn Pro Leu Lys Glu
285                 290                 295

Met Ser Asn Ile Asn His Pro Asp Ile Arg Leu Lys Gln Leu Glu Cys
300                 305                 310                 315

Val Leu Gln Ile Leu Gln Ser Gln Gly Asp Asn Leu Gly Pro Gly Trp
                320                 325                 330

Pro Leu Val Leu Gly Val Met Gly Ala Ile Arg Asn Asp Gln Gly Glu
                335                 340                 345

Ser Leu Ile Arg Thr Ala Phe Gln Cys Leu Gln Leu Val Val Thr Asp
                350                 355                 360

Phe Leu Pro Thr Met Pro Cys Thr Cys Leu Gln Ile Val Val Asp Val
            365                 370                 375

Ala Gly Ser Phe Gly Leu His Asn Gln Glu Leu Asn Ile Ser Leu Thr
380                 385                 390                 395

Ser Ile Gly Leu Leu Trp Asn Ile Ser Asp Tyr Phe Phe Gln Arg Gly
                400                 405                 410

Glu Thr Ile Glu Lys Glu Leu Asn Lys Glu Glu Ala Ala Gln Gln Lys
            415                 420                 425

Gln Ala Glu Glu Lys Gly Val Val Leu Asn Arg Pro Phe His Pro Ala
            430                 435                 440

Pro Pro Phe Asp Cys Leu Trp Leu Cys Leu Tyr Ala Lys Leu Gly Glu
            445                 450                 455

Leu Cys Val Asp Pro Arg Pro Ala Val Arg Lys Ser Ala Gly Gln Thr
460                 465                 470                 475

Leu Phe Ser Thr Ile Gly Ala His Gly Thr Leu Leu Gln His Ser Thr
                480                 485                 490

Trp Arg Thr Val Ile Trp Lys Val Leu
            495                 500

<210> SEQ ID NO 29
<211> LENGTH: 1563
<212> TYPE: DNA
<213> ORGANISM: Homo sapiens

<400> SEQUENCE: 29

```
atggtgaatg cctgctggtg tggtcttctt gctgcactct cactccttct tgatgccagc      60
acagatgaag ttgccactga gaatatttta aaagctgaac tgactatggc tgctctttgt     120
ggaagactgg gccttgtaac ttcaagagat gcctttataa ctgcaatatg caaaggttcc     180
ctgcctcccc attatgctct tactgtattg aataccacca ctgcagctac actttccaac     240
aaatcatatt ccgttcaggg ccaaagtgtt atgatgataa gtccatcaag tgaatctcac     300
caacaagttg tggcagtggg tcaacctta gcagtccagc ctcaagggac agtaatgctg     360
acttccaaaa atatccagtg tatgaggact ttacttaact ggcgcattg ccatggggct     420
gttcttggaa catcatggca acttgtcttg caactcttc agcatcttgt gtggattctg     480
ggattaaagc ctagtagtgg cggtgccttg aaacctggga gagctgtaga aggacccagt     540
acagttctaa caacagcagt gatgacagat ttaccagtga tttccaatat actttcaaga     600
```

-continued

```
ttgtttgaaa gctcacagta tcttgatgat gtatcactgc atcatttaat aaatgcactt    660
tgctccttgt ctctagaagc aatggatatg gcctatggaa ataataagga accatctctt    720
tttgctgttg ccaaattgtt agaaactggt ttagttaata tgcaccgaat agaaattctg    780
tggagacctc tgactggcca tctacttgag aaggtctgcc agcatccaaa ctctcgaatg    840
ggagaatggg gagcagaagc tttaacttct cttattaaag caggattaac atttaaccat    900
gatcctccac tctcacaaaa ccagaggctg cagttgcttt tattgaaccc gttaaaggag    960
atgtccaata ttaatcatcc agatattcga ctcaagcagt tagaatgcgt gttgcagatt   1020
ctgcagagtc agggagacaa tcttgggcct ggatggccat tagtgcttgg agtcatggga   1080
gcaatcagaa atgatcaagg agaatccttg atacgaactg cattccagtg tcttcagttg   1140
gttgtgacag attttctacc aacaatgcct tgtacttgcc tgcaaatagt tgtagatgtt   1200
gcaggtagct ttggcctcca taaccaagaa ctcaatatta gtttaacttc aataggttta   1260
ttgtggaata tttcagatta ttttttccaa agagggaaa ctattgaaaa agaactaaat   1320
aaggaagagg cagcacagca aaagcaggca gaagagaaag gagttgtttt aaatcggcca   1380
ttccaccctg caccgccatt tgattgcttg tggttatgtc tttatgcaaa attgggtgaa   1440
ctatgtgtgg atccccgtcc tgctgtcagg aagagtgcag ggcaaactct gttttctaca   1500
attggtgcgc atggaacttt attacagcat tcaacctggc gcactgttat ctggaaggta   1560
ttg                                                                 1563

<210> SEQ ID NO 30
<211> LENGTH: 1768
<212> TYPE: DNA
<213> ORGANISM: Homo sapiens
<220> FEATURE:
<221> NAME/KEY: sig_peptide
<222> LOCATION: (8)..(70)
<220> FEATURE:
<221> NAME/KEY: mat_peptide
<222> LOCATION: (71)..(1570)
<220> FEATURE:
<221> NAME/KEY: CDS
<222> LOCATION: (8)..(1570)

<400> SEQUENCE: 30 ggaagaa atg gtg aat gcc tgc tgg tgt ggt ctt ctt gct gca ctc tca          49
        Met Val Asn Ala Cys Trp Cys Gly Leu Leu Ala Ala Leu Ser
            -20             -15                 -10 ctc ctt ctt gat gcc agc aca gat gaa gtt gcc act gag aat att tta         97
Leu Leu Leu Asp Ala Ser Thr Asp Glu Val Ala Thr Glu Asn Ile Leu
        -5              -1  1               5 aaa gct gaa ctg act atg gct gct ctt tgt gga aga ctg ggc ctt gta        145
Lys Ala Glu Leu Thr Met Ala Ala Leu Cys Gly Arg Leu Gly Leu Val
 10              15              20              25 act tca aga gat gcc ttt ata act gca ata tgc aaa ggt tcc ctg cct        193
Thr Ser Arg Asp Ala Phe Ile Thr Ala Ile Cys Lys Gly Ser Leu Pro
             30              35              40 ccc cat tat gct ctt act gta ttg aat acc acc act gca gct aca ctt        241
Pro His Tyr Ala Leu Thr Val Leu Asn Thr Thr Thr Ala Ala Thr Leu
     45              50              55 tcc aac aaa tca tat tcc gtt cag ggc caa agt gtt atg atg ata agt        289
Ser Asn Lys Ser Tyr Ser Val Gln Gly Gln Ser Val Met Met Ile Ser
 60              65              70 cca tca agt gaa tct cac caa caa gtt gtg gca gtg ggt caa cct tta        337
Pro Ser Ser Glu Ser His Gln Gln Val Val Ala Val Gly Gln Pro Leu
 75              80              85
```

-continued

```
gca gtc cag cct caa ggg aca gta atg ctg act tcc aaa aat atc cag       385
Ala Val Gln Pro Gln Gly Thr Val Met Leu Thr Ser Lys Asn Ile Gln
 90              95                 100                 105 tgt atg agg act tta ctt aac ttg gcg cat tgc cat ggg gct gtt ctt       433
Cys Met Arg Thr Leu Leu Asn Leu Ala His Cys His Gly Ala Val Leu
             110                 115                 120 gga aca tca tgg caa ctt gtc ttg gca act ctt cag cat ctt gtg tgg      481
Gly Thr Ser Trp Gln Leu Val Leu Ala Thr Leu Gln His Leu Val Trp
         125                 130                 135 att ctg gga tta aag cct agt agt ggc ggt gcc ttg aaa cct ggg aga      529
Ile Leu Gly Leu Lys Pro Ser Ser Gly Gly Ala Leu Lys Pro Gly Arg
     140                 145                 150 gct gta gaa gga ccc agt aca gtt cta aca aca gca gtg atg aca gat      577
Ala Val Glu Gly Pro Ser Thr Val Leu Thr Thr Ala Val Met Thr Asp
155                 160                 165 tta cca gtg att tcc aat ata ctt tca aga ttg ttt gaa agc tca cag      625
Leu Pro Val Ile Ser Asn Ile Leu Ser Arg Leu Phe Glu Ser Ser Gln
170                 175                 180                 185 tat ctt gat gat gta tca ctg cat cat tta ata aat gca ctt tgc tcc      673
Tyr Leu Asp Asp Val Ser Leu His His Leu Ile Asn Ala Leu Cys Ser
             190                 195                 200 ttg tct cta gaa gca atg gat atg gcc tat gga aat aat aag gaa cca      721
Leu Ser Leu Glu Ala Met Asp Met Ala Tyr Gly Asn Asn Lys Glu Pro
         205                 210                 215 tct ctt ttt gct gtt gcc aaa ttg tta gaa act ggt tta gtt aat atg      769
Ser Leu Phe Ala Val Ala Lys Leu Leu Glu Thr Gly Leu Val Asn Met
     220                 225                 230 cac cga ata gaa att ctg tgg aga cct ctg act ggc cat cta ctt gag      817
His Arg Ile Glu Ile Leu Trp Arg Pro Leu Thr Gly His Leu Leu Glu
235                 240                 245 aag gtc tgc cag cat cca aac tct cga atg gga gaa tgg gga gca gaa      865
Lys Val Cys Gln His Pro Asn Ser Arg Met Gly Glu Trp Gly Ala Glu
250                 255                 260                 265 gct tta act tct ctt att aaa gca gga tta aca ttt aac cat gat cct      913
Ala Leu Thr Ser Leu Ile Lys Ala Gly Leu Thr Phe Asn His Asp Pro
             270                 275                 280 cca ctc tca caa aac cag agg ctg cag ttg ctt tta ttg aac ccg tta      961
Pro Leu Ser Gln Asn Gln Arg Leu Gln Leu Leu Leu Leu Asn Pro Leu
         285                 290                 295 aag gag atg tcc aat att aat cat cca gat att cga ctc aag cag tta     1009
Lys Glu Met Ser Asn Ile Asn His Pro Asp Ile Arg Leu Lys Gln Leu
     300                 305                 310 gaa tgc gtg ttg cag att ctg cag agt cag gga gac aat ctt ggg cct     1057
Glu Cys Val Leu Gln Ile Leu Gln Ser Gln Gly Asp Asn Leu Gly Pro
315                 320                 325 gga tgg cca tta gtg ctt gga gtc atg gga gca atc aga aat gat caa     1105
Gly Trp Pro Leu Val Leu Gly Val Met Gly Ala Ile Arg Asn Asp Gln
330                 335                 340                 345 gga gaa tcc ttg ata cga act gca ttc cag tgt ctt cag ttg gtt gtg     1153
Gly Glu Ser Leu Ile Arg Thr Ala Phe Gln Cys Leu Gln Leu Val Val
             350                 355                 360 aca gat ttt cta cca aca atg cct tgt act tgc ctg caa ata gtt gta     1201
Thr Asp Phe Leu Pro Thr Met Pro Cys Thr Cys Leu Gln Ile Val Val
         365                 370                 375 gat gtt gca ggt agc ttt ggc ctc cat aac caa gaa ctc aat att agt     1249
Asp Val Ala Gly Ser Phe Gly Leu His Asn Gln Glu Leu Asn Ile Ser
     380                 385                 390 tta act tca ata ggt tta ttg tgg aat att tca gat tat ttt ttc caa     1297
Leu Thr Ser Ile Gly Leu Leu Trp Asn Ile Ser Asp Tyr Phe Phe Gln
395                 400                 405
```

-continued

```
aga ggg gaa act att gaa aaa gaa cta aat aag gaa gag gca gca cag      1345
Arg Gly Glu Thr Ile Glu Lys Glu Leu Asn Lys Glu Glu Ala Ala Gln
    410                 415                 420                 425 caa aag cag gca gaa gag aaa gga gtt gtt tta aat cgg cca ttc cac      1393
Gln Lys Gln Ala Glu Glu Lys Gly Val Val Leu Asn Arg Pro Phe His
                430                 435                 440 cct gca ccg cca ttt gat tgc ttg tgg tta tgt ctt tat gca aaa ttg      1441
Pro Ala Pro Pro Phe Asp Cys Leu Trp Leu Cys Leu Tyr Ala Lys Leu
            445                 450                 455 ggt gaa cta tgt gtg gat ccc cgt cct gct gtc agg aag agt gca ggg      1489
Gly Glu Leu Cys Val Asp Pro Arg Pro Ala Val Arg Lys Ser Ala Gly
        460                 465                 470 caa act ctg ttt tct aca att ggt gcg cat gga act tta tta cag cat      1537
Gln Thr Leu Phe Ser Thr Ile Gly Ala His Gly Thr Leu Leu Gln His
    475                 480                 485 tca acc tgg cgc act gtt atc tgg aag gta ttg taaaatagat tggactatca   1590
Ser Thr Trp Arg Thr Val Ile Trp Lys Val Leu
490                 495                 500 gcttttaatg agtcatgctt atatattaat acttttcag ttaaacttat ttctttaat     1650 ttttaaagaa tttccatgca tttgtgtatt tgacaaaaca ggaataaact gtgtcatatt   1710
gtaaattgta cctcataaag agcaaattaa atattaacag ccttaaaaaa aaaaaaaa     1768

<210> SEQ ID NO 31
<211> LENGTH: 459
<212> TYPE: PRT
<213> ORGANISM: Homo sapiens

<400> SEQUENCE: 31

Met Val Asn Ala Cys Trp Cys Gly Leu Leu Ala Ala Leu Ser Leu Leu
    -20                 -15                 -10

Leu Asp Ala Ser Thr Asp Glu Val Ala Thr Glu Asn Ile Leu Lys Ala
 -5              -1   1              5                    10

Glu Leu Thr Met Ala Ala Leu Cys Gly Arg Leu Gly Leu Val Thr Ser
                15                  20                  25

Arg Asp Ala Phe Ile Thr Ala Ile Cys Lys Gly Ser Leu Pro Pro His
            30                  35                  40

Tyr Ala Leu Thr Val Leu Asn Thr Thr Ala Thr Leu Ser Asn
        45                  50                  55

Lys Ser Tyr Ser Val Gln Gly Gln Ser Val Met Met Ile Ser Pro Ser
60                  65                  70                  75

Ser Glu Ser His Gln Gln Val Val Ala Val Gly Gln Pro Leu Ala Val
                80                  85                  90

Gln Pro Gln Gly Thr Val Met Leu Thr Ser Lys Asn Ile Gln Cys Met
                95                  100                 105

Arg Thr Leu Leu Asn Leu Ala His Cys His Gly Ala Val Leu Gly Thr
            110                 115                 120

Ser Trp Gln Leu Val Leu Ala Thr Leu Gln His Leu Val Trp Ile Leu
        125                 130                 135

Gly Leu Lys Pro Ser Gly Gly Ala Leu Lys Pro Gly Arg Ala Val
140                 145                 150                 155

Glu Gly Pro Ser Thr Val Leu Thr Thr Ala Val Met Thr Asp Leu Pro
                160                 165                 170

Val Ile Ser Asn Ile Leu Ser Arg Leu Phe Glu Ser Ser Arg Tyr Leu
            175                 180                 185

Asp Asp Val Ser Leu His His Leu Ile Asn Ala Leu Cys Ser Leu Ser
```

```
                190              195                  200
Leu Glu Ala Met Asp Met Ala Tyr Gly Asn Asn Lys Glu Pro Ser Leu
    205                 210                 215

Phe Ala Val Ala Lys Leu Leu Glu Thr Gly Leu Val Asn Met His Arg
220                 225                 230                 235

Ile Glu Ile Leu Trp Arg Pro Leu Thr Gly His Leu Leu Glu Val Cys
                240                 245                 250

Gln His Pro Asn Ser Arg Met Arg Glu Trp Gly Ala Glu Ala Leu Thr
                    255                 260                 265

Ser Leu Ile Lys Ala Gly Leu Thr Phe Asn His Asp Pro Pro Leu Ser
                270                 275                 280

Gln Asn Gln Arg Leu Gln Leu Leu Leu Asn Pro Leu Lys Glu Met
    285                 290                 295

Ser Asn Ile Asn His Pro Asp Ile Arg Leu Lys Gln Leu Glu Cys Val
300                 305                 310                 315

Leu Gln Ile Leu Gln Ser Gln Gly Asp Ser Leu Gly Pro Gly Trp Pro
                320                 325                 330

Leu Val Leu Gly Val Met Gly Ala Ile Arg Asn Asp Gln Gly Glu Ser
                335                 340                 345

Leu Ile Arg Thr Ala Phe Gln Cys Leu Gln Leu Val Val Thr Glu Ile
                350                 355                 360

Ile Phe Val Leu Lys Ala Val Ser Thr Leu Ile Asp Ser Leu Lys Lys
                365                 370                 375

Thr Gln Pro Glu Asn Val Asp Gly Asn Thr Trp Ala Gln Val Ile Ala
380                 385                 390                 395

Leu Tyr Pro Thr Leu Val Glu Cys Ile Ala Cys Pro Ser Ser Glu Val
                400                 405                 410

Cys Ser Ala Leu Lys Glu Ala Leu Val Pro Phe Lys Asp Phe Met Gln
                415                 420                 425

Pro Pro Ala Ser Arg Val Gln Asn Gly Glu Ser
                430                 435

<210> SEQ ID NO 32
<211> LENGTH: 1377
<212> TYPE: DNA
<213> ORGANISM: Homo sapiens

<400> SEQUENCE: 32
atggtgaatg cctgctggtg tggtcttctt gctgcactct cactccttct tgatgccagc    60
acagatgaag ttgccactga aatattttta aaagctgaac tgactatggc tgctctttgt   120
ggaagactgg gccttgtaac ttcaagagat gcctttataa ctgcaatatg caaaggttcc   180
ctgcctcccc attatgctct tactgtattg aataccacca ctgcagctac actttccaac   240
aaatcatatt ccgttcaggg ccaaagtgtt atgatgataa gtccatcaag tgaatctcac   300
caacaagttg tggcagtggg tcaacccttta gcagtccagc ctcaagggac agtaatgctg   360
acttccaaaa atatccagtg tatgaggact ttacttaact ggcgcattg ccatggggct   420 gttcttggaa catcatggca acttgtcttg caactcttc agcatcttgt gtggattctg   480
ggattaaagc ctagtagtgg cggtgccttg aaacctggga gagctgtaga aggacccagt   540
acagttctaa caacagcagt gatgacagat ttaccagtga tttccaatat acttttcaaga   600 ttgtttgaaa gctcacgta tcttgatgat gtatcactgc atcatttaat aaatgcactt   660
tgctccttgt ctctagaagc aatggatatg gcctatggaa ataataagga accatctctt   720
```

```
tttgctgttg ccaaattgtt agaaactggt ttagttaata tgcaccgaat agaaattctg    780
tggagacctc tgactggcca tctacttgag gtctgccagc atccaaactc tcgaatgaga    840
gaatggggag cagaagcttt aacttctctt attaaagcag gattaacatt taaccatgat    900
cctccactct cacaaaacca gaggctgcag ttgcttttat tgaacccgtt aaaggagatg    960
tccaatatta atcatccaga tattcgactc aagcagttag aatgcgtgtt gcagattctg   1020
cagagtcagg gagacagtct tgggcctgga tggccattag tgcttggagt catgggagca   1080
atcagaaatg atcaaggaga atccttgata cgaactgcat tccagtgtct tcagttggtt   1140
gtaacagaaa ttatatttgt tttaaaagca gtcagtactc ttattgattc acttaagaaa   1200
actcagcctg agaatgttga tggaaatacc tgggcacaag taattgcctt atacccaact   1260
ttagtagaat gcatcgcctg tccttcttca gaagtctgtt ctgcacttaa agaggcacta   1320
gttcctttta aggatttcat gcagccacca gcatccagag ttcaaaatgg agaatct     1377
```

<210> SEQ ID NO 33
<211> LENGTH: 2009
<212> TYPE: DNA
<213> ORGANISM: Homo sapiens
<220> FEATURE:
<221> NAME/KEY: sig_peptide
<222> LOCATION: (8)..(70)
<220> FEATURE:
<221> NAME/KEY: mat_peptide
<222> LOCATION: (71)..(1384)
<220> FEATURE:
<221> NAME/KEY: CDS
<222> LOCATION: (8)..(1384)

<400> SEQUENCE: 33

```
ggaagaa atg gtg aat gcc tgc tgg tgt ggt ctt ctt gct gca ctc tca     49
        Met Val Asn Ala Cys Trp Cys Gly Leu Leu Ala Ala Leu Ser
            -20             -15                 -10 ctc ctt ctt gat gcc agc aca gat gaa gtt gcc act gag aat att tta    97
Leu Leu Leu Asp Ala Ser Thr Asp Glu Val Ala Thr Glu Asn Ile Leu
     -5              -1  1               5 aaa gct gaa ctg act atg gct gct ctt tgt gga aga ctg ggc ctt gta   145
Lys Ala Glu Leu Thr Met Ala Ala Leu Cys Gly Arg Leu Gly Leu Val
 10              15                  20                  25 act tca aga gat gcc ttt ata act gca ata tgc aaa ggt tcc ctg cct   193
Thr Ser Arg Asp Ala Phe Ile Thr Ala Ile Cys Lys Gly Ser Leu Pro
                 30                  35                  40 ccc cat tat gct ctt act gta ttg aat acc acc act gca gct aca ctt   241
Pro His Tyr Ala Leu Thr Val Leu Asn Thr Thr Thr Ala Ala Thr Leu
             45                  50                  55 tcc aac aaa tca tat tcc gtt cag ggc caa agt gtt atg atg ata agt   289
Ser Asn Lys Ser Tyr Ser Val Gln Gly Gln Ser Val Met Met Ile Ser
         60                  65                  70 cca tca agt gaa tct cac caa caa gtt gtg gca gtg ggt caa cct tta   337
Pro Ser Ser Glu Ser His Gln Gln Val Val Ala Val Gly Gln Pro Leu
     75                  80                  85 gca gtc cag cct caa ggg aca gta atg ctg act tcc aaa aat atc cag   385
Ala Val Gln Pro Gln Gly Thr Val Met Leu Thr Ser Lys Asn Ile Gln
 90                  95                 100                 105 tgt atg agg act tta ctt aac ttg gcg cat tgc cat ggg gct gtt ctt   433
Cys Met Arg Thr Leu Leu Asn Leu Ala His Cys His Gly Ala Val Leu
                110                 115                 120 gga aca tca tgg caa ctt gtc ttg gca act ctt cag cat ctt gtg tgg   481
Gly Thr Ser Trp Gln Leu Val Leu Ala Thr Leu Gln His Leu Val Trp
            125                 130                 135
```

```
att ctg gga tta aag cct agt agt ggc ggt gcc ttg aaa cct ggg aga       529
Ile Leu Gly Leu Lys Pro Ser Ser Gly Gly Ala Leu Lys Pro Gly Arg
        140                 145                 150 gct gta gaa gga ccc agt aca gtt cta aca aca gca gtg atg aca gat       577
Ala Val Glu Gly Pro Ser Thr Val Leu Thr Thr Ala Val Met Thr Asp
        155                 160                 165 tta cca gtg att tcc aat ata ctt tca aga ttg ttt gaa agc tca cgg       625
Leu Pro Val Ile Ser Asn Ile Leu Ser Arg Leu Phe Glu Ser Ser Arg
170                 175                 180                 185 tat ctt gat gat gta tca ctg cat cat tta ata aat gca ctt tgc tcc       673
Tyr Leu Asp Asp Val Ser Leu His His Leu Ile Asn Ala Leu Cys Ser
                190                 195                 200 ttg tct cta gaa gca atg gat atg gcc tat gga aat aat aag gaa cca       721
Leu Ser Leu Glu Ala Met Asp Met Ala Tyr Gly Asn Asn Lys Glu Pro
        205                 210                 215 tct ctt ttt gct gtt gcc aaa ttg tta gaa act ggt tta gtt aat atg       769
Ser Leu Phe Ala Val Ala Lys Leu Leu Glu Thr Gly Leu Val Asn Met
        220                 225                 230 cac cga ata gaa att ctg tgg aga cct ctg act ggc cat cta ctt gag       817
His Arg Ile Glu Ile Leu Trp Arg Pro Leu Thr Gly His Leu Leu Glu
        235                 240                 245 gtc tgc cag cat cca aac tct cga atg aga gaa tgg gga gca gaa gct       865
Val Cys Gln His Pro Asn Ser Arg Met Arg Glu Trp Gly Ala Glu Ala
250                 255                 260                 265 tta act tct ctt att aaa gca gga tta aca ttt aac cat gat cct cca       913
Leu Thr Ser Leu Ile Lys Ala Gly Leu Thr Phe Asn His Asp Pro Pro
                270                 275                 280 ctc tca caa aac cag agg ctg cag ttg ctt tta ttg aac ccg tta aag       961
Leu Ser Gln Asn Gln Arg Leu Gln Leu Leu Leu Leu Asn Pro Leu Lys
        285                 290                 295 gag atg tcc aat att aat cat cca gat att cga ctc aag cag tta gaa      1009
Glu Met Ser Asn Ile Asn His Pro Asp Ile Arg Leu Lys Gln Leu Glu
        300                 305                 310 tgc gtg ttg cag att ctg cag agt cag gga gac agt ctt ggg cct gga      1057
Cys Val Leu Gln Ile Leu Gln Ser Gln Gly Asp Ser Leu Gly Pro Gly
        315                 320                 325 tgg cca tta gtg ctt gga gtc atg gga gca atc aga aat gat caa gga      1105
Trp Pro Leu Val Leu Gly Val Met Gly Ala Ile Arg Asn Asp Gln Gly
330                 335                 340                 345 gaa tcc ttg ata cga act gca ttc cag tgt ctt cag ttg gtt gta aca      1153
Glu Ser Leu Ile Arg Thr Ala Phe Gln Cys Leu Gln Leu Val Val Thr
                350                 355                 360 gaa att ata ttt gtt tta aaa gca gtc agt act ctt att gat tca ctt      1201
Glu Ile Ile Phe Val Leu Lys Ala Val Ser Thr Leu Ile Asp Ser Leu
        365                 370                 375 aag aaa act cag cct gag aat gtt gat gga aat acc tgg gca caa gta      1249
Lys Lys Thr Gln Pro Glu Asn Val Asp Gly Asn Thr Trp Ala Gln Val
        380                 385                 390 att gcc tta tac cca act tta gta gaa tgc atc gcc tgt cct tct tca      1297
Ile Ala Leu Tyr Pro Thr Leu Val Glu Cys Ile Ala Cys Pro Ser Ser
        395                 400                 405 gaa gtc tgt tct gca ctt aaa gag gca cta gtt cct ttt aag gat ttc      1345
Glu Val Cys Ser Ala Leu Lys Glu Ala Leu Val Pro Phe Lys Asp Phe
410                 415                 420                 425 atg cag cca cca gca tcc aga gtt caa aat gga gaa tct tgaccggcta       1394
Met Gln Pro Pro Ala Ser Arg Val Gln Asn Gly Glu Ser
                430                 435 caatatattt gaaagcagga agatagtcta aaaaatgttt gctcctaatt gagtcttctg    1454
tgagaaggac atttcttact gcagataatt cttggcagct gttgttggcc tcctttaaat   1514
```

```
tctacttacc tgagttcagt aattcatatt acaggcttgc acatcaacaa aggctcctga    1574
atgaacagca gtgcaaggct ttaataaatt aaactgatgg gagggataat taacactaca    1634
gtatacatgc taccatatct ccagttggtg atttaaagtg agcttatgta cagtttgtgg    1694
tgtatgtgtt aatgatgtac tttttaaaaa gaaagaagag atatttcaat tcagtcagat    1754
ttattagtct ggtgttttg cacccttttt caagtacaaa atcgtactag aatttatgc     1814 aagatggtac tgtaacattc catattatct ataaccagcc tctgttaaca aagggaactg    1874
atatacttgt gtgtataata aatggtacag ttctgtataa aatagtgcat ttatttaaat    1934
tttaaaagta ttgataatgt taaatgctta aagctctatt tattactaaa aaaaaaaaaa    1994
aaaaaaaaaa aaaaa                                                    2009
```

<210> SEQ ID NO 34
<211> LENGTH: 185
<212> TYPE: PRT
<213> ORGANISM: Homo sapiens

<400> SEQUENCE: 34

```
Met Phe Ser His Leu Pro Phe Asp Cys Val Leu Leu Leu Leu
    -20             -15                 -10

Leu Leu Thr Arg Ser Ser Glu Val Glu Tyr Arg Ala Glu Val Gly Gln
 -5              -1  1               5                  10

Asn Ala Tyr Leu Pro Cys Phe Tyr Thr Pro Ala Ala Pro Gly Asn Leu
                15                  20                  25

Val Pro Val Cys Trp Gly Lys Gly Ala Cys Pro Val Phe Glu Cys Gly
            30                  35                  40

Asn Val Val Leu Arg Thr Asp Glu Arg Asp Val Asn Tyr Trp Thr Ser
        45                  50                  55

Arg Tyr Trp Leu Asn Gly Asp Phe Arg Lys Gly Asp Val Ser Leu Thr
 60                  65                  70                  75

Ile Glu Asn Val Thr Leu Ala Asp Ser Gly Ile Tyr Cys Cys Arg Ile
                80                  85                  90

Gln Ile Pro Gly Ile Met Asn Asp Glu Lys Phe Asn Leu Lys Leu Val
                95                  100                 105

Ile Lys Pro Ala Lys Val Thr Pro Ala Pro Thr Leu Gln Arg Asp Phe
            110                 115                 120

Thr Ala Ala Phe Pro Arg Met Leu Thr Thr Arg Gly His Gly Pro Ala
        125                 130                 135

Glu Thr Gln Thr Leu Gly Ser Leu Pro Asp Ile Asn Leu Thr Gly Ile
140                 145                 150                 155

Leu Ile Ala Lys Arg Arg Tyr Arg Ile
                160
```

<210> SEQ ID NO 35
<211> LENGTH: 555
<212> TYPE: DNA
<213> ORGANISM: Homo sapiens

<400> SEQUENCE: 35

```
atgttttcac atcttcctt tgactgtgtc ctgctgctgc tgctgctact acttacaagg      60
tcctcagaag tggaatacag agcggaggtc ggtcagaatg cctatctgcc ctgcttctac    120
accccagccg ccccaggaa cctcgtgccc gtctgctggg gcaaggagc ctgtcctgtg      180 tttgaatgtg gcaacgtggt gctcaggact gatgaaaggg atgtgaatta ttggacatcc    240
```

```
agatactggc taaatgggga tttccgcaaa ggagatgtgt ccctgaccat agagaatgtg      300
actctagcag acagtgggat ctactgctgc cggatccaaa tcccaggcat aatgaatgat      360
gaaaaattta acctgaagtt ggtcatcaaa ccagccaagg tcaccctgc accgactctg       420 cagagagact tcactgcagc ctttccaagg atgcttacca ccaggggaca tggcccagca      480
gagacacaga cactggggag cctccctgat ataaatctaa caggtattct catagcaaag      540
agaagataca gaatt                                                      555

<210> SEQ ID NO 36
<211> LENGTH: 2091
<212> TYPE: DNA
<213> ORGANISM: Homo sapiens
<220> FEATURE:
<221> NAME/KEY: sig_peptide
<222> LOCATION: (53)..(115)
<220> FEATURE:
<221> NAME/KEY: mat_peptide
<222> LOCATION: (116)..(607)
<220> FEATURE:
<221> NAME/KEY: CDS
<222> LOCATION: (53)..(607)

<400> SEQUENCE: 36
gttaaaactg tgcctaacag aggtgtcctc tgacttttct tctgcaagct cc atg ttt      58
                                                         Met Phe
                                                         -20 tca cat ctt ccc ttt gac tgt gtc ctg ctg ctg ctg ctg cta cta ctt      106
Ser His Leu Pro Phe Asp Cys Val Leu Leu Leu Leu Leu Leu Leu Leu
         -15                 -10                  -5 aca agg tcc tca gaa gtg gaa tac aga gcg gag gtc ggt cag aat gcc      154
Thr Arg Ser Ser Glu Val Glu Tyr Arg Ala Glu Val Gly Gln Asn Ala
 -1   1               5                  10 tat ctg ccc tgc ttc tac acc cca gcc gcc cca ggg aac ctc gtg ccc      202
Tyr Leu Pro Cys Phe Tyr Thr Pro Ala Ala Pro Gly Asn Leu Val Pro
     15                  20                  25 gtc tgc tgg ggc aaa gga gcc tgt cct gtg ttt gaa tgt ggc aac gtg      250
Val Cys Trp Gly Lys Gly Ala Cys Pro Val Phe Glu Cys Gly Asn Val
 30              35                  40                  45 gtg ctc agg act gat gaa agg gat gtg aat tat tgg aca tcc aga tac      298
Val Leu Arg Thr Asp Glu Arg Asp Val Asn Tyr Trp Thr Ser Arg Tyr
                 50                  55                  60 tgg cta aat ggg gat ttc cgc aaa gga gat gtg tcc ctg acc ata gag      346
Trp Leu Asn Gly Asp Phe Arg Lys Gly Asp Val Ser Leu Thr Ile Glu
             65                  70                  75 aat gtg act cta gca gac agt ggg atc tac tgc tgc cgg atc caa atc      394
Asn Val Thr Leu Ala Asp Ser Gly Ile Tyr Cys Cys Arg Ile Gln Ile
         80                  85                  90 cca ggc ata atg aat gat gaa aaa ttt aac ctg aag ttg gtc atc aaa      442
Pro Gly Ile Met Asn Asp Glu Lys Phe Asn Leu Lys Leu Val Ile Lys
     95                 100                 105 cca gcc aag gtc acc cct gca ccg act ctg cag aga gac ttc act gca      490
Pro Ala Lys Val Thr Pro Ala Pro Thr Leu Gln Arg Asp Phe Thr Ala
110                 115                 120                 125 gcc ttt cca agg atg ctt acc acc agg gga cat ggc cca gca gag aca      538
Ala Phe Pro Arg Met Leu Thr Thr Arg Gly His Gly Pro Ala Glu Thr
                130                 135                 140 cag aca ctg ggg agc ctc cct gat ata aat cta aca ggt att ctc ata      586
Gln Thr Leu Gly Ser Leu Pro Asp Ile Asn Leu Thr Gly Ile Leu Ile
            145                 150                 155 gca aag aga aga tac aga att taagcctcat ctctttggcc aacctccctc          637
Ala Lys Arg Arg Tyr Arg Ile
```

```
                                                                 160
cctcaggatt ggcaaatgca gtagcagagg gaattcgctc agaagaaaac atctatacca    697
ttgaagagaa cgtatatgaa gtggaggagc ccaatgagta ttattgctat gtcagcagca    757
ggcagcaacc ctcacaacct tggggttgtc gctttgcaat gccatagatc caaccacctt    817
atttttgagc ttggtgtttt gtcttttca  gaaactatga gctgtgtcac ctgactggtt    877
ttggaggttc tgtccactgc tatggagcag agttttccca ttttcagaag ataatgactc    937
acatgggaat tgaactggga cctgcactga acttaaacag gcatgtcatt gcctctgtat    997
ttaagccaac agagttaccc aacccagaga ctgttaatca tggatgttag agctcaaacg   1057 ggctttttata tacactagga attcttgacg tggggtctct ggagctccag gaaattcggg   1117
cacatcatat gtccatgaaa cttcagataa actagggaaa actgggtgct gaggtgaaag   1177
cataactttt ttggcacaga aagtctaaag gggccactga ttttcaaaga gatctgtgat   1237
ccctttttgt tttttgtttt tgagatggag tcttgctctg ttgcccaggc tggagtgcaa   1297
tggcacaatc tcggctcact gcaagccccg cctcctgggt tcaagcgatt ctcctgcctc   1357
agcctcctga gtggctggga ttacaggcat gcaccaccat gcccagctaa tttgttgtat   1417
ttttagtaga cagggtttt  caccatgttg gccagtgtgg tctcaaactc ctgacctcat   1477
gatttgcctg cctcggcccc caaaagcact gggattacag gcgtgagcca ccacatccag   1537
ccagtgatcc ttaaaagatt aagagatgac tggactaggt ctaccttgat cttgaagatt   1597 ccctggaat  gttgagattt aggcttattt gagcactacc tgcccaactg tcagtgccag   1657
tgcatagccc ttcttttgtc tcccttatga agactgccct gcagggctga gatgtggcag   1717
gagctcccag ggaaaaagga agtgcatttg attggtgtgt attggccaag ttttgcttgt   1777
tgtgtgcttg aaagaaaata tctctgacca acttctgtat tcgtggacca aactgaagct   1837 atattttca  cagaagaaga agcagtgacg gggacacaaa ttctgttgcc tggtggaaag   1897
aaggcaaagg ccttcagcaa tctatattac cagcgctgga tcctttgaca gagagtggtc   1957
cctaaactta aatttcaaga cggtataggc ttgatctgtc ttgcttattg ttgcccctg    2017 cgcctagcac aattctgaca cacaattgga acttactaaa aatttttttt actgaaaaaa   2077
aaaaaaaaaa aaaa                                                     2091
```

<210> SEQ ID NO 37
<211> LENGTH: 98
<212> TYPE: PRT
<213> ORGANISM: Homo sapiens

<400> SEQUENCE: 37

```
Met Val Arg Ile Leu Arg Thr Val Pro Phe Leu Pro Leu Leu Gly Gly
    -15                 -10                  -5                  -1

Cys Ile Asp Asp Thr Ile Leu Ser Arg Gln Gly Phe Ile Asn Tyr Ser
  1               5                  10                  15

Lys Leu Pro Ser Leu Pro Leu Val Gln Gly Glu Leu Val Gly Gly Leu
             20                  25                  30

Thr Cys Leu Thr Ala Gln Thr His Ser Leu Leu Gln His Gln Pro Leu
         35                  40                  45

Gln Leu Thr Thr Leu Leu Asp Gln Tyr Ile Arg Glu Gln Arg Glu Lys
     50                  55                  60

Asp Ser Val Met Ser Ala Asn Gly Lys Pro Asp Pro Asp Thr Val Pro
 65                  70                  75                  80

Asp Ser
```

<210> SEQ ID NO 38
<211> LENGTH: 294
<212> TYPE: DNA
<213> ORGANISM: Homo sapiens

<400> SEQUENCE: 38

```
atggtacgga tcttaaggac tgtgccattc ctgccgctgc taggtggctg cattgatgac    60
accatcctca gcaggcaggg ctttatcaac tactccaagc tccccagcct gcccctggtg   120 caggggagc ttgtaggagg cctcacctgc ctcacagccc agaccactc cctgctccag    180 caccagcccc tccagctgac caccctgttg gaccagtaca tcagagagca acgcgagaag   240
gattctgtca tgtcggccaa tgggaagcca gatcctgaca ctgttccgga ctcg         294
```

<210> SEQ ID NO 39
<211> LENGTH: 1094
<212> TYPE: DNA
<213> ORGANISM: Homo sapiens
<220> FEATURE:
<221> NAME/KEY: sig_peptide
<222> LOCATION: (22)..(69)
<220> FEATURE:
<221> NAME/KEY: mat_peptide
<222> LOCATION: (70)..(315)
<220> FEATURE:
<221> NAME/KEY: CDS
<222> LOCATION: (22)..(315)

<400> SEQUENCE: 39

```
gaagagccca aggtcaagga g atg gta cgg atc tta agg act gtg cca ttc      51
                        Met Val Arg Ile Leu Arg Thr Val Pro Phe
                            -15             -10 ctg ccg ctg cta ggt ggc tgc att gat gac acc atc ctc agc agg cag      99
Leu Pro Leu Leu Gly Gly Cys Ile Asp Asp Thr Ile Leu Ser Arg Gln
 -5              -1   1               5                       10 ggc ttt atc aac tac tcc aag ctc ccc agc ctg ccc ctg gtg cag ggg     147
Gly Phe Ile Asn Tyr Ser Lys Leu Pro Ser Leu Pro Leu Val Gln Gly
            15                  20                      25 gag ctt gta gga ggc ctc acc tgc ctc aca gcc cag acc cac tcc ctg     195
Glu Leu Val Gly Gly Leu Thr Cys Leu Thr Ala Gln Thr His Ser Leu
         30                  35                  40 ctc cag cac cag ccc ctc cag ctg acc acc ctg ttg gac cag tac atc     243
Leu Gln His Gln Pro Leu Gln Leu Thr Thr Leu Leu Asp Gln Tyr Ile
     45                  50                  55 aga gag caa cgc gag aag gat tct gtc atg tcg gcc aat ggg aag cca     291
Arg Glu Gln Arg Glu Lys Asp Ser Val Met Ser Ala Asn Gly Lys Pro
 60                  65                  70 gat cct gac act gtt ccg gac tcg tagccagcct gtttagccag ccctgcgcat    345
Asp Pro Asp Thr Val Pro Asp Ser
 75                  80 aaatacactc tgcgttattg gctgtgctct cctcaatggg acatgtggaa gaacttgggg   405
tcgaggagtg tgtttgtcac ttggttttca ctagtaatga tattgtcagg tatagggcca   465
cttggagatg cagaggattc catttcagat gtcagtcacc ggcttcgtcc ttagttttcc   525
caacttggga cgtgatagga gcaaagtctc tccattctcc aggtccaagg cagagatcct   585
gaaaagatag ggctattgtc ccctgcctcc ttggtcactg cctcttgctg cacgggctcc   645
tgagcccacc cccttggggc acaacctgcc actgccacag tagctcaacc aagcagttgt   705
gctgagaatg gcacctggtg agagcctgct gtgtgccagg ctttgtgctg agtgctgtac   765
atgtattagt tcctttactg ctgaccacat tgtacccatt tcacagagaa ggagcagaga   825
```

```
aattaagtgg cttgctcaag gtcatgcagt tagtaagtgg cagaacaggg acttggaacc      885
aagccctctg ctctgaagac cgcgtcctga atttcttcac tagagcttcc tcatcaggtt      945
acccagaagt gggtcccatc caccatccag gtgtgcttgg atgttagttc tccaccctcg     1005
aggtgtacgc tgtgaaaagt ttgggagcac tgctttataa taaaatgaaa tatattataa     1065
aaaaaaaaaa aaaaaaaaaa aaaaaaaaa                                        1094

<210> SEQ ID NO 40
<211> LENGTH: 474
<212> TYPE: PRT
<213> ORGANISM: Homo sapiens

<400> SEQUENCE: 40

Met Tyr Thr Val Gly Ala Pro His Thr Trp Pro His Ile Val Ala Ala
            -20                 -15                 -10

Leu Val Trp Leu Ile Asp Cys Ile Lys Ile His Thr Ala Met Lys Glu
         -5          -1   1                5

Ser Ser Pro Leu Phe Asp Asp Gly Gln Pro Trp Gly Glu Glu Thr Glu
 10                  15                  20                  25

Asp Gly Ile Met His Asn Lys Leu Phe Leu Asp Tyr Thr Ile Lys Cys
                 30                  35                  40

Tyr Glu Ser Phe Met Ser Gly Ala Asp Ser Phe Asp Glu Met Asn Ala
             45                  50                  55

Glu Leu Gln Ser Lys Leu Lys Asp Leu Phe Asn Val Asp Ala Phe Lys
         60                  65                  70

Leu Glu Ser Leu Glu Ala Lys Asn Arg Ala Leu Asn Glu Gln Ile Ala
 75                  80                  85

Arg Leu Glu Gln Glu Arg Glu Lys Glu Pro Asn Arg Leu Glu Ser Leu
 90                  95                 100                 105

Arg Lys Leu Lys Ala Ser Leu Gln Gly Asp Val Gln Lys Tyr Gln Ala
             110                 115                 120

Tyr Met Ser Asn Leu Glu Ser His Ser Ala Ile Leu Asp Gln Lys Leu
             125                 130                 135

Asn Gly Leu Asn Glu Glu Ile Ala Arg Val Glu Leu Glu Cys Glu Thr
         140                 145                 150

Ile Lys Gln Glu Asn Thr Arg Leu Gln Asn Ile Asp Asn Gln Lys
 155                 160                 165

Tyr Ser Val Ala Asp Ile Glu Arg Ile Asn His Glu Arg Asn Glu Leu
 170                 175                 180                 185

Gln Gln Thr Ile Asn Lys Leu Thr Lys Asp Leu Glu Ala Glu Gln Gln
             190                 195                 200

Lys Leu Trp Asn Glu Glu Leu Lys Tyr Ala Arg Gly Lys Glu Ala Ile
         205                 210                 215

Glu Thr Gln Leu Ala Glu Tyr His Lys Leu Ala Arg Lys Leu Lys Leu
             220                 225                 230

Ile Pro Lys Gly Ala Glu Asn Ser Lys Gly Tyr Asp Phe Glu Ile Lys
         235                 240                 245

Phe Asn Pro Glu Ala Gly Ala Asn Cys Leu Val Lys Tyr Arg Ala Gln
 250                 255                 260                 265

Val Tyr Val Pro Leu Lys Glu Leu Leu Asn Glu Thr Glu Glu Ile
             270                 275                 280

Asn Lys Ala Leu Asn Lys Lys Met Gly Leu Glu Asp Thr Leu Glu Gln
             285                 290                 295
```

```
Leu Asn Ala Met Ile Thr Glu Ser Lys Arg Ser Val Gly Thr Leu Lys
            300                 305                 310

Glu Glu Val Gln Lys Leu Asp Asp Leu Tyr Gln Gln Lys Ile Lys Glu
        315                 320                 325

Ala Glu Glu Asp Glu Lys Cys Ala Ser Glu Leu Glu Ser Leu Glu
330                 335                 340                 345

Lys His Lys His Leu Leu Glu Ser Thr Val Asn Gln Gly Leu Ser Glu
                350                 355                 360

Ala Met Asn Glu Leu Asp Ala Val Gln Arg Glu Tyr Gln Leu Val Val
            365                 370                 375

Gln Thr Thr Thr Glu Glu Arg Arg Lys Val Gly Asn Asn Leu Gln Arg
        380                 385                 390

Leu Leu Glu Met Val Ala Thr His Val Gly Ser Val Glu Lys His Leu
    395                 400                 405

Glu Glu Gln Ile Ala Lys Val Asp Arg Glu Tyr Glu Glu Cys Met Ser
410                 415                 420                 425

Glu Asp Leu Ser Glu Asn Ile Lys Glu Ile Arg Asp Lys Tyr Glu Lys
                430                 435                 440

Lys Ala Thr Leu Ile Lys Ser Ser Glu Glu
            445                 450

<210> SEQ ID NO 41
<211> LENGTH: 1422
<212> TYPE: DNA
<213> ORGANISM: Homo sapiens

<400> SEQUENCE: 41
atgtacacag tgggggctcc tcatacatgg cctcacattg tggcagcctt agtttggcta      60
atagactgca tcaagataca tactgccatg aaagaaagct cacctttatt tgatgatggg     120
cagccttggg gagaagaaac tgaagatgga attatgcata ataagttgtt tttggactac     180
accataaaat gctatgagag ttttatgagt ggtgccgaca gctttgatga gatgaatgca     240
gagctgcagt caaaactgaa ggattttattt aatgtggatg cttttaagct ggaatcatta     300
gaagcaaaaa acagagcatt gaatgaacag attgcaagat ggaacaaga agagaaaaa     360 gaaccgaatc gtctagagtc gttgagaaaa ctgaaggctt ccttacaagg agatgttcaa     420
aagtatcagg catacatgag caatttggag tctcattcag ccattcttga ccagaaatta     480
aatggtctca atgaggaaat tgctagagta gaactagaat gtgaaacaat aaaacaggag     540
aacactcgac tacagaatat cattgacaac cagaagtact cagttgcaga cattgagcga     600
ataaatcatg aaagaaatga attgcagcag actattaata aattaaccaa ggacctggaa     660
gctgaacaac agaagttgtg gaatgaggag ttaaatatg ccagaggcaa agaagcgatt     720
gaaacacaat tagcagagta tcacaaattg gctagaaaat taaaacttat tcctaaaggt     780
gctgagaatt ccaaaggtta tgactttgaa attaagtttta tcccgaggc tggtgccaac     840 tgccttgtca atacagggc tcaagtttat gtacctctta aggaactcct gaatgaaact     900
gaagaagaaa ttaataaagc cctaaataaa aaatgggtt tggaggatac tttagaacaa     960
ttgaatgcaa tgataacaga aagcaagaga gtgtgggaa ctctgaaaga agaagttcaa    1020
aagctggatg atctttacca acaaaaaatt aaggaagcag aggaagagga tgaaaaatgt    1080
gccagtgagc ttgagtcctt ggagaaacac aagcacctgc tagaaagtac tgttaaccag    1140
gggctcagtg aagctatgaa tgaattagat gctgttcagc gggaatacca actagttgtg    1200
caaaccacga ctgaagaaag acgaaaagtg ggaaataact tgcaacgtct gttagagatg    1260
```

-continued

```
gttgctacac atgttgggtc tgtagagaaa catcttgagg agcagattgc taaagttgat    1320
agagaatatg aagaatgcat gtcagaagat ctctcggaaa atattaaaga gattagagat    1380
aagtatgaga agaaagctac tctaattaag tcttctgaag aa                      1422

<210> SEQ ID NO 42
<211> LENGTH: 1613
<212> TYPE: DNA
<213> ORGANISM: Homo sapiens
<220> FEATURE:
<221> NAME/KEY: sig_peptide
<222> LOCATION: (99)..(167)
<220> FEATURE:
<221> NAME/KEY: mat_peptide
<222> LOCATION: (168)..(1520)
<220> FEATURE:
<221> NAME/KEY: CDS
<222> LOCATION: (99)..(1520)

<400> SEQUENCE: 42
tgtgcccctc atacgaactt cctgacacaa agtttgaaga agaggttcca agaatcttta     60
aagaccttgg gtatcctttt gcactatcca aaagctcc atg tac aca gtg ggg gct    116
                                          Met Tyr Thr Val Gly Ala
                                                            -20 cct cat aca tgg cct cac att gtg gca gcc tta gtt tgg cta ata gac      164
Pro His Thr Trp Pro His Ile Val Ala Ala Leu Val Trp Leu Ile Asp
        -15                 -10                  -5 tgc atc aag ata cat act gcc atg aaa gaa agc tca cct tta ttt gat      212
Cys Ile Lys Ile His Thr Ala Met Lys Glu Ser Ser Pro Leu Phe Asp
 -1   1               5                  10                  15 gat ggg cag cct tgg gga gaa gaa act gaa gat gga att atg cat aat      260
Asp Gly Gln Pro Trp Gly Glu Glu Thr Glu Asp Gly Ile Met His Asn
                 20                  25                  30 aag ttg ttt ttg gac tac acc ata aaa tgc tat gag agt ttt atg agt      308
Lys Leu Phe Leu Asp Tyr Thr Ile Lys Cys Tyr Glu Ser Phe Met Ser
             35                  40                  45 ggt gcc gac agc ttt gat gag atg aat gca gag ctg cag tca aaa ctg      356
Gly Ala Asp Ser Phe Asp Glu Met Asn Ala Glu Leu Gln Ser Lys Leu
         50                  55                  60 aag gat tta ttt aat gtg gat gct ttt aag ctg gaa tca tta gaa gca      404
Lys Asp Leu Phe Asn Val Asp Ala Phe Lys Leu Glu Ser Leu Glu Ala
 65                  70                  75 aaa aac aga gca ttg aat gaa cag att gca aga ttg gaa caa gaa aga      452
Lys Asn Arg Ala Leu Asn Glu Gln Ile Ala Arg Leu Glu Gln Glu Arg
 80                  85                  90                  95 gaa aaa gaa ccg aat cgt cta gag tcg ttg aga aaa ctg aag gct tcc      500
Glu Lys Glu Pro Asn Arg Leu Glu Ser Leu Arg Lys Leu Lys Ala Ser
                100                 105                 110 tta caa gga gat gtt caa aag tat cag gca tac atg agc aat ttg gag      548
Leu Gln Gly Asp Val Gln Lys Tyr Gln Ala Tyr Met Ser Asn Leu Glu
            115                 120                 125 tct cat tca gcc att ctt gac cag aaa tta aat ggt ctc aat gag gaa      596
Ser His Ser Ala Ile Leu Asp Gln Lys Leu Asn Gly Leu Asn Glu Glu
        130                 135                 140 att gct aga gta gaa cta gaa tgt gaa aca ata aaa cag gag aac act      644
Ile Ala Arg Val Glu Leu Glu Cys Glu Thr Ile Lys Gln Glu Asn Thr
    145                 150                 155 cga cta cag aat atc att gac aac cag aag tac tca gtt gca gac att      692
Arg Leu Gln Asn Ile Ile Asp Asn Gln Lys Tyr Ser Val Ala Asp Ile
160                 165                 170                 175 gag cga ata aat cat gaa aga aat gaa ttg cag cag act att aat aaa      740
Glu Arg Ile Asn His Glu Arg Asn Glu Leu Gln Gln Thr Ile Asn Lys
```

```
Glu Arg Ile Asn His Glu Arg Asn Glu Leu Gln Gln Thr Ile Asn Lys
            180                 185                 190 tta acc aag gac ctg gaa gct gaa caa cag aag ttg tgg aat gag gag      788
Leu Thr Lys Asp Leu Glu Ala Glu Gln Gln Lys Leu Trp Asn Glu Glu
        195                 200                 205 tta aaa tat gcc aga ggc aaa gaa gcg att gaa aca caa tta gca gag      836
Leu Lys Tyr Ala Arg Gly Lys Glu Ala Ile Glu Thr Gln Leu Ala Glu
    210                 215                 220 tat cac aaa ttg gct aga aaa tta aaa ctt att cct aaa ggt gct gag      884
Tyr His Lys Leu Ala Arg Lys Leu Lys Leu Ile Pro Lys Gly Ala Glu
225                 230                 235 aat tcc aaa ggt tat gac ttt gaa att aag ttt aat ccc gag gct ggt      932
Asn Ser Lys Gly Tyr Asp Phe Glu Ile Lys Phe Asn Pro Glu Ala Gly
240                 245                 250                 255 gcc aac tgc ctt gtc aaa tac agg gct caa gtt tat gta cct ctt aag      980
Ala Asn Cys Leu Val Lys Tyr Arg Ala Gln Val Tyr Val Pro Leu Lys
            260                 265                 270 gaa ctc ctg aat gaa act gaa gaa gaa att aat aaa gcc cta aat aaa     1028
Glu Leu Leu Asn Glu Thr Glu Glu Glu Ile Asn Lys Ala Leu Asn Lys
        275                 280                 285 aaa atg ggt ttg gag gat act tta gaa caa ttg aat gca atg ata aca     1076
Lys Met Gly Leu Glu Asp Thr Leu Glu Gln Leu Asn Ala Met Ile Thr
    290                 295                 300 gaa agc aag aga agt gtg gga act ctg aaa gaa gaa gtt caa aag ctg     1124
Glu Ser Lys Arg Ser Val Gly Thr Leu Lys Glu Glu Val Gln Lys Leu
305                 310                 315 gat gat ctt tac caa caa aaa att aag gaa gca gag gaa gag gat gaa     1172
Asp Asp Leu Tyr Gln Gln Lys Ile Lys Glu Ala Glu Glu Glu Asp Glu
320                 325                 330                 335 aaa tgt gcc agt gag ctt gag tcc ttg gag aaa cac aag cac ctg cta     1220
Lys Cys Ala Ser Glu Leu Glu Ser Leu Glu Lys His Lys His Leu Leu
            340                 345                 350 gaa agt act gtt aac cag ggg ctc agt gaa gct atg aat gaa tta gat     1268
Glu Ser Thr Val Asn Gln Gly Leu Ser Glu Ala Met Asn Glu Leu Asp
        355                 360                 365 gct gtt cag cgg gaa tac caa cta gtt gtg caa acc acg act gaa gaa     1316
Ala Val Gln Arg Glu Tyr Gln Leu Val Val Gln Thr Thr Thr Glu Glu
    370                 375                 380 aga cga aaa gtg gga aat aac ttg caa cgt ctg tta gag atg gtt gct     1364
Arg Arg Lys Val Gly Asn Asn Leu Gln Arg Leu Leu Glu Met Val Ala
385                 390                 395 aca cat gtt ggg tct gta gag aaa cat ctt gag gag cag att gct aaa     1412
Thr His Val Gly Ser Val Glu Lys His Leu Glu Glu Gln Ile Ala Lys
400                 405                 410                 415 gtt gat aga gaa tat gaa gaa tgc atg tca gaa gat ctc tcg gaa aat     1460
Val Asp Arg Glu Tyr Glu Glu Cys Met Ser Glu Asp Leu Ser Glu Asn
            420                 425                 430 att aaa gag att aga gat aag tat gag aag aaa gct act cta att aag     1508
Ile Lys Glu Ile Arg Asp Lys Tyr Glu Lys Lys Ala Thr Leu Ile Lys
        435                 440                 445 tct tct gaa gaa tgaagataaa atgttgatca tgtatatata tccatagtga         1560
Ser Ser Glu Glu
            450 ataaaattgt ctcagtaaag taaaaaaaaa aaaaaaaaaa aaa                     1613

<210> SEQ ID NO 43
<211> LENGTH: 78
<212> TYPE: PRT
<213> ORGANISM: Homo sapiens
```

-continued

<400> SEQUENCE: 43

Met Tyr Tyr Ile Leu Ile Tyr Pro Phe Pro Leu Phe Leu Phe Leu Leu
        -20                 -15                 -10

Ser Leu Leu Ile Tyr Asn Gln Lys Met Lys Lys Ser Val His Leu Val
    -5              -1   1               5                   10

Phe Asp Leu Pro Lys His Leu Val Asn Leu Ile Phe Val Thr Leu Trp
                15                  20                  25

Met Val Asn Leu Thr Phe Thr Gln Val Gly Phe Cys Phe Val Glu Asn
            30                  35                  40

Asp Leu Leu Gly Gly Thr Thr Thr Glu Arg Thr Lys Leu
            45                  50                  55

<210> SEQ ID NO 44
<211> LENGTH: 234
<212> TYPE: DNA
<213> ORGANISM: Homo sapiens

<400> SEQUENCE: 44
atgtattata ttttaatcta tccttttcct ttgttttgt tcttattatc tcttctgata      60
tataaccaaa aaatgaaaaa atctgtacac ttggtgtttg atttacctaa gcacctagtt    120
aatttaatct tgtaacact tggatggtt aacttaacct ttactcaagt tggttttgt      180 tttgttgaaa atgacttact tggtggaacc actactactg aaagaacgaa actt          234

<210> SEQ ID NO 45
<211> LENGTH: 511
<212> TYPE: DNA
<213> ORGANISM: Homo sapiens
<220> FEATURE:
<221> NAME/KEY: sig_peptide
<222> LOCATION: (49)..(114)
<220> FEATURE:
<221> NAME/KEY: mat_peptide
<222> LOCATION: (115)..(282)
<220> FEATURE:
<221> NAME/KEY: CDS
<222> LOCATION: (49)..(282)

<400> SEQUENCE: 45
attttatcaa ttgtttgtat ttccctttaa ggtaacattt taaatgaa atg tat tat     57
                                                     Met Tyr Tyr
                                                         -20 att tta atc tat cct ttt cct ttg ttt ttg ttc tta tta tct ctt ctg    105
Ile Leu Ile Tyr Pro Phe Pro Leu Phe Leu Phe Leu Leu Ser Leu Leu
            -15                 -10                 -5 ata tat aac caa aaa atg aaa aaa tct gta cac ttg gtg ttt gat tta    153
Ile Tyr Asn Gln Lys Met Lys Lys Ser Val His Leu Val Phe Asp Leu
        -1   1               5                   10 cct aag cac cta gtt aat tta atc ttt gta aca ctt tgg atg gtt aac    201
Pro Lys His Leu Val Asn Leu Ile Phe Val Thr Leu Trp Met Val Asn
        15                  20                  25 tta acc ttt act caa gtt ggt ttt tgt ttt gtt gaa aat gac tta ctt    249
Leu Thr Phe Thr Gln Val Gly Phe Cys Phe Val Glu Asn Asp Leu Leu
30                  35                  40                  45 ggt gga acc act act act gaa aga acg aaa ctt tgatattaca ttgttaagta   302
Gly Gly Thr Thr Thr Thr Glu Arg Thr Lys Leu
                50                  55 tcagagctgt tacagagcaa gtccttttaa agagatgtaa aaattaagta cctgtgccaa   362
actgattttt attagaaacc ctgttttctt taagtaaaag tatattctac cagcatggct   422
tggtaagaaa aatcccctat ctttttttcc ctgtcctcaa aattcagaat ttttccggaa   482

-continued

```
aaaaaaaaaa aaaaaaaaaa aaaaaaaaa                                          511

<210> SEQ ID NO 46
<211> LENGTH: 73
<212> TYPE: PRT
<213> ORGANISM: Homo sapiens

<400> SEQUENCE: 46

Met Gln Phe Met Asn Leu Leu Val Gly Phe Ser Cys Ser Trp Gly Asn
-15                 -10                 -5                  -1  1

Thr Cys Ala Cys His Thr Arg Pro Phe Leu Ala Pro Ser Val Phe Ser
            5                   10                  15

Leu Cys Asp Gly Gly Leu Ile Val Ser Val Phe Thr Gln Gly Trp Phe
            20                  25                  30

Pro Gly Cys Thr Ala Pro Val Pro Thr Pro Thr Val Pro Leu Ile Arg
            35                  40                  45

Cys His Asp Phe Ser Ala Thr Ser Pro
50                  55

<210> SEQ ID NO 47
<211> LENGTH: 219
<212> TYPE: DNA
<213> ORGANISM: Homo sapiens

<400> SEQUENCE: 47
atgcagttca tgaacttgct ggttggtttt tcctgctcct ggggtaacac atgcgcttgt      60
catacacgcc ccttccttgc cccttcagta ttctctcttt gcgatggagg tctcatagtg     120
agtgtcttca ctcaagggtg gtttcctggc tgcacggcac ctgttccaac acctactgtg     180
cctctcatca ggtgtcacga tttttctgcc acttcacct                             219

<210> SEQ ID NO 48
<211> LENGTH: 903
<212> TYPE: DNA
<213> ORGANISM: Homo sapiens
<220> FEATURE:
<221> NAME/KEY: sig_peptide
<222> LOCATION: (31)..(75)
<220> FEATURE:
<221> NAME/KEY: mat_peptide
<222> LOCATION: (76)..(249)
<220> FEATURE:
<221> NAME/KEY: CDS
<222> LOCATION: (31)..(249)

<400> SEQUENCE: 48
ggagtttcgt aagcaaaata gaggacagaa atg cag ttc atg aac ttg ctg gtt        54
                                 Met Gln Phe Met Asn Leu Leu Val
                                 -15                 -10 ggt ttt tcc tgc tcc tgg ggt aac aca tgc gct tgt cat aca cgc ccc        102
Gly Phe Ser Cys Ser Trp Gly Asn Thr Cys Ala Cys His Thr Arg Pro
        -5              -1  1               5 ttc ctt gcc cct tca gta ttc tct ctt tgc gat gga ggt ctc ata gtg        150
Phe Leu Ala Pro Ser Val Phe Ser Leu Cys Asp Gly Gly Leu Ile Val
10                  15                  20                  25 agt gtc ttc act caa ggg tgg ttt cct ggc tgc acg gca cct gtt cca        198
Ser Val Phe Thr Gln Gly Trp Phe Pro Gly Cys Thr Ala Pro Val Pro
                30                  35                  40 aca cct act gtg cct ctc atc agg tgt cac gat ttt tct gcc act tca        246
Thr Pro Thr Val Pro Leu Ile Arg Cys His Asp Phe Ser Ala Thr Ser
            45                  50                  55
```

```
cct tagggagctt ccagtgattg attttaggag gcccacgcca agctccccag      299
Pro gaaatgactg ccttccttgg gaccaaggac cgttccaacg gcattcactg ccagttctaa   359
taggcgagga aaatgcccga ggcgctgtct tctgtccccc acacgtacca gaaagtgaaa   419
aatgcagcga gtcctctggg cggttatgag cctccaggcg catgctgtcc agttggacgg   479
aacatctggc ggttggttga ttgctctctt ttgtcttggt cgctgcttct agaatctatg   539
cagggataga cagtgaggtc agaagtcttt cccgggagag agatggcctg ggttatcatt    599
gctgatagct ttggctgcat gagttgggct tccccttacc cagggctgca cagccaggtg   659
tgggggtcac cggcaggtgg gctggtggct gcagcctcag agccctccca ggttgctgct   719
gtttccagtg aatcacattt cgtcatttga agcccatgag gaccattgtg tggatccatg   779
gtgattctag acttcagata tatttaggaa ggcgcagatt tcaaatctgt gtttgatttt   839
ctgtaataag agaaatccaa tttgtaaaac ttgaaaaaaa aaaaaaaaaa aaaaaaaaa    899 aaaa                                                                903
```

<210> SEQ ID NO 49
<211> LENGTH: 421
<212> TYPE: PRT
<213> ORGANISM: Homo sapiens

<400> SEQUENCE: 49

```
Met Arg Trp Ile Leu Phe Ile Gly Ala Leu Ile Gly Ser Ser Ile Cys
    -15                 -10                  -5                  -1

Gly Gln Glu Lys Phe Phe Gly Asp Gln Val Phe Arg Ile Asn Val Arg
  1               5                  10                  15

Asn Gly Asp Glu Ile Ser Lys Leu Ser Gln Leu Val Asn Ser Asn
             20                  25                  30

Leu Lys Leu Asn Phe Trp Lys Ser Pro Ser Ser Phe Asn Arg Pro Val
             35                  40                  45

Asp Val Leu Val Pro Ser Val Ser Leu Gln Ala Phe Lys Ser Phe Leu
 50                  55                  60

Arg Ser Gln Gly Leu Glu Tyr Ala Val Thr Ile Glu Asp Leu Gln Ala
 65                  70                  75                  80

Leu Leu Asp Asn Glu Asp Glu Met Gln His Asn Glu Gly Gln Glu
                 85                  90                  95

Arg Ser Ser Asn Asn Phe Asn Tyr Gly Ala Tyr His Ser Leu Glu Ala
                100                 105                 110

Thr Tyr His Glu Met Asp Asn Ile Ala Ala Asp Phe Pro Asp Leu Ala
            115                 120                 125

Arg Arg Val Lys Ile Gly His Ser Phe Glu Asn Arg Thr Met Tyr Val
        130                 135                 140

Leu Lys Phe Ser Thr Gly Lys Gly Val Arg Arg Pro Ala Val Trp Leu
145                 150                 155                 160

Asn Ala Gly Ile His Ser Arg Glu Trp Ile Ser Gln Ala Thr Ala Ile
                165                 170                 175

Trp Thr Ala Arg Lys Ile Val Ser Asp Tyr Gln Arg Asp Pro Ala Ile
            180                 185                 190

Thr Ser Ile Leu Glu Lys Met Asp Ile Phe Leu Leu Pro Val Ala Asn
        195                 200                 205

Pro Asp Gly Tyr Val Tyr Thr Gln Thr Gln Asn Arg Leu Trp Arg Lys
    210                 215                 220

Thr Arg Ser Arg Asn Pro Gly Ser Ser Cys Ile Gly Ala Asp Pro Asn
```

```
                225                 230                 235                 240
Arg Asn Trp Asn Ala Ser Phe Ala Gly Lys Gly Ala Ser Asp Asn Pro
            245                 250                 255

Cys Ser Glu Val Tyr His Gly Pro His Ala Asn Ser Glu Val Glu Val
            260                 265                 270

Lys Ser Val Val Asp Phe Ile Gln Lys His Gly Asn Phe Lys Gly Phe
            275                 280                 285

Ile Asp Leu His Ser Tyr Ser Gln Leu Leu Met Tyr Pro Tyr Gly Tyr
            290                 295                 300

Ser Val Lys Lys Ala Pro Asp Ala Glu Glu Leu Asp Lys Val Ala Arg
305                 310                 315                 320

Leu Ala Ala Lys Ala Leu Ala Ser Val Ser Gly Thr Glu Tyr Gln Val
                325                 330                 335

Gly Pro Thr Cys Thr Thr Val Tyr Pro Ala Ser Gly Ser Ser Ile Asp
            340                 345                 350

Trp Ala Tyr Asp Asn Gly Ile Lys Phe Ala Phe Thr Phe Glu Leu Arg
            355                 360                 365

Asp Thr Gly Thr Tyr Gly Phe Leu Leu Pro Ala Asn Gln Ile Ile Pro
        370                 375                 380

Thr Ala Glu Glu Thr Trp Leu Gly Leu Lys Thr Ile Met Glu His Val
385                 390                 395                 400

Arg Asp Asn Leu Tyr
                405

<210> SEQ ID NO 50
<211> LENGTH: 1263
<212> TYPE: DNA
<213> ORGANISM: Homo sapiens

<400> SEQUENCE: 50
atgaggtgga tactgttcat tggggcccctt attgggtcca gcatctgtgg ccaagaaaaa       60
ttttttgggg accaagtttt taggattaat gtcagaaatg agacgagat cagcaaattg      120 agtcaactag tgaattcaaa caacttgaag ctcaatttct ggaaatctcc ctcctccttc      180
aatcggcctg tggatgtcct ggtcccatct gtcagtctgc aggcatttaa atccttcctg      240
agatcccagg gcttagagta cgcagtgaca attgaggacc tgcaggccct tttagacaat      300
gaagatgatg aaatgcaaca caatgaaggg caagaacgga gcagtaataa cttcaactac      360
ggggcttacc attccctgga agctacttac cacgagatgg acaacattgc cgcagacttt      420
cctgacctgg cgaggagggt gaagattgga cattcgtttg aaaaccggac gatgtatgta      480
ctgaagttca gcactgggaa aggcgtgagg cggccggccg tttggctgaa tgcaggcatc      540
cattcccgag agtggatctc ccaggccact gcaatctgga cggcaaggaa gattgtatct      600
gattaccaga gggatccagc tatcacctcc atcttggaga aatgatatat tttcttgttg      660
cctgtggcca atcctgatgg atatgtgtat actcaaactc aaaaccgatt atggaggaag      720
acgcggtccc gaaatcctgg aagctcctgc attggtgctg acccaaatag aaactggaac      780
gctagttttg caggaaaggg agccagcgac aacccttgct ccgaagtgta ccatggaccc      840
cacgccaatt cggaagtgga ggtgaaatca gtggtagatt tcatccaaaa acatgggaat      900
ttcaagggct tcatcgacct gcacagctac tcgcagctgc tgatgtatcc atatgggtac      960
tcagtcaaaa aggcccccaga tgccgaggaa ctcgacaagg tggcgaggct tgcggccaaa     1020
gctctggctt ctgtgtcggg cactgagtac caagtgggtc ccacctgcac cactgtctat     1080
```

```
ccagctagcg ggagcagcat cgactgggcg tatgacaacg gcatcaaatt tgcattcaca    1140
tttgagttga gagataccgg gacctatggc ttcctcctgc cagctaacca gatcatcccc    1200
actgcagagg agacgtggct ggggctgaag accatcatgg agcatgtgcg ggacaacctc    1260
tac                                                                 1263

<210> SEQ ID NO 51
<211> LENGTH: 2796
<212> TYPE: DNA
<213> ORGANISM: Homo sapiens
<220> FEATURE:
<221> NAME/KEY: sig_peptide
<222> LOCATION: (11)..(58)
<220> FEATURE:
<221> NAME/KEY: mat_peptide
<222> LOCATION: (59)..(1273)
<220> FEATURE:
<221> NAME/KEY: CDS
<222> LOCATION: (11)..(1273)

<400> SEQUENCE: 51
ccccggggac atg agg tgg ata ctg ttc att ggg gcc ctt att ggg tcc         49
            Met Arg Trp Ile Leu Phe Ile Gly Ala Leu Ile Gly Ser
               -15             -10                  -5 agc atc tgt ggc caa gaa aaa ttt ttt ggg gac caa gtt ttt agg att        97
Ser Ile Cys Gly Gln Glu Lys Phe Phe Gly Asp Gln Val Phe Arg Ile
    -1  1               5                  10 aat gtc aga aat gga gac gag atc agc aaa ttg agt caa cta gtg aat       145
Asn Val Arg Asn Gly Asp Glu Ile Ser Lys Leu Ser Gln Leu Val Asn
 15              20                  25 tca aac aac ttg aag ctc aat ttc tgg aaa tct ccc tcc tcc ttc aat       193
Ser Asn Asn Leu Lys Leu Asn Phe Trp Lys Ser Pro Ser Ser Phe Asn
30              35                  40                  45 cgg cct gtg gat gtc ctg gtc cca tct gtc agt ctg cag gca ttt aaa       241
Arg Pro Val Asp Val Leu Val Pro Ser Val Ser Leu Gln Ala Phe Lys
                50                  55                  60 tcc ttc ctg aga tcc cag ggc tta gag tac gca gtg aca att gag gac       289
Ser Phe Leu Arg Ser Gln Gly Leu Glu Tyr Ala Val Thr Ile Glu Asp
            65                  70                  75 ctg cag gcc ctt tta gac aat gaa gat gat gaa atg caa cac aat gaa       337
Leu Gln Ala Leu Leu Asp Asn Glu Asp Asp Glu Met Gln His Asn Glu
        80                  85                  90 ggg caa gaa cgg agc agt aat aac ttc aac tac ggg gct tac cat tcc       385
Gly Gln Glu Arg Ser Ser Asn Asn Phe Asn Tyr Gly Ala Tyr His Ser
    95                  100                 105 ctg gaa gct act tac cac gag atg gac aac att gcc gca gac ttt cct       433
Leu Glu Ala Thr Tyr His Glu Met Asp Asn Ile Ala Ala Asp Phe Pro
110                 115                 120                 125 gac ctg gcg agg agg gtg aag att gga cat tcg ttt gaa aac cgg acg       481
Asp Leu Ala Arg Arg Val Lys Ile Gly His Ser Phe Glu Asn Arg Thr
                130                 135                 140 atg tat gta ctg aag ttc agc act ggg aaa ggc gtg agg cgg ccg gcc       529
Met Tyr Val Leu Lys Phe Ser Thr Gly Lys Gly Val Arg Arg Pro Ala
            145                 150                 155 gtt tgg ctg aat gca ggc atc cat tcc cga gag tgg atc tcc cag gcc       577
Val Trp Leu Asn Ala Gly Ile His Ser Arg Glu Trp Ile Ser Gln Ala
        160                 165                 170 act gca atc tgg acg gca agg aag att gta tct gat tac cag agg gat       625
Thr Ala Ile Trp Thr Ala Arg Lys Ile Val Ser Asp Tyr Gln Arg Asp
    175                 180                 185 cca gct atc acc tcc atc ttg gag aaa atg gat att ttc ttg ttg cct       673
Pro Ala Ile Thr Ser Ile Leu Glu Lys Met Asp Ile Phe Leu Leu Pro
```

```
              190                 195                 200                 205
gtg gcc aat cct gat gga tat gtg tat act caa act caa aac cga tta          721
Val Ala Asn Pro Asp Gly Tyr Val Tyr Thr Gln Thr Gln Asn Arg Leu
                    210                 215                 220 tgg agg aag acg cgg tcc cga aat cct gga agc tcc tgc att ggt gct          769
Trp Arg Lys Thr Arg Ser Arg Asn Pro Gly Ser Ser Cys Ile Gly Ala
                225                 230                 235 gac cca aat aga aac tgg aac gct agt ttt gca gga aag gga gcc agc          817
Asp Pro Asn Arg Asn Trp Asn Ala Ser Phe Ala Gly Lys Gly Ala Ser
            240                 245                 250 gac aac cct tgc tcc gaa gtg tac cat gga ccc cac gcc aat tcg gaa          865
Asp Asn Pro Cys Ser Glu Val Tyr His Gly Pro His Ala Asn Ser Glu
        255                 260                 265 gtg gag gtg aaa tca gtg gta gat ttc atc caa aaa cat ggg aat ttc          913
Val Glu Val Lys Ser Val Val Asp Phe Ile Gln Lys His Gly Asn Phe
    270                 275                 280                 285 aag ggc ttc atc gac ctg cac agc tac tcg cag ctg ctg atg tat cca          961
Lys Gly Phe Ile Asp Leu His Ser Tyr Ser Gln Leu Leu Met Tyr Pro
                    290                 295                 300 tat ggg tac tca gtc aaa aag gcc cca gat gcc gag gaa ctc gac aag         1009
Tyr Gly Tyr Ser Val Lys Lys Ala Pro Asp Ala Glu Glu Leu Asp Lys
                305                 310                 315 gtg gcg agg ctt gcg gcc aaa gct ctg gct tct gtg tcg ggc act gag         1057
Val Ala Arg Leu Ala Ala Lys Ala Leu Ala Ser Val Ser Gly Thr Glu
            320                 325                 330 tac caa gtg ggt ccc acc tgc acc act gtc tat cca gct agc ggg agc         1105
Tyr Gln Val Gly Pro Thr Cys Thr Thr Val Tyr Pro Ala Ser Gly Ser
        335                 340                 345 agc atc gac tgg gcg tat gac aac ggc atc aaa ttt gca ttc aca ttt         1153
Ser Ile Asp Trp Ala Tyr Asp Asn Gly Ile Lys Phe Ala Phe Thr Phe
350                 355                 360                 365 gag ttg aga gat acc ggg acc tat ggc ttc ctc ctg cca gct aac cag         1201
Glu Leu Arg Asp Thr Gly Thr Tyr Gly Phe Leu Leu Pro Ala Asn Gln
                    370                 375                 380 atc atc ccc act gca gag gag acg tgg ctg ggg ctg aag acc atc atg         1249
Ile Ile Pro Thr Ala Glu Glu Thr Trp Leu Gly Leu Lys Thr Ile Met
                385                 390                 395 gag cat gtg cgg gac aac ctc tac taggcgatgg ctctgctctg tctacattta        1303
Glu His Val Arg Asp Asn Leu Tyr
            400                 405 tttgtaccca cacgtgcacg cactgaggcc attgttaaag gagctctttc ctacctgtgt       1363
gagtcagagc cctctgggtt tgtggagcac acaggcctgc ccctctccag ccagctccct       1423
ggagtcgtgt gtcctggcgg tgtccctgca agaactggtt ctgccagcct gctcaatttt       1483
ggtcctgctg tttttgatga gccttttgtc tgtttctcct tccaccctgc tggctgggcg       1543
gctgcactca gcatcacccc ttcctgggtg gcatgtctct ctctacctca tttttagaac       1603
caaagaacat ctgagatgat tctctaccct catccacatc tagccaagcc agtgaccttg       1663
ctctggtggc actgtgggag acaccacttg tctttaggtg ggtctcaaag atgatgtaga       1723 atttcccttta atttctcgca gtcttcctgg aaaatatttt cctttgagca gcaaatcttg      1783
tagggatatc agtgaaggtc tctccctccc tcctctcctg ttttttttttt tgagacagag      1843 ttttgctctt gttgcccaga ctggagtgtg atggctcgac cttggctcac cacaacctct       1903
gcctcctggg ttcaagcaat tctcctgcct cagcctcttg agtagcttgg tttataggcg       1963
catgccacca tgcctggcta attttgtgtt tttagtagag acagggtttc tccatgttgg       2023
tcaggctggt ctcaaactcc caacctcagg tgatctgccc tccttggcct cccagagtgc       2083
```

```
tgggattaca ggtgtgagcc actgtgccgg tcccgtcccc tcctttttta ggcctgaata    2143
caaagtagaa gatcactttc cttcactgtg ctgagaattt ctagatacta cagttcttac    2203
tcctctcttc cctttgttat tcagtgtgac caggatggcg ggaggggatc tgtgtcactg    2263
taggtactgt gcccaggaag gctgggtgaa gtgaccatct aaattgcagg atggtgaaat    2323
tatccccatc tgtcctaatg ggcttaccte ctctttgcct tttgaactca cttcaaagat    2383
ctaggcctca tcttacaggt cctaaatcac tcatctggcc tggataatct cactgccctg    2443
gcacattccc atttgtgctg tggtgtatcc tgtgtttcct tgtcctggtt tgtgtgtgtg    2503
tgtgtgtgtg tgtgtgtgtg tgtgtgtgtt tgtgtgtgtg tgtctgtcta ttttgtatcc    2563
tggaccacaa gttcctaagt agagcaagaa ttcatcaacc agctgcctct tgtttcattt    2623
cacctcagca cgtaccatct gtccttttgt tgttgttgtt ttgttttttgt tttttgctt    2683 ttaccaaaca tgtctgtaaa tcttaacctc ctgcctagga tttgtacagc atctggtgtg    2743
tgcttataag ccaataaata ttcaatgtca aaaaaaaaaa aaaaaaaaaa aaa    2796
```

<210> SEQ ID NO 52
<211> LENGTH: 111
<212> TYPE: PRT
<213> ORGANISM: Homo sapiens

<400> SEQUENCE: 52

```
Met Leu Ile Ile Val Leu Val Asn Ala Phe Val Ser Ile Thr Val Glu
            -10                 -5                  -1   1
Asn Phe Phe Leu Asp Met Val Leu Trp Lys Val Val Phe Asn Arg Asp
             5                  10                  15
Lys Gln Gly Glu Tyr Arg Phe Ser Thr Thr Gln Pro Pro Gln Glu Ser
         20                  25                  30
Val Asp Arg Trp Gly Lys Cys Cys Leu Pro Trp Ala Leu Gly Cys Arg
 35                  40                  45                  50
Lys Lys Thr Pro Lys Ala Lys Tyr Met Tyr Leu Ala Gln Glu Leu Leu
                 55                  60                  65
Val Asp Pro Glu Trp Pro Pro Lys Gln Thr Thr Thr Glu Ala Lys
             70                  75                  80
Ala Leu Val Lys Glu Asn Gly Ser Cys Gln Ile Ile Thr Ile Thr
         85                  90                  95
```

<210> SEQ ID NO 53
<211> LENGTH: 333
<212> TYPE: DNA
<213> ORGANISM: Homo sapiens

<400> SEQUENCE: 53

```
atgctcatca ttgttcttgt caatgccttt gtgtctatca cagtggagaa cttcttcctt    60
gacatggtcc tttggaaagt tgtgttcaac cgagacaaac aaggagagta tcggttcagc    120
accacacagc caccgcagga gtcagtggat cggtggggaa atgctgcctt accctgggcc    180
ctgggctgta gaagaagac accaaaggca aagtacatgt atctggcgca ggagctcttg    240
gttgatccag aatggccacc aaaacctcag acaaccacag aagctaaagc tttagttaag    300
gagaatggat catgtcaaat catcaccata aca    333
```

<210> SEQ ID NO 54
<211> LENGTH: 3635
<212> TYPE: DNA
<213> ORGANISM: Homo sapiens

```
<220> FEATURE:
<221> NAME/KEY: sig_peptide
<222> LOCATION: (36)..(77)
<220> FEATURE:
<221> NAME/KEY: mat_peptide
<222> LOCATION: (78)..(368)
<220> FEATURE:
<221> NAME/KEY: CDS
<222> LOCATION: (36)..(368)

<400> SEQUENCE: 54
```

| | | |
|---|---|---|
| agatagtgtg tgtaccatat cagtggcgtg taact atg ctc atc att gtt ctt<br>                                              Met Leu Ile Ile Val Leu<br>                                                                                         -10 | | 53 |

```
gtc aat gcc ttt gtg tct atc aca gtg gag aac ttc ttc gac atg       101
Val Asn Ala Phe Val Ser Ile Thr Val Glu Asn Phe Phe Asp Met
       -5              -1   1               5 gtc ctt tgg aaa gtt gtg ttc aac cga gac aaa caa gga gag tat cgg   149
Val Leu Trp Lys Val Val Phe Asn Arg Asp Lys Gln Gly Glu Tyr Arg
 10                  15                  20 ttc agc acc aca cag cca ccg cag gag tca gtg gat cgg tgg gga aaa   197
Phe Ser Thr Thr Gln Pro Pro Gln Glu Ser Val Asp Arg Trp Gly Lys
 25              30                  35                  40 tgc tgc tta ccc tgg gcc ctg ggc tgt aga aag aag aca cca aag gca   245
Cys Cys Leu Pro Trp Ala Leu Gly Cys Arg Lys Lys Thr Pro Lys Ala
             45                  50                  55 aag tac atg tat ctg gcg cag gag ctc ttg gtt gat cca gaa tgg cca   293
Lys Tyr Met Tyr Leu Ala Gln Glu Leu Leu Val Asp Pro Glu Trp Pro
                 60                  65                  70 cca aaa cct cag aca acc aca gaa gct aaa gct tta gtt aag gag aat   341
Pro Lys Pro Gln Thr Thr Thr Glu Ala Lys Ala Leu Val Lys Glu Asn
             75                  80                  85 gga tca tgt caa atc atc acc ata aca tagcagtgaa tcagtctcag         388
Gly Ser Cys Gln Ile Ile Thr Ile Thr
 90                  95 tggtattgct gatagcagta ttcaggaata tgtgatttta ggagtttctg atcctgtgtg  448
tcagaatggc actagttcag tttatgtccc ttctgatata gtagcttatt tgacagcttt  508
gctcttcctt aaaataaaaa cagaaaaata tatcgtccta acagttaaat taacaatcaa  568
tccataaagt cctatatctt cattcagcaa cccaaatatt acatacattt ccagaatttt  628
cttgattgtt actttcagtg atattcttta tattgggtac aggagaagtt tggtgtttgg  688
taggtttttc aacattagtt tttgagacta gtttacctct tcacatttat gctcacaacc  748
ctcttgttag aaaagtctgt gtttatatac aggctgtaag tttgtgattg ataaaaagaa  808
gatgagtgtt aattagcctc cagtgaaaat atactgaaag cctgttttca tttgattcca  868
atgtttcttc caaagaattc tgtataaaca tatgccaatt ccctatgatg gtctagagtt  928
aggaatgagt gtttatggtg ttgcttatag aacaactcag gtaatctcca tttctggttt  988
tatattttct gtacaaactg cctgggtttt attttttctaa tcagcaaggt gcttcactgc 1048
cttcttgaga cgcctctcaa agctcttaaa tggctcctgt gctatgtgtg gtgttggcag 1108
tctaatttgc ttctgttaaa tgttgtagaa ccttttttcac taggaaataa gattcatttc 1168
tttcggcagt agatgtagat tcatctttta acgtttcttc aaatttgttt ctgtcaggct 1228
ttgtgttatt ttaaatggtt ttttaaaatt ttcttctatg ttttcaatta cctaaagaca 1288
taggataata gttttttttta agttagaatt ttacctcata aaattttttg aggtttgatg 1348
tatgtctctg tcttatcaat aatgaggctt aaaaaatact ggatttgaat ggctgccgtt 1408
ttttcaaagc aatatgaatt tgatgagttt gtttatgcc attaggtggc gccagaggtc  1468
```

```
agaacatgtc tattttgaat tggatcgtta caaatgagca tatttgatgc ggaaatttct    1528
gggagaaaaa aaattgagga aataaagtta aaaaattgac attcattgag ccaaaagaga    1588
tgtggagaaa catttttcac ctttctgttt ggcctgatta acatttaaat tcttgccaaa    1648
attaaggtaa cttttaaaaa cacctttat aggtggatcc agcagtctgg caacgcccac     1708
agttaccaca acacagaaaa ctgatcgtgc tataaaatgg acgctaaact atgaaaacag    1768
tgtgacattg ttctctgttc ttccagagcc agtaacatgc ttgctcgtgc tttctacttc    1828
tagctgatca ttcttttccc aacatatatt tacaaattta ccaattttta cctagaattt    1888
taggaccaaa tggttctcac tctttatgct gcaaagacct ggatgatgtt tggtaactat    1948
agaaaaatag aaattacact caggatcact gttactgcta ttgccactga tgattcctgc    2008
aaaatataat cgaagttttc catcaaatgt ataaatgct attaatacac attagatgat     2068
aacagttgtt ccatgaatga ttctatgaag ctatgcatct tagacctctt gagctgtgaa    2128
ttagcactat tttctatagt tacttattct ctggatcatt ttataatttc catattaatt    2188
tcaaatatgc tcgtgttatt cttcagtgat ttccacaatt gtgcatttta ttctttggtt    2248
taagtactga agcatataat gaagtaatt gctaagtagc agcttaaaaa ttcaattatc      2308
cgattgtatt taacatcttt aagagcatga tcataaagag ctattttga cccccccccc      2368
cactttttta acatttagag ttaataaggg ttttatatct cttctgtcca tattgttttc    2428
aaaggaatga ggtgtttagg tggctggaaa agcatttgta ggaagttaga tttgaatata    2488
gacaaggtgg gttattcacg ttgagaatgt tatttgaaga atgcctgtga agccaggtgt    2548
gggttctact cagtgccata gatagactga gtcttctctc gtaggtcacc attacatagt    2608
aattttgatt ctgaatttca cattaaatta tttgagttta tacagaccta aattttaaaa    2668
tctgtacata tattattttg atgtattaag atgaatattg ctgatttaaa ttttatttat    2728
gcacatactt aaaggacaga aatgtctggg aaagtaattg ttaaataatg atatgtaact    2788
ttttaacttt ttaaataaat aacaagattt ttaatgtgtg tctccctcag ggttgtttaa    2848
agttttttt ctccctcaag tataaatagt ggtaactata tgttttgtat cttctagcac     2908
caactgctgt aaagcaatgc tgcaaataat gcttgaatac aagtggctaa gccaacaaca    2968
gaataaatac ttttatagta gttttataat cctgaaattc gaaagctttc ccaattgcac    3028
ttgcatctaa acaaaactgt tgcagttttt actctatta ttttgttccc catgtttatg     3088
aaagtcctgc acagtttcaa aggcatggta ataatatat caatgtttat gtagtctgtt     3148
acagaaacag ctatagataa cattatccag tgaagagcaa aattcaagct ttagaaaata    3208
ttcatgcatg caattttgac atatctaaaa ataggttttt gtatatttat ggtgggaggt    3268
ggttgggaac ttttaacaaa atggggtgtt aattttgta cagtctgtgg gcatttacac     3328
atttttaatg tattaaaatt tggtaattat gtgtacatta aattaataaa agttacttct    3388
agttatgatt tgtgaattcc ctaagacctt ggatttttt aagtaacttt atatcagaaa     3448
tgatactgca tctttatatt tttaaaattg tattgctgct caagaatggt accctcttgt    3508
caaaaaggca tacattcata attgtacatt cagcattgta ataatctta tgaaacccttt    3568
tttgattgaa gctattcaaa ataaaaattt taatgaacga aaaaaaaaa aaaaaaaaa      3628
aaaaaaa                                                              3635
```

<210> SEQ ID NO 55
<211> LENGTH: 1109
<212> TYPE: PRT
<213> ORGANISM: Homo sapiens

```
<400> SEQUENCE: 55

Met Leu Ile Glu His Pro Leu Arg Cys Leu Val Leu Cys Ala Gln Val
                -15                 -10                  -5

His Ala Gly Met Trp Arg Arg Asn Gly Phe Ser Leu Val Asn Gln Ile
 -1   1              5                  10

Tyr Tyr Tyr His Asn Val Lys Cys Arg Arg Glu Met Phe Asp Lys Asp
 15              20                  25                  30

Val Val Met Leu Gln Thr Gly Val Ser Met Met Asp Pro Asn His Phe
                 35                  40                  45

Leu Met Ile Met Leu Ser Arg Phe Glu Leu Tyr Gln Ile Phe Ser Thr
                 50                  55                  60

Pro Asp Tyr Gly Lys Arg Phe Ser Ser Glu Ile Thr His Lys Asp Val
             65                  70                  75

Val Gln Gln Asn Asn Thr Leu Ile Glu Glu Met Leu Tyr Leu Ile Ile
 80                  85                  90

Met Leu Val Gly Glu Arg Phe Ser Pro Gly Val Gly Gln Val Asn Ala
 95             100                 105                     110

Thr Asp Glu Ile Lys Arg Glu Ile Ile His Gln Leu Ser Ile Lys Pro
                115                 120                 125

Met Ala His Ser Glu Leu Val Lys Ser Leu Pro Glu Asp Glu Asn Lys
                130                 135                 140

Glu Thr Gly Met Glu Ser Val Ile Glu Ala Val Ala His Phe Lys Lys
                145                 150                 155

Pro Gly Leu Thr Gly Arg Gly Met Tyr Glu Leu Lys Pro Glu Cys Ala
                160                 165                 170

Lys Glu Phe Asn Leu Tyr Phe Tyr His Phe Ser Arg Ala Glu Gln Ser
175                 180                 185                 190

Lys Ala Glu Glu Ala Gln Arg Lys Leu Lys Arg Gln Asn Arg Glu Asp
                195                 200                 205

Thr Ala Leu Pro Pro Pro Val Leu Pro Pro Phe Cys Pro Leu Phe Ala
                210                 215                 220

Ser Leu Val Asn Ile Leu Gln Ser Asp Val Met Leu Cys Ile Met Gly
                225                 230                 235

Thr Ile Leu Gln Trp Ala Val Glu His Asn Gly Tyr Ala Trp Ser Glu
240                 245                 250

Ser Met Leu Gln Arg Val Leu His Leu Ile Gly Met Ala Leu Gln Glu
255                 260                 265                 270

Glu Lys Gln His Leu Glu Asn Val Thr Glu Glu His Val Val Thr Phe
                275                 280                 285

Thr Phe Thr Gln Lys Ile Ser Lys Pro Gly Glu Ala Pro Lys Asn Ser
                290                 295                 300

Pro Ser Ile Leu Ala Met Leu Glu Thr Leu Gln Asn Ala Pro Tyr Leu
                305                 310                 315

Glu Val His Lys Asp Met Ile Arg Trp Ile Leu Lys Thr Phe Asn Ala
                320                 325                 330

Val Lys Lys Met Arg Glu Ser Ser Pro Thr Ser Pro Val Ala Glu Thr
335                 340                 345                 350

Glu Gly Thr Ile Met Glu Glu Ser Ser Arg Asp Lys Asp Lys Ala Glu
                355                 360                 365

Arg Lys Arg Lys Ala Glu Ile Ala Arg Leu Arg Arg Glu Lys Ile Met
                370                 375                 380

Ala Gln Met Ser Glu Met Gln Arg His Phe Ile Asp Glu Asn Lys Glu
```

-continued

```
                385                 390                 395
Leu Phe Gln Gln Thr Leu Glu Leu Asp Ala Ser Thr Ser Ala Val Leu
400                 405                 410

Asp His Ser Pro Val Ala Ser Asp Met Thr Leu Thr Ala Leu Gly Pro
415                 420                 425                 430

Ala Gln Thr Gln Val Pro Glu Gln Arg Gln Phe Val Thr Cys Ile Leu
                435                 440                 445

Cys Gln Glu Glu Gln Val Lys Val Glu Ser Arg Ala Met Val Leu
            450                 455                 460

Ala Ala Phe Val Gln Arg Ser Thr Val Leu Ser Lys Asn Arg Ser Lys
            465                 470                 475

Phe Ile Gln Asp Pro Glu Lys Tyr Asp Pro Leu Phe Met His Pro Asp
        480                 485                 490

Leu Ser Cys Gly Thr His Thr Ser Ser Cys Gly His Ile Met His Ala
495                 500                 505                 510

His Cys Trp Gln Arg Tyr Phe Asp Ser Val Gln Ala Lys Glu Gln Arg
                515                 520                 525

Arg Gln Gln Arg Leu Arg Leu His Thr Ser Tyr Asp Val Glu Asn Gly
            530                 535                 540

Glu Phe Leu Cys Pro Leu Cys Glu Cys Leu Ser Asn Thr Val Ile Pro
            545                 550                 555

Leu Leu Leu Ser Pro Arg Asn Ile Phe Asn Asn Arg Leu Asn Phe Ser
        560                 565                 570

Asp Gln Pro Asn Leu Thr Gln Trp Ile Arg Thr Ile Ser Gln Gln Ile
575                 580                 585                 590

Lys Ala Leu Gln Phe Leu Arg Lys Glu Glu Ser Thr Pro Asn Asn Ala
                595                 600                 605

Ser Thr Lys Asn Ser Glu Asn Val Asp Glu Leu Gln Leu Pro Glu Gly
            610                 615                 620

Phe Arg Pro Asp Phe Arg Pro Lys Ile Pro Tyr Ser Glu Ser Ile Lys
            625                 630                 635

Glu Met Leu Thr Thr Phe Gly Thr Ala Thr Tyr Lys Val Gly Leu Lys
        640                 645                 650

Val His Pro Asn Glu Glu Asp Pro Arg Val Pro Ile Met Cys Trp Gly
655                 660                 665                 670

Ser Cys Ala Tyr Thr Ile Gln Ser Ile Glu Arg Ile Leu Ser Asp Glu
                675                 680                 685

Asp Lys Pro Leu Phe Gly Pro Leu Pro Cys Arg Leu Asp Asp Cys Leu
            690                 695                 700

Arg Ser Leu Thr Arg Phe Ala Ala Ala His Trp Thr Val Ala Ser Val
            705                 710                 715

Ser Val Val Gln Gly His Phe Cys Lys Leu Phe Ala Ser Leu Val Pro
        720                 725                 730

Asn Asp Ser His Glu Glu Leu Pro Cys Ile Leu Asp Ile Asp Met Phe
735                 740                 745                 750

His Leu Leu Val Gly Leu Val Leu Ala Phe Pro Ala Leu Gln Cys Gln
                755                 760                 765

Asp Phe Ser Gly Ile Ser Leu Gly Thr Gly Asp Leu His Ile Phe His
            770                 775                 780

Leu Val Thr Met Ala His Ile Ile Gln Ile Leu Leu Thr Ser Cys Thr
            785                 790                 795

Glu Glu Asn Gly Met Asp Gln Glu Asn Pro Pro Cys Glu Glu Glu Ser
        800                 805                 810
```

| | | | | | | | | | | | |
|---|---|---|---|---|---|---|---|---|---|---|---|
|Ala|Val|Leu|Ala|Leu|Tyr|Lys|Thr|Leu|His|Gln|Tyr|Thr|Gly|Ser|Ala|
|815| | | |820| | | |825| | | |830| | |

Ala Val Leu Ala Leu Tyr Lys Thr Leu His Gln Tyr Thr Gly Ser Ala
815                 820                 825                 830

Leu Lys Glu Ile Pro Ser Gly Trp His Leu Trp Arg Ser Val Arg Ala
            835                 840                 845

Gly Ile Met Pro Phe Leu Lys Cys Ser Ala Leu Phe Phe His Tyr Leu
            850                 855                 860

Asn Gly Val Pro Ser Pro Pro Asp Ile Gln Val Pro Gly Thr Ser His
            865                 870                 875

Phe Glu His Leu Cys Ser Tyr Leu Ser Leu Pro Asn Asn Leu Ile Cys
            880                 885                 890

Leu Phe Gln Glu Asn Ser Glu Ile Met Asn Ser Leu Ile Glu Ser Trp
895                 900                 905                 910

Cys Arg Asn Ser Glu Val Lys Arg Tyr Leu Glu Gly Glu Arg Asp Ala
            915                 920                 925

Ile Arg Tyr Pro Arg Glu Ser Asn Lys Leu Ile Asn Leu Pro Glu Asp
            930                 935                 940

Tyr Ser Ser Leu Ile Asn Gln Ala Ser Asn Phe Ser Cys Pro Lys Ser
            945                 950                 955

Gly Gly Asp Lys Ser Arg Ala Pro Thr Leu Cys Leu Val Cys Gly Ser
            960                 965                 970

Leu Leu Cys Ser Gln Ser Tyr Cys Cys Gln Thr Glu Leu Glu Gly Glu
975                 980                 985                 990

Asp Val Gly Ala Cys Thr Ala His Thr Tyr Ser Cys Gly Ser Gly Val
            995                 1000                1005

Gly Ile Phe Leu Arg Val Arg Glu Cys Gln Val Leu Phe Leu Ala Gly
            1010                1015                1020

Lys Thr Lys Gly Cys Phe Tyr Ser Pro Pro Tyr Leu Asp Asp Tyr Gly
            1025                1030                1035

Glu Thr Asp Gln Gly Leu Arg Arg Gly Asn Pro Leu His Leu Cys Lys
            1040                1045                1050

Glu Arg Phe Lys Lys Ile Gln Lys Leu Trp His Gln His Ser Val Thr
1055                1060                1065                1070

Glu Glu Ile Gly His Ala Gln Glu Ala Asn Gln Thr Leu Val Gly Ile
            1075                1080                1085

Asp Trp Gln His Leu
            1090

<210> SEQ ID NO 56
<211> LENGTH: 3327
<212> TYPE: DNA
<213> ORGANISM: Homo sapiens

<400> SEQUENCE: 56

```
atgttgatag aacaccctct tagatgtctt gttctgtgtg cccaagtaca tgccggaatg     60
tggagaagaa atgggttctc tctagtaaac cagatttatt actaccataa tgtgaaatgc    120
agacgtgaga tgtttgacaa ggatgtagta atgcttcaga caggtgtctc catgatggat    180
ccaaatcatt tcctgatgat catgctcagc cgctttgaac tttatcagat tttcagtact    240
ccagactatg gaaaaagatt tagttctgag attacccata aggatgttgt tcagcagaac    300
aatactctaa tagaagaaat gctatacctc attataatgc ttgttggaga gagatttagt    360
cctggagttg acaggtaaa tgctacagat gaaatcaagc gagagattat ccatcagttg    420
agtatcaagc ctatggctca tagtgaattg gtaaagtctt tacctgaaga tgagaacaag    480
```

```
gagactggca tggagagtgt aatcgaagca gttgcccatt tcaagaaacc tggattaaca    540
ggacgaggca tgtatgaact gaaaccagaa tgtgccaaag agttcaactt gtatttctat    600
cacttttcaa gggcagaaca gtccaaggca gaagaagcgc aacggaaatt gaaaagacaa    660
aatagagaag atacagcact cccacctccg gtgttgcctc cattctgccc tctgtttgca    720
agcctggtta acattttgca gtcagatgtc atgttgtgca tcatgggaac aattctgcaa    780
tgggctgtgg aacataatgg atatgcctgg tcagagtcca tgctgcaaag ggtgttacat    840
ttaattggca tggcactaca agaagaaaaa caacatttag agaatgtcac ggaagagcat    900
gtagtaacat ttaccttcac tcagaagata tcaaaacctg tgaagcgcc aaaaaattct     960 cctagcatac tagctatgct ggaaacacta caaaatgctc cctacctaga agtccacaaa   1020
gacatgattc ggtggatatt gaagactttt aatgctgtta aaaagatgag ggagagttca   1080
cctaccagtc ccgtggcaga gacagaagga accataatgg aagagagttc aagggacaaa   1140
gacaaagctg agaggaagag aaaagcagag attgccagac tgcgcagaga aaagatcatg   1200
gctcagatgt ctgaaatgca gcggcatttt attgatgaaa caaagaact ctttcagcag     1260 acattagaac tggatgcctc aacctctgct gttcttgatc atagccctgt ggcttcagat   1320
atgacactta cagcactggg ccccgcacaa actcaggttc ctgaacaaag acaattcgtt   1380
acatgtatat tgtgtcaaga ggagcaagaa gttaaagtgg aaagcagggc aatggtcttg   1440
gcagcatttg ttcagagatc aactgtatta tcaaaaaaca gaagtaaatt tattcaagat   1500
ccagaaaaat atgatccatt attcatgcac cctgatctgt cttgtggaac acacactagt   1560
agctgtgggc acattatgca tgcccattgt tggcaaaggt attttgattc cgttcaagct   1620
aaagaacagc gaaggcaaca gagattacgc ttacatacga gctatgatgt agaaaacgga   1680
gaattccttt gccccctttg tgaatgcttg agtaatactg ttattcctct gctgctttct   1740
ccaagaaata ttttttaacaa caggttaaat ttttcagacc aaccaaatct gactcagtgg   1800
attagaacaa tatctcagca aataaaagca ttacagtttc ttaggaaaga agaaagtact   1860
cctaataatg cctctacaaa gaattcagaa aatgtggatg aattacagct ccctgaaggg   1920
ttcaggcctg attttcgtcc taagatccct tattctgaga gcataaaaga aatgctaacg   1980
acatttggaa ctgctaccta caaggtggga ctaaaggttc atcccaatga agaggatcct   2040
cgtgttccca taatgtgttg gggtagctgc gcgtacacca tccaaagcat agaaagaatt   2100
ttgagtgatg aagataaacc attgtttggt cctttacctt gcagactgga tgactgtctt   2160
aggtcattga cgagatttgc cgcagcacac tggacagtgg catcagtttc agtggtgcaa   2220
ggacattttt gtaaactttt tgcatcactg gtgcctaatg acagccatga ggaacttcca   2280
tgcatattag atattgacat gtttcattta ttggtgggct tggtgcttgc atttcctgcg   2340
ttgcagtgtc aggattttc agggatcagc cttggcactg agaccttca cattttccat     2400 ctggttacta tggcacacat catacagatc ttacttacct catgtacaga agagaatggc   2460
atggatcaag aaaatccccc ttgtgaagaa gaatcagcag ttcttgcttt gtataaaaca   2520
cttcaccagt atacgggaag tgccttgaaa gaaataccat ccggctggca tctgtgggag   2580
agtgtcagag ctggaatcat gcctttcctg aagtgttctg ctttatttt tcattactta   2640 aatggagttc cttccccacc cgacattcaa gttcctggaa caagccattt tgaacattta   2700
tgtagctatc tttccctacc aaacaacctc atttgccttt tcaagaaaaa tagtgagata   2760
atgaattcac tgattgaaag ttggtgccgt aacagtgaag ttaaaagata tctagaaggt   2820
gaaagagatg ctataagata tccaagagaa tctaacaaat taataaaacct tccagaggat   2880
```

-continued

```
tacagcagcc tcattaatca agcatccaat ttctcgtgcc cgaaatcagg tggtgataag      2940
agcagagccc caactctgtg ccttgtgtgc ggatctctgc tgtgctccca gagttactgc      3000
tgccagactg aactggaagg ggaggatgta ggagcctgca cagctcacac ctactcctgt      3060
ggctctggag tgggcatctt cctgagagta cgggaatgtc aggtgctatt tttagctggc      3120
aaaaccaaag gctgttttta ttctcctcct taccttgatg actatgggga gaccgaccag      3180
ggactcagac ggggaaatcc tttacattta tgcaaagagc gattcaagaa gattcagaag      3240
ctctggcacc aacacagtgt cacagaggaa attggacatg cacaggaagc caatcagaca      3300
ctggttggca ttgactggca acattta                                          3327

<210> SEQ ID NO 57
<211> LENGTH: 3502
<212> TYPE: DNA
<213> ORGANISM: Homo sapiens
<220> FEATURE:
<221> NAME/KEY: sig_peptide
<222> LOCATION: (56)..(109)
<220> FEATURE:
<221> NAME/KEY: mat_peptide
<222> LOCATION: (110)..(3382)
<220> FEATURE:
<221> NAME/KEY: CDS
<222> LOCATION: (56)..(3382)

<400> SEQUENCE: 57
tttttgtttt ctgttttttt attttttgta tatatagagt gaacttagcc caccc atg       58
                                                                 Met
ttg ata gaa cac cct ctt aga tgt ctt gtt ctg tgt gcc caa gta cat       106
Leu Ile Glu His Pro Leu Arg Cys Leu Val Leu Cys Ala Gln Val His
        -15                 -10                  -5 gcc gga atg tgg aga aga aat ggg ttc tct cta gta aac cag att tat       154
Ala Gly Met Trp Arg Arg Asn Gly Phe Ser Leu Val Asn Gln Ile Tyr
 -1   1               5                  10                  15 tac tac cat aat gtg aaa tgc aga cgt gag atg ttt gac aag gat gta       202
Tyr Tyr His Asn Val Lys Cys Arg Arg Glu Met Phe Asp Lys Asp Val
                 20                  25                  30 gta atg ctt cag aca ggt gtc tcc atg atg gat cca aat cat ttc ctg       250
Val Met Leu Gln Thr Gly Val Ser Met Met Asp Pro Asn His Phe Leu
             35                  40                  45 atg atc atg ctc agc cgc ttt gaa ctt tat cag att ttc agt act cca       298
Met Ile Met Leu Ser Arg Phe Glu Leu Tyr Gln Ile Phe Ser Thr Pro
         50                  55                  60 gac tat gga aaa aga ttt agt tct gag att acc cat aag gat gtt gtt       346
Asp Tyr Gly Lys Arg Phe Ser Ser Glu Ile Thr His Lys Asp Val Val
     65                  70                  75 cag cag aac aat act cta ata gaa gaa atg cta tac ctc att ata atg       394
Gln Gln Asn Asn Thr Leu Ile Glu Glu Met Leu Tyr Leu Ile Ile Met
 80                  85                  90                  95 ctt gtt gga gag aga ttt agt cct gga gtt gga cag gta aat gct aca       442
Leu Val Gly Glu Arg Phe Ser Pro Gly Val Gly Gln Val Asn Ala Thr
                    100                 105                 110 gat gaa atc aag cga gag att atc cat cag ttg agt atc aag cct atg       490
Asp Glu Ile Lys Arg Glu Ile Ile His Gln Leu Ser Ile Lys Pro Met
                115                 120                 125 gct cat agt gaa ttg gta aag tct tta cct gaa gat gag aac aag gag       538
Ala His Ser Glu Leu Val Lys Ser Leu Pro Glu Asp Glu Asn Lys Glu
            130                 135                 140 act ggc atg gag agt gta atc gaa gca gtt gcc cat ttc aag aaa cct       586
Thr Gly Met Glu Ser Val Ile Glu Ala Val Ala His Phe Lys Lys Pro
        145                 150                 155
```

-continued

```
gga tta aca gga cga ggc atg tat gaa ctg aaa cca gaa tgt gcc aaa    634
Gly Leu Thr Gly Arg Gly Met Tyr Glu Leu Lys Pro Glu Cys Ala Lys
160                 165                 170                 175 gag ttc aac ttg tat ttc tat cac ttt tca agg gca gaa cag tcc aag    682
Glu Phe Asn Leu Tyr Phe Tyr His Phe Ser Arg Ala Glu Gln Ser Lys
            180                 185                 190 gca gaa gaa gcg caa cgg aaa ttg aaa aga caa aat aga gaa gat aca    730
Ala Glu Glu Ala Gln Arg Lys Leu Lys Arg Gln Asn Arg Glu Asp Thr
        195                 200                 205 gca ctc cca cct ccg gtg ttg cct cca ttc tgc cct ctg ttt gca agc    778
Ala Leu Pro Pro Pro Val Leu Pro Pro Phe Cys Pro Leu Phe Ala Ser
        210                 215                 220 ctg gtt aac att ttg cag tca gat gtc atg ttg tgc atc atg gga aca    826
Leu Val Asn Ile Leu Gln Ser Asp Val Met Leu Cys Ile Met Gly Thr
    225                 230                 235 att ctg caa tgg gct gtg gaa cat aat gga tat gcc tgg tca gag tcc    874
Ile Leu Gln Trp Ala Val Glu His Asn Gly Tyr Ala Trp Ser Glu Ser
240                 245                 250                 255 atg ctg caa agg gtg tta cat tta att ggc atg gca cta caa gaa gaa    922
Met Leu Gln Arg Val Leu His Leu Ile Gly Met Ala Leu Gln Glu Glu
            260                 265                 270 aaa caa cat tta gag aat gtc acg gaa gag cat gta gta aca ttt acc    970
Lys Gln His Leu Glu Asn Val Thr Glu Glu His Val Val Thr Phe Thr
        275                 280                 285 ttc act cag aag ata tca aaa cct ggt gaa gcg cca aaa aat tct cct   1018
Phe Thr Gln Lys Ile Ser Lys Pro Gly Glu Ala Pro Lys Asn Ser Pro
        290                 295                 300 agc ata cta gct atg ctg gaa aca cta caa aat gct ccc tac cta gaa   1066
Ser Ile Leu Ala Met Leu Glu Thr Leu Gln Asn Ala Pro Tyr Leu Glu
    305                 310                 315 gtc cac aaa gac atg att cgg tgg ata ttg aag act ttt aat gct gtt   1114
Val His Lys Asp Met Ile Arg Trp Ile Leu Lys Thr Phe Asn Ala Val
320                 325                 330                 335 aaa aag atg agg gag agt tca cct acc agt ccc gtg gca gag aca gaa   1162
Lys Lys Met Arg Glu Ser Ser Pro Thr Ser Pro Val Ala Glu Thr Glu
            340                 345                 350 gga acc ata atg gaa gag agt tca agg gac aaa gac aaa gct gag agg   1210
Gly Thr Ile Met Glu Glu Ser Ser Arg Asp Lys Asp Lys Ala Glu Arg
        355                 360                 365 aag aga aaa gca gag att gcc aga ctg cgc aga gaa aag atc atg gct   1258
Lys Arg Lys Ala Glu Ile Ala Arg Leu Arg Arg Glu Lys Ile Met Ala
        370                 375                 380 cag atg tct gaa atg cag cgg cat ttt att gat gaa aac aaa gaa ctc   1306
Gln Met Ser Glu Met Gln Arg His Phe Ile Asp Glu Asn Lys Glu Leu
    385                 390                 395 ttt cag cag aca tta gaa ctg gat gcc tca acc tct gct gtt ctt gat   1354
Phe Gln Gln Thr Leu Glu Leu Asp Ala Ser Thr Ser Ala Val Leu Asp
400                 405                 410                 415 cat agc cct gtg gct tca gat atg aca ctt aca gca ctg ggc ccc gca   1402
His Ser Pro Val Ala Ser Asp Met Thr Leu Thr Ala Leu Gly Pro Ala
            420                 425                 430 caa act cag gtt cct gaa caa aga caa ttc gtt aca tgt ata ttg tgt   1450
Gln Thr Gln Val Pro Glu Gln Arg Gln Phe Val Thr Cys Ile Leu Cys
        435                 440                 445 caa gag gag caa gaa gtt aaa gtg gaa agc agg gca atg gtc ttg gca   1498
Gln Glu Glu Gln Glu Val Lys Val Glu Ser Arg Ala Met Val Leu Ala
    450                 455                 460 gca ttt gtt cag aga tca act gta tta tca aaa aac aga agt aaa ttt   1546
Ala Phe Val Gln Arg Ser Thr Val Leu Ser Lys Asn Arg Ser Lys Phe
```

```
              465                 470                 475
att caa gat cca gaa aaa tat gat cca tta ttc atg cac cct gat ctg    1594
Ile Gln Asp Pro Glu Lys Tyr Asp Pro Leu Phe Met His Pro Asp Leu
480                 485                 490                 495 tct tgt gga aca cac act agt agc tgt ggg cac att atg cat gcc cat    1642
Ser Cys Gly Thr His Thr Ser Ser Cys Gly His Ile Met His Ala His
                500                 505                 510 tgt tgg caa agg tat ttt gat tcc gtt caa gct aaa gaa cag cga agg    1690
Cys Trp Gln Arg Tyr Phe Asp Ser Val Gln Ala Lys Glu Gln Arg Arg
                    515                 520                 525 caa cag aga tta cgc tta cat acg agc tat gat gta gaa aac gga gaa    1738
Gln Gln Arg Leu Arg Leu His Thr Ser Tyr Asp Val Glu Asn Gly Glu
            530                 535                 540 ttc ctt tgc ccc ctt tgt gaa tgc ttg agt aat act gtt att cct ctg    1786
Phe Leu Cys Pro Leu Cys Glu Cys Leu Ser Asn Thr Val Ile Pro Leu
        545                 550                 555 ctg ctt tct cca aga aat att ttt aac aac agg tta aat ttt tca gac    1834
Leu Leu Ser Pro Arg Asn Ile Phe Asn Asn Arg Leu Asn Phe Ser Asp
560                 565                 570                 575 caa cca aat ctg act cag tgg att aga aca ata tct cag caa ata aaa    1882
Gln Pro Asn Leu Thr Gln Trp Ile Arg Thr Ile Ser Gln Gln Ile Lys
                580                 585                 590 gca tta cag ttt ctt agg aaa gaa gaa agt act cct aat aat gcc tct    1930
Ala Leu Gln Phe Leu Arg Lys Glu Glu Ser Thr Pro Asn Asn Ala Ser
                    595                 600                 605 aca aag aat tca gaa aat gtg gat gaa tta cag ctc cct gaa ggg ttc    1978
Thr Lys Asn Ser Glu Asn Val Asp Glu Leu Gln Leu Pro Glu Gly Phe
            610                 615                 620 agg cct gat ttt cgt cct aag atc cct tat tct gag agc ata aaa gaa    2026
Arg Pro Asp Phe Arg Pro Lys Ile Pro Tyr Ser Glu Ser Ile Lys Glu
        625                 630                 635 atg cta acg aca ttt gga act gct acc tac aag gtg gga cta aag gtt    2074
Met Leu Thr Thr Phe Gly Thr Ala Thr Tyr Lys Val Gly Leu Lys Val
640                 645                 650                 655 cat ccc aat gaa gag gat cct cgt gtt ccc ata atg tgt tgg ggt agc    2122
His Pro Asn Glu Glu Asp Pro Arg Val Pro Ile Met Cys Trp Gly Ser
                660                 665                 670 tgc gcg tac acc atc caa agc ata gaa aga att ttg agt gat gaa gat    2170
Cys Ala Tyr Thr Ile Gln Ser Ile Glu Arg Ile Leu Ser Asp Glu Asp
                    675                 680                 685 aaa cca ttg ttt ggt cct tta cct tgc aga ctg gat gac tgt ctt agg    2218
Lys Pro Leu Phe Gly Pro Leu Pro Cys Arg Leu Asp Asp Cys Leu Arg
            690                 695                 700 tca ttg acg aga ttt gcc gca gca cac tgg aca gtg gca tca gtt tca    2266
Ser Leu Thr Arg Phe Ala Ala Ala His Trp Thr Val Ala Ser Val Ser
        705                 710                 715 gtg gtg caa gga cat ttt tgt aaa ctt ttt gca tca ctg gtg cct aat    2314
Val Val Gln Gly His Phe Cys Lys Leu Phe Ala Ser Leu Val Pro Asn
720                 725                 730                 735 gac agc cat gag gaa ctt cca tgc ata tta gat att gac atg ttt cat    2362
Asp Ser His Glu Glu Leu Pro Cys Ile Leu Asp Ile Asp Met Phe His
                740                 745                 750 tta ttg gtg ggc ttg gtg ctt gca ttt cct gcg ttg cag tgt cag gat    2410
Leu Leu Val Gly Leu Val Leu Ala Phe Pro Ala Leu Gln Cys Gln Asp
                    755                 760                 765 ttt tca ggg atc agc ctt ggc act gga gac ctt cac att ttc cat ctg    2458
Phe Ser Gly Ile Ser Leu Gly Thr Gly Asp Leu His Ile Phe His Leu
            770                 775                 780 gtt act atg gca cac atc ata cag atc tta ctt acc tca tgt aca gaa    2506
```

|     |     |     |     |     |     |     |     |     |     |     |     |     |     |     |     |
|---|---|---|---|---|---|---|---|---|---|---|---|---|---|---|---|
| Val | Thr | Met | Ala | His | Ile | Ile | Gln | Ile | Leu | Leu | Thr | Ser | Cys | Thr | Glu |
|     | 785 |     |     |     | 790 |     |     |     |     | 795 |     |     |     |     |     |

| gag | aat | ggc | atg | gat | caa | gaa | aat | ccc | cct | tgt | gaa | gaa | gaa | tca | gca | 2554 |
|---|---|---|---|---|---|---|---|---|---|---|---|---|---|---|---|---|
| Glu | Asn | Gly | Met | Asp | Gln | Glu | Asn | Pro | Pro | Cys | Glu | Glu | Glu | Ser | Ala |  |
| 800 |  |  |  |  | 805 |  |  |  |  | 810 |  |  |  |  | 815 |  |

| gtt | ctt | gct | ttg | tat | aaa | aca | ctt | cac | cag | tat | acg | gga | agt | gcc | ttg | 2602 |
|---|---|---|---|---|---|---|---|---|---|---|---|---|---|---|---|---|
| Val | Leu | Ala | Leu | Tyr | Lys | Thr | Leu | His | Gln | Tyr | Thr | Gly | Ser | Ala | Leu |  |
|  |  |  |  |  | 820 |  |  |  |  | 825 |  |  |  |  | 830 |  |

| aaa | gaa | ata | cca | tcc | ggc | tgg | cat | ctg | tgg | agg | agt | gtc | aga | gct | gga | 2650 |
|---|---|---|---|---|---|---|---|---|---|---|---|---|---|---|---|---|
| Lys | Glu | Ile | Pro | Ser | Gly | Trp | His | Leu | Trp | Arg | Ser | Val | Arg | Ala | Gly |  |
|  |  |  |  | 835 |  |  |  |  | 840 |  |  |  |  | 845 |  |  |

| atc | atg | cct | ttc | ctg | aag | tgt | tct | gct | tta | ttt | ttt | cat | tac | tta | aat | 2698 |
|---|---|---|---|---|---|---|---|---|---|---|---|---|---|---|---|---|
| Ile | Met | Pro | Phe | Leu | Lys | Cys | Ser | Ala | Leu | Phe | Phe | His | Tyr | Leu | Asn |  |
|  |  | 850 |  |  |  |  | 855 |  |  |  |  | 860 |  |  |  |  |

| gga | gtt | cct | tcc | cca | ccc | gac | att | caa | gtt | cct | gga | aca | agc | cat | ttt | 2746 |
|---|---|---|---|---|---|---|---|---|---|---|---|---|---|---|---|---|
| Gly | Val | Pro | Ser | Pro | Pro | Asp | Ile | Gln | Val | Pro | Gly | Thr | Ser | His | Phe |  |
| 865 |  |  |  |  | 870 |  |  |  |  | 875 |  |  |  |  |  |  |

| gaa | cat | tta | tgt | agc | tat | ctt | tcc | cta | cca | aac | aac | ctc | att | tgc | ctt | 2794 |
|---|---|---|---|---|---|---|---|---|---|---|---|---|---|---|---|---|
| Glu | His | Leu | Cys | Ser | Tyr | Leu | Ser | Leu | Pro | Asn | Asn | Leu | Ile | Cys | Leu |  |
| 880 |  |  |  | 885 |  |  |  |  | 890 |  |  |  |  | 895 |  |  |

| ttt | caa | gaa | aat | agt | gag | ata | atg | aat | tca | ctg | att | gaa | agt | tgg | tgc | 2842 |
|---|---|---|---|---|---|---|---|---|---|---|---|---|---|---|---|---|
| Phe | Gln | Glu | Asn | Ser | Glu | Ile | Met | Asn | Ser | Leu | Ile | Glu | Ser | Trp | Cys |  |
|  |  |  |  | 900 |  |  |  |  | 905 |  |  |  |  | 910 |  |  |

| cgt | aac | agt | gaa | gtt | aaa | aga | tat | cta | gaa | ggt | gaa | aga | gat | gct | ata | 2890 |
|---|---|---|---|---|---|---|---|---|---|---|---|---|---|---|---|---|
| Arg | Asn | Ser | Glu | Val | Lys | Arg | Tyr | Leu | Glu | Gly | Glu | Arg | Asp | Ala | Ile |  |
|  |  |  |  | 915 |  |  |  |  | 920 |  |  |  |  | 925 |  |  |

| aga | tat | cca | aga | gaa | tct | aac | aaa | tta | ata | aac | ctt | cca | gag | gat | tac | 2938 |
|---|---|---|---|---|---|---|---|---|---|---|---|---|---|---|---|---|
| Arg | Tyr | Pro | Arg | Glu | Ser | Asn | Lys | Leu | Ile | Asn | Leu | Pro | Glu | Asp | Tyr |  |
|  |  | 930 |  |  |  |  | 935 |  |  |  |  | 940 |  |  |  |  |

| agc | agc | ctc | att | aat | caa | gca | tcc | aat | ttc | tcg | tgc | ccg | aaa | tca | ggt | 2986 |
|---|---|---|---|---|---|---|---|---|---|---|---|---|---|---|---|---|
| Ser | Ser | Leu | Ile | Asn | Gln | Ala | Ser | Asn | Phe | Ser | Cys | Pro | Lys | Ser | Gly |  |
| 945 |  |  |  |  | 950 |  |  |  |  | 955 |  |  |  |  |  |  |

| ggt | gat | aag | agc | aga | gcc | cca | act | ctg | tgc | ctt | gtg | tgc | gga | tct | ctg | 3034 |
|---|---|---|---|---|---|---|---|---|---|---|---|---|---|---|---|---|
| Gly | Asp | Lys | Ser | Arg | Ala | Pro | Thr | Leu | Cys | Leu | Val | Cys | Gly | Ser | Leu |  |
| 960 |  |  |  |  | 965 |  |  |  |  | 970 |  |  |  |  | 975 |  |

| ctg | tgc | tcc | cag | agt | tac | tgc | tgc | cag | act | gaa | ctg | gaa | ggg | gag | gat | 3082 |
|---|---|---|---|---|---|---|---|---|---|---|---|---|---|---|---|---|
| Leu | Cys | Ser | Gln | Ser | Tyr | Cys | Cys | Gln | Thr | Glu | Leu | Glu | Gly | Glu | Asp |  |
|  |  |  | 980 |  |  |  |  | 985 |  |  |  |  | 990 |  |  |  |

| gta | gga | gcc | tgc | aca | gct | cac | acc | tac | tcc | tgt | ggc | tct | gga | gtg | ggc | 3130 |
|---|---|---|---|---|---|---|---|---|---|---|---|---|---|---|---|---|
| Val | Gly | Ala | Cys | Thr | Ala | His | Thr | Tyr | Ser | Cys | Gly | Ser | Gly | Val | Gly |  |
|  |  | 995 |  |  |  |  | 1000 |  |  |  |  | 1005 |  |  |  |  |

| atc | ttc | ctg | aga | gta | cgg | gaa | tgt | cag | gtg | cta | ttt | tta | gct | ggc | aaa | 3178 |
|---|---|---|---|---|---|---|---|---|---|---|---|---|---|---|---|---|
| Ile | Phe | Leu | Arg | Val | Arg | Glu | Cys | Gln | Val | Leu | Phe | Leu | Ala | Gly | Lys |  |
|  |  | 1010 |  |  |  |  | 1015 |  |  |  |  | 1020 |  |  |  |  |

| acc | aaa | ggc | tgt | ttt | tat | tct | cct | cct | tac | ctt | gat | gac | tat | ggg | gag | 3226 |
|---|---|---|---|---|---|---|---|---|---|---|---|---|---|---|---|---|
| Thr | Lys | Gly | Cys | Phe | Tyr | Ser | Pro | Pro | Tyr | Leu | Asp | Asp | Tyr | Gly | Glu |  |
|  | 1025 |  |  |  |  | 1030 |  |  |  |  | 1035 |  |  |  |  |  |

| acc | gac | cag | gga | ctc | aga | cgg | gga | aat | cct | tta | cat | tta | tgc | aaa | gag | 3274 |
|---|---|---|---|---|---|---|---|---|---|---|---|---|---|---|---|---|
| Thr | Asp | Gln | Gly | Leu | Arg | Arg | Gly | Asn | Pro | Leu | His | Leu | Cys | Lys | Glu |  |
| 1040 |  |  |  |  | 1045 |  |  |  |  | 1050 |  |  |  |  | 1055 |  |

| cga | ttc | aag | aag | att | cag | aag | ctc | tgg | cac | caa | cac | agt | gtc | aca | gag | 3322 |
|---|---|---|---|---|---|---|---|---|---|---|---|---|---|---|---|---|
| Arg | Phe | Lys | Lys | Ile | Gln | Lys | Leu | Trp | His | Gln | His | Ser | Val | Thr | Glu |  |
|  |  |  |  | 1060 |  |  |  |  | 1065 |  |  |  |  | 1070 |  |  |

| gaa | att | gga | cat | gca | cag | gaa | gcc | aat | cag | aca | ctg | gtt | ggc | att | gac | 3370 |
|---|---|---|---|---|---|---|---|---|---|---|---|---|---|---|---|---|
| Glu | Ile | Gly | His | Ala | Gln | Glu | Ala | Asn | Gln | Thr | Leu | Val | Gly | Ile | Asp |  |
|  |  |  | 1075 |  |  |  |  | 1080 |  |  |  |  | 1085 |  |  |  |

| tgg | caa | cat | tta | taattattgc | accaccaaaa | aacacaaact | tggattttt |  |  |  |  |  |  |  |  | 3422 |
|---|---|---|---|---|---|---|---|---|---|---|---|---|---|---|---|---|
| Trp | Gln | His | Leu |  |  |  |  |  |  |  |  |  |  |  |  |  |
|  |  |  | 1090 |  |  |  |  |  |  |  |  |  |  |  |  |  |

```
taacccagtt ggcttttttaa gaaagaaaga agttctgctg aatttggaaa taaattcttt    3482
atttaaactt taaaaaaaaa                                                 3502
```

<210> SEQ ID NO 58
<211> LENGTH: 1726
<212> TYPE: PRT
<213> ORGANISM: Homo sapiens

<400> SEQUENCE: 58

```
Met Leu Ala Cys Leu Gln Ala Cys Ala Gly Ser Val Ser Gln Glu Leu
            -10                 -5                  -1   1

Ser Glu Thr Ile Leu Thr Met Val Ala Asn Cys Ser Asn Val Met Asn
 5                      10                  15

Lys Ala Arg Gln Pro Pro Gly Val Met Pro Lys Gly Arg Pro Pro
20                  25                  30                  35

Ser Ala Ser Ser Leu Asp Ala Ile Ser Pro Val Gln Ile Asp Pro Leu
                40                  45                  50

Ala Gly Met Thr Ser Leu Ser Ile Gly Gly Ser Ala Ala Pro His Thr
                55                  60                  65

Gln Ser Met Gln Gly Phe Pro Pro Asn Leu Gly Ser Ala Phe Ser Thr
            70                  75                  80

Pro Gln Ser Pro Ala Lys Ala Phe Pro Pro Leu Ser Thr Pro Asn Gln
85                  90                  95

Thr Thr Ala Phe Ser Gly Ile Gly Gly Leu Ser Ser Gln Leu Pro Val
100                 105                 110                 115

Gly Gly Leu Gly Thr Gly Ser Leu Thr Gly Ile Gly Thr Gly Ala Leu
                120                 125                 130

Gly Leu Pro Ala Val Asn Asn Asp Pro Phe Val Gln Arg Lys Leu Gly
                135                 140                 145

Thr Ser Gly Leu Asn Gln Pro Thr Phe Gln Gln Ser Lys Met Lys Pro
            150                 155                 160

Ser Asp Leu Ser Gln Val Trp Pro Glu Ala Asn Gln His Phe Ser Lys
165                 170                 175

Glu Ile Asp Asp Glu Ala Asn Ser Tyr Phe Gln Arg Ile Tyr Asn His
180                 185                 190                 195

Pro Pro His Pro Thr Met Ser Val Asp Glu Val Leu Glu Met Leu Gln
                200                 205                 210

Arg Phe Lys Asp Ser Thr Ile Lys Arg Glu Arg Glu Val Phe Asn Cys
                215                 220                 225

Met Leu Arg Asn Leu Phe Glu Glu Tyr Arg Phe Phe Pro Gln Tyr Pro
            230                 235                 240

Asp Lys Glu Leu His Ile Thr Ala Cys Leu Phe Gly Gly Ile Ile Glu
245                 250                 255

Lys Gly Leu Val Thr Tyr Met Ala Leu Gly Leu Ala Leu Arg Tyr Val
260                 265                 270                 275

Leu Glu Ala Leu Arg Lys Pro Phe Gly Ser Lys Met Tyr Tyr Phe Gly
                280                 285                 290

Ile Ala Ala Leu Asp Arg Phe Lys Asn Arg Leu Lys Asp Tyr Pro Gln
                295                 300                 305

Tyr Cys Gln His Leu Ala Ser Ile Ser His Phe Met Gln Phe Pro His
            310                 315                 320

His Leu Gln Glu Tyr Ile Glu Tyr Gly Gln Gln Ser Arg Asp Pro Pro
325                 330                 335

Val Lys Met Gln Gly Ser Ile Thr Thr Pro Gly Ser Ile Ala Leu Ala
```

-continued

```
                340                 345                 350                 355
Gln Ala Gln Ala Gln Ala Gln Val Pro Ala Lys Ala Pro Leu Ala Gly
                360                 365                 370
Gln Val Ser Thr Met Val Thr Thr Ser Thr Thr Thr Thr Val Ala Lys
                375                 380                 385
Thr Val Thr Val Thr Arg Pro Thr Gly Val Ser Phe Lys Lys Asp Val
                390                 395                 400
Pro Pro Ser Ile Asn Thr Thr Asn Ile Asp Thr Leu Leu Val Ala Thr
            405                 410                 415
Asp Gln Thr Glu Arg Ile Val Glu Pro Glu Asn Ile Gln Glu Lys
420                 425                 430                 435
Ile Ala Phe Ile Phe Asn Asn Leu Ser Gln Ser Asn Met Thr Gln Lys
                440                 445                 450
Val Glu Glu Leu Lys Glu Thr Val Lys Glu Glu Phe Met Pro Trp Val
                455                 460                 465
Ser Gln Tyr Leu Val Met Lys Arg Val Ser Ile Glu Pro Asn Phe His
                470                 475                 480
Ser Leu Tyr Ser Asn Phe Leu Asp Thr Leu Lys Asn Pro Glu Phe Asn
            485                 490                 495
Lys Met Val Leu Asn Glu Thr Tyr Arg Asn Ile Lys Val Leu Leu Thr
500                 505                 510                 515
Ser Asp Lys Ala Ala Ala Asn Phe Ser Asp Arg Ser Leu Leu Lys Asn
                520                 525                 530
Leu Gly His Trp Leu Gly Met Ile Thr Leu Ala Lys Asn Lys Pro Ile
                535                 540                 545
Leu His Thr Asp Leu Asp Val Lys Ser Leu Leu Leu Glu Ala Tyr Val
                550                 555                 560
Lys Gly Gln Gln Glu Leu Leu Tyr Val Val Pro Phe Val Ala Lys Val
            565                 570                 575
Leu Glu Ser Ser Ile Arg Ser Val Val Phe Arg Pro Pro Asn Pro Trp
580                 585                 590                 595
Thr Met Ala Ile Met Asn Val Leu Ala Glu Leu His Gln Glu His Asp
                600                 605                 610
Leu Lys Leu Asn Leu Lys Phe Glu Ile Glu Val Leu Cys Lys Asn Leu
            615                 620                 625
Ala Leu Asp Ile Asn Glu Leu Lys Pro Gly Asn Leu Leu Lys Asp Lys
            630                 635                 640
Asp Arg Leu Lys Asn Leu Asp Glu Gln Leu Ser Ala Pro Lys Lys Asp
            645                 650                 655
Val Lys Gln Pro Glu Glu Leu Pro Pro Ile Thr Thr Thr Thr Ser
660                 665                 670                 675
Thr Thr Pro Ala Thr Asn Thr Thr Cys Thr Ala Thr Val Pro Pro Gln
                680                 685                 690
Pro Gln Tyr Ser Tyr His Asp Ile Asn Val Tyr Ser Leu Ala Gly Leu
            695                 700                 705
Ala Pro His Ile Thr Leu Asn Pro Thr Ile Pro Leu Phe Gln Ala His
            710                 715                 720
Pro Gln Leu Lys Gln Cys Val Arg Gln Ala Ile Glu Arg Ala Val Gln
            725                 730                 735
Glu Leu Val His Pro Val Val Asp Arg Ser Ile Lys Ile Ala Met Thr
740                 745                 750                 755
Thr Cys Glu Gln Ile Val Arg Lys Asp Phe Ala Leu Asp Ser Glu Glu
                760                 765                 770
```

-continued

```
Ser Arg Met Arg Ile Ala Ala His His Met Met Arg Asn Leu Thr Ala
            775                 780                 785
Gly Met Ala Met Ile Thr Cys Arg Glu Pro Leu Leu Met Ser Ile Ser
            790                 795                 800
Thr Asn Leu Lys Asn Ser Phe Ala Ser Ala Leu Arg Thr Ala Ser Pro
            805                 810                 815
Gln Gln Arg Glu Met Met Asp Gln Ala Ala Gln Leu Ala Gln Asp
820                 825                 830                 835
Asn Cys Glu Leu Ala Cys Cys Phe Ile Gln Lys Thr Ala Val Glu Lys
            840                 845                 850
Ala Gly Pro Glu Met Asp Lys Arg Leu Ala Thr Glu Phe Glu Leu Arg
            855                 860                 865
Lys His Ala Arg Gln Glu Gly Arg Arg Tyr Cys Asp Pro Val Val Leu
            870                 875                 880
Thr Tyr Gln Ala Glu Arg Met Pro Glu Gln Ile Arg Leu Lys Val Gly
            885                 890                 895
Gly Val Asp Pro Lys Gln Leu Ala Val Tyr Glu Glu Phe Ala Arg Asn
900                 905                 910                 915
Val Pro Gly Phe Leu Pro Thr Asn Asp Leu Ser Gln Pro Thr Gly Phe
            920                 925                 930
Leu Ala Gln Pro Met Lys Gln Ala Trp Ala Thr Asp Val Ala Gln
            935                 940                 945
Ile Tyr Asp Lys Cys Ile Thr Glu Leu Glu Gln His Leu His Ala Ile
            950                 955                 960
Pro Pro Thr Leu Ala Met Asn Pro Gln Ala Gln Ala Leu Arg Ser Leu
            965                 970                 975
Leu Glu Val Val Val Leu Ser Arg Asn Ser Arg Asp Ala Ile Ala Ala
980                 985                 990                 995
Leu Gly Leu Leu Gln Lys Ala Val Glu Gly Leu Leu Asp Ala Thr Ser
                1000                1005                1010
Gly Ala Asp Ala Asp Leu Leu Leu Arg Tyr Arg Glu Cys His Leu Leu
                1015                1020                1025
Val Leu Lys Ala Leu Gln Asp Gly Arg Ala Tyr Gly Ser Pro Trp Cys
                1030                1035                1040
Asn Lys Gln Ile Thr Arg Cys Leu Ile Glu Cys Arg Asp Glu Tyr Lys
                1045                1050                1055
Tyr Asn Val Glu Ala Val Glu Leu Leu Ile Arg Asn His Leu Val Asn
1060                1065                1070                1075
Met Gln Gln Tyr Asp Phe His Leu Ala Gln Ser Met Glu Asn Gly Leu
                1080                1085                1090
Asn Tyr Met Ala Val Ala Phe Ala Met Gln Leu Val Lys Ile Leu Leu
                1095                1100                1105
Val Asp Glu Arg Ser Val Ala His Val Thr Glu Ala Asp Leu Phe His
                1110                1115                1120
Thr Ile Glu Thr Leu Met Arg Ile Asn Ala His Ser Arg Gly Asn Ala
                1125                1130                1135
Pro Glu Gly Leu Ser Gln Leu Met Glu Val Val Arg Ser Asn Tyr Glu
1140                1145                1150                1155
Ala Met Ile Asp Arg Ala His Gly Gly Pro Asn Phe Met Met His Ser
                1160                1165                1170
Gly Ile Ser Gln Ala Ser Glu Tyr Asp Asp Pro Pro Gly Leu Arg Glu
                1175                1180                1185
```

```
Lys Ala Glu Tyr Leu Leu Arg Glu Trp Val Asn Leu Tyr His Ser Ala
        1190                1195                1200

Ala Ala Gly Arg Asp Ser Thr Lys Ala Phe Ser Ala Phe Val Gly Gln
        1205                1210                1215

Met His Gln Gln Gly Ile Leu Lys Thr Asp Asp Leu Ile Thr Arg Phe
1220                1225                1230                1235

Phe Arg Leu Cys Thr Glu Met Cys Val Glu Ile Ser Tyr Arg Ala Gln
                1240                1245                1250

Ala Glu Gln Gln His Asn Pro Ala Ala Asn Pro Thr Met Ile Arg Ala
        1255                1260                1265

Lys Cys Tyr His Asn Leu Asp Ala Phe Val Arg Leu Ile Ala Leu Leu
        1270                1275                1280

Val Lys His Ser Gly Glu Ala Thr Asn Thr Val Thr Lys Ile Asn Leu
        1285                1290                1295

Leu Asn Lys Val Leu Gly Ile Val Val Gly Val Leu Leu Gln Asp His
1300                1305                1310                1315

Asp Val Arg Gln Ser Glu Phe Gln Gln Leu Pro Tyr His Arg Ile Phe
                1320                1325                1330

Ile Met Leu Leu Leu Glu Leu Asn Ala Pro Glu His Val Leu Glu Thr
        1335                1340                1345

Ile Asn Phe Gln Thr Leu Thr Ala Phe Cys Asn Thr Phe His Ile Leu
        1350                1355                1360

Arg Pro Thr Lys Ala Pro Gly Phe Val Tyr Ala Trp Leu Glu Leu Ile
        1365                1370                1375

Ser His Arg Ile Phe Ile Ala Arg Met Leu Ala His Thr Pro Gln Gln
1380                1385                1390                1395

Lys Gly Trp Pro Met Tyr Ala Gln Leu Leu Ile Asp Leu Phe Lys Tyr
                1400                1405                1410

Leu Ala Pro Phe Leu Arg Asn Val Glu Leu Thr Lys Pro Met Gln Ile
        1415                1420                1425

Leu Tyr Lys Gly Thr Leu Arg Val Leu Leu Val Leu Leu His Asp Phe
        1430                1435                1440

Pro Glu Phe Leu Cys Asp Tyr His Tyr Gly Phe Cys Asp Val Ile Pro
        1445                1450                1455

Pro Asn Cys Ile Gln Leu Arg Asn Leu Ile Leu Ser Ala Phe Pro Arg
1460                1465                1470                1475

Asn Met Arg Leu Pro Asp Pro Phe Thr Pro Asn Leu Lys Val Asp Met
                1480                1485                1490

Leu Ser Glu Ile Asn Ile Ala Pro Arg Ile Leu Thr Asn Phe Thr Gly
        1495                1500                1505

Val Met Pro Pro Gln Phe Lys Lys Asp Leu Asp Ser Tyr Leu Lys Thr
        1510                1515                1520

Arg Ser Pro Val Thr Phe Leu Ser Asp Leu Arg Ser Asn Leu Gln Val
        1525                1530                1535

Ser Asn Glu Pro Gly Asn Arg Tyr Asn Leu Gln Leu Ile Asn Ala Leu
1540                1545                1550                1555

Val Leu Tyr Val Gly Thr Gln Ala Ile Ala His Ile His Asn Lys Gly
                1560                1565                1570

Ser Thr Pro Ser Met Ser Thr Ile Thr His Ser Ala His Met Asp Ile
        1575                1580                1585

Phe Gln Asn Leu Ala Val Asp Leu Asp Thr Glu Gly Arg Tyr Leu Phe
        1590                1595                1600

Leu Asn Ala Ile Ala Asn Gln Leu Arg Tyr Pro Asn Ser His Thr His
```

```
                       1605                1610                1615
Tyr Phe Ser Cys Thr Met Leu Tyr Leu Phe Ala Glu Ala Asn Thr Glu
1620                1625                1630                1635

Ala Ile Gln Glu Gln Ile Thr Arg Val Leu Leu Glu Arg Leu Ile Val
                1640                1645                1650

Asn Arg Pro His Pro Trp Gly Leu Leu Ile Thr Phe Ile Glu Leu Ile
            1655                1660                1665

Lys Asn Pro Ala Phe Lys Phe Trp Asn His Glu Phe Val His Cys Ala
        1670                1675                1680

Pro Glu Ile Glu Lys Leu Phe Gln Ser Val Ala Gln Cys Cys Met Gly
    1685                1690                1695

Gln Lys Gln Ala Gln Gln Val Met Glu Gly Thr Gly Ala Ser
1700                1705                1710

<210> SEQ ID NO 59
<211> LENGTH: 5178
<212> TYPE: DNA
<213> ORGANISM: Homo sapiens

<400> SEQUENCE: 59
atgttggcct gtctgcaagc ttgtgcaggg agtgtttctc aggagctatc agaaactatc      60
ctcaccatgg tagccaattg cagtaatgtt atgaataagg ccagacaacc accacctgga     120
gttatgccaa aggacgtcc tcctagtgct agcagcttag atgccatttc tcctgttcag      180
attgaccctc ttgctggaat gacatctctt agtataggtg gttcagctgc ccctcacacc     240
cagagtatgc agggttttcc tccaaatttg ggttctgcat tcagtacccc tcagtcacca     300
gcaaaagcat ttccaccccct ttcaaccccc aatcagacca ctgcattcag tggtattgga     360
ggactttcat cacagcttcc agtaggtggt cttggcacag gcagcctgac tggtatagga     420
actggtgctc ttggactccc tgcagtgaat aacgaccctt ttgtacagag gaaactgggc     480
acctctggac tgaatcagcc tacattccag cagagtaaga tgaaaccttc ggacttgtct     540
caggtgtggc cagaggcaaa ccagcacttt agtaaagaga tagatgatga agcaaacagc     600
tatttccagc gaatatataa tcatccacca catccaacca tgtctgttga tgaggtatta     660
gaaatgctgc agagatttaa agactctact ataaagaggg aacgagaagt atttaactgt     720
atgctaagga acttgtttga agaatatcgt ttttttcccc agtatcctga taagagtta     780
catataacag cctgcctatt tggtggtata attgagaaag gactggtcac ttacatggca     840
ctaggtctgg ctctacgata tgttcttgaa gccttacgca gcctttttgg atccaaaatg     900
tattatttcg ggattgctgc actagataga tttaaaaaca gattgaagga ctatccccag     960
tattgtcaac atttggcttc tatcagtcac tttatgcaat ttccacatca tttacaggag    1020
tatattgagt atggacagca gtctagagat cctcctgtga aaatgcaagg ctctatcaca    1080
acccctggaa gtattgcact ggctcaggcc caggctcagg cccaggttcc agcaaaagct    1140
cctcttgctg gtcaagttag cactatggta accacctcaa caactaccac tgttgctaaa    1200
acggttacgg tcaccaggcc aactggagtc agctttaaga agatgtgcc accttctatt    1260
aatactacaa atatagatac gttgcttgtg gccacagatc aaactgagag aattgtggag    1320
cccccagaaa atatccagga gaaaattgct tttattttca ataatctctc acagtcaaat    1380
atgacacaaa aggttgaaga gctaaaggaa acggtgaaag aagaatttat gccttgggtt    1440
tcacagtatc tggttatgaa gagagtcagt attgagccaa actttcatag cctgtattca    1500
aacttccttg acacgctgaa gaatcctgaa tttaacaaga tggttctgaa tgagacctac    1560
```

-continued

```
agaaacatta aagtgctcct gacctctgat aaagctgcag ccaatttctc agatcgttct    1620
ttgctgaaga acttgggaca ttggctagga atgatcacat tagctaaaaa caaacccatc    1680
ttacacactg acttggatgt gaaatcattg ctgctagagg cttatgttaa aggacaacaa    1740
gaattgctct atgtagtgcc ctttgttgcc aaagtcttag aatctagcat tcgtagtgtg    1800
gtttttaggc caccaaaccc ttggacaatg gcaattatga atgtattagc tgagctacat    1860
caggagcatg acttaaagtt aaacttgaag tttgaaatcg aggttctctg caagaacctt    1920
gcattagaca tcaatgagct aaaacctgga aacctcctaa aggataaaga tcgcctgaag    1980
aatttagatg agcaactctc tgctccaaag aaagatgtca agcagccaga agaactccct    2040
cccatcacaa ccacaacaac ttctactaca ccagctacca acaccacttg tacagccacg    2100
gttccaccac agccacagta cagctaccac gacatcaatg tctattccct tgcgggcttg    2160
gcaccacaca ttactctgaa tccaacaatt cccttgtttc aggcccatcc acagttgaag    2220
cagtgtgtgc gtcaggcaat tgaacgggct gtccaggagc tggtccatcc tgtggtggat    2280
cgatcaatta agattgccat gactacttgt gagcaaatag tcaggaagga ttttgccctg    2340
gattcggagg aatctcgaat gcgaatagca gctcatcaca tgatgcgtaa cttgacagct    2400
ggaatggcta tgattacatg cagggaacct ttgctcatga gcatatctac caacttaaaa    2460
aacagttttg cctcagccct tcgtactgct tccccacaac aaagagaaat gatggatcag    2520
gcagctgctc aattagctca ggacaattgt gagttggctt gctgttttat tcagaagact    2580
gcagtagaaa aagcaggccc tgagatggac aagagattag caactgaatt tgagctgaga    2640
aaacatgcta ggcaagaagg acgcagatac tgtgatcctg ttgtttttaac atatcaagct    2700
gaacggatgc cagagcaaat caggctgaaa gttggtggtg tggacccaaa gcagttggct    2760
gtttatgaag agtttgcacg caatgttcct ggcttcttac ctacaaatga cttaagtcag    2820
cccacgggat ttttagccca gcccatgaag caagcttggg caacagatga tgtagctcag    2880
atttatgata agtgtattac agaactggag caacatctac atgccatccc accaactttg    2940
gccatgaacc ctcaagctca ggctcttcga agtctcttgg aggttgtagt tttatctcga    3000
aactctcggg atgccatagc tgctcttgga ttgctccaaa aggctgtaga gggcttacta    3060
gatgccacaa gtggtgctga tgctgacctt ctgctgcgct acagggaatg ccacctcttg    3120
gtcctaaaag ctctgcagga tggccgggca tatgggtctc catggtgcaa caaacagatc    3180
acaaggtgcc taattgaatg tcgagatgaa tataaatata atgtggaggc tgtggagctg    3240
ctaattcgca atcatttggt taatatgcag cagtatgatt ttcacctagc gcagtcaatg    3300
gagaatggct taaactacat ggctgtggca tttgctatgc agttagtaaa aatcctgctg    3360
gtggatgaaa ggagtgttgc tcatgttact gaggcagatc tgttccacac cattgaaacc    3420
ctcatgagga ttaatgctca ttccagaggc aatgctccag aaggattgtc ccagctgatg    3480
gaagtagtgc gatccaacta tgaagcaatg attgatcgtg ctcatggagg cccaaacttt    3540
atgatgcatt ctgggatctc tcaagcctca gagtatgatg accctccagg cctgagggag    3600
aaggcagagt atcttctgag ggaatgggtg aatctctacc attcagcagc agctggccgc    3660
gacagtacca aagcttttctc tgcatttgtt ggacagatgc accagcaagg aatactgaag    3720
accgatgatc tcataacaag gttctttcgt ctgtgtactg aaatgtgtgt tgaaatcagt    3780
taccgtgctc aggctgagca gcagcacaat cctgctgcca atcccaccat gatccgagcc    3840
aagtgctatc acaacctgga tgcctttgtt cgactcattg cactgctcgt gaaacactca    3900
```

```
ggggaggcca ccaacactgt cacaaagatt aatctgctga acaaggtcct tggtatagta    3960
gtgggagttc tccttcagga tcatgatgtt cgtcagagtg aatttcagca acttccctac    4020
catcgaattt ttatcatgct tctcttggaa ctcaatgcac ctgagcatgt gttggaaacc    4080
attaatttcc agacacttac agctttctgc aatacattcc acatcttgag gcctaccaaa    4140
gctcctggct ttgtatatgc ctggcttgaa ctgatttccc atcggatatt tattgcaaga    4200
atgctggcac atacgccaca gcagaagggg tggcctatgt atgcacagct actgattgat    4260
ttattcaaat atttagcgcc tttccttaga aatgtggaac tcaccaaacc tatgcaaatc    4320
ctctacaagg gcactttaag agtgctgctg gttcttttgc atgatttccc agagttcctt    4380
tgtgattacc attatgggtt ctgtgatgtg atcccaccta attgtatcca gttaagaaat    4440
ttgatcctga gtgcctttcc aagaaacatg aggctccccg acccattcac tcctaatcta    4500
aaggtggaca tgttgagtga aattaacatt gctccccgga ttctcaccaa tttcactgga    4560
gtaatgccac tcagttcaa aaaggatttg gattcctatc ttaaaactcg atcaccagtc    4620
actttcctgt ctgatctgcg cagcaaccta caggtatcca atgaacctgg gaatcgctac    4680
aacctccagc tcatcaatgc actggtgctc tatgtcggga ctcaggccat gcgcacatc     4740 cacaacaagg gcagcacacc ttcaatgagc accatcactc actcagcaca catggatatc    4800
ttccagaatt tggctgtgga cttggacact gagggtcgct atctcttttt gaatgcaatt    4860
gcaaatcagc tccggtaccc aaatagccac actcactact tcagttgcac catgctgtac    4920 cttttttgcag aggccaatac ggaagccatc caagaacaga tcacaagagt tctcttggaa    4980
cggttgattg taaataggcc acatccttgg ggtcttctta ttaccttcat tgagctgatt    5040
aaaaacccag cgtttaagtt ctggaaccat gaatttgtac actgtgcccc agaaatcgaa    5100
aagttattcc agtcggtcgc acagtgctgc atgggacaga agcaggccca gcaagtaatg    5160
gaagggacag gtgccagt                                                  5178

<210> SEQ ID NO 60
<211> LENGTH: 5457
<212> TYPE: DNA
<213> ORGANISM: Homo sapiens
<220> FEATURE:
<221> NAME/KEY: sig_peptide
<222> LOCATION: (8)..(46)
<220> FEATURE:
<221> NAME/KEY: mat_peptide
<222> LOCATION: (47)..(5185)
<220> FEATURE:
<221> NAME/KEY: CDS
<222> LOCATION: (8)..(5185)

<400> SEQUENCE: 60 ggcgaca atg ttg gcc tgt ctg caa gct tgt gca ggg agt gtt tct cag           49
        Met Leu Ala Cys Leu Gln Ala Cys Ala Gly Ser Val Ser Gln
            -10              -5                   -1  1 gag cta tca gaa act atc ctc acc atg gta gcc aat tgc agt aat gtt           97
Glu Leu Ser Glu Thr Ile Leu Thr Met Val Ala Asn Cys Ser Asn Val
            5                   10                  15 atg aat aag gcc aga caa cca cca cct gga gtt atg cca aaa gga cgt          145
Met Asn Lys Ala Arg Gln Pro Pro Pro Gly Val Met Pro Lys Gly Arg
        20                  25                  30 cct cct agt gct agc agc tta gat gcc att tct cct gtt cag att gac          193
Pro Pro Ser Ala Ser Ser Leu Asp Ala Ile Ser Pro Val Gln Ile Asp
    35                  40                  45 cct ctt gct gga atg aca tct ctt agt ata ggt ggt tca gct gcc cct          241
Pro Leu Ala Gly Met Thr Ser Leu Ser Ile Gly Gly Ser Ala Ala Pro
```

-continued

```
           50                   55                   60                   65
cac acc cag agt atg cag ggt ttt cct cca aat ttg ggt tct gca ttc          289
His Thr Gln Ser Met Gln Gly Phe Pro Pro Asn Leu Gly Ser Ala Phe
                     70                   75                   80 agt acc cct cag tca cca gca aaa gca ttt cca ccc ctt tca acc ccc          337
Ser Thr Pro Gln Ser Pro Ala Lys Ala Phe Pro Pro Leu Ser Thr Pro
                 85                   90                   95 aat cag acc act gca ttc agt ggt att gga gga ctt tca tca cag ctt          385
Asn Gln Thr Thr Ala Phe Ser Gly Ile Gly Gly Leu Ser Ser Gln Leu
            100                  105                  110 cca gta ggt ggt ctt ggc aca ggc agc ctg act ggt ata gga act ggt          433
Pro Val Gly Gly Leu Gly Thr Gly Ser Leu Thr Gly Ile Gly Thr Gly
        115                  120                  125 gct ctt gga ctc cct gca gtg aat aac gac cct ttt gta cag agg aaa          481
Ala Leu Gly Leu Pro Ala Val Asn Asn Asp Pro Phe Val Gln Arg Lys
130                  135                  140                  145 ctg ggc acc tct gga ctg aat cag cct aca ttc cag cag agt aag atg          529
Leu Gly Thr Ser Gly Leu Asn Gln Pro Thr Phe Gln Gln Ser Lys Met
                     150                  155                  160 aaa cct tcg gac ttg tct cag gtg tgg cca gag gca aac cag cac ttt          577
Lys Pro Ser Asp Leu Ser Gln Val Trp Pro Glu Ala Asn Gln His Phe
                 165                  170                  175 agt aaa gag ata gat gat gaa gca aac agc tat ttc cag cga ata tat          625
Ser Lys Glu Ile Asp Asp Glu Ala Asn Ser Tyr Phe Gln Arg Ile Tyr
            180                  185                  190 aat cat cca cca cat cca acc atg tct gtt gat gag gta tta gaa atg          673
Asn His Pro Pro His Pro Thr Met Ser Val Asp Glu Val Leu Glu Met
        195                  200                  205 ctg cag aga ttt aaa gac tct act ata aag agg gaa cga gaa gta ttt          721
Leu Gln Arg Phe Lys Asp Ser Thr Ile Lys Arg Glu Arg Glu Val Phe
210                  215                  220                  225 aac tgt atg cta agg aac ttg ttt gaa gaa tat cgt ttt ttt ccc cag          769
Asn Cys Met Leu Arg Asn Leu Phe Glu Glu Tyr Arg Phe Phe Pro Gln
                     230                  235                  240 tat cct gat aaa gag tta cat ata aca gcc tgc cta ttt ggt ggt ata          817
Tyr Pro Asp Lys Glu Leu His Ile Thr Ala Cys Leu Phe Gly Gly Ile
                 245                  250                  255 att gag aaa gga ctg gtc act tac atg gca cta ggt ctg gct cta cga          865
Ile Glu Lys Gly Leu Val Thr Tyr Met Ala Leu Gly Leu Ala Leu Arg
            260                  265                  270 tat gtt ctt gaa gcc tta cgc aag cct ttt gga tcc aaa atg tat tat          913
Tyr Val Leu Glu Ala Leu Arg Lys Pro Phe Gly Ser Lys Met Tyr Tyr
        275                  280                  285 ttc ggg att gct gca cta gat aga ttt aaa aac aga ttg aag gac tat          961
Phe Gly Ile Ala Ala Leu Asp Arg Phe Lys Asn Arg Leu Lys Asp Tyr
290                  295                  300                  305 ccc cag tat tgt caa cat ttg gct tct atc agt cac ttt atg caa ttt         1009
Pro Gln Tyr Cys Gln His Leu Ala Ser Ile Ser His Phe Met Gln Phe
                     310                  315                  320 cca cat cat tta cag gag tat att gag tat gga cag cag tct aga gat         1057
Pro His His Leu Gln Glu Tyr Ile Glu Tyr Gly Gln Gln Ser Arg Asp
                 325                  330                  335 cct cct gtg aaa atg caa ggc tct atc aca acc cct gga agt att gca         1105
Pro Pro Val Lys Met Gln Gly Ser Ile Thr Thr Pro Gly Ser Ile Ala
            340                  345                  350 ctg gct cag gcc cag gct cag gcc cag gtt cca gca aaa gct cct ctt         1153
Leu Ala Gln Ala Gln Ala Gln Ala Gln Val Pro Ala Lys Ala Pro Leu
        355                  360                  365 gct ggt caa gtt agc act atg gta acc acc tca aca act acc act gtt         1201
```

```
                Ala Gly Gln Val Ser Thr Met Val Thr Thr Ser Thr Thr Thr Val
                370                 375                 380                 385 gct aaa acg gtt acg gtc acc agg cca act gga gtc agc ttt aag aaa            1249
Ala Lys Thr Val Thr Val Thr Arg Pro Thr Gly Val Ser Phe Lys Lys
                390                 395                 400 gat gtg cca cct tct att aat act aca aat ata gat acg ttg ctt gtg            1297
Asp Val Pro Pro Ser Ile Asn Thr Thr Asn Ile Asp Thr Leu Leu Val
                405                 410                 415 gcc aca gat caa act gag aga att gtg gag ccc cca gaa aat atc cag            1345
Ala Thr Asp Gln Thr Glu Arg Ile Val Glu Pro Pro Glu Asn Ile Gln
                420                 425                 430 gag aaa att gct ttt att ttc aat aat ctc tca cag tca aat atg aca            1393
Glu Lys Ile Ala Phe Ile Phe Asn Asn Leu Ser Gln Ser Asn Met Thr
    435                 440                 445 caa aag gtt gaa gag cta aag gaa acg gtg aaa gaa gaa ttt atg cct            1441
Gln Lys Val Glu Glu Leu Lys Glu Thr Val Lys Glu Glu Phe Met Pro
450                 455                 460                 465 tgg gtt tca cag tat ctg gtt atg aag aga gtc agt att gag cca aac            1489
Trp Val Ser Gln Tyr Leu Val Met Lys Arg Val Ser Ile Glu Pro Asn
                470                 475                 480 ttt cat agc ctg tat tca aac ttc ctt gac acg ctg aag aat cct gaa            1537
Phe His Ser Leu Tyr Ser Asn Phe Leu Asp Thr Leu Lys Asn Pro Glu
                485                 490                 495 ttt aac aag atg gtt ctg aat gag acc tac aga aac att aaa gtg ctc            1585
Phe Asn Lys Met Val Leu Asn Glu Thr Tyr Arg Asn Ile Lys Val Leu
                500                 505                 510 ctg acc tct gat aaa gct gca gcc aat ttc tca gat cgt tct ttg ctg            1633
Leu Thr Ser Asp Lys Ala Ala Ala Asn Phe Ser Asp Arg Ser Leu Leu
    515                 520                 525 aag aac ttg gga cat tgg cta gga atg atc aca tta gct aaa aac aaa            1681
Lys Asn Leu Gly His Trp Leu Gly Met Ile Thr Leu Ala Lys Asn Lys
530                 535                 540                 545 ccc atc tta cac act gac ttg gat gtg aaa tca ttg ctg cta gag gct            1729
Pro Ile Leu His Thr Asp Leu Asp Val Lys Ser Leu Leu Leu Glu Ala
                550                 555                 560 tat gtt aaa gga caa caa gaa ttg ctc tat gta gtg ccc ttt gtt gcc            1777
Tyr Val Lys Gly Gln Gln Glu Leu Leu Tyr Val Val Pro Phe Val Ala
                565                 570                 575 aaa gtc tta gaa tct agc att cgt agt gtg gtt ttt agg cca cca aac            1825
Lys Val Leu Glu Ser Ser Ile Arg Ser Val Val Phe Arg Pro Pro Asn
                580                 585                 590 cct tgg aca atg gca att atg aat gta tta gct gag cta cat cag gag            1873
Pro Trp Thr Met Ala Ile Met Asn Val Leu Ala Glu Leu His Gln Glu
    595                 600                 605 cat gac tta aag tta aac ttg aag ttt gaa atc gag gtt ctc tgc aag            1921
His Asp Leu Lys Leu Asn Leu Lys Phe Glu Ile Glu Val Leu Cys Lys
610                 615                 620                 625 aac ctt gca tta gac atc aat gag cta aaa cct gga aac ctc cta aag            1969
Asn Leu Ala Leu Asp Ile Asn Glu Leu Lys Pro Gly Asn Leu Leu Lys
                630                 635                 640 gat aaa gat cgc ctg aag aat tta gat gag caa ctc tct gct cca aag            2017
Asp Lys Asp Arg Leu Lys Asn Leu Asp Glu Gln Leu Ser Ala Pro Lys
                645                 650                 655 aaa gat gtc aag cag cca gaa gaa ctc cct ccc atc aca acc aca aca            2065
Lys Asp Val Lys Gln Pro Glu Glu Leu Pro Pro Ile Thr Thr Thr Thr
                660                 665                 670 act tct act aca cca gct acc aac acc act tgt aca gcc acg gtt cca            2113
Thr Ser Thr Thr Pro Ala Thr Asn Thr Thr Cys Thr Ala Thr Val Pro
    675                 680                 685
```

-continued

| | | |
|---|---|---|
| cca cag cca cag tac agc tac cac gac atc aat gtc tat tcc ctt gcg<br>Pro Gln Pro Gln Tyr Ser Tyr His Asp Ile Asn Val Tyr Ser Leu Ala<br>690                    695                      700                    705 | 2161 |
| ggc ttg gca cca cac att act ctg aat cca aca att ccc ttg ttt cag<br>Gly Leu Ala Pro His Ile Thr Leu Asn Pro Thr Ile Pro Leu Phe Gln<br>                    710                      715                    720 | 2209 |
| gcc cat cca cag ttg aag cag tgt gtg cgt cag gca att gaa cgg gct<br>Ala His Pro Gln Leu Lys Gln Cys Val Arg Gln Ala Ile Glu Arg Ala<br>725                    730                      735 | 2257 |
| gtc cag gag ctg gtc cat cct gtg gtg gat cga tca att aag att gcc<br>Val Gln Glu Leu Val His Pro Val Val Asp Arg Ser Ile Lys Ile Ala<br>                    740                      745                    750 | 2305 |
| atg act act tgt gag caa ata gtc agg aag gat ttt gcc ctg gat tcg<br>Met Thr Thr Cys Glu Gln Ile Val Arg Lys Asp Phe Ala Leu Asp Ser<br>755                    760                      765 | 2353 |
| gag gaa tct cga atg cga ata gca gct cat cac atg atg cgt aac ttg<br>Glu Glu Ser Arg Met Arg Ile Ala Ala His His Met Met Arg Asn Leu<br>770                    775                      780                    785 | 2401 |
| aca gct gga atg gct atg att aca tgc agg gaa cct ttg ctc atg agc<br>Thr Ala Gly Met Ala Met Ile Thr Cys Arg Glu Pro Leu Leu Met Ser<br>                    790                      795                    800 | 2449 |
| ata tct acc aac tta aaa aac agt ttt gcc tca gcc ctt cgt act gct<br>Ile Ser Thr Asn Leu Lys Asn Ser Phe Ala Ser Ala Leu Arg Thr Ala<br>805                    810                      815 | 2497 |
| tcc cca caa caa aga gaa atg atg gat cag gca gct gct caa tta gct<br>Ser Pro Gln Gln Arg Glu Met Met Asp Gln Ala Ala Ala Gln Leu Ala<br>                    820                      825                    830 | 2545 |
| cag gac aat tgt gag ttg gct tgc tgt ttt att cag aag act gca gta<br>Gln Asp Asn Cys Glu Leu Ala Cys Cys Phe Ile Gln Lys Thr Ala Val<br>835                    840                      845 | 2593 |
| gaa aaa gca ggc cct gag atg gac aag aga tta gca act gaa ttt gag<br>Glu Lys Ala Gly Pro Glu Met Asp Lys Arg Leu Ala Thr Glu Phe Glu<br>850                    855                      860                    865 | 2641 |
| ctg aga aaa cat gct agg caa gaa gga cgc aga tac tgt gat cct gtt<br>Leu Arg Lys His Ala Arg Gln Glu Gly Arg Arg Tyr Cys Asp Pro Val<br>                    870                      875                    880 | 2689 |
| gtt tta aca tat caa gct gaa cgg atg cca gag caa atc agg ctg aaa<br>Val Leu Thr Tyr Gln Ala Glu Arg Met Pro Glu Gln Ile Arg Leu Lys<br>885                    890                      895 | 2737 |
| gtt ggt ggt gtg gac cca aag cag ttg gct gtt tat gaa gag ttt gca<br>Val Gly Gly Val Asp Pro Lys Gln Leu Ala Val Tyr Glu Glu Phe Ala<br>                    900                      905                    910 | 2785 |
| cgc aat gtt cct ggc ttc tta cct aca aat gac tta agt cag ccc acg<br>Arg Asn Val Pro Gly Phe Leu Pro Thr Asn Asp Leu Ser Gln Pro Thr<br>915                    920                      925 | 2833 |
| gga ttt tta gcc cag ccc atg aag caa gct tgg gca aca gat gat gta<br>Gly Phe Leu Ala Gln Pro Met Lys Gln Ala Trp Ala Thr Asp Asp Val<br>930                    935                      940                    945 | 2881 |
| gct cag att tat gat aag tgt att aca gaa ctg gag caa cat cta cat<br>Ala Gln Ile Tyr Asp Lys Cys Ile Thr Glu Leu Glu Gln His Leu His<br>                    950                      955                    960 | 2929 |
| gcc atc cca cca act ttg gcc atg aac cct caa gct cag gct ctt cga<br>Ala Ile Pro Pro Thr Leu Ala Met Asn Pro Gln Ala Gln Ala Leu Arg<br>965                    970                      975 | 2977 |
| agt ctc ttg gag gtt gta gtt tta tct cga aac tct cgg gat gcc ata<br>Ser Leu Leu Glu Val Val Val Leu Ser Arg Asn Ser Arg Asp Ala Ile<br>                    980                      985                    990 | 3025 |
| gct gct ctt gga ttg ctc caa aag gct gta gag ggc tta cta gat gcc<br>Ala Ala Leu Gly Leu Leu Gln Lys Ala Val Glu Gly Leu Leu Asp Ala<br>995                    1000                    1005 | 3073 |

| | | |
|---|---|---|
| aca agt ggt gct gat gct gac ctt ctg ctg cgc tac agg gaa tgc cac<br>Thr Ser Gly Ala Asp Ala Asp Leu Leu Leu Arg Tyr Arg Glu Cys His<br>1010                  1015                  1020                  1025 | | 3121 |
| ctc ttg gtc cta aaa gct ctg cag gat ggc cgg gca tat ggg tct cca<br>Leu Leu Val Leu Lys Ala Leu Gln Asp Gly Arg Ala Tyr Gly Ser Pro<br>                  1030                  1035                  1040 | | 3169 |
| tgg tgc aac aaa cag atc aca agg tgc cta att gaa tgt cga gat gaa<br>Trp Cys Asn Lys Gln Ile Thr Arg Cys Leu Ile Glu Cys Arg Asp Glu<br>            1045                  1050                  1055 | | 3217 |
| tat aaa tat aat gtg gag gct gtg gag ctg cta att cgc aat cat ttg<br>Tyr Lys Tyr Asn Val Glu Ala Val Glu Leu Leu Ile Arg Asn His Leu<br>                1060                  1065                  1070 | | 3265 |
| gtt aat atg cag cag tat gat ttt cac cta gcg cag tca atg gag aat<br>Val Asn Met Gln Gln Tyr Asp Phe His Leu Ala Gln Ser Met Glu Asn<br>1075                  1080                  1085 | | 3313 |
| ggc tta aac tac atg gct gtg gca ttt gct atg cag tta gta aaa atc<br>Gly Leu Asn Tyr Met Ala Val Ala Phe Ala Met Gln Leu Val Lys Ile<br>1090                  1095                  1100                  1105 | | 3361 |
| ctg ctg gtg gat gaa agg agt gtt gct cat gtt act gag gca gat ctg<br>Leu Leu Val Asp Glu Arg Ser Val Ala His Val Thr Glu Ala Asp Leu<br>                1110                  1115                  1120 | | 3409 |
| ttc cac acc att gaa acc ctc atg agg att aat gct cat tcc aga ggc<br>Phe His Thr Ile Glu Thr Leu Met Arg Ile Asn Ala His Ser Arg Gly<br>            1125                  1130                  1135 | | 3457 |
| aat gct cca gaa gga ttg tcc cag ctg atg gaa gta gtg cga tcc aac<br>Asn Ala Pro Glu Gly Leu Ser Gln Leu Met Glu Val Val Arg Ser Asn<br>                1140                  1145                  1150 | | 3505 |
| tat gaa gca atg att gat cgt gct cat gga ggc cca aac ttt atg atg<br>Tyr Glu Ala Met Ile Asp Arg Ala His Gly Gly Pro Asn Phe Met Met<br>            1155                  1160                  1165 | | 3553 |
| cat tct ggg atc tct caa gcc tca gag tat gat gac cct cca ggc ctg<br>His Ser Gly Ile Ser Gln Ala Ser Glu Tyr Asp Asp Pro Pro Gly Leu<br>1170                  1175                  1180                  1185 | | 3601 |
| agg gag aag gca gag tat ctt ctg agg gaa tgg gtg aat ctc tac cat<br>Arg Glu Lys Ala Glu Tyr Leu Leu Arg Glu Trp Val Asn Leu Tyr His<br>                1190                  1195                  1200 | | 3649 |
| tca gca gca gct ggc cgc gac agt acc aaa gct ttc tct gca ttt gtt<br>Ser Ala Ala Ala Gly Arg Asp Ser Thr Lys Ala Phe Ser Ala Phe Val<br>            1205                  1210                  1215 | | 3697 |
| gga cag atg cac cag caa gga ata ctg aag acc gat gat ctc ata aca<br>Gly Gln Met His Gln Gln Gly Ile Leu Lys Thr Asp Asp Leu Ile Thr<br>                1220                  1225                  1230 | | 3745 |
| agg ttc ttt cgt ctg tgt act gaa atg tgt gtt gaa atc agt tac cgt<br>Arg Phe Phe Arg Leu Cys Thr Glu Met Cys Val Glu Ile Ser Tyr Arg<br>            1235                  1240                  1245 | | 3793 |
| gct cag gct gag cag cag cac aat cct gct gcc aat ccc acc atg atc<br>Ala Gln Ala Glu Gln Gln His Asn Pro Ala Ala Asn Pro Thr Met Ile<br>1250                  1255                  1260                  1265 | | 3841 |
| cga gcc aag tgc tat cac aac ctg gat gcc ttt gtt cga ctc att gca<br>Arg Ala Lys Cys Tyr His Asn Leu Asp Ala Phe Val Arg Leu Ile Ala<br>1270                  1275                  1280 | | 3889 |
| ctg ctc gtg aaa cac tca ggg gag gcc acc aac act gtc aca aag att<br>Leu Leu Val Lys His Ser Gly Glu Ala Thr Asn Thr Val Thr Lys Ile<br>1285                  1290                  1295 | | 3937 |
| aat ctg ctg aac aag gtc ctt ggt ata gta gtg gga gtt ctc ctt cag<br>Asn Leu Leu Asn Lys Val Leu Gly Ile Val Val Gly Val Leu Leu Gln<br>1300                  1305                  1310 | | 3985 |
| gat cat gat gtt cgt cag agt gaa ttt cag caa ctt ccc tac cat cga<br>Asp His Asp Val Arg Gln Ser Glu Phe Gln Gln Leu Pro Tyr His Arg | | 4033 |

-continued

```
        1315                1320                1325
att ttt atc atg ctt ctc ttg gaa ctc aat gca cct gag cat gtg ttg     4081
Ile Phe Ile Met Leu Leu Leu Glu Leu Asn Ala Pro Glu His Val Leu
1330                1335                1340                1345 gaa acc att aat ttc cag aca ctt aca gct ttc tgc aat aca ttc cac     4129
Glu Thr Ile Asn Phe Gln Thr Leu Thr Ala Phe Cys Asn Thr Phe His
                    1350                1355                1360 atc ttg agg cct acc aaa gct cct ggc ttt gta tat gcc tgg ctt gaa     4177
Ile Leu Arg Pro Thr Lys Ala Pro Gly Phe Val Tyr Ala Trp Leu Glu
            1365                1370                1375 ctg att tcc cat cgg ata ttt att gca aga atg ctg gca cat acg cca     4225
Leu Ile Ser His Arg Ile Phe Ile Ala Arg Met Leu Ala His Thr Pro
        1380                1385                1390 cag cag aag ggg tgg cct atg tat gca cag cta ctg att gat tta ttc     4273
Gln Gln Lys Gly Trp Pro Met Tyr Ala Gln Leu Leu Ile Asp Leu Phe
    1395                1400                1405 aaa tat tta gcg cct ttc ctt aga aat gtg gaa ctc acc aaa cct atg     4321
Lys Tyr Leu Ala Pro Phe Leu Arg Asn Val Glu Leu Thr Lys Pro Met
1410                1415                1420                1425 caa atc ctc tac aag ggc act tta aga gtg ctg ctg gtt ctt ttg cat     4369
Gln Ile Leu Tyr Lys Gly Thr Leu Arg Val Leu Leu Val Leu Leu His
                    1430                1435                1440 gat ttc cca gag ttc ctt tgt gat tac cat tat ggg ttc tgt gat gtg     4417
Asp Phe Pro Glu Phe Leu Cys Asp Tyr His Tyr Gly Phe Cys Asp Val
            1445                1450                1455 atc cca cct aat tgt atc cag tta aga aat ttg atc ctg agt gcc ttt     4465
Ile Pro Pro Asn Cys Ile Gln Leu Arg Asn Leu Ile Leu Ser Ala Phe
        1460                1465                1470 cca aga aac atg agg ctc ccc gac cca ttc act cct aat cta aag gtg     4513
Pro Arg Asn Met Arg Leu Pro Asp Pro Phe Thr Pro Asn Leu Lys Val
    1475                1480                1485 gac atg ttg agt gaa att aac att gct ccc cgg att ctc acc aat ttc     4561
Asp Met Leu Ser Glu Ile Asn Ile Ala Pro Arg Ile Leu Thr Asn Phe
1490                1495                1500                1505 act gga gta atg cca cct cag ttc aaa aag gat ttg gat tcc tat ctt     4609
Thr Gly Val Met Pro Pro Gln Phe Lys Lys Asp Leu Asp Ser Tyr Leu
                    1510                1515                1520 aaa act cga tca cca gtc act ttc ctg tct gat ctg cgc agc aac cta     4657
Lys Thr Arg Ser Pro Val Thr Phe Leu Ser Asp Leu Arg Ser Asn Leu
            1525                1530                1535 cag gta tcc aat gaa cct ggg aat cgc tac aac ctc cag ctc atc aat     4705
Gln Val Ser Asn Glu Pro Gly Asn Arg Tyr Asn Leu Gln Leu Ile Asn
        1540                1545                1550 gca ctg gtg ctc tat gtc ggg act cag gcc att gcg cac atc cac aac     4753
Ala Leu Val Leu Tyr Val Gly Thr Gln Ala Ile Ala His Ile His Asn
    1555                1560                1565 aag ggc agc aca cct tca atg agc acc atc act cac tca gca cac atg     4801
Lys Gly Ser Thr Pro Ser Met Ser Thr Ile Thr His Ser Ala His Met
1570                1575                1580                1585 gat atc ttc cag aat ttg gct gtg gac ttg gac act gag ggt cgc tat     4849
Asp Ile Phe Gln Asn Leu Ala Val Asp Leu Asp Thr Glu Gly Arg Tyr
                    1590                1595                1600 ctc ttt ttg aat gca att gca aat cag ctc cgg tac cca aat agc cac     4897
Leu Phe Leu Asn Ala Ile Ala Asn Gln Leu Arg Tyr Pro Asn Ser His
            1605                1610                1615 act cac tac ttc agt tgc acc atg ctg tac ctt ttt gca gag gcc aat     4945
Thr His Tyr Phe Ser Cys Thr Met Leu Tyr Leu Phe Ala Glu Ala Asn
        1620                1625                1630 acg gaa gcc atc caa gaa cag atc aca aga gtt ctc ttg gaa cgg ttg     4993
```

-continued

```
Thr Glu Ala Ile Gln Glu Gln Ile Thr Arg Val Leu Leu Glu Arg Leu
    1635                1640                1645 att gta aat agg cca cat cct tgg ggt ctt ctt att acc ttc att gag    5041
Ile Val Asn Arg Pro His Pro Trp Gly Leu Leu Ile Thr Phe Ile Glu
1650                1655                1660                1665 ctg att aaa aac cca gcg ttt aag ttc tgg aac cat gaa ttt gta cac    5089
Leu Ile Lys Asn Pro Ala Phe Lys Phe Trp Asn His Glu Phe Val His
            1670                1675                1680 tgt gcc cca gaa atc gaa aag tta ttc cag tcg gtc gca cag tgc tgc    5137
Cys Ala Pro Glu Ile Glu Lys Leu Phe Gln Ser Val Ala Gln Cys Cys
        1685                1690                1695 atg gga cag aag cag gcc cag caa gta atg gaa ggg aca ggt gcc agt    5185
Met Gly Gln Lys Gln Ala Gln Gln Val Met Glu Gly Thr Gly Ala Ser
    1700                1705                1710 tagacgaaac tgcatctctg ttgtacgtgt cagtctagag gtctcactgc accgagttca    5245
taaactgact gaagaatcct ttcagctctt cctgactttc ccagcccttt ggtttgtggg    5305
tatctgcccc aactactgtt gggatcagcc tcctgtctta tgtgggcacg ttccaaagtt    5365
taaatgcatt tttttgactc ttggccaaaa tttagaagat gctgtgaata tcattttgaa    5425
cttgtgtaaa tacatgaaaa aaaaaaaaaa aa                                   5457
```

<210> SEQ ID NO 61
<211> LENGTH: 453
<212> TYPE: PRT
<213> ORGANISM: Homo sapiens

<400> SEQUENCE: 61

```
Met Lys Leu Leu Val Ile Leu Phe Ser Gly Leu Ile Thr Gly Phe
-15                 -10                 -5                  -1  1

Arg Ser Asp Ser Ser Ser Leu Pro Pro Lys Leu Leu Leu Val Ser
                5                   10                  15

Phe Asp Gly Phe Arg Ala Asp Tyr Leu Lys Asn Tyr Glu Phe Pro His
                20                  25                  30

Leu Gln Asn Phe Ile Lys Glu Gly Val Leu Val Glu His Val Lys Asn
            35                  40                  45

Val Phe Ile Thr Lys Thr Phe Pro Asn His Tyr Ser Ile Val Thr Gly
50                  55                  60                  65

Leu Tyr Glu Glu Ser His Gly Ile Val Ala Asn Ser Met Tyr Asp Ala
                70                  75                  80

Val Thr Lys Lys His Phe Ser Asp Ser Asn Lys Asp Pro Phe Trp
            85                  90                  95

Trp Asn Glu Ala Val Pro Ile Trp Val Thr Asn Gln Leu Gln Glu Asn
        100                 105                 110

Arg Ser Ser Ala Ala Ala Met Trp Pro Gly Thr Asp Val Pro Ile His
    115                 120                 125

Asp Thr Ile Ser Ser Tyr Phe Met Asn Tyr Asn Ser Val Ser Phe
130                 135                 140                 145

Glu Glu Arg Leu Asn Asn Ile Thr Met Trp Leu Asn Asn Ser Asn Pro
                150                 155                 160

Pro Val Thr Phe Ala Thr Leu Tyr Trp Glu Glu Pro Asp Ala Ser Gly
            165                 170                 175

His Lys Tyr Gly Pro Glu Asp Lys Glu Asn Met Ser Arg Val Leu Lys
        180                 185                 190

Lys Ile Asp Asp Leu Ile Gly Asp Leu Val Gln Arg Leu Lys Met Leu
    195                 200                 205
```

Gly Leu Trp Glu Asn Leu Asn Val Ile Ile Thr Ser Asp His Gly Met
210                 215                 220                 225

Thr Gln Cys Ser Gln Asp Arg Leu Ile Asn Leu Asp Ser Cys Ile Asp
            230                 235                 240

His Ser Tyr Tyr Thr Leu Ile Asp Leu Ser Pro Val Ala Ala Ile Leu
        245                 250                 255

Pro Lys Ile Asn Arg Thr Glu Val Tyr Asn Lys Leu Lys Asn Cys Ser
    260                 265                 270

Pro His Met Asn Val Tyr Leu Lys Glu Asp Ile Pro Asn Arg Phe Tyr
275                 280                 285

Tyr Gln His Asn Asp Arg Ile Gln Pro Ile Ile Leu Val Ala Asp Glu
290                 295                 300                 305

Gly Trp Thr Ile Val Leu Asn Glu Ser Ser Gln Lys Leu Gly Asp His
                310                 315                 320

Gly Tyr Asp Asn Ser Leu Pro Ser Met His Pro Phe Leu Ala Ala His
            325                 330                 335

Gly Pro Ala Phe His Lys Gly Tyr Lys His Ser Thr Ile Asn Ile Val
        340                 345                 350

Asp Ile Tyr Pro Met Met Cys His Ile Leu Gly Leu Lys Pro His Pro
    355                 360                 365

Asn Asn Gly Thr Phe Gly His Thr Lys Cys Leu Leu Val Asp Gln Trp
370                 375                 380                 385

Cys Ile Asn Leu Pro Glu Ala Ile Ala Ile Val Ile Gly Ser Leu Leu
                390                 395                 400

Val Leu Thr Met Leu Thr Cys Leu Ile Ile Met Gln Asn Arg Leu
            405                 410                 415

Ser Val Pro Arg Pro Phe Ser Arg Leu Gln Leu Gln Glu Asp Asp
        420                 425                 430

Asp Pro Leu Ile Gly
    435

<210> SEQ ID NO 62
<211> LENGTH: 1359
<212> TYPE: DNA
<213> ORGANISM: Homo sapiens

<400> SEQUENCE: 62
atgaagttat tagtaatact tttgttttct ggacttataa ctggttttag aagtgactct      60
tcctctagtt tgccacctaa gttactacta gtatcctttg atggcttcag agctgattat     120
ctgaagaact atgaatttcc tcatctccag aattttatca agaaggtgt tttggtagag      180 catgttaaaa atgttttat cacaaaaaca tttccaaacc actacagtat tgtgacaggc      240
ttgtatgaag aaagccatgg cattgtggct aattccatgt atgatgcagt cacaaagaaa     300 cactttctg actctaatga caaggatcct ttttggtgga atgaggcagt acctatttgg      360
gtgaccaatc agcttcagga aaacagatca agtgctgctg ctatgtggcc tggtactgat     420
gtacccattc acgataccat ctcttcctat tttatgaatt acaactcctc agtgtcattt     480
gaggaaagac taaataatat tactatgtgg ctaaacaatt cgaacccacc agtcaccttt     540
gcaacactat attgggaaga accagatgca agtggccaca atacggacc tgaagataaa     600 gaaaacatga gcagagtgtt gaaaaaata tgatgatctta tcggtgactt agtccaaaga     660
ctcaagatgt tagggctatg ggaaaatctt aatgtgatca ttacaagtga tcatgggatg     720
acccagtgtt ctcaggacag actgataaac ctggattcct gcatcgatca ttcatactac     780

-continued

```
actcttatag atttgagccc agttgctgca atacttccca aaataaatag aacagaggtt      840
tataacaaac tgaaaaactg tagccctcat atgaatgttt atctcaaaga agacattcct      900
aacagatttt attaccaaca taatgatcga attcagccca ttattttggt tgccgatgaa      960
ggctggacaa ttgtgctaaa tgaatcatca caaaaattag gtgaccatgg ttatgataat     1020
tctttgccta gtatgcatcc atttctagct gcccacggac ctgcatttca caaaggctac     1080
aagcatagca caattaacat tgtggatatt tatccaatga tgtgccacat cctgggatta     1140
aaaccacatc ccaataatgg gacctttggt catactaagt gcttgttagt tgaccagtgg     1200
tgcattaatc tcccagaagc catcgcgatt gttatcggtt cactcttggt gttaaccatg     1260
ctaacatgcc tcataataat catgcagaat agactttctg tacctcgtcc attttctcga     1320
cttcagctac aagaagatga tgatgatccc ttaattggg                            1359
```

<210> SEQ ID NO 63
<211> LENGTH: 2044
<212> TYPE: DNA
<213> ORGANISM: Homo sapiens
<220> FEATURE:
<221> NAME/KEY: sig_peptide
<222> LOCATION: (70)..(114)
<220> FEATURE:
<221> NAME/KEY: mat_peptide
<222> LOCATION: (115)..(1428)
<220> FEATURE:
<221> NAME/KEY: CDS
<222> LOCATION: (70)..(1428)

<400> SEQUENCE: 63

```
gttccgcgca ttggaaagaa gcgaccgcgg cggctggaac cctgattgct gtccttcaac       60 gtgttcatt atg aag tta tta gta ata ctt ttg ttt tct gga ctt ata act      111
           Met Lys Leu Leu Val Ile Leu Leu Phe Ser Gly Leu Ile Thr
               -15                 -10                  -5 ggt ttt aga agt gac tct tcc tct agt ttg cca cct aag tta cta cta       159
Gly Phe Arg Ser Asp Ser Ser Ser Ser Leu Pro Pro Lys Leu Leu Leu
 -1   1               5                  10                  15 gta tcc ttt gat ggc ttc aga gct gat tat ctg aag aac tat gaa ttt       207
Val Ser Phe Asp Gly Phe Arg Ala Asp Tyr Leu Lys Asn Tyr Glu Phe
                 20                  25                  30 cct cat ctc cag aat ttt atc aaa gaa ggt gtt ttg gta gag cat gtt       255
Pro His Leu Gln Asn Phe Ile Lys Glu Gly Val Leu Val Glu His Val
             35                  40                  45 aaa aat gtt ttt atc aca aaa aca ttt cca aac cac tac agt att gtg       303
Lys Asn Val Phe Ile Thr Lys Thr Phe Pro Asn His Tyr Ser Ile Val
         50                  55                  60 aca ggc ttg tat gaa gaa agc cat ggc att gtg gct aat tcc atg tat       351
Thr Gly Leu Tyr Glu Glu Ser His Gly Ile Val Ala Asn Ser Met Tyr
     65                  70                  75 gat gca gtc aca aag aaa cac ttt tct gac tct aat gac aag gat cct       399
Asp Ala Val Thr Lys Lys His Phe Ser Asp Ser Asn Asp Lys Asp Pro
 80                  85                  90                  95 ttt tgg tgg aat gag gca gta cct att tgg gtg acc aat cag ctt cag       447
Phe Trp Trp Asn Glu Ala Val Pro Ile Trp Val Thr Asn Gln Leu Gln
                100                 105                 110 gaa aac aga tca agt gct gct gct atg tgg cct ggt act gat gta ccc       495
Glu Asn Arg Ser Ser Ala Ala Ala Met Trp Pro Gly Thr Asp Val Pro
             115                 120                 125 att cac gat acc atc tct tcc tat ttt atg aat tac aac tcc tca gtg       543
Ile His Asp Thr Ile Ser Ser Tyr Phe Met Asn Tyr Asn Ser Ser Val
         130                 135                 140
```

```
tca ttt gag gaa aga cta aat aat att act atg tgg cta aac aat tcg    591
Ser Phe Glu Glu Arg Leu Asn Asn Ile Thr Met Trp Leu Asn Asn Ser
    145                 150                 155 aac cca cca gtc acc ttt gca aca cta tat tgg gaa gaa cca gat gca    639
Asn Pro Pro Val Thr Phe Ala Thr Leu Tyr Trp Glu Glu Pro Asp Ala
160                 165                 170                 175 agt ggc cac aaa tac gga cct gaa gat aaa gaa aac atg agc aga gtg    687
Ser Gly His Lys Tyr Gly Pro Glu Asp Lys Glu Asn Met Ser Arg Val
                180                 185                 190 ttg aaa aaa ata gat gat ctt atc ggt gac tta gtc caa aga ctc aag    735
Leu Lys Lys Ile Asp Asp Leu Ile Gly Asp Leu Val Gln Arg Leu Lys
                    195                 200                 205 atg tta ggg cta tgg gaa aat ctt aat gtg atc att aca agt gat cat    783
Met Leu Gly Leu Trp Glu Asn Leu Asn Val Ile Ile Thr Ser Asp His
            210                 215                 220 ggg atg acc cag tgt tct cag gac aga ctg ata aac ctg gat tcc tgc    831
Gly Met Thr Gln Cys Ser Gln Asp Arg Leu Ile Asn Leu Asp Ser Cys
        225                 230                 235 atc gat cat tca tac tac act ctt ata gat ttg agc cca gtt gct gca    879
Ile Asp His Ser Tyr Tyr Thr Leu Ile Asp Leu Ser Pro Val Ala Ala
240                 245                 250                 255 ata ctt ccc aaa ata aat aga aca gag gtt tat aac aaa ctg aaa aac    927
Ile Leu Pro Lys Ile Asn Arg Thr Glu Val Tyr Asn Lys Leu Lys Asn
                260                 265                 270 tgt agc cct cat atg aat gtt tat ctc aaa gaa gac att cct aac aga    975
Cys Ser Pro His Met Asn Val Tyr Leu Lys Glu Asp Ile Pro Asn Arg
                275                 280                 285 ttt tat tac caa cat aat gat cga att cag ccc att att ttg gtt gcc   1023
Phe Tyr Tyr Gln His Asn Asp Arg Ile Gln Pro Ile Ile Leu Val Ala
            290                 295                 300 gat gaa ggc tgg aca att gtg cta aat gaa tca tca caa aaa tta ggt   1071
Asp Glu Gly Trp Thr Ile Val Leu Asn Glu Ser Ser Gln Lys Leu Gly
        305                 310                 315 gac cat ggt tat gat aat tct ttg cct agt atg cat cca ttt cta gct   1119
Asp His Gly Tyr Asp Asn Ser Leu Pro Ser Met His Pro Phe Leu Ala
320                 325                 330                 335 gcc cac gga cct gca ttt cac aaa ggc tac aag cat agc aca att aac   1167
Ala His Gly Pro Ala Phe His Lys Gly Tyr Lys His Ser Thr Ile Asn
                340                 345                 350 att gtg gat att tat cca atg atg tgc cac atc ctg gga tta aaa cca   1215
Ile Val Asp Ile Tyr Pro Met Met Cys His Ile Leu Gly Leu Lys Pro
                355                 360                 365 cat ccc aat aat ggg acc ttt ggt cat act aag tgc ttg tta gtt gac   1263
His Pro Asn Asn Gly Thr Phe Gly His Thr Lys Cys Leu Leu Val Asp
            370                 375                 380 cag tgg tgc att aat ctc cca gaa gcc atc gcg att gtt atc ggt tca   1311
Gln Trp Cys Ile Asn Leu Pro Glu Ala Ile Ala Ile Val Ile Gly Ser
385                 390                 395 ctc ttg gtg tta acc atg cta aca tgc ctc ata ata atc atg cag aat   1359
Leu Leu Val Leu Thr Met Leu Thr Cys Leu Ile Ile Ile Met Gln Asn
400                 405                 410                 415 aga ctt tct gta cct cgt cca ttt tct cga ctt cag cta caa gaa gat   1407
Arg Leu Ser Val Pro Arg Pro Phe Ser Arg Leu Gln Leu Gln Glu Asp
                420                 425                 430 gat gat gat ccc tta att ggg tgacatgtgc tagggcttat acaaagtgtc      1458
Asp Asp Asp Pro Leu Ile Gly
                435 tttgattaat cacaaaacta agaatacatc caaagaatag tgttgtaact atgaaaaga   1518 atactttgaa agacaaagaa cttagactaa gcatgttaaa attattactt tgttttcctt   1578
```

-continued

```
gtgttttgtt tcggtgcatt tgctaataag ataacgctga ccatagtaaa attgttagta    1638
aatcattagg taacatcttg tggtaggaaa tcattaggta acatcaatcc taactagaaa    1698
tactaaaaat ggcttttgag aaaaatactt cctctgcttg tattttgcga tgaagatgtg    1758
atacatcttt aaatgaaaat ataccaaaat ttagtaggca tgttttcta ataaatttat     1818 atatttgtaa agaaacaac agaaatcttt atgcaatttg tgaattttgt atattaggga     1878
ggaaaagctt cctatatttt tatatttacc tttaattagt ttgtatctca agtaccctct    1938
tgaggtagga aatgctctgt gatggtaaat aaaattggag cagacagaaa agatatagca    1998
aatgaagaaa tattttaagg aaacctattt gaaaaaaaaa aacaaa                   2044
```

<210> SEQ ID NO 64
<211> LENGTH: 708
<212> TYPE: PRT
<213> ORGANISM: Homo sapiens

<400> SEQUENCE: 64

```
Met Lys Asp Met Pro Leu Arg Ile His Val Leu Leu Gly Leu Ala Ile
        -20             -15                 -10

Thr Thr Leu Val Gln Ala Val Asp Lys Lys Val Asp Cys Pro Arg Leu
    -5                  -1   1               5                  10

Cys Thr Cys Glu Ile Arg Pro Trp Phe Thr Pro Arg Ser Ile Tyr Met
                15                  20                  25

Glu Ala Ser Thr Val Asp Cys Asn Asp Leu Gly Leu Leu Thr Phe Pro
                30                  35                  40

Ala Arg Leu Pro Ala Asn Thr Gln Ile Leu Leu Leu Gln Thr Asn Asn
                45                  50                  55

Ile Ala Lys Ile Glu Tyr Ser Thr Asp Phe Pro Val Asn Leu Thr Gly
    60                  65                  70

Leu Asp Leu Ser Gln Asn Asn Leu Ser Ser Val Thr Asn Ile Asn Val
75                  80                  85                  90

Lys Lys Met Pro Gln Leu Leu Ser Val Tyr Leu Glu Glu Asn Lys Leu
                95                  100                 105

Thr Glu Leu Pro Glu Lys Cys Leu Ser Glu Leu Ser Asn Leu Gln Glu
                110                 115                 120

Leu Tyr Ile Asn His Asn Leu Leu Ser Thr Ile Ser Pro Gly Ala Phe
                125                 130                 135

Ile Gly Leu His Asn Leu Leu Arg Leu His Leu Asn Ser Asn Arg Leu
                140                 145                 150

Gln Met Ile Asn Ser Lys Trp Phe Asp Ala Leu Pro Asn Leu Glu Ile
155                 160                 165                 170

Leu Met Ile Gly Glu Asn Pro Ile Ile Arg Ile Lys Asp Met Asn Phe
                175                 180                 185

Lys Pro Leu Ile Asn Leu Arg Ser Leu Val Ile Ala Gly Ile Asn Leu
                190                 195                 200

Thr Glu Ile Pro Asp Asn Ala Leu Val Gly Leu Glu Asn Leu Glu Ser
                205                 210                 215

Ile Ser Phe Tyr Asp Asn Arg Leu Ile Lys Val Pro His Val Ala Leu
                220                 225                 230

Gln Lys Val Val Asn Leu Lys Phe Leu Asp Leu Asn Lys Asn Pro Ile
235                 240                 245                 250

Asn Arg Ile Arg Arg Gly Asp Phe Ser Asn Met Leu His Leu Lys Glu
                255                 260                 265
```

```
Leu Gly Ile Asn Asn Met Pro Glu Leu Ile Ser Ile Asp Ser Leu Ala
            270                 275                 280

Val Asp Asn Leu Pro Asp Leu Arg Lys Ile Glu Ala Thr Asn Asn Pro
        285                 290                 295

Arg Leu Ser Tyr Ile His Pro Asn Ala Phe Phe Arg Leu Pro Lys Leu
    300                 305                 310

Glu Ser Leu Met Leu Asn Ser Asn Ala Leu Ser Ala Leu Tyr His Gly
315                 320                 325                 330

Thr Ile Glu Ser Leu Pro Asn Leu Lys Glu Ile Ser Ile His Ser Asn
                335                 340                 345

Pro Ile Arg Cys Asp Cys Val Ile Arg Trp Met Asn Met Asn Lys Thr
            350                 355                 360

Asn Ile Arg Phe Met Glu Pro Asp Ser Leu Phe Cys Val Asp Pro Pro
        365                 370                 375

Glu Phe Gln Gly Gln Asn Val Arg Gln Val His Phe Arg Asp Met Met
    380                 385                 390

Glu Ile Cys Leu Pro Leu Ile Ala Pro Glu Ser Phe Pro Ser Asn Leu
395                 400                 405                 410

Asn Val Glu Ala Gly Ser Tyr Val Ser Phe His Cys Arg Ala Thr Ala
                415                 420                 425

Glu Pro Gln Pro Glu Ile Tyr Trp Ile Thr Pro Ser Gly Gln Lys Leu
            430                 435                 440

Leu Pro Asn Thr Leu Thr Asp Lys Phe Tyr Val His Ser Glu Gly Thr
        445                 450                 455

Leu Asp Ile Asn Gly Val Thr Pro Lys Glu Gly Leu Tyr Thr Cys
    460                 465                 470

Ile Ala Thr Asn Leu Val Gly Ala Asp Leu Lys Ser Val Met Ile Lys
475                 480                 485                 490

Val Asp Gly Ser Phe Pro Gln Asp Asn Gly Ser Leu Asn Ile Lys
                495                 500                 505

Ile Arg Asp Ile Gln Ala Asn Ser Val Leu Val Ser Trp Lys Ala Ser
            510                 515                 520

Ser Lys Ile Leu Lys Ser Ser Val Lys Trp Thr Ala Phe Val Lys Thr
        525                 530                 535

Glu Asn Ser His Ala Ala Gln Ser Ala Arg Ile Pro Ser Asp Val Lys
    540                 545                 550

Val Tyr Asn Leu Thr His Leu Asn Pro Ser Thr Glu Tyr Lys Ile Cys
555                 560                 565                 570

Ile Asp Ile Pro Thr Ile Tyr Gln Lys Asn Arg Lys Cys Val Asn
                575                 580                 585

Val Thr Thr Lys Gly Leu His Pro Asp Gln Lys Glu Tyr Glu Lys Asn
            590                 595                 600

Asn Thr Thr Thr Leu Met Ala Cys Leu Gly Gly Leu Leu Gly Ile Ile
        605                 610                 615

Gly Val Ile Cys Leu Ile Ser Cys Leu Ser Pro Glu Met Asn Cys Asp
    620                 625                 630

Gly Gly His Ser Tyr Val Arg Asn Tyr Leu Gln Lys Pro Thr Phe Ala
635                 640                 645                 650

Leu Gly Glu Leu Tyr Pro Pro Leu Ile Asn Leu Trp Glu Ala Gly Lys
                655                 660                 665

Glu Lys Ser Thr Ser Leu Lys Val Lys Ala Thr Val Ile Gly Leu Pro
            670                 675                 680

Thr Asn Met Ser
```

<210> SEQ ID NO 65
<211> LENGTH: 2124
<212> TYPE: DNA
<213> ORGANISM: Homo sapiens

<400> SEQUENCE: 65

| | | | | | |
|---|---|---|---|---|---|
| atgaaggaca | tgccactccg | aattcatgtg | ctacttggcc | tagctatcac | tacactagta | 60 |
| caagctgtag | ataaaaaagt | ggattgtcca | cggttatgta | cgtgtgaaat | caggccttgg | 120 |
| tttacaccca | gatccattta | tatggaagca | tctacagtgg | attgtaatga | tttaggtctt | 180 |
| ttaactttcc | cagccagatt | gccagctaac | acacagattc | ttctcctaca | gactaacaat | 240 |
| attgcaaaaa | ttgaatactc | cacagacttt | ccagtaaacc | ttactggcct | ggatttatct | 300 |
| caaaacaatt | tatcttcagt | caccaatatt | aatgtaaaaa | agatgcctca | gctcctttct | 360 |
| gtgtacctag | aggaaaacaa | acttactgaa | ctgcctgaaa | aatgtctgtc | cgaactgagc | 420 |
| aacttacaag | aactctatat | taatcacaac | ttgctttcta | caatttcacc | tggagccttt | 480 |
| attggcctac | ataatcttct | tcgacttcat | ctcaattcaa | atagattgca | gatgatcaac | 540 |
| agtaagtggt | ttgatgctct | tccaaatcta | gagattctga | tgattgggga | aaatccaatt | 600 |
| atcagaatca | agacatgaa | ctttaagcct | cttatcaatc | ttcgcagcct | ggttatagct | 660 |
| ggtataaacc | tcacagaaat | accagataac | gccttggttg | gactggaaaa | cttagaaagc | 720 |
| atctcttttt | acgataacag | gcttattaaa | gtaccccatg | ttgctcttca | aaaagttgta | 780 |
| aatctcaaat | ttttggatct | aaataaaaat | cctattaata | gaatacgaag | gggtgatttt | 840 |
| agcaatatgc | tacacttaaa | agagttgggg | ataaataata | tgcctgagct | gatttccatc | 900 |
| gatagtcttg | ctgtggataa | cctgccagat | ttaagaaaaa | tagaagctac | taacaaccct | 960 |
| agattgtctt | acattcaccc | caatgcattt | ttcagactcc | ccaagctgga | atcactcatg | 1020 |
| ctgaacagca | atgctctcag | tgccctgtac | catggtacca | ttgagtctct | gccaaacctc | 1080 |
| aaggaaatca | gcatacacag | taaccccatc | aggtgtgact | gtgtcatccg | ttggatgaac | 1140 |
| atgaacaaaa | ccaacattcg | attcatggag | ccagattcac | tgttttgcgt | ggacccacct | 1200 |
| gaattccaag | tcagaatgt | tcggcaagtg | catttcaggg | acatgatgga | aatttgtctc | 1260 |
| cctcttatag | ctcctgagag | cttccttct | aatctaaatg | tagaagctgg | gagctatgtt | 1320 |
| tcctttcact | gtagagctac | tgcagaacca | cagcctgaaa | tctactggat | aacaccttct | 1380 |
| ggtcaaaaac | tcttgcctaa | taccctgaca | gacaagttct | atgtccattc | tgagggaaca | 1440 |
| ctagatataa | atggcgtaac | tcccaaagaa | gggggtttat | atacttgtat | agcaactaac | 1500 |
| ctagttggcg | ctgacttgaa | gtctgttatg | atcaaagtgg | atggatcttt | tccacaagat | 1560 |
| aacaatggct | ctttgaatat | taaaataaga | gatattcagg | ccaattcagt | tttggtgtcc | 1620 |
| tggaaagcaa | gttctaaaat | tctcaaatct | agtgttaaat | ggacagcctt | tgtcaagact | 1680 |
| gaaaattctc | atgctgcgca | aagtgctcga | ataccatctg | atgtcaaggt | atataatctt | 1740 |
| actcatctga | atcatcaac | tgagtataaa | atttgtattg | atattccac | catctatcag | 1800 |
| aaaaacagaa | aaaatgtgt | aaatgtcacc | accaaaggtt | tgcaccctga | tcaaaaagag | 1860 |
| tatgaaaaga | ataataccac | aacacttatg | gcctgtcttg | gaggccttct | ggggattatt | 1920 |
| ggtgtgatat | gtcttatcag | ctgcctctct | ccagaaatga | actgtgatgg | tggacacagc | 1980 |
| tatgtgagga | attacttaca | gaaaccaacc | tttgcattag | gtgagcttta | tcctcctctg | 2040 |
| ataaatctct | gggaagcagg | aaaagaaaaa | agtacatcac | tgaaagtaaa | agcaactgtt | 2100 |

-continued

```
ataggtttac caacaaatat gtcc                                          2124
```

<210> SEQ ID NO 66
<211> LENGTH: 3068
<212> TYPE: DNA
<213> ORGANISM: Homo sapiens
<220> FEATURE:
<221> NAME/KEY: sig_peptide
<222> LOCATION: (894)..(959)
<220> FEATURE:
<221> NAME/KEY: mat_peptide
<222> LOCATION: (960)..(3017)
<220> FEATURE:
<221> NAME/KEY: CDS
<222> LOCATION: (894)..(3017)

<400> SEQUENCE: 66

```
gtctgaagcg attggctcct ctctggggag tggagggtgt tcagttatta atgaccgctg    60
agcaggcagc accatgtcag tgtgacaact gatcgggtga acgatgcacc actaaccacc   120
atggaaacaa ggaaaaataa agccagctca caggatctct cttcactgga ttgagagcct   180
cagcctgccg actgagaaaa agagttccag gaaaagaag gaatcccggc tgcagcctcc    240
tgccttcctt tatattttaa aatagagaga taagattgcg tgcatgtgtg catatctata   300
gtatatattt tgtacacttt gttacacaga cacacaaatg cacctatta taccgggcaa    360 gaacacaacc atgtgattat ctcaaccaag gaactgagga atccagcacg caaggacatc   420
ggaggtgggc tagcactgaa actgcttttc aagacgagga agaggaggag aaagagaaag   480
aagaggaaga tgttgggcaa catttattta acatgctcca cagcccggac cctggcatca   540
tgctgctatt cctgcaaata ctgaagaagc atgggattta atattttac ttctaaataa    600 atgaattact caatctccta tgaccatcta tacatactcc accttcaaaa agtacatcaa   660
tattatatca ttaaggaaat agtaaccttc tcttctccaa tatgcatgac attttttggac  720 aatgcaattg tggcactggc acttatttca gtgaagaaaa actttgtggt tctatggcat   780
tcatcatttg acaaatgcaa gcatcttcct tatcaatcag ctcctattga acttactagc   840
actgactgtg gaatccttaa gggcccatta catttctgaa gaagaaagct aag atg      896
                                                             Met
```

```
aag gac atg cca ctc cga att cat gtg cta ctt ggc cta gct atc act    944
Lys Asp Met Pro Leu Arg Ile His Val Leu Leu Gly Leu Ala Ile Thr
        -20                 -15                 -10 aca cta gta caa gct gta gat aaa aaa gtg gat tgt cca cgg tta tgt    992
Thr Leu Val Gln Ala Val Asp Lys Lys Val Asp Cys Pro Arg Leu Cys
 -5                 -1  1               5                 10 acg tgt gaa atc agg cct tgg ttt aca ccc aga tcc att tat atg gaa   1040
Thr Cys Glu Ile Arg Pro Trp Phe Thr Pro Arg Ser Ile Tyr Met Glu
             15                  20                 25 gca tct aca gtg gat tgt aat gat tta ggt ctt tta act ttc cca gcc   1088
Ala Ser Thr Val Asp Cys Asn Asp Leu Gly Leu Leu Thr Phe Pro Ala
         30                  35                  40 aga ttg cca gct aac aca cag att ctt ctc cta cag act aac aat att   1136
Arg Leu Pro Ala Asn Thr Gln Ile Leu Leu Leu Gln Thr Asn Asn Ile
     45                  50                  55 gca aaa att gaa tac tcc aca gac ttt cca gta aac ctt act ggc ctg   1184
Ala Lys Ile Glu Tyr Ser Thr Asp Phe Pro Val Asn Leu Thr Gly Leu
 60                  65                  70                  75 gat tta tct caa aac aat tta tct tca gtc acc aat att aat gta aaa   1232
Asp Leu Ser Gln Asn Asn Leu Ser Ser Val Thr Asn Ile Asn Val Lys
                 80                  85                  90
```

| | | | | | | | | | | | | | | | |
|---|---|---|---|---|---|---|---|---|---|---|---|---|---|---|---|
| aag | atg | cct | cag | ctc | ctt | tct | gtg | tac | cta | gag | gaa | aac | aaa | ctt | act | 1280
| Lys | Met | Pro | Gln | Leu | Leu | Ser | Val | Tyr | Leu | Glu | Glu | Asn | Lys | Leu | Thr |
| | | | 95 | | | | | 100 | | | | | 105 | | |

```
aag atg cct cag ctc ctt tct gtg tac cta gag gaa aac aaa ctt act     1280
Lys Met Pro Gln Leu Leu Ser Val Tyr Leu Glu Glu Asn Lys Leu Thr
            95                  100                 105 gaa ctg cct gaa aaa tgt ctg tcc gaa ctg agc aac tta caa gaa ctc     1328
Glu Leu Pro Glu Lys Cys Leu Ser Glu Leu Ser Asn Leu Gln Glu Leu
        110                 115                 120 tat att aat cac aac ttg ctt tct aca att tca cct gga gcc ttt att     1376
Tyr Ile Asn His Asn Leu Leu Ser Thr Ile Ser Pro Gly Ala Phe Ile
    125                 130                 135 ggc cta cat aat ctt ctt cga ctt cat ctc aat tca aat aga ttg cag     1424
Gly Leu His Asn Leu Leu Arg Leu His Leu Asn Ser Asn Arg Leu Gln
140                 145                 150                 155 atg atc aac agt aag tgg ttt gat gct ctt cca aat cta gag att ctg     1472
Met Ile Asn Ser Lys Trp Phe Asp Ala Leu Pro Asn Leu Glu Ile Leu
                160                 165                 170 atg att ggg gaa aat cca att atc aga atc aaa gac atg aac ttt aag     1520
Met Ile Gly Glu Asn Pro Ile Ile Arg Ile Lys Asp Met Asn Phe Lys
            175                 180                 185 cct ctt atc aat ctt cgc agc ctg gtt ata gct ggt ata aac ctc aca     1568
Pro Leu Ile Asn Leu Arg Ser Leu Val Ile Ala Gly Ile Asn Leu Thr
        190                 195                 200 gaa ata cca gat aac gcc ttg gtt gga ctg gaa aac tta gaa agc atc     1616
Glu Ile Pro Asp Asn Ala Leu Val Gly Leu Glu Asn Leu Glu Ser Ile
    205                 210                 215 tct ttt tac gat aac agg ctt att aaa gta ccc cat gtt gct ctt caa     1664
Ser Phe Tyr Asp Asn Arg Leu Ile Lys Val Pro His Val Ala Leu Gln
220                 225                 230                 235 aaa gtt gta aat ctc aaa ttt ttg gat cta aat aaa aat cct att aat     1712
Lys Val Val Asn Leu Lys Phe Leu Asp Leu Asn Lys Asn Pro Ile Asn
                240                 245                 250 aga ata cga agg ggt gat ttt agc aat atg cta cac tta aaa gag ttg     1760
Arg Ile Arg Arg Gly Asp Phe Ser Asn Met Leu His Leu Lys Glu Leu
            255                 260                 265 ggg ata aat aat atg cct gag ctg att tcc atc gat agt ctt gct gtg     1808
Gly Ile Asn Asn Met Pro Glu Leu Ile Ser Ile Asp Ser Leu Ala Val
        270                 275                 280 gat aac ctg cca gat tta aga aaa ata gaa gct act aac aac cct aga     1856
Asp Asn Leu Pro Asp Leu Arg Lys Ile Glu Ala Thr Asn Asn Pro Arg
    285                 290                 295 ttg tct tac att cac ccc aat gca ttt ttc aga ctc ccc aag ctg gaa     1904
Leu Ser Tyr Ile His Pro Asn Ala Phe Phe Arg Leu Pro Lys Leu Glu
300                 305                 310                 315 tca ctc atg ctg aac agc aat gct ctc agt gcc ctg tac cat ggt acc     1952
Ser Leu Met Leu Asn Ser Asn Ala Leu Ser Ala Leu Tyr His Gly Thr
                320                 325                 330 att gag tct ctg cca aac ctc aag gaa atc agc ata cac agt aac ccc     2000
Ile Glu Ser Leu Pro Asn Leu Lys Glu Ile Ser Ile His Ser Asn Pro
            335                 340                 345 atc agg tgt gac tgt gtc atc cgt tgg atg aac atg aac aaa acc aac     2048
Ile Arg Cys Asp Cys Val Ile Arg Trp Met Asn Met Asn Lys Thr Asn
        350                 355                 360 att cga ttc atg gag cca gat tca ctg ttt tgc gtg gac cca cct gaa     2096
Ile Arg Phe Met Glu Pro Asp Ser Leu Phe Cys Val Asp Pro Pro Glu
    365                 370                 375 ttc caa ggt cag aat gtt cgg caa gtg cat ttc agg gac atg atg gaa     2144
Phe Gln Gly Gln Asn Val Arg Gln Val His Phe Arg Asp Met Met Glu
380                 385                 390                 395 att tgt ctc cct ctt ata gct cct gag agc ttt cct tct aat cta aat     2192
Ile Cys Leu Pro Leu Ile Ala Pro Glu Ser Phe Pro Ser Asn Leu Asn
                400                 405                 410
```

```
gta gaa gct ggg agc tat gtt tcc ttt cac tgt aga gct act gca gaa      2240
Val Glu Ala Gly Ser Tyr Val Ser Phe His Cys Arg Ala Thr Ala Glu
        415                 420                 425 cca cag cct gaa atc tac tgg ata aca cct tct ggt caa aaa ctc ttg      2288
Pro Gln Pro Glu Ile Tyr Trp Ile Thr Pro Ser Gly Gln Lys Leu Leu
430                 435                 440 cct aat acc ctg aca gac aag ttc tat gtc cat tct gag gga aca cta      2336
Pro Asn Thr Leu Thr Asp Lys Phe Tyr Val His Ser Glu Gly Thr Leu
    445                 450                 455 gat ata aat ggc gta act ccc aaa gaa ggg ggt tta tat act tgt ata      2384
Asp Ile Asn Gly Val Thr Pro Lys Glu Gly Gly Leu Tyr Thr Cys Ile
460                 465                 470                 475 gca act aac cta gtt ggc gct gac ttg aag tct gtt atg atc aaa gtg      2432
Ala Thr Asn Leu Val Gly Ala Asp Leu Lys Ser Val Met Ile Lys Val
                480                 485                 490 gat gga tct ttt cca caa gat aac aat ggc tct ttg aat att aaa ata      2480
Asp Gly Ser Phe Pro Gln Asp Asn Asn Gly Ser Leu Asn Ile Lys Ile
            495                 500                 505 aga gat att cag gcc aat tca gtt ttg gtg tcc tgg aaa gca agt tct      2528
Arg Asp Ile Gln Ala Asn Ser Val Leu Val Ser Trp Lys Ala Ser Ser
        510                 515                 520 aaa att ctc aaa tct agt gtt aaa tgg aca gcc ttt gtc aag act gaa      2576
Lys Ile Leu Lys Ser Ser Val Lys Trp Thr Ala Phe Val Lys Thr Glu
525                 530                 535 aat tct cat gct gcg caa agt gct cga ata cca tct gat gtc aag gta      2624
Asn Ser His Ala Ala Gln Ser Ala Arg Ile Pro Ser Asp Val Lys Val
540                 545                 550                 555 tat aat ctt act cat ctg aat cca tca act gag tat aaa att tgt att      2672
Tyr Asn Leu Thr His Leu Asn Pro Ser Thr Glu Tyr Lys Ile Cys Ile
                560                 565                 570 gat att ccc acc atc tat cag aaa aac aga aaa aaa tgt gta aat gtc      2720
Asp Ile Pro Thr Ile Tyr Gln Lys Asn Arg Lys Lys Cys Val Asn Val
            575                 580                 585 acc acc aaa ggt ttg cac cct gat caa aaa gag tat gaa aag aat aat      2768
Thr Thr Lys Gly Leu His Pro Asp Gln Lys Glu Tyr Glu Lys Asn Asn
        590                 595                 600 acc aca aca ctt atg gcc tgt ctt gga ggc ctt ctg ggg att att ggt      2816
Thr Thr Thr Leu Met Ala Cys Leu Gly Gly Leu Leu Gly Ile Ile Gly
605                 610                 615 gtg ata tgt ctt atc agc tgc ctc tct cca gaa atg aac tgt gat ggt      2864
Val Ile Cys Leu Ile Ser Cys Leu Ser Pro Glu Met Asn Cys Asp Gly
620                 625                 630                 635 gga cac agc tat gtg agg aat tac tta cag aaa cca acc ttt gca tta      2912
Gly His Ser Tyr Val Arg Asn Tyr Leu Gln Lys Pro Thr Phe Ala Leu
                640                 645                 650 ggt gag ctt tat cct cct ctg ata aat ctc tgg gaa gca gga aaa gaa      2960
Gly Glu Leu Tyr Pro Pro Leu Ile Asn Leu Trp Glu Ala Gly Lys Glu
            655                 660                 665 aaa agt aca tca ctg aaa gta aaa gca act gtt ata ggt tta cca aca      3008
Lys Ser Thr Ser Leu Lys Val Lys Ala Thr Val Ile Gly Leu Pro Thr
        670                 675                 680 aat atg tcc taaaaccac caaggaaacc tactccaaaa atgaacaaaa               3057
Asn Met Ser
        685 aaaaaaaaaa a                                                         3068

<210> SEQ ID NO 67
<211> LENGTH: 255
<212> TYPE: PRT
```

<213> ORGANISM: Homo sapiens

<400> SEQUENCE: 67

```
Met Ser Tyr Tyr Gly Ser Ser Tyr His Ile Ile Asn Ala Asp Ala Lys
1               5                   10                  15
Tyr Pro Gly Tyr Pro Pro Glu His Ile Ile Ala Glu Lys Arg Arg Ala
            20                  25                  30
Arg Arg Arg Leu Leu His Lys Asp Gly Ser Cys Asn Val Tyr Phe Lys
        35                  40                  45
His Ile Phe Gly Glu Trp Gly Ser Tyr Val Val Asp Ile Phe Thr Thr
    50                  55                  60
Leu Val Asp Thr Lys Trp Arg His Met Phe Val Ile Phe Ser Leu Ser
65                  70                  75                  80
Tyr Ile Leu Ser Trp Leu Ile Phe Gly Ser Val Phe Trp Leu Ile Ala
                85                  90                  95
Phe His His Gly Asp Leu Leu Asn Asp Pro Asp Ile Thr Pro Cys Val
            100                 105                 110
Asp Asn Val His Ser Phe Thr Gly Ala Phe Leu Phe Ser Leu Glu Thr
        115                 120                 125
Gln Thr Thr Ile Gly Tyr Gly Tyr Arg Cys Val Thr Glu Glu Cys Ser
    130                 135                 140
Val Ala Val Leu Met Val Ile Leu Gln Ser Ile Leu Ser Cys Ile Ile
145                 150                 155                 160
Asn Thr Phe Ile Ile Gly Ala Ala Leu Ala Lys Met Ala Thr Ala Arg
                165                 170                 175
Lys Arg Ala Gln Thr Ile Arg Phe Ser Tyr Phe Ala Leu Ile Gly Met
            180                 185                 190
Arg Asp Gly Lys Leu Cys Leu Met Trp Arg Ile Gly Asp Phe Arg Pro
        195                 200                 205
Asn His Val Val Glu Gly Thr Val Arg Ala Gln Leu Leu Arg Tyr Thr
    210                 215                 220
Glu Asp Ser Glu Gly Arg Met Thr Met Ala Phe Lys Asp Leu Lys Leu
225                 230                 235                 240
Val Asn Asp Gln Ile Ile Leu Val Thr Pro Val Thr Ile Val Pro
                245                 250                 255
```

<210> SEQ ID NO 68
<211> LENGTH: 765
<212> TYPE: DNA
<213> ORGANISM: Homo sapiens

<400> SEQUENCE: 68

```
atgagctatt acggcagcag ctatcatatt atcaatgcgg acgcaaaata cccaggctac     60
ccgccagagc acattatagc tgagaagaga agagcaagaa gacgattact tcacaaagat    120
ggcagctgta atgtctactt caagcacatt tttggagaat ggggaagcta tgtggttgac    180
atcttcacca ctcttgtgga caccaagtgg cgccatatgt ttgtgatatt tctttatct    240
tatattctct cgtggttgat atttggctct gtcttttggc tcatagcctt tcatcatggc    300
gatctattaa atgatccaga catcacacct tgtgttgaca acgtccattc tttcacaggg    360
gcctttttgt tctccctaga gacccaaacc accataggat atggttatcg ctgtgttact    420
gaagaatgtt ctgtggccgt gctcatggtg atcctccagt ccatcttaag ttgcatcata    480
aatacccttta tcattggagc tgccttggcc aaaatggcaa ctgctcgaaa gagagcccaa    540
accattcgtt tcagctactt tgcacttata ggtatgagag atgggaagct ttgcctcatg    600
```

```
tggcgcattg gtgattttcg gccaaaccac gtggtagaag gaacagttag agcccaactt    660
ctccgctata cagaagacag tgaagggagg atgacgatgg catttaaaga cctcaaatta    720
gtcaacgacc aaatcatcct ggtcaccccg gtaactattg tccca                    765

<210> SEQ ID NO 69
<211> LENGTH: 907
<212> TYPE: DNA
<213> ORGANISM: Homo sapiens
<220> FEATURE:
<221> NAME/KEY: CDS
<222> LOCATION: (78)..(842)

<400> SEQUENCE: 69
caaaccaaga aatagcaaca agtctagaat tcttactact acaaaactca cctggatccc    60
taagggcaca gcaaaga atg agc tat tac ggc agc agc tat cat att atc       110
                   Met Ser Tyr Tyr Gly Ser Ser Tyr His Ile Ile
                   1               5                   10 aat gcg gac gca aaa tac cca ggc tac ccg cca gag cac att ata gct      158
Asn Ala Asp Ala Lys Tyr Pro Gly Tyr Pro Pro Glu His Ile Ile Ala
            15                  20                  25 gag aag aga aga gca aga aga cga tta ctt cac aaa gat ggc agc tgt      206
Glu Lys Arg Arg Ala Arg Arg Arg Leu Leu His Lys Asp Gly Ser Cys
        30                  35                  40 aat gtc tac ttc aag cac att ttt gga gaa tgg gga agc tat gtg gtt      254
Asn Val Tyr Phe Lys His Ile Phe Gly Glu Trp Gly Ser Tyr Val Val
    45                  50                  55 gac atc ttc acc act ctt gtg gac acc aag tgg cgc cat atg ttt gtg      302
Asp Ile Phe Thr Thr Leu Val Asp Thr Lys Trp Arg His Met Phe Val
60                  65                  70                  75 ata ttt tct tta tct tat att ctc tcg tgg ttg ata ttt ggc tct gtc      350
Ile Phe Ser Leu Ser Tyr Ile Leu Ser Trp Leu Ile Phe Gly Ser Val
                80                  85                  90 ttt tgg ctc ata gcc ttt cat cat ggc gat cta tta aat gat cca gac      398
Phe Trp Leu Ile Ala Phe His His Gly Asp Leu Leu Asn Asp Pro Asp
            95                  100                 105 atc aca cct tgt gtt gac aac gtc cat tct ttc aca ggg gcc ttt ttg      446
Ile Thr Pro Cys Val Asp Asn Val His Ser Phe Thr Gly Ala Phe Leu
        110                 115                 120 ttc tcc cta gag acc caa acc acc ata gga tat ggt tat cgc tgt gtt      494
Phe Ser Leu Glu Thr Gln Thr Thr Ile Gly Tyr Gly Tyr Arg Cys Val
    125                 130                 135 act gaa gaa tgt tct gtg gcc gtg ctc atg gtg atc ctc cag tcc atc      542
Thr Glu Glu Cys Ser Val Ala Val Leu Met Val Ile Leu Gln Ser Ile
140                 145                 150                 155 tta agt tgc atc ata aat acc ttt atc att gga gct gcc ttg gcc aaa      590
Leu Ser Cys Ile Ile Asn Thr Phe Ile Ile Gly Ala Ala Leu Ala Lys
                160                 165                 170 atg gca act gct cga aag aga gcc caa acc att cgt ttc agc tac ttt      638
Met Ala Thr Ala Arg Lys Arg Ala Gln Thr Ile Arg Phe Ser Tyr Phe
            175                 180                 185 gca ctt ata ggt atg aga gat ggg aag ctt tgc ctc atg tgg cgc att      686
Ala Leu Ile Gly Met Arg Asp Gly Lys Leu Cys Leu Met Trp Arg Ile
        190                 195                 200 ggt gat ttt cgg cca aac cac gtg gta gaa gga aca gtt aga gcc caa      734
Gly Asp Phe Arg Pro Asn His Val Val Glu Gly Thr Val Arg Ala Gln
    205                 210                 215 ctt ctc cgc tat aca gaa gac agt gaa ggg agg atg acg atg gca ttt      782
Leu Leu Arg Tyr Thr Glu Asp Ser Glu Gly Arg Met Thr Met Ala Phe
220                 225                 230                 235
```

```
aaa gac ctc aaa tta gtc aac gac caa atc atc ctg gtc acc ccg gta      830
Lys Asp Leu Lys Leu Val Asn Asp Gln Ile Ile Leu Val Thr Pro Val
            240                 245                 250 act att gtc cca tgaccctgcc aaatccccct ctgtgagaaa cacccaaaaa           882
Thr Ile Val Pro
        255 aaaaaaaaaa aaaaaaaaaa aaaaa                                           907

<210> SEQ ID NO 70
<211> LENGTH: 859
<212> TYPE: PRT
<213> ORGANISM: Homo sapiens

<400> SEQUENCE: 70

Met Ala Cys Arg Trp Ser Thr Lys Glu Ser Pro Arg Trp Arg Ser Ala
        -25                 -20                 -15

Leu Leu Leu Leu Phe Leu Ala Gly Val Tyr Gly Asn Gly Ala Leu Ala
    -10                  -5              -1   1                5

Glu His Ser Glu Asn Val His Ile Ser Gly Val Ser Thr Ala Cys Gly
                10                  15                  20

Glu Thr Pro Glu Gln Ile Arg Ala Pro Ser Gly Ile Ile Thr Ser Pro
            25                  30                  35

Gly Trp Pro Ser Glu Tyr Pro Ala Lys Ile Asn Cys Ser Trp Phe Ile
        40                  45                  50

Arg Ala Asn Pro Gly Glu Ile Ile Thr Ile Ser Phe Gln Asp Phe Asp
    55                  60                  65

Ile Gln Gly Ser Arg Arg Cys Asn Leu Asp Trp Leu Thr Ile Glu Thr
70                  75                  80                  85

Tyr Lys Asn Ile Glu Ser Tyr Arg Ala Cys Gly Ser Thr Ile Pro Pro
                90                  95                  100

Pro Tyr Ile Ser Ser Gln Asp His Ile Trp Ile Arg Phe His Ser Asp
            105                 110                 115

Asp Asn Ile Ser Arg Lys Gly Phe Arg Leu Ala Tyr Phe Ser Gly Lys
        120                 125                 130

Ser Glu Glu Pro Asn Cys Ala Cys Asp Gln Phe Arg Cys Gly Asn Gly
    135                 140                 145

Lys Cys Ile Pro Glu Ala Trp Lys Cys Asn Asn Met Asp Glu Cys Gly
150                 155                 160                 165

Asp Ser Ser Asp Glu Glu Ile Cys Ala Lys Glu Ala Asn Pro Pro Thr
                170                 175                 180

Ala Ala Ala Phe Gln Pro Cys Ala Tyr Asn Gln Phe Gln Cys Leu Ser
            185                 190                 195

Arg Phe Thr Lys Val Tyr Thr Cys Leu Pro Glu Ser Leu Lys Cys Asp
        200                 205                 210

Gly Asn Ile Asp Cys Leu Asp Leu Gly Asp Glu Ile Asp Cys Asp Val
    215                 220                 225

Pro Thr Cys Gly Gln Trp Leu Lys Tyr Phe Tyr Gly Thr Phe Asn Ser
230                 235                 240                 245

Pro Asn Tyr Pro Asp Phe Tyr Pro Pro Gly Ser Asn Cys Thr Trp Leu
                250                 255                 260

Ile Asp Thr Gly Asp His Arg Lys Val Ile Leu Arg Phe Thr Asp Phe
            265                 270                 275

Lys Leu Asp Gly Thr Gly Tyr Gly Asp Tyr Val Lys Ile Tyr Asp Gly
        280                 285                 290
```

-continued

```
Leu Glu Glu Asn Pro His Lys Leu Leu Arg Val Leu Thr Ala Phe Asp
295                 300                 305

Ser His Ala Pro Leu Thr Val Val Ser Ser Gly Gln Ile Arg Val
310                 315                 320                 325

His Phe Cys Ala Asp Lys Val Asn Ala Ala Arg Gly Phe Asn Ala Thr
                330                 335                 340

Tyr Gln Val Asp Gly Phe Cys Leu Pro Trp Glu Ile Pro Cys Gly Gly
                345                 350                 355

Asn Trp Gly Cys Tyr Thr Glu Gln Gln Arg Cys Asp Gly Tyr Trp His
            360                 365                 370

Cys Pro Asn Gly Arg Asp Glu Thr Asn Cys Thr Met Cys Gln Lys Glu
    375                 380                 385

Glu Phe Pro Cys Ser Arg Asn Gly Val Cys Tyr Pro Arg Ser Asp Arg
390                 395                 400                 405

Cys Asn Tyr Gln Asn His Cys Pro Asn Gly Ser Asp Glu Lys Asn Cys
                410                 415                 420

Phe Phe Cys Gln Pro Gly Asn Phe His Cys Lys Asn Asn Arg Cys Val
                425                 430                 435

Phe Glu Ser Trp Val Cys Asp Ser Gln Asp Cys Gly Asp Gly Ser
            440                 445                 450

Asp Glu Glu Asn Cys Pro Val Ile Val Pro Thr Arg Val Ile Thr Ala
            455                 460                 465

Ala Val Ile Gly Ser Leu Ile Cys Gly Leu Leu Val Ile Ala Leu
470                 475                 480                 485

Gly Cys Thr Cys Lys Leu Tyr Ser Leu Arg Met Phe Glu Arg Ser
                490                 495                 500

Phe Glu Thr Gln Leu Ser Arg Val Glu Ala Glu Leu Leu Arg Arg Glu
                505                 510                 515

Ala Pro Pro Ser Tyr Gly Gln Leu Ile Ala Gln Gly Leu Ile Pro Pro
            520                 525                 530

Val Glu Asp Phe Pro Val Cys Ser Pro Asn Gln Ala Ser Val Leu Glu
535                 540                 545

Asn Leu Arg Leu Ala Val Arg Ser Gln Leu Gly Phe Thr Ser Val Arg
550                 555                 560                 565

Leu Pro Met Ala Gly Arg Ser Ser Asn Ile Trp Asn Arg Ile Phe Asn
                570                 575                 580

Phe Ala Arg Ser Arg His Ser Gly Ser Leu Ala Leu Val Ser Ala Asp
                585                 590                 595

Gly Asp Glu Val Val Pro Ser Gln Ser Thr Ser Arg Glu Pro Glu Arg
            600                 605                 610

Asn His Thr His Arg Ser Leu Phe Ser Val Glu Ser Asp Asp Thr Asp
    615                 620                 625

Thr Glu Asn Glu Arg Arg Asp Met Ala Gly Ala Ser Gly Gly Val Ala
630                 635                 640                 645

Ala Pro Leu Pro Gln Lys Val Pro Pro Thr Thr Ala Val Glu Ala Thr
                650                 655                 660

Val Gly Ala Cys Ala Ser Ser Ser Gln Ser Thr Arg Gly Gly His
                665                 670                 675

Ala Asp Asn Gly Arg Asp Val Thr Ser Val Glu Pro Pro Ser Val Ser
            680                 685                 690

Pro Ala Arg His Gln Leu Thr Ser Ala Leu Ser Arg Met Thr Gln Gly
    695                 700                 705

Leu Arg Trp Val Arg Phe Thr Leu Gly Arg Ser Ser Ser Leu Ser Gln
```

```
         710                 715                 720                 725
Asn Gln Ser Pro Leu Arg Gln Leu Asp Asn Gly Val Ser Gly Arg Glu
                730                 735                 740

Asp Asp Asp Val Glu Met Leu Ile Pro Ile Ser Asp Gly Ser Ser
            745                 750                 755

Asp Phe Asp Val Asn Asp Cys Ser Arg Pro Leu Leu Asp Leu Ala Ser
        760                 765                 770

Asp Gln Gly Gln Gly Leu Arg Gln Pro Tyr Asn Ala Thr Asn Pro Gly
    775                 780                 785

Val Arg Pro Ser Asn Arg Asp Gly Pro Cys Glu Arg Cys Gly Ile Val
790                 795                 800                 805

His Thr Ala Gln Ile Pro Asp Thr Cys Leu Glu Val Thr Leu Lys Asn
                810                 815                 820

Glu Thr Ser Asp Asp Glu Ala Leu Leu Leu Cys
                825                 830

<210> SEQ ID NO 71
<211> LENGTH: 2577
<212> TYPE: DNA
<213> ORGANISM: Homo sapiens

<400> SEQUENCE: 71
atggcctgtc gctggagcac aaaagagtct ccgcggtgga ggtctgcgtt gctcttgctt      60
ttcctcgctg gggtgtacgg aaatggtgct cttgcagaac attctgaaaa tgtgcatatt     120
tcaggagtgt caactgcttg tgagagact ccagagcaaa tacgagcacc aagtggcata     180
atcacaagcc aggctggcc ttctgaatat cctgcaaaaa tcaactgtag ctggttcata     240
agggcaaacc caggcgaaat cattactata agttttcagg attttgatat tcaaggatcc     300
agaaggtgca atttggactg gttgacaata gaaacataca agaatattga agttacaga     360 gcttgtggtt ccacaattcc acctccgtat atctcttcac aagaccacat ctggattagg     420
tttcattcgg atgacaacat ctctagaaag ggtttcagac tggcatattt ttcagggaaa     480
tctgaggaac caaattgtgc ttgtgatcag tttcgttgtg gtaatggaaa gtgtataccca     540 gaagcctgga atgtaataa catggatgaa tgtggagata gttccgatga gagatctgt     600 gccaaagaag caaatcctcc aactgctgct gcttttcaac cctgtgctta caaccagttc     660
cagtgtttat cccgttttac caagtttac acttgcctcc ccgaatcttt aaaatgtgat     720
gggaacattg actgccttga cctaggagat gagatagact gtgatgtgcc aacatgtggg     780
caatggctaa atatttttta tggtactttt aattctccca attatccaga cttttatcct     840
cctggaagca attgcacctg ttaatagac actggtgatc accgtaaagt cattttacgc     900
ttcactgact taaacttga tggtactggt tatggtgatt atgtcaaaat atatgatgga     960
ttagaggaga atccacacaa gcttttgcgt gtgttgacag cttttgattc tcatgcacct    1020
cttacagttg tttcttcttc tggacagata agggtacatt tttgtgctga taaagtgaat    1080
gctgcaaggg gatttaatgc tacttaccaa gtagatgggt tctgtttgcc atgggaaata    1140
ccctgtggag gtaactgggg gtgttatact gagcagcagc gttgtgatgg gtattggcat    1200
tgcccaaatg aagggatga aaccaattgt accatgtgcc agaaggaaga atttccatgt    1260
tcccgaaatg gtgtctgtta tcctcgttct gatcgctgca actaccagaa tcattgccca    1320
aatggctcag atgaaaaaaa ctgcttttt tgccaaccag gaaatttcca ttgtaaaaac    1380
aatcgttgtg tgtttgaaag ttgggtgtgt gattctcaag atgactgtgg tgatggcagc    1440
```

```
gatgaagaaa attgcccagt aatcgtgcct acaagagtca tcactgctgc cgtcataggg    1500
agcctcatct gtggcctgtt actcgtcata gcattgggat gtacttgtaa gctttattct    1560
ctgagaatgt ttgaaagaag atcatttgaa acacagttgt caagagtgga agcagaattg    1620
ttaagaagag aagctcctcc ctcgtatgga caattgattg ctcagggttt aattccacca    1680
gttgaagatt ttcctgtttg ttcacctaat caggcttctg ttttggaaaa tctgaggcta    1740
gcggtacgat ctcagcttgg atttacttca gtcaggcttc ctatggcagg cagatcaagc    1800
aacatttgga accgtatttt taattttgca agatcacgtc attctgggtc attggctttg    1860
gtctcagcag atggagatga ggttgtccct agtcagagta ccagtagaga acctgagaga    1920
aatcatactc acagaagttt gttttccgtg gagtctgatg atacagacac agaaaatgag    1980
agaagagata tggcaggagc atctggtggg gttgcagctc ctttgcctca aaaagtccct    2040
cccacaacgg cagtagaagc gacagtagga gcatgtgcaa gttcctcaac tcagagtacc    2100
cgaggtggcc atgcagataa tggaagggat gtgacaagtg tggaaccccc aagtgtgagt    2160
ccagcacgtc accagcttac aagtgcactc agtcgtatga ctcaggggct acgctgggta    2220
cgttttacat taggacgatc aagttcccta agtcagaacc agagtccttt gagacaactt    2280
gataatgggg taagtggaag agaagatgat gatgatgttg aaatgctaat tccaatttct    2340
gatggatctt cagactttga tgtgaatgac tgctccagac tcttcttga tcttgcctca    2400 gatcaaggac aagggcttag acaaccatat aatgcaacaa atcctggagt aaggccaagt    2460
aatcgagatg gccctgtgat gcgctgtggt attgtcccaca ctgcccagat accagacact    2520
tgcttagaag taacactgaa aaacgaaacg agtgatgatg aggctttgtt actttgt      2577

<210> SEQ ID NO 72
<211> LENGTH: 3088
<212> TYPE: DNA
<213> ORGANISM: Homo sapiens
<220> FEATURE:
<221> NAME/KEY: CDS
<222> LOCATION: (41)..(2617)
<220> FEATURE:
<221> NAME/KEY: sig_peptide
<222> LOCATION: (41)..(121)
<220> FEATURE:
<221> NAME/KEY: mat_peptide
<222> LOCATION: (122)..(2617)

<400> SEQUENCE: 72
ctcctccgtc tcctcctctc tctctccatc tgctgtggtt atg gcc tgt cgc tgg         55
                                             Met Ala Cys Arg Trp
                                                     -25 agc aca aaa gag tct ccg cgg tgg agg tct gcg ttg ctc ttg ctt ttc         103
Ser Thr Lys Glu Ser Pro Arg Trp Arg Ser Ala Leu Leu Leu Leu Phe
        -20                 -15                 -10 ctc gct ggg gtg tac gga aat ggt gct ctt gca gaa cat tct gaa aat         151
Leu Ala Gly Val Tyr Gly Asn Gly Ala Leu Ala Glu His Ser Glu Asn
    -5                  -1  1                 5                  10 gtg cat att tca gga gtg tca act gct tgt gga gag act cca gag caa         199
Val His Ile Ser Gly Val Ser Thr Ala Cys Gly Glu Thr Pro Glu Gln
                15                  20                  25 ata cga gca cca agt ggc ata atc aca agc cca ggc tgg cct tct gaa         247
Ile Arg Ala Pro Ser Gly Ile Ile Thr Ser Pro Gly Trp Pro Ser Glu
            30                  35                  40 tat cct gca aaa atc aac tgt agc tgg ttc ata agg gca aac cca ggc         295
Tyr Pro Ala Lys Ile Asn Cys Ser Trp Phe Ile Arg Ala Asn Pro Gly
        45                  50                  55
```

-continued

| | |
|---|---|
| gaa atc att act ata agt ttt cag gat ttt gat att caa gga tcc aga<br>Glu Ile Ile Thr Ile Ser Phe Gln Asp Phe Asp Ile Gln Gly Ser Arg<br>60                             65                           70 | 343 |
| agg tgc aat ttg gac tgg ttg aca ata gaa aca tac aag aat att gaa<br>Arg Cys Asn Leu Asp Trp Leu Thr Ile Glu Thr Tyr Lys Asn Ile Glu<br>75                           80                         85                        90 | 391 |
| agt tac aga gct tgt ggt tcc aca att cca cct ccg tat atc tct tca<br>Ser Tyr Arg Ala Cys Gly Ser Thr Ile Pro Pro Pro Tyr Ile Ser Ser<br>                        95                       100                       105 | 439 |
| caa gac cac atc tgg att agg ttt cat tcg gat gac aac atc tct aga<br>Gln Asp His Ile Trp Ile Arg Phe His Ser Asp Asp Asn Ile Ser Arg<br>                  110                       115                       120 | 487 |
| aag ggt ttc aga ctg gca tat ttt tca ggg aaa tct gag gaa cca aat<br>Lys Gly Phe Arg Leu Ala Tyr Phe Ser Gly Lys Ser Glu Glu Pro Asn<br>         125                       130                       135 | 535 |
| tgt gct tgt gat cag ttt cgt tgt ggt aat gga aag tgt ata cca gaa<br>Cys Ala Cys Asp Gln Phe Arg Cys Gly Asn Gly Lys Cys Ile Pro Glu<br>140                          145                       150 | 583 |
| gcc tgg aaa tgt aat aac atg gat gaa tgt gga gat agt tcc gat gaa<br>Ala Trp Lys Cys Asn Asn Met Asp Glu Cys Gly Asp Ser Ser Asp Glu<br>155                          160                       165             170 | 631 |
| gag atc tgt gcc aaa gaa gca aat cct cca act gct gct gct ttt caa<br>Glu Ile Cys Ala Lys Glu Ala Asn Pro Pro Thr Ala Ala Ala Phe Gln<br>                  175                       180                       185 | 679 |
| ccc tgt gct tac aac cag ttc cag tgt tta tcc cgt ttt acc aaa gtt<br>Pro Cys Ala Tyr Asn Gln Phe Gln Cys Leu Ser Arg Phe Thr Lys Val<br>                       190                       195                     200 | 727 |
| tac act tgc ctc ccc gaa tct tta aaa tgt gat ggg aac att gac tgc<br>Tyr Thr Cys Leu Pro Glu Ser Leu Lys Cys Asp Gly Asn Ile Asp Cys<br>             205                       210                       215 | 775 |
| ctt gac cta gga gat gag ata gac tgt gat gtg cca aca tgt ggg caa<br>Leu Asp Leu Gly Asp Glu Ile Asp Cys Asp Val Pro Thr Cys Gly Gln<br>220                          225                       230 | 823 |
| tgg cta aaa tat ttt tat ggt act ttt aat tct ccc aat tat cca gac<br>Trp Leu Lys Tyr Phe Tyr Gly Thr Phe Asn Ser Pro Asn Tyr Pro Asp<br>235                          240                       245             250 | 871 |
| ttt tat cct cct gga agc aat tgc acc tgg tta ata gac act ggt gat<br>Phe Tyr Pro Pro Gly Ser Asn Cys Thr Trp Leu Ile Asp Thr Gly Asp<br>                  255                       260                       265 | 919 |
| cac cgt aaa gtc att tta cgc ttc act gac ttt aaa ctt gat ggt act<br>His Arg Lys Val Ile Leu Arg Phe Thr Asp Phe Lys Leu Asp Gly Thr<br>             270                       275                       280 | 967 |
| ggt tat ggt gat tat gtc aaa ata tat gat gga tta gag gag aat cca<br>Gly Tyr Gly Asp Tyr Val Lys Ile Tyr Asp Gly Leu Glu Glu Asn Pro<br>         285                       290                       295 | 1015 |
| cac aag ctt ttg cgt gtg ttg aca gct ttt gat tct cat gca cct ctt<br>His Lys Leu Leu Arg Val Leu Thr Ala Phe Asp Ser His Ala Pro Leu<br>300                          305                       310 | 1063 |
| aca gtt gtt tct tct tct gga cag ata agg gta cat ttt tgt gct gat<br>Thr Val Val Ser Ser Ser Gly Gln Ile Arg Val His Phe Cys Ala Asp<br>315                          320                       325             330 | 1111 |
| aaa gtg aat gct gca agg gga ttt aat gct act tac caa gta gat ggg<br>Lys Val Asn Ala Ala Arg Gly Phe Asn Ala Thr Tyr Gln Val Asp Gly<br>                  335                       340                       345 | 1159 |
| ttc tgt ttg cca tgg gaa ata ccc tgt gga ggt aac tgg ggg tgt tat<br>Phe Cys Leu Pro Trp Glu Ile Pro Cys Gly Gly Asn Trp Gly Cys Tyr<br>                  350                       355                     360 | 1207 |
| act gag cag cag cgt tgt gat ggg tat tgg cat tgc cca aat gga agg<br>Thr Glu Gln Gln Arg Cys Asp Gly Tyr Trp His Cys Pro Asn Gly Arg<br>365                          370                       375 | 1255 |

-continued

| | |
|---|---|
| gat gaa acc aat tgt acc atg tgc cag aag gaa gaa ttt cca tgt tcc<br>Asp Glu Thr Asn Cys Thr Met Cys Gln Lys Glu Glu Phe Pro Cys Ser<br>380                          385                        390 | 1303 |
| cga aat ggt gtc tgt tat cct cgt tct gat cgc tgc aac tac cag aat<br>Arg Asn Gly Val Cys Tyr Pro Arg Ser Asp Arg Cys Asn Tyr Gln Asn<br>395                        400                          405                    410 | 1351 |
| cat tgc cca aat ggc tca gat gaa aaa aac tgc ttt ttt tgc caa cca<br>His Cys Pro Asn Gly Ser Asp Glu Lys Asn Cys Phe Phe Cys Gln Pro<br>                    415                          420                        425 | 1399 |
| gga aat ttc cat tgt aaa aac aat cgt tgt gtg ttt gaa agt tgg gtg<br>Gly Asn Phe His Cys Lys Asn Asn Arg Cys Val Phe Glu Ser Trp Val<br>                430                          435                        440 | 1447 |
| tgt gat tct caa gat gac tgt ggt gat ggc agc gat gaa gaa aat tgc<br>Cys Asp Ser Gln Asp Asp Cys Gly Asp Gly Ser Asp Glu Glu Asn Cys<br>              445                          450                        455 | 1495 |
| cca gta atc gtg cct aca aga gtc atc act gct gcc gtc ata ggg agc<br>Pro Val Ile Val Pro Thr Arg Val Ile Thr Ala Ala Val Ile Gly Ser<br>460                          465                          470 | 1543 |
| ctc atc tgt ggc ctg tta ctc gtc ata gca ttg gga tgt act tgt aag<br>Leu Ile Cys Gly Leu Leu Leu Val Ile Ala Leu Gly Cys Thr Cys Lys<br>475                          480                          485                    490 | 1591 |
| ctt tat tct ctg aga atg ttt gaa aga aga tca ttt gaa aca cag ttg<br>Leu Tyr Ser Leu Arg Met Phe Glu Arg Arg Ser Phe Glu Thr Gln Leu<br>                        495                        500                        505 | 1639 |
| tca aga gtg gaa gca gaa ttg tta aga aga gaa gct cct ccc tcg tat<br>Ser Arg Val Glu Ala Glu Leu Leu Arg Arg Glu Ala Pro Pro Ser Tyr<br>                  510                          515                        520 | 1687 |
| gga caa ttg att gct cag ggt tta att cca cca gtt gaa gat ttt cct<br>Gly Gln Leu Ile Ala Gln Gly Leu Ile Pro Pro Val Glu Asp Phe Pro<br>              525                          530                        535 | 1735 |
| gtt tgt tca cct aat cag gct tct gtt ttg gaa aat ctg agg cta gcg<br>Val Cys Ser Pro Asn Gln Ala Ser Val Leu Glu Asn Leu Arg Leu Ala<br>540                          545                          550 | 1783 |
| gta cga tct cag ctt gga ttt act tca gtc agg ctt cct atg gca ggc<br>Val Arg Ser Gln Leu Gly Phe Thr Ser Val Arg Leu Pro Met Ala Gly<br>555                          560                          565                    570 | 1831 |
| aga tca agc aac att tgg aac cgt att ttt aat ttt gca aga tca cgt<br>Arg Ser Ser Asn Ile Trp Asn Arg Ile Phe Asn Phe Ala Arg Ser Arg<br>                  575                          580                        585 | 1879 |
| cat tct ggg tca ttg gct ttg gtc tca gca gat gga gat gag gtt gtc<br>His Ser Gly Ser Leu Ala Leu Val Ser Ala Asp Gly Asp Glu Val Val<br>              590                          595                        600 | 1927 |
| cct agt cag agt acc agt aga gaa cct gag aga aat cat act cac aga<br>Pro Ser Gln Ser Thr Ser Arg Glu Pro Glu Arg Asn His Thr His Arg<br>                    605                        610                        615 | 1975 |
| agt ttg ttt tcc gtg gag tct gat gat aca gac aca gaa aat gag aga<br>Ser Leu Phe Ser Val Glu Ser Asp Asp Thr Asp Thr Glu Asn Glu Arg<br>              620                          625                        630 | 2023 |
| aga gat atg gca gga gca tct ggt ggg gtt gca gct cct ttg cct caa<br>Arg Asp Met Ala Gly Ala Ser Gly Gly Val Ala Ala Pro Leu Pro Gln<br>635                          640                          645                    650 | 2071 |
| aaa gtc cct ccc aca acg gca gta gaa gcg aca gta gga gca tgt gca<br>Lys Val Pro Pro Thr Thr Ala Val Glu Ala Thr Val Gly Ala Cys Ala<br>                    655                          660                        665 | 2119 |
| agt tcc tca act cag agt acc cga ggt ggc cat gca gat aat gga agg<br>Ser Ser Ser Thr Gln Ser Thr Arg Gly Gly His Ala Asp Asn Gly Arg<br>              670                          675                        680 | 2167 |
| gat gtg aca agt gtg gaa ccc cca agt gtg agt cca gca cgt cac cag<br>Asp Val Thr Ser Val Glu Pro Pro Ser Val Ser Pro Ala Arg His Gln | 2215 |

```
                    685                 690                 695
ctt aca agt gca ctc agt cgt atg act cag ggg cta cgc tgg gta cgt    2263
Leu Thr Ser Ala Leu Ser Arg Met Thr Gln Gly Leu Arg Trp Val Arg
        700                 705                 710 ttt aca tta gga cga tca agt tcc cta agt cag aac cag agt cct ttg    2311
Phe Thr Leu Gly Arg Ser Ser Ser Leu Ser Gln Asn Gln Ser Pro Leu
715                 720                 725                 730 aga caa ctt gat aat ggg gta agt gga aga gaa gat gat gat gat gtt    2359
Arg Gln Leu Asp Asn Gly Val Ser Gly Arg Glu Asp Asp Asp Asp Val
                735                 740                 745 gaa atg cta att cca att tct gat gga tct tca gac ttt gat gtg aat    2407
Glu Met Leu Ile Pro Ile Ser Asp Gly Ser Ser Asp Phe Asp Val Asn
            750                 755                 760 gac tgc tcc aga cct ctt ctt gat ctt gcc tca gat caa gga caa ggg    2455
Asp Cys Ser Arg Pro Leu Leu Asp Leu Ala Ser Asp Gln Gly Gln Gly
        765                 770                 775 ctt aga caa cca tat aat gca aca aat cct gga gta agg cca agt aat    2503
Leu Arg Gln Pro Tyr Asn Ala Thr Asn Pro Gly Val Arg Pro Ser Asn
    780                 785                 790 cga gat ggc ccc tgt gag cgc tgt ggt att gtc cac act gcc cag ata    2551
Arg Asp Gly Pro Cys Glu Arg Cys Gly Ile Val His Thr Ala Gln Ile
795                 800                 805                 810 cca gac act tgc tta gaa gta aca ctg aaa aac gaa acg agt gat gat    2599
Pro Asp Thr Cys Leu Glu Val Thr Leu Lys Asn Glu Thr Ser Asp Asp
                815                 820                 825 gag gct ttg tta ctt tgt taggtacgaa tcacataagg gagattgtat           2647
Glu Ala Leu Leu Leu Cys
                830 acaagttgga gcaatatcca tttattattt tgtaacttta cagttaaact agttttagtt   2707 taaaagaaa aaatgcaggg tgatttctta ttattatatg ttagcctgca tggttaaatt    2767 cgacaacttg taactctatg aacttagagt ttactatttt agcagctaaa aatgcatcac   2827 atattcatat tgttcaataa tgtcctttca tttgtttctg attgttttca tcctgatact   2887 gtagttcact gtagaaatgt ggctgctgaa actcatttga ttgtcatttt tatctatcct   2947 atgttaaatg gtttgttttt acaaaataat acctattttt aattgaaacg tttatgcttt   3007 tgccaacaca tcttgtaact taatatacta gatgttaagg ttgttaatgt acaaaaaaaa   3067 aaaaaaaaa aaaaaaaaa a                                              3088

<210> SEQ ID NO 73
<211> LENGTH: 687
<212> TYPE: PRT
<213> ORGANISM: Homo sapiens

<400> SEQUENCE: 73

Met Thr Pro Gln Ser Leu Leu Gln Thr Thr Leu Phe Leu Leu Ser Leu
-25                 -20                 -15                 -10

Leu Phe Leu Val Gln Gly Ala His Gly Arg Gly His Arg Glu Asp Phe
                -5                  -1  1                   5

Arg Phe Cys Ser Gln Arg Asn Gln Thr His Arg Ser Ser Leu His Tyr
            10                  15                  20

Lys Pro Thr Pro Asp Leu Arg Ile Ser Ile Glu Asn Ser Glu Glu Ala
        25                  30                  35

Leu Thr Val His Ala Pro Phe Pro Ala Ala His Pro Ala Ser Arg Ser
40                  45                  50                  55

Phe Pro Asp Pro Arg Gly Leu Tyr His Phe Cys Leu Tyr Trp Asn Arg
                60                  65                  70
```

```
His Ala Gly Arg Leu His Leu Leu Tyr Gly Lys Arg Asp Phe Leu Leu
         75                  80                  85

Ser Asp Lys Ala Ser Ser Leu Leu Cys Phe Gln His Gln Glu Glu Ser
         90                  95                 100

Leu Ala Gln Gly Pro Pro Leu Leu Ala Thr Ser Val Thr Ser Trp Trp
        105                 110                 115

Ser Pro Gln Asn Ile Ser Leu Pro Ser Ala Ala Ser Phe Thr Phe Ser
120                 125                 130                 135

Phe His Ser Pro Pro His Thr Ala Ala His Asn Ala Ser Val Asp Met
                140                 145                 150

Cys Glu Leu Lys Arg Asp Leu Gln Leu Leu Ser Gln Phe Leu Lys His
                155                 160                 165

Pro Gln Lys Ala Ser Arg Arg Pro Ser Ala Ala Pro Ala Ser Gln Gln
                170                 175                 180

Leu Gln Ser Leu Glu Ser Lys Leu Thr Ser Val Arg Phe Met Gly Asp
        185                 190                 195

Met Val Ser Phe Glu Glu Asp Arg Ile Asn Ala Thr Val Trp Lys Leu
200                 205                 210                 215

Gln Pro Thr Ala Gly Leu Gln Asp Leu His Ile His Ser Arg Gln Glu
                220                 225                 230

Glu Glu Gln Ser Glu Ile Met Glu Tyr Ser Val Leu Leu Pro Arg Thr
        235                 240                 245

Leu Phe Gln Arg Thr Lys Gly Arg Arg Gly Glu Ala Glu Lys Arg Leu
        250                 255                 260

Leu Leu Val Asp Phe Ser Ser Gln Ala Leu Phe Gln Asp Lys Asn Ser
        265                 270                 275

Ser Gln Val Leu Gly Glu Lys Val Leu Gly Ile Val Val Gln Asn Thr
280                 285                 290                 295

Lys Val Ala Asn Leu Thr Glu Pro Val Val Leu Thr Phe Gln His Gln
                300                 305                 310

Leu Gln Pro Lys Asn Val Thr Leu Gln Cys Val Phe Trp Val Glu Asp
                315                 320                 325

Pro Thr Leu Ser Ser Pro Gly His Trp Ser Ser Ala Gly Cys Glu Thr
        330                 335                 340

Val Arg Arg Glu Thr Gln Thr Ser Cys Phe Cys Asn His Leu Thr Tyr
        345                 350                 355

Phe Ala Val Leu Met Val Ser Ser Val Glu Val Asp Ala Val His Lys
360                 365                 370                 375

His Tyr Leu Ser Leu Leu Ser Tyr Val Gly Cys Val Val Ser Ala Leu
                380                 385                 390

Ala Cys Leu Val Ser Ile Ala Ala Tyr Leu Cys Ser Arg Arg Lys Pro
                395                 400                 405

Arg Asp Tyr Thr Ile Lys Val His Met Asn Leu Leu Leu Ala Val Phe
                410                 415                 420

Leu Leu Asp Thr Ser Phe Leu Leu Ser Glu Pro Val Ala Leu Thr Gly
        425                 430                 435

Ser Glu Ala Gly Cys Arg Ala Ser Ala Ile Phe Leu His Phe Ser Leu
440                 445                 450                 455

Leu Thr Cys Leu Ser Trp Met Gly Leu Glu Gly Tyr Asn Leu Tyr Arg
                460                 465                 470

Leu Val Val Glu Val Phe Gly Thr Tyr Val Pro Gly Tyr Leu Leu Lys
                475                 480                 485
```

```
Leu Ser Ala Met Gly Trp Gly Phe Pro Ile Phe Leu Val Thr Leu Val
        490                 495                 500

Ala Leu Val Asp Val Asp Asn Tyr Gly Pro Ile Ile Leu Ala Val His
        505                 510                 515

Arg Thr Pro Glu Gly Val Ile Tyr Pro Ser Met Cys Trp Ile Arg Asp
520                 525                 530                 535

Ser Leu Val Ser Tyr Ile Thr Asn Leu Gly Leu Phe Ser Leu Val Phe
                540                 545                 550

Leu Phe Asn Met Ala Met Leu Ala Thr Met Val Val Gln Ile Leu Arg
                555                 560                 565

Leu Arg Pro His Thr Gln Lys Trp Ser His Val Leu Thr Leu Leu Gly
        570                 575                 580

Leu Ser Leu Val Leu Gly Leu Pro Trp Ala Leu Ile Phe Phe Ser Phe
        585                 590                 595

Ala Ser Gly Thr Phe Gln Leu Val Val Leu Tyr Leu Phe Ser Ile Ile
600                 605                 610                 615

Thr Ser Phe Gln Gly Phe Leu Ile Phe Ile Trp Tyr Trp Ser Met Arg
                620                 625                 630

Leu Gln Ala Arg Gly Gly Pro Ser Pro Leu Lys Ser Asn Ser Asp Ser
                635                 640                 645

Ala Arg Leu Pro Ile Ser Ser Gly Ser Thr Ser Ser Arg Ile
        650                 655                 660

<210> SEQ ID NO 74
<211> LENGTH: 2061
<212> TYPE: DNA
<213> ORGANISM: Homo sapiens

<400> SEQUENCE: 74
atgactcccc agtcgctgct gcagacgaca ctgttcctgc tgagtctgct cttcctggtc      60
caaggtgccc acggcagggg ccacagggaa gactttcgct tctgcagcca gcggaaccag     120
acacacagga gcagcctcca ctacaaaccc acaccagacc tgcgcatctc catcgagaac     180
tccgaagagg ccctcacagt ccatgcccct ttccctgcag cccaccctgc ttcccgatcc     240
ttccctgacc caggggcct ctaccacttc tgcctctact ggaaccgaca tgctgggaga     300
ttacatcttc tctatggcaa gcgtgacttc ttgctgagtg acaaagcctc tagcctcctc     360
tgcttccagc accaggagga gagcctggct cagggccccc cgctgttagc cacttctgtc     420
acctcctggt ggagccctca gaacatcagc ctgcccagtg ccgccagctt caccttctcc     480
ttccacagtc ctccccacac ggccgctcac aatgcctcgg tggacatgtg cgagctcaaa     540
agggacctcc agctgctcag ccagttcctg aagcatcccc agaaggcctc aaggaggccc     600
tcggctgccc ccgccagcca gcagttgcag agcctggagt cgaaactgac ctctgtgaga     660
ttcatggggg acatggtgtc cttcgaggag gaccggatca cgccacggt gtggaagctc     720 cagcccacag ccggcctcca ggacctgcac atccactccc ggcaggagga ggagcagagc     780
gagatcatgg agtactcggt gctgctgcct cgaacactct tccagaggac gaaaggccgg     840 agggggagg ctgagaagag actcctcctg gtggacttca gcagccaagc cctgttccag     900
gacaagaatt ccagccaagt cctgggtgag aaggtcttgg ggattgtggt acagaacacc     960
aaagtagcca acctcacgga gcccgtggtg ctcaccttcc agcaccagct acagccgaag    1020
aatgtgactc tgcaatgtgt gttctgggtt gaagacccca cattgagcag cccggggcat    1080
tggagcagtg ctgggtgtga gaccgtcagg agagaaccag aaacatcctg cttctgcaac    1140
```

-continued

```
cacttgacct actttgcagt gctgatggtc tcctcggtgg aggtggacgc cgtgcacaag    1200
cactacctga gcctcctctc ctacgtgggc tgtgtcgtct ctgccctggc ctgccttgtc    1260
agcattgccg cctacctctg ctccaggagg aaacctcggg actacaccat caaggtgcac    1320
atgaacctgc tgctggccgt cttcctgctg gacacgagct tcctgctcag cgagccggtg    1380
gccctgacag gctctgaggc tggctgccga gccagtgcca tcttcctgca cttctccctg    1440
ctcacctgcc tttcctggat gggcctcgag gggtacaacc tctaccgact cgtggtggag    1500
gtctttggca cctatgtccc tggctaccta ctcaagctga gcgccatggg ctggggcttc    1560
cccatctttc tggtgacgct ggtggccctg gtggatgtgg acaactatgg ccccatcatc    1620
ttggctgtgc ataggactcc agagggcgtc atctacccct tccatgtgct gatccgggac    1680
tccctggtca gctacatcac caacctgggc ctcttcagcc tggtgtttct gttcaacatg    1740
gccatgctag ccaccatggt ggtgcagatc ctgcggctgc gcccccacac ccaaaagtgg    1800
tcacatgtgc tgacactgct gggcctcagc ctggtccttg cctgccctg ggccttgatc     1860
ttcttctcct ttgcttctgg caccttccag cttgtcgtcc tctacctttt cagcatcatc    1920
acctccttcc aaggcttcct catcttcatc tggtactggt ccatgcggct gcaggcccgg    1980
ggtggcccct cccctctgaa gagcaactca gacagcgcca ggctccccat cagctcgggc    2040
agcacctcgt ccagccgcat c                                              2061
```

```
<210> SEQ ID NO 75
<211> LENGTH: 3564
<212> TYPE: DNA
<213> ORGANISM: Homo sapiens
<220> FEATURE:
<221> NAME/KEY: sig_peptide
<222> LOCATION: (43)..(2103)
<220> FEATURE:
<221> NAME/KEY: mat_peptide
<222> LOCATION: (118)..(2103)
<220> FEATURE:
<221> NAME/KEY: CDS
<222> LOCATION: (43)..(2103)

<400> SEQUENCE: 75
attacaggtg gtgacttcca agagtgactc cgtcggagga aa atg act ccc cag         54
                                              Met Thr Pro Gln
                                                  -25 tcg ctg ctg cag acg aca ctg ttc ctg ctg agt ctg ctc ttc ctg gtc       102
Ser Leu Leu Gln Thr Thr Leu Phe Leu Leu Ser Leu Leu Phe Leu Val
    -20                 -15                 -10 caa ggt gcc cac ggc agg ggc cac agg gaa gac ttt cgc ttc tgc agc       150
Gln Gly Ala His Gly Arg Gly His Arg Glu Asp Phe Arg Phe Cys Ser
-5               -1  1               5                   10 cag cgg aac cag aca cac agg agc agc ctc cac tac aaa ccc aca cca       198
Gln Arg Asn Gln Thr His Arg Ser Ser Leu His Tyr Lys Pro Thr Pro
            15                  20                  25 gac ctg cgc atc tcc atc gag aac tcc gaa gag gcc ctc aca gtc cat       246
Asp Leu Arg Ile Ser Ile Glu Asn Ser Glu Glu Ala Leu Thr Val His
        30                  35                  40 gcc cct ttc cct gca gcc cac cct gct tcc cga tcc ttc cct gac ccc       294
Ala Pro Phe Pro Ala Ala His Pro Ala Ser Arg Ser Phe Pro Asp Pro
    45                  50                  55 agg ggc ctc tac cac ttc tgc ctc tac tgg aac cga cat gct ggg aga       342
Arg Gly Leu Tyr His Phe Cys Leu Tyr Trp Asn Arg His Ala Gly Arg
60                  65                  70                  75 tta cat ctt ctc tat ggc aag cgt gac ttc ttg ctg agt gac aaa gcc       390
Leu His Leu Leu Tyr Gly Lys Arg Asp Phe Leu Leu Ser Asp Lys Ala
```

-continued

```
                    80                      85                      90
tct agc ctc ctc tgc ttc cag cac cag gag gag agc ctg gct cag ggc        438
Ser Ser Leu Leu Cys Phe Gln His Gln Glu Glu Ser Leu Ala Gln Gly
         95                     100                     105 ccc ccg ctg tta gcc act tct gtc acc tcc tgg tgg agc cct cag aac        486
Pro Pro Leu Leu Ala Thr Ser Val Thr Ser Trp Trp Ser Pro Gln Asn
            110                     115                     120 atc agc ctg ccc agt gcc gcc agc ttc acc ttc tcc ttc cac agt cct        534
Ile Ser Leu Pro Ser Ala Ala Ser Phe Thr Phe Ser Phe His Ser Pro
        125                     130                     135 ccc cac acg gcc gct cac aat gcc tcg gtg gac atg tgc gag ctc aaa        582
Pro His Thr Ala Ala His Asn Ala Ser Val Asp Met Cys Glu Leu Lys
140                     145                     150                     155 agg gac ctc cag ctg ctc agc cag ttc ctg aag cat ccc cag aag gcc        630
Arg Asp Leu Gln Leu Leu Ser Gln Phe Leu Lys His Pro Gln Lys Ala
                    160                     165                     170 tca agg agg ccc tcg gct gcc ccc gcc agc cag cag ttg cag agc ctg        678
Ser Arg Arg Pro Ser Ala Ala Pro Ala Ser Gln Gln Leu Gln Ser Leu
            175                     180                     185 gag tcg aaa ctg acc tct gtg aga ttc atg ggg gac atg gtg tcc ttc        726
Glu Ser Lys Leu Thr Ser Val Arg Phe Met Gly Asp Met Val Ser Phe
        190                     195                     200 gag gag gac cgg atc aac gcc acg gtg tgg aag ctc cag ccc aca gcc        774
Glu Glu Asp Arg Ile Asn Ala Thr Val Trp Lys Leu Gln Pro Thr Ala
205                     210                     215 ggc ctc cag gac ctg cac atc cac tcc cgg cag gag gag gag cag agc        822
Gly Leu Gln Asp Leu His Ile His Ser Arg Gln Glu Glu Glu Gln Ser
220                     225                     230                     235 gag atc atg gag tac tcg gtg ctg ctg cct cga aca ctc ttc cag agg        870
Glu Ile Met Glu Tyr Ser Val Leu Leu Pro Arg Thr Leu Phe Gln Arg
                    240                     245                     250 acg aaa ggc cgg agg ggg gag gct gag aag aga ctc ctc ctg gtg gac        918
Thr Lys Gly Arg Arg Gly Glu Ala Glu Lys Arg Leu Leu Leu Val Asp
            255                     260                     265 ttc agc agc caa gcc ctg ttc cag gac aag aat tcc agc caa gtc ctg        966
Phe Ser Ser Gln Ala Leu Phe Gln Asp Lys Asn Ser Ser Gln Val Leu
        270                     275                     280 ggt gag aag gtc ttg ggg att gtg gta cag aac acc aaa gta gcc aac       1014
Gly Glu Lys Val Leu Gly Ile Val Val Gln Asn Thr Lys Val Ala Asn
285                     290                     295 ctc acg gag ccc gtg gtg ctc acc ttc cag cac cag cta cag ccg aag       1062
Leu Thr Glu Pro Val Val Leu Thr Phe Gln His Gln Leu Gln Pro Lys
300                     305                     310                     315 aat gtg act ctg caa tgt gtg ttc tgg gtt gaa gac ccc aca ttg agc       1110
Asn Val Thr Leu Gln Cys Val Phe Trp Val Glu Asp Pro Thr Leu Ser
                    320                     325                     330 agc ccg ggg cat tgg agc agt gct ggg tgt gag acc gtc agg aga gaa       1158
Ser Pro Gly His Trp Ser Ser Ala Gly Cys Glu Thr Val Arg Arg Glu
            335                     340                     345 acc caa aca tcc tgc ttc tgc aac cac ttg acc tac ttt gca gtg ctg       1206
Thr Gln Thr Ser Cys Phe Cys Asn His Leu Thr Tyr Phe Ala Val Leu
        350                     355                     360 atg gtc tcc tcg gtg gag gtg gac gcc gtg cac aag cac tac ctg agc       1254
Met Val Ser Ser Val Glu Val Asp Ala Val His Lys His Tyr Leu Ser
365                     370                     375 ctc ctc tcc tac gtg ggc tgt gtc gtc tct gcc ctg gcc tgc ctt gtc       1302
Leu Leu Ser Tyr Val Gly Cys Val Val Ser Ala Leu Ala Cys Leu Val
380                     385                     390                     395 agc att gcc gcc tac ctc tgc tcc agg agg aaa cct cgg gac tac acc       1350
```

-continued

| | | |
|---|---|---|
| Ser Ile Ala Ala Tyr Leu Cys Ser Arg Arg Lys Pro Arg Asp Tyr Thr<br>              400                        405                410 | | |

```
atc aag gtg cac atg aac ctg ctg ctg gcc gtc ttc ctg ctg gac acg      1398
Ile Lys Val His Met Asn Leu Leu Leu Ala Val Phe Leu Leu Asp Thr
            415                 420                 425 agc ttc ctg ctc agc gag ccg gtg gcc ctg aca ggc tct gag gct ggc      1446
Ser Phe Leu Leu Ser Glu Pro Val Ala Leu Thr Gly Ser Glu Ala Gly
        430                 435                 440 tgc cga gcc agt gcc atc ttc ctg cac ttc tcc ctc acc tgc ctt          1494
Cys Arg Ala Ser Ala Ile Phe Leu His Phe Ser Leu Leu Thr Cys Leu
    445                 450                 455 tcc tgg atg ggc ctc gag ggg tac aac ctc tac cga ctc gtg gtg gag      1542
Ser Trp Met Gly Leu Glu Gly Tyr Asn Leu Tyr Arg Leu Val Val Glu
460                 465                 470                 475 gtc ttt ggc acc tat gtc cct ggc tac cta ctc aag ctg agc gcc atg      1590
Val Phe Gly Thr Tyr Val Pro Gly Tyr Leu Leu Lys Leu Ser Ala Met
                480                 485                 490 ggc tgg ggc ttc ccc atc ttt ctg gtg acg ctg gtg gcc ctg gtg gat      1638
Gly Trp Gly Phe Pro Ile Phe Leu Val Thr Leu Val Ala Leu Val Asp
            495                 500                 505 gtg gac aac tat ggc ccc atc atc ttg gct gtg cat agg act cca gag      1686
Val Asp Asn Tyr Gly Pro Ile Ile Leu Ala Val His Arg Thr Pro Glu
        510                 515                 520 ggc gtc atc tac cct tcc atg tgc tgg atc cgg gac tcc ctg gtc agc      1734
Gly Val Ile Tyr Pro Ser Met Cys Trp Ile Arg Asp Ser Leu Val Ser
    525                 530                 535 tac atc acc aac ctg ggc ctc ttc agc ctg gtg ttt ctg ttc aac atg      1782
Tyr Ile Thr Asn Leu Gly Leu Phe Ser Leu Val Phe Leu Phe Asn Met
540                 545                 550                 555 gcc atg cta gcc acc atg gtg gtg cag atc ctg cgg ctg cgc ccc cac      1830
Ala Met Leu Ala Thr Met Val Val Gln Ile Leu Arg Leu Arg Pro His
                560                 565                 570 acc caa aag tgg tca cat gtg ctg aca ctg ctg ggc ctc agc ctg gtc      1878
Thr Gln Lys Trp Ser His Val Leu Thr Leu Leu Gly Leu Ser Leu Val
            575                 580                 585 ctt ggc ctg ccc tgg gcc ttg atc ttc ttc tcc ttt gct tct ggc acc      1926
Leu Gly Leu Pro Trp Ala Leu Ile Phe Phe Ser Phe Ala Ser Gly Thr
        590                 595                 600 ttc cag ctt gtc gtc ctc tac ctt ttc agc atc atc acc tcc ttc caa      1974
Phe Gln Leu Val Val Leu Tyr Leu Phe Ser Ile Ile Thr Ser Phe Gln
    605                 610                 615 ggc ttc ctc atc ttc atc tgg tac tgg tcc atg cgg ctg cag gcc cgg      2022
Gly Phe Leu Ile Phe Ile Trp Tyr Trp Ser Met Arg Leu Gln Ala Arg
620                 625                 630                 635 ggt ggc ccc tcc cct ctg aag agc aac tca gac agc gcc agg ctc ccc      2070
Gly Gly Pro Ser Pro Leu Lys Ser Asn Ser Asp Ser Ala Arg Leu Pro
                640                 645                 650 atc agc tcg ggc agc acc tcg tcc agc cgc atc taggcctcca gcccacctgc   2123
Ile Ser Ser Gly Ser Thr Ser Ser Ser Arg Ile
            655                 660 ccatgtgatg aagcagagat gcggcctcgt cgcacactgc ctgtggcccc cgagccaggc   2183
ccagccccag gccagtcagc cgcagacttt ggaaagccca acgaccatgg agagatgggc   2243
cgttgccatg gtggacggac tcccgggctg ggcttttgaa ttggccttgg ggactactcg   2303
gctctcactc agctcccacg ggactcagaa gtgcgccgcc atgctgccta gggtactgtc   2363
cccacatctg tcccaaccca gctggaggcc tggtctctcc ttacaacccc tgggcccagc   2423
cctcattgct gggggccagg ccttggatct tgagggtctg gcacatcctt aatcctgtgc   2483
```

-continued

```
cccctgcctgg gacagaaatg tggctccagt tgctctgtct ctcgtggtca ccctgagggc    2543
actctgcatc ctctgtcatt ttaacctcag gtggcaccca gggcgaatgg ggcccagggc    2603
agaccttcag ggccagagcc ctggcggagg agaggcccct tgccaggagc acagcagcag    2663
ctcgcctacc tctgagccca ggccccctcc ctccctcagc ccccagtcc tccctccatc     2723 ttccctgggg ttctcctcct ctcccagggc ctccttgctc cttcgttcac agctgggggt    2783
ccccgattcc aatgctgttt tttggggagt ggtttccagg agctgcctgg tgtctgctgt    2843
aaatgtttgt ctactgcaca agcctcggcc tgcccctgag ccaggctcgg taccgatgcg    2903
tgggctgggc taggtccctc tgtccatctg ggcctttgta tgagctgcat tgcccttgct    2963
caccctgacc aagcacacgc ctcagagggg ccctcagcct ctcctgaagc cctcttgtgg    3023
caagaactgt ggaccatgcc agtcccgtct ggtttccatc ccaccactcc aaggactgag    3083
actgacctcc tctggtgaca ctggcctaga gcctgacact ctcctaagag gttctctcca    3143
agcccccaaa tagctccagg cgccctcggc cgcccatcat ggttaattct gtccaacaaa    3203
cacacacggg tagattgctg gcctgttgta ggtggtaggg acacagatga ccgacctggt    3263
cactcctcct gccaacattc agtctggtat gtgaggcgtg cgtgaagcaa gaactcctgg    3323
agctacaggg acagggagcc atcattcctg cctgggaatc ctggaagact tcctgcagga    3383
gtcagcgttc aatcttgacc ttgaagatgg gaaggatgtt ctttttacgt accaattctt    3443
ttgtcttttg atattaaaaa gaagtacatg ttcattgtag agaatttgga aactgtagaa    3503
gagaatcaag aagaaaaata aaaatcagct gttgtaatcg cctagcaaaa aaaaaaaaaa    3563
a                                                                    3564
```

<210> SEQ ID NO 76
<211> LENGTH: 704
<212> TYPE: PRT
<213> ORGANISM: Homo sapiens

<400> SEQUENCE: 76

```
Met Phe Thr Phe Leu Leu Thr Cys Ile Phe Leu Pro Leu Leu Arg Gly
    -15             -10                  -5                  -1

His Ser Leu Phe Thr Cys Glu Pro Ile Thr Val Pro Arg Cys Met Lys
1               5                   10                  15

Met Ala Tyr Asn Met Thr Phe Phe Pro Asn Leu Met Gly His Tyr Asp
            20                  25                  30

Gln Ser Ile Ala Ala Val Glu Met Glu His Phe Leu Pro Leu Ala Asn
        35                  40                  45

Leu Glu Cys Ser Pro Asn Ile Glu Thr Phe Leu Cys Lys Ala Phe Val
    50                  55                  60

Pro Thr Cys Ile Glu Gln Ile His Val Val Pro Cys Arg Lys Leu
65              70                  75                  80

Cys Glu Lys Val Tyr Ser Asp Cys Lys Lys Leu Ile Asp Thr Phe Gly
                85                  90                  95

Ile Arg Trp Pro Glu Glu Leu Glu Cys Asp Arg Leu Gln Tyr Cys Asp
            100                 105                 110

Glu Thr Val Pro Val Thr Phe Asp Pro His Thr Glu Phe Leu Gly Pro
        115                 120                 125

Gln Lys Lys Thr Glu Gln Val Gln Arg Asp Ile Gly Phe Trp Cys Pro
    130                 135                 140

Arg His Leu Lys Thr Ser Gly Gly Gln Gly Tyr Lys Phe Leu Gly Ile
145                 150                 155                 160
```

-continued

```
Asp Gln Cys Ala Pro Pro Cys Pro Asn Met Tyr Phe Lys Ser Asp Glu
            165                 170                 175

Leu Glu Phe Ala Lys Ser Phe Ile Gly Thr Val Ser Ile Phe Cys Leu
            180                 185                 190

Cys Ala Thr Leu Phe Thr Phe Leu Thr Phe Leu Ile Asp Val Arg Arg
            195                 200                 205

Phe Arg Tyr Pro Glu Arg Pro Ile Ile Tyr Tyr Ser Val Cys Tyr Ser
            210                 215                 220

Ile Val Ser Leu Met Tyr Phe Ile Gly Phe Leu Leu Gly Asp Ser Thr
225                 230                 235                 240

Ala Cys Asn Lys Ala Asp Glu Lys Leu Glu Leu Gly Asn Thr Val Val
                245                 250                 255

Leu Asp Ser Gln Asn Lys Ala Cys Thr Val Leu Phe Met Leu Leu Tyr
            260                 265                 270

Phe Phe Thr Met Ala Gly Thr Val Trp Trp Val Ile Leu Thr Ile Thr
            275                 280                 285

Trp Phe Leu Ala Ala Gly Arg Lys Trp Ser Cys Glu Ala Ile Glu Gln
            290                 295                 300

Lys Ala Val Trp Phe His Ala Val Ala Trp Gly Thr Pro Gly Phe Leu
305                 310                 315                 320

Thr Val Met Leu Leu Ala Met Asn Lys Val Glu Gly Asp Asn Ile Ser
                325                 330                 335

Gly Val Cys Phe Val Gly Leu Tyr Asp Leu Asp Ala Ser Arg Tyr Phe
            340                 345                 350

Val Leu Leu Pro Leu Cys Leu Cys Val Phe Val Gly Leu Ser Leu Leu
            355                 360                 365

Leu Ala Gly Ile Ile Ser Leu Asn His Val Arg Gln Val Ile Gln His
            370                 375                 380

Asp Gly Arg Asn Gln Glu Lys Leu Lys Lys Phe Met Ile Arg Ile Gly
385                 390                 395                 400

Val Phe Ser Gly Leu Tyr Leu Val Pro Leu Val Thr Leu Leu Gly Cys
            405                 410                 415

Tyr Val Tyr Glu Gln Val Asn Arg Ile Thr Trp Glu Ile Thr Trp Val
            420                 425                 430

Ser Asp His Cys Arg Gln Tyr His Ile Pro Cys Pro Tyr Gln Ala Lys
            435                 440                 445

Ala Lys Ala Arg Pro Glu Leu Ala Leu Phe Met Ile Lys Tyr Leu Met
450                 455                 460

Thr Leu Ile Val Gly Ile Ser Ala Val Phe Trp Val Gly Ser Lys Lys
465                 470                 475                 480

Thr Cys Thr Glu Trp Ala Gly Phe Phe Lys Arg Asn Arg Lys Arg Asp
            485                 490                 495

Pro Ile Ser Glu Ser Arg Arg Val Leu Gln Glu Ser Cys Glu Phe Phe
            500                 505                 510

Leu Lys His Asn Ser Lys Val Lys His Lys Lys His Tyr Lys Pro
            515                 520                 525

Ser Ser His Lys Leu Lys Val Ile Ser Lys Ser Met Gly Thr Ser Thr
530                 535                 540

Gly Ala Thr Ala Asn His Gly Thr Ser Ala Val Ala Ile Thr Ser His
545                 550                 555                 560

Asp Tyr Leu Gly Gln Glu Thr Leu Thr Glu Ile Gln Thr Ser Pro Glu
            565                 570                 575

Thr Ser Met Arg Glu Val Lys Ala Asp Gly Ala Ser Thr Pro Arg Leu
```

```
                    580             585             590
Arg Glu Gln Asp Cys Gly Glu Pro Ala Ser Pro Ala Ala Ser Ile Ser
            595                 600                 605

Arg Leu Ser Gly Glu Gln Val Asp Gly Lys Gly Gln Ala Gly Ser Val
        610                 615                 620

Ser Glu Ser Ala Arg Ser Glu Gly Arg Ile Ser Pro Lys Ser Asp Ile
625                 630                 635                 640

Thr Asp Thr Gly Leu Ala Gln Ser Asn Asn Leu Gln Val Pro Ser Ser
                645                 650                 655

Ser Glu Pro Ser Ser Leu Lys Gly Ser Thr Ser Leu Leu Val His Pro
            660                 665                 670

Val Ser Gly Val Arg Lys Glu Gln Gly Gly Gly Cys His Ser Asp Thr
        675                 680                 685

<210> SEQ ID NO 77
<211> LENGTH: 2112
<212> TYPE: DNA
<213> ORGANISM: Homo sapiens

<400> SEQUENCE: 77
```

| | | | | | |
|---|---|---|---|---|---|
| atgtttacat | ttttgttgac | gtgtattttt | ctacccctcc | taagagggca | cagtctcttc | 60 |
| acctgtgaac | caattactgt | tcccagatgt | atgaaaatgg | cctacaacat | gacgttttc | 120 |
| cctaatctga | tgggtcatta | tgaccagagt | attgccgcgg | tggaaatgga | gcattttctt | 180 |
| cctctcgcaa | atctggaatg | ttcaccaaac | attgaaactt | tcctctgcaa | agcatttgta | 240 |
| ccaacctgca | tagaacaaat | tcatgtggtt | ccaccttgtc | gtaaactttg | tgagaaagta | 300 |
| tattctgatt | gcaaaaaatt | aattgacact | tttgggatcc | gatggcctga | ggagcttgaa | 360 |
| tgtgacagat | acaatactg  | tgatgagact | gttcctgtaa | cttttgatcc | acacacagaa | 420 |
| tttcttggtc | ctcagaagaa | aacagaacaa | gtccaaagag | acattggatt | tggtgtcca  | 480 |
| aggcatctta | agacttctgg | gggacaagga | tataagtttc | tgggaattga | ccagtgtgcg | 540 |
| cctccatgcc | ccaacatgta | ttttaaaagt | gatgagctag | agtttgcaaa | aagttttatt | 600 |
| ggaacagttt | caatattttg | tctttgtgca | actctgttca | cattccttac | ttttttaatt | 660 |
| gatgttagaa | gattcagata | cccagagaga | ccaattatat | attactctgt | ctgttacagc | 720 |
| attgtatctc | ttatgtactt | cattggattt | ttgctaggcg | atagcacagc | ctgcaataag | 780 |
| gcagatgaga | agctagaact | tggtaacact | gttgtcctag | actctcaaaa | taaggcttgc | 840 |
| accgtttgt  | tcatgctttt | gtatttttc  | acaatggctg | gcactgtgtg | gtgggtgatt | 900 |
| cttaccatta | cttggttctt | agctgcagga | agaaaatgga | gttgtgaagc | catcgagcaa | 960 |
| aaagcagtgt | ggtttcatgc | tgttcatgg  | ggaacaccag | gttcctgac  | tgttatgctt | 1020 |
| cttgctatga | acaaagttga | aggagacaac | attagtggag | tttgctttgt | tggccttat  | 1080 |
| gacctggatg | cttctcgcta | ctttgtactc | ttgccactgt | gcctttgtgt | gtttgttggg | 1140 |
| ctctctcttc | ttttagctgg | cattatttcc | ttaaatcatg | ttcgacaagt | catacaacat | 1200 |
| gatggccgga | accaagaaaa | actaaagaaa | tttatgattc | gaattggagt | cttcagcggc | 1260 |
| ttgtatcttg | tgccattagt | gacacttctc | ggatgttacg | tctatagca  | agtgaacagg | 1320 |
| attacctggg | agataacttg | ggtctctgat | cattgtcgtc | agtaccatat | cccatgtcct | 1380 |
| tatcaggcaa | aagcaaaagc | tcgaccagaa | ttggctttat | ttatgataaa | atacctgatg | 1440 |
| acattaattg | ttggcatctc | tgctgtcttc | tgggttggaa | gcaaaaagac | atgcacagaa | 1500 |
| tgggctgggt | tttttaaacg | aaatcgcaag | agagatccaa | tcagtgaaag | tcgaagagta | 1560 |

```
ctacaggaat catgtgagtt tttcttaaag cacaattcta aagttaaaca caaaagaag      1620 cactataaac caagttcaca caagctgaag gtcatttcca aatccatggg aaccagcaca      1680
ggagctacag caaatcatgg cacttctgca gtagcaatta ctagccatga ttacctagga      1740
caagaaactt tgacagaaat ccaaacctca ccagaaacat caatgagaga ggtgaaagcg      1800
gacggagcta gcaccccag gttaagagaa caggactgtg gtgaacctgc ctcgccagca      1860
gcatccatct ccagactctc tggggaacag gtcgacggga agggccaggc aggcagtgta      1920
tctgaaagtg cgcggagtga aggaaggatt agtccaaaga gtgatattac tgacactggc      1980
ctggcacaga gcaacaattt gcaggtcccc agttcttcag aaccaagcag cctcaaaggt      2040
tccacatctc tgcttgttca cccggtttca ggagtgagaa aagagcaggg aggtggttgt      2100
cattcagata ct                                                          2112

<210> SEQ ID NO 78
<211> LENGTH: 3492
<212> TYPE: DNA
<213> ORGANISM: Homo sapiens
<220> FEATURE:
<221> NAME/KEY: sig_peptide
<222> LOCATION: (6)..(53)
<220> FEATURE:
<221> NAME/KEY: mat_peptide
<222> LOCATION: (54)..(2117)
<220> FEATURE:
<221> NAME/KEY: CDS
<222> LOCATION: (6)..(2117)

<400> SEQUENCE: 78 tggaa atg ttt aca ttt ttg ttg acg tgt att ttt cta ccc ctc cta aga     50
      Met Phe Thr Phe Leu Leu Thr Cys Ile Phe Leu Pro Leu Leu Arg
      -15              -10                 -5 ggg cac agt ctc ttc acc tgt gaa cca att act gtt ccc aga tgt atg      98
Gly His Ser Leu Phe Thr Cys Glu Pro Ile Thr Val Pro Arg Cys Met
-1  1               5                  10                  15 aaa atg gcc tac aac atg acg ttt ttc cct aat ctg atg ggt cat tat     146
Lys Met Ala Tyr Asn Met Thr Phe Phe Pro Asn Leu Met Gly His Tyr
                20                  25                  30 gac cag agt att gcc gcg gtg gaa atg gag cat ttt ctt cct ctc gca     194
Asp Gln Ser Ile Ala Ala Val Glu Met Glu His Phe Leu Pro Leu Ala
            35                  40                  45 aat ctg gaa tgt tca cca aac att gaa act ttc ctc tgc aaa gca ttt     242
Asn Leu Glu Cys Ser Pro Asn Ile Glu Thr Phe Leu Cys Lys Ala Phe
        50                  55                  60 gta cca acc tgc ata gaa caa att cat gtg gtt cca cct tgt cgt aaa     290
Val Pro Thr Cys Ile Glu Gln Ile His Val Val Pro Pro Cys Arg Lys
    65                  70                  75 ctt tgt gag aaa gta tat tct gat tgc aaa aaa tta att gac act ttt     338
Leu Cys Glu Lys Val Tyr Ser Asp Cys Lys Lys Leu Ile Asp Thr Phe
80                  85                  90                  95 ggg atc cga tgg cct gag gag ctt gaa tgt gac aga tta caa tac tgt     386
Gly Ile Arg Trp Pro Glu Glu Leu Glu Cys Asp Arg Leu Gln Tyr Cys
                100                 105                 110 gat gag act gtt cct gta act ttt gat cca cac aca gaa ttt ctt ggt     434
Asp Glu Thr Val Pro Val Thr Phe Asp Pro His Thr Glu Phe Leu Gly
            115                 120                 125 cct cag aag aaa aca gaa caa gtc caa aga gac att gga ttt tgg tgt     482
Pro Gln Lys Lys Thr Glu Gln Val Gln Arg Asp Ile Gly Phe Trp Cys
        130                 135                 140 cca agg cat ctt aag act tct ggg gga caa gga tat aag ttt ctg gga     530
```

```
            Pro Arg His Leu Lys Thr Ser Gly Gly Gln Gly Tyr Lys Phe Leu Gly
                145                 150                 155 att gac cag tgt gcg cct cca tgc ccc aac atg tat ttt aaa agt gat            578
Ile Asp Gln Cys Ala Pro Pro Cys Pro Asn Met Tyr Phe Lys Ser Asp
160                 165                 170                 175 gag cta gag ttt gca aaa agt ttt att gga aca gtt tca ata ttt tgt            626
Glu Leu Glu Phe Ala Lys Ser Phe Ile Gly Thr Val Ser Ile Phe Cys
                180                 185                 190 ctt tgt gca act ctg ttc aca ttc ctt act ttt tta att gat gtt aga            674
Leu Cys Ala Thr Leu Phe Thr Phe Leu Thr Phe Leu Ile Asp Val Arg
            195                 200                 205 aga ttc aga tac cca gag aga cca att ata tat tac tct gtc tgt tac            722
Arg Phe Arg Tyr Pro Glu Arg Pro Ile Ile Tyr Tyr Ser Val Cys Tyr
        210                 215                 220 agc att gta tct ctt atg tac ttc att gga ttt ttg cta ggc gat agc            770
Ser Ile Val Ser Leu Met Tyr Phe Ile Gly Phe Leu Leu Gly Asp Ser
    225                 230                 235 aca gcc tgc aat aag gca gat gag aag cta gaa ctt ggt aac act gtt            818
Thr Ala Cys Asn Lys Ala Asp Glu Lys Leu Glu Leu Gly Asn Thr Val
240                 245                 250                 255 gtc cta gac tct caa aat aag gct tgc acc gtt ttg ttc atg ctt ttg            866
Val Leu Asp Ser Gln Asn Lys Ala Cys Thr Val Leu Phe Met Leu Leu
                260                 265                 270 tat ttt ttc aca atg gct ggc act gtg tgg tgg gtg att ctt acc att            914
Tyr Phe Phe Thr Met Ala Gly Thr Val Trp Trp Val Ile Leu Thr Ile
            275                 280                 285 act tgg ttc tta gct gca gga aga aaa tgg agt tgt gaa gcc atc gag            962
Thr Trp Phe Leu Ala Ala Gly Arg Lys Trp Ser Cys Glu Ala Ile Glu
        290                 295                 300 caa aaa gca gtg tgg ttt cat gct gtt gca tgg gga aca cca ggt ttc           1010
Gln Lys Ala Val Trp Phe His Ala Val Ala Trp Gly Thr Pro Gly Phe
    305                 310                 315 ctg act gtt atg ctt ctt gct atg aac aaa gtt gaa gga gac aac att           1058
Leu Thr Val Met Leu Leu Ala Met Asn Lys Val Glu Gly Asp Asn Ile
320                 325                 330                 335 agt gga gtt tgc ttt gtt ggc ctt tat gac ctg gat gct tct cgc tac           1106
Ser Gly Val Cys Phe Val Gly Leu Tyr Asp Leu Asp Ala Ser Arg Tyr
                340                 345                 350 ttt gta ctc ttg cca ctg tgc ctt tgt gtg ttt gtt ggg ctc tct ctt           1154
Phe Val Leu Leu Pro Leu Cys Leu Cys Val Phe Val Gly Leu Ser Leu
            355                 360                 365 ctt tta gct ggc att att tcc tta aat cat gtt cga caa gtc ata caa           1202
Leu Leu Ala Gly Ile Ile Ser Leu Asn His Val Arg Gln Val Ile Gln
        370                 375                 380 cat gat ggc cgg aac caa gaa aaa cta aag aaa ttt atg att cga att           1250
His Asp Gly Arg Asn Gln Glu Lys Leu Lys Lys Phe Met Ile Arg Ile
    385                 390                 395 gga gtc ttc agc ggc ttg tat ctt gtg cca tta gtg aca ctt ctc gga           1298
Gly Val Phe Ser Gly Leu Tyr Leu Val Pro Leu Val Thr Leu Leu Gly
400                 405                 410                 415 tgt tac gtc tat gag caa gtg aac agg att acc tgg gag ata act tgg           1346
Cys Tyr Val Tyr Glu Gln Val Asn Arg Ile Thr Trp Glu Ile Thr Trp
                420                 425                 430 gtc tct gat cat tgt cgt cag tac cat atc cca tgt cct tat cag gca           1394
Val Ser Asp His Cys Arg Gln Tyr His Ile Pro Cys Pro Tyr Gln Ala
            435                 440                 445 aaa gca aaa gct cga cca gaa ttg gct tta ttt atg ata aaa tac ctg           1442
Lys Ala Lys Ala Arg Pro Glu Leu Ala Leu Phe Met Ile Lys Tyr Leu
        450                 455                 460
```

| | | |
|---|---|---|
| atg aca tta att gtt ggc atc tct gct gtc ttc tgg gtt gga agc aaa<br>Met Thr Leu Ile Val Gly Ile Ser Ala Val Phe Trp Val Gly Ser Lys<br>465                     470                     475 | | 1490 |
| aag aca tgc aca gaa tgg gct ggg ttt ttt aaa cga aat cgc aag aga<br>Lys Thr Cys Thr Glu Trp Ala Gly Phe Phe Lys Arg Asn Arg Lys Arg<br>480                   485                   490                   495 | | 1538 |
| gat cca atc agt gaa agt cga aga gta cta cag gaa tca tgt gag ttt<br>Asp Pro Ile Ser Glu Ser Arg Arg Val Leu Gln Glu Ser Cys Glu Phe<br>                   500                   505                   510 | | 1586 |
| ttc tta aag cac aat tct aaa gtt aaa cac aaa aag aag cac tat aaa<br>Phe Leu Lys His Asn Ser Lys Val Lys His Lys Lys Lys His Tyr Lys<br>                515                   520                   525 | | 1634 |
| cca agt tca cac aag ctg aag gtc att tcc aaa tcc atg gga acc agc<br>Pro Ser Ser His Lys Leu Lys Val Ile Ser Lys Ser Met Gly Thr Ser<br>               530                   535                   540 | | 1682 |
| aca gga gct aca gca aat cat ggc act tct gca gta gca att act agc<br>Thr Gly Ala Thr Ala Asn His Gly Thr Ser Ala Val Ala Ile Thr Ser<br>545                     550                   555 | | 1730 |
| cat gat tac cta gga caa gaa act ttg aca gaa atc caa acc tca cca<br>His Asp Tyr Leu Gly Gln Glu Thr Leu Thr Glu Ile Gln Thr Ser Pro<br>560                     565                   570                   575 | | 1778 |
| gaa aca tca atg aga gag gtg aaa gcg gac gga gct agc acc ccc agg<br>Glu Thr Ser Met Arg Glu Val Lys Ala Asp Gly Ala Ser Thr Pro Arg<br>                   580                   585                   590 | | 1826 |
| tta aga gaa cag gac tgt ggt gaa cct gcc tcg cca gca gca tcc atc<br>Leu Arg Glu Gln Asp Cys Gly Glu Pro Ala Ser Pro Ala Ala Ser Ile<br>               595                   600                   605 | | 1874 |
| tcc aga ctc tct ggg gaa cag gtc gac ggg aag ggc cag gca ggc agt<br>Ser Arg Leu Ser Gly Glu Gln Val Asp Gly Lys Gly Gln Ala Gly Ser<br>         610                   615                   620 | | 1922 |
| gta tct gaa agt gcg cgg agt gaa gga agg att agt cca aag agt gat<br>Val Ser Glu Ser Ala Arg Ser Glu Gly Arg Ile Ser Pro Lys Ser Asp<br>625                     630                   635 | | 1970 |
| att act gac act ggc ctg gca cag agc aac aat ttg cag gtc ccc agt<br>Ile Thr Asp Thr Gly Leu Ala Gln Ser Asn Asn Leu Gln Val Pro Ser<br>640                     645                   650                   655 | | 2018 |
| tct tca gaa cca agc agc ctc aaa ggt tcc aca tct ctg ctt gtt cac<br>Ser Ser Glu Pro Ser Ser Leu Lys Gly Ser Thr Ser Leu Leu Val His<br>                   660                   665                   670 | | 2066 |
| ccg gtt tca gga gtg aga aaa gag cag gga ggt ggt tgt cat tca gat<br>Pro Val Ser Gly Val Arg Lys Glu Gln Gly Gly Gly Cys His Ser Asp<br>               675                   680                   685 | | 2114 |
| act tgaagaacat tttctctcgt tactcagaag caaatttgtg ttacactgga<br>Thr | | 2167 |
| agtgacctat gcactgtttt gtaagaatca ctgttacgtt cttcttttgc acttaaagtt | | 2227 |
| gcattgccta ctgttatact ggaaaaaata gagttcaaga ataatatgac tcatttcaca | | 2287 |
| caaaggttaa tgacaacaat atacctgaaa acagagatgt gcaggttaat aatattttt | | 2347 |
| taatagtgtg ggaggacaga gttagaggaa tcttcctttt ctatttatga agattctact | | 2407 |
| cttggtaaga gtattttaag atgtactatg ctatttact tttttgatat aaaatcaaga | | 2467 |
| tatttctttg ctgaagtatt taaatcttat ccttgtatct tttatacat atttgaaaat | | 2527 |
| aagcttatat gtatttgaac tttttgaaa tcctattcaa gtattttat catgctattg | | 2587 |
| tgatatttta gcactttggt agcttttaca ctgaattct aagaaaattg taaaatagtc | | 2647 |
| ttcttttata ctgtaaaaaa agatatacca aaagtctta taataggaat ttaactttaa | | 2707 |
| aaacccactt attgataacct taccatctaa atgtgtgat ttttatagtc tcgttttagg | | 2767 |

-continued

```
aatttcacag atctaaatta tgtagctgaa ataaggtgct tactcaaaga gtgtccacta    2827
ttgattgtat tatgctgctc actgatcctt ctgcatattt aaaataaaat gtcctaaagg    2887
gttagtagac aaaatgttag tcttttgtat attaggccaa gtgcaattga cttcccittt   2947 ttaatgtttc atgaccaccc attgattgta ttataaccac ttacagttgc ttatattttt    3007
tgttttaact tttgttttt aacatttaga atattacatt ttgtattata cagtaccttt      3067
ctcagacatt ttgtagaatt catttcggca gctcactagg attttgctga acattaaaaa    3127
gtgtgatagc gatattagtg ccaatcaaat ggaaaaaagg tagtcttaat aaacaagaca    3187
caacgttttt atacaacata ctttaaaata ttaaggagtt ttcttaattt tgtttcctat    3247
taagtattat tctttgggca agattttctg atgcttttga ttttctctca atttagcatt    3307
tgcttttggt ttttttctct atttagcatt ctgttaaggc acaaaaacta tgtactgtat    3367
gggaaatgtt gtaaatatta ccttttccac atttttaaaca gacaactttg aatacaaaaa   3427
ctttgttttg tgtgatcttt tcattaataa aattatcttt gtataagaaa aaaaaaaaaa    3487
aaaaa                                                                3492
```

<210> SEQ ID NO 79
<211> LENGTH: 551
<212> TYPE: PRT
<213> ORGANISM: Homo sapiens

<400> SEQUENCE: 79

```
Met Leu Cys Ser Leu Leu Cys Glu Cys Leu Leu Val Ala Gly
        -15             -10                 -5

Tyr Ala His Asp Asp Asp Trp Ile Asp Pro Thr Asp Met Leu Asn Tyr
 -1   1               5                  10

Asp Ala Ala Ser Gly Thr Met Arg Lys Ser Gln Ala Lys Tyr Gly Ile
 15                  20                  25                  30

Ser Gly Glu Lys Asp Val Ser Pro Asp Leu Ser Cys Ala Asp Glu Ile
                 35                  40                  45

Ser Glu Cys Tyr His Lys Leu Asp Ser Leu Thr Tyr Lys Ile Asp Glu
             50                  55                  60

Cys Glu Lys Lys Lys Arg Glu Asp Tyr Glu Ser Gln Ser Asn Pro Val
         65                  70                  75

Phe Arg Arg Tyr Leu Asn Lys Ile Leu Ile Glu Ala Gly Lys Leu Gly
     80                  85                  90

Leu Pro Asp Glu Asn Lys Gly Asp Met His Tyr Asp Ala Glu Ile Ile
 95                 100                 105                 110

Leu Lys Arg Glu Thr Leu Leu Glu Ile Gln Lys Phe Leu Asn Gly Glu
                115                 120                 125

Asp Trp Lys Pro Gly Ala Leu Asp Asp Ala Leu Ser Asp Ile Leu Ile
            130                 135                 140

Asn Phe Lys Phe His Asp Phe Glu Thr Trp Lys Trp Arg Phe Glu Asp
        145                 150                 155

Ser Phe Gly Val Asp Pro Tyr Asn Val Leu Met Val Leu Leu Cys Leu
    160                 165                 170

Leu Cys Ile Val Val Leu Val Ala Thr Glu Leu Trp Thr Tyr Val Arg
175                 180                 185                 190

Trp Tyr Thr Gln Leu Arg Arg Val Leu Ile Ser Phe Leu Phe Ser
                195                 200                 205

Leu Gly Trp Asn Trp Met Tyr Leu Tyr Lys Leu Ala Phe Ala Gln His
            210                 215                 220
```

```
Gln Ala Glu Val Ala Lys Met Glu Pro Leu Asn Asn Val Cys Ala Lys
        225                 230                 235
Lys Met Asp Trp Thr Gly Ser Ile Trp Glu Trp Phe Arg Ser Ser Trp
    240                 245                 250
Thr Tyr Lys Asp Asp Pro Cys Gln Lys Tyr Tyr Glu Leu Leu Leu Val
255                 260                 265                 270
Asn Pro Ile Trp Leu Val Pro Pro Thr Lys Ala Leu Ala Val Thr Phe
                275                 280                 285
Thr Thr Phe Val Thr Glu Pro Leu Lys His Ile Gly Lys Gly Thr Gly
            290                 295                 300
Glu Phe Ile Lys Ala Leu Met Lys Glu Ile Pro Ala Leu Leu His Leu
        305                 310                 315
Pro Val Leu Ile Ile Met Ala Leu Ala Ile Leu Ser Phe Cys Tyr Gly
    320                 325                 330
Ala Gly Lys Ser Val His Val Leu Arg His Ile Gly Gly Pro Glu Ser
335                 340                 345                 350
Glu Pro Pro Gln Ala Leu Arg Pro Arg Asp Arg Arg Gln Glu Glu
                355                 360                 365
Ile Asp Tyr Arg Pro Asp Gly Gly Ala Gly Ala Asp Phe His Tyr
            370                 375                 380
Arg Gly Gln Met Gly Pro Thr Glu Gln Gly Pro Tyr Ala Lys Thr Tyr
        385                 390                 395
Glu Gly Arg Arg Glu Ile Leu Arg Glu Arg Asp Val Asp Leu Arg Phe
    400                 405                 410
Gln Thr Gly Asn Lys Ser Pro Glu Val Leu Arg Ala Phe Asp Val Pro
415                 420                 425                 430
Asp Ala Glu Ala Arg Glu His Pro Thr Val Val Pro Ser His Lys Ser
                435                 440                 445
Pro Val Leu Asp Thr Lys Pro Lys Glu Thr Gly Gly Ile Leu Gly Glu
            450                 455                 460
Gly Thr Pro Lys Glu Ser Ser Thr Glu Ser Ser Gln Ser Ala Lys Pro
        465                 470                 475
Val Ser Gly Gln Asp Thr Ser Gly Asn Thr Glu Gly Ser Pro Ala Ala
    480                 485                 490
Glu Lys Ala Gln Leu Lys Ser Glu Ala Ala Gly Ser Pro Asp Gln Gly
495                 500                 505                 510
Ser Thr Tyr Ser Pro Ala Arg Gly Val Ala Gly Pro Arg Gly Gln Asp
                515                 520                 525
Pro Val Ser Ser Pro Cys Gly
            530
```

<210> SEQ ID NO 80
<211> LENGTH: 1653
<212> TYPE: DNA
<213> ORGANISM: Homo sapiens

<400> SEQUENCE: 80

```
atgctgtgtt ctttgctcct ttgtgaatgt ctgttgctgg tagctggtta tgctcatgat      60
gatgactgga ttgaccccac agacatgctt aactatgatg ctgcttcagg aacaatgaga     120
aaatctcagg caaatatgg tatttcaggg gaaaaggatg tcagtcctga cttgtcatgt     180
gctgatgaaa tatcagaatg ttatcacaaa cttgattctt aacttataa gattgatgag      240 tgtgaaaaga aaagaggga agactatgaa agtcaaagca atcctgtttt taggagatac     300
ttaaataaga tttttaattga agctggaaag cttggacttc ctgatgaaaa caaaggcgat     360
```

```
atgcattatg atgctgagat tatccttaaa agagaaactt tgttagaaat acagaagttt     420
ctcaatggag aagactggaa accaggtgcc ttggatgatg cactaagtga tatttttaatt    480 aattttaagt ttcatgattt tgaaacatgg aagtggcgat cgaagattc ctttggagtg     540 gatccatata atgtgttaat ggtacttctt tgtctgctct gcatcgtggt tttagtggct    600
accgagctgt ggacatatgt acgttggtac actcagttga cgtgttttt aatcatcagc    660 tttctgttca gtttgggatg gaattggatg tatttatata agctagcttt tgcacagcat    720
caggctgaag tcgccaagat ggagccatta acaatgtgt gtgccaaaaa gatggactgg    780 actgaagta tctgggaatg gtttagaagt tcatggacct ataaggatga cccatgccaa    840
aaatactatg agctcttact agtcaaccct atttggttgg tcccaccaac aaaggcactt    900
gcagttacat tcaccacatt tgtaacggag ccattgaagc atattggaaa aggaactggg    960
gaatttatta agcactcat gaaggaaatt ccagcgctgc ttcatcttcc agtgctgata    1020
attatggcat tagccatcct gagttttctgc tatggtgctg gaaaatcagt tcatgtgctg   1080
agacatatag gcggtcctga gagcgaacct ccccaggcac ttcggccacg ggatagaaga   1140
cggcaggagg aaattgatta tagacctgat ggtggagcag gtgatgccga tttccattat   1200
aggggccaaa tgggccccac tgagcaaggc cctatatgcca aaacgtatga gggtagaaga   1260 gagatttga gagagagaga tgttgacttg agatttcaga ctggcaacaa gagccctgaa    1320
gtgctccggg catttgatgt accagacgca gaggcacgag agcatccac ggtggtaccc     1380 agtcataaat cacctgttttt ggatacaaag cccaaggaga caggtggaat cctgggggaa   1440
ggcacaccga agaaagcag tactgaaagc agccagtcgg ccaagcctgt ctctggccaa    1500
gacacatcag gaatacaga aggttcaccc gcagcggaaa aggcccagct caagtctgaa    1560
gccgcaggca gcccagacca aggcagcaca tacagccccg caagaggtgt ggctggacca    1620
cgtggacagg atccggtcag cagcccctgt ggc                                  1653

<210> SEQ ID NO 81
<211> LENGTH: 2000
<212> TYPE: DNA
<213> ORGANISM: Homo sapiens
<220> FEATURE:
<221> NAME/KEY: sig_peptide
<222> LOCATION: (82)..(135)
<220> FEATURE:
<221> NAME/KEY: mat_peptide
<222> LOCATION: (136)..(1734)
<220> FEATURE:
<221> NAME/KEY: CDS
<222> LOCATION: (82)..(1734)

<400> SEQUENCE: 81
gcggcggcaa gctgtgcgac ctcttctgcg gccggcctgg gcaggtgtct tcctcgagag      60
gcaggcaggg gatcccggac g atg ctg tgt tct ttg ctc ctt tgt gaa tgt        111
                        Met Leu Cys Ser Leu Leu Leu Cys Glu Cys
                                    -15                 -10 ctg ttg ctg gta gct ggt tat gct cat gat gat gac tgg att gac ccc        159
Leu Leu Leu Val Ala Gly Tyr Ala His Asp Asp Asp Trp Ile Asp Pro
        -5                  -1  1                   5 aca gac atg ctt aac tat gat gct gct tca gga aca atg aga aaa tct       207
Thr Asp Met Leu Asn Tyr Asp Ala Ala Ser Gly Thr Met Arg Lys Ser
        10                  15                  20 cag gca aaa tat ggt att tca ggg gaa aag gat gtc agt cct gac ttg       255
Gln Ala Lys Tyr Gly Ile Ser Gly Glu Lys Asp Val Ser Pro Asp Leu
25                  30                  35                  40
```

-continued

| | | |
|---|---|---|
| tca tgt gct gat gaa ata tca gaa tgt tat cac aaa ctt gat tct tta<br>Ser Cys Ala Asp Glu Ile Ser Glu Cys Tyr His Lys Leu Asp Ser Leu<br>                            45                                  50                           55 | | 303 |
| act tat aag att gat gag tgt gaa aag aaa aag agg gaa gac tat gaa<br>Thr Tyr Lys Ile Asp Glu Cys Glu Lys Lys Lys Arg Glu Asp Tyr Glu<br>               60                         65                      70 | | 351 |
| agt caa agc aat cct gtt ttt agg aga tac tta aat aag att tta att<br>Ser Gln Ser Asn Pro Val Phe Arg Arg Tyr Leu Asn Lys Ile Leu Ile<br>        75                        80                      85 | | 399 |
| gaa gct gga aag ctt gga ctt cct gat gaa aac aaa ggc gat atg cat<br>Glu Ala Gly Lys Leu Gly Leu Pro Asp Glu Asn Lys Gly Asp Met His<br>    90                        95                      100 | | 447 |
| tat gat gct gag att atc ctt aaa aga gaa act ttg tta gaa ata cag<br>Tyr Asp Ala Glu Ile Ile Leu Lys Arg Glu Thr Leu Leu Glu Ile Gln<br>105                      110                      115                      120 | | 495 |
| aag ttt ctc aat gga gaa gac tgg aaa cca ggt gcc ttg gat gat gca<br>Lys Phe Leu Asn Gly Glu Asp Trp Lys Pro Gly Ala Leu Asp Asp Ala<br>                            125                      130                      135 | | 543 |
| cta agt gat att tta att aat ttt aag ttt cat gat ttt gaa aca tgg<br>Leu Ser Asp Ile Leu Ile Asn Phe Lys Phe His Asp Phe Glu Thr Trp<br>            140                      145                      150 | | 591 |
| aag tgg cga ttc gaa gat tcc ttt gga gtg gat cca tat aat gtg tta<br>Lys Trp Arg Phe Glu Asp Ser Phe Gly Val Asp Pro Tyr Asn Val Leu<br>                155                      160                      165 | | 639 |
| atg gta ctt ctt tgt ctg ctc tgc atc gtg gtt tta gtg gct acc gag<br>Met Val Leu Leu Cys Leu Leu Cys Ile Val Val Leu Val Ala Thr Glu<br>170                      175                      180 | | 687 |
| ctg tgg aca tat gta cgt tgg tac act cag ttg aga cgt gtt tta atc<br>Leu Trp Thr Tyr Val Arg Trp Tyr Thr Gln Leu Arg Arg Val Leu Ile<br>185                      190                      195                      200 | | 735 |
| atc agc ttt ctg ttc agt ttg gga tgg aat tgg atg tat tta tat aag<br>Ile Ser Phe Leu Phe Ser Leu Gly Trp Asn Trp Met Tyr Leu Tyr Lys<br>                      205                      210                      215 | | 783 |
| cta gct ttt gca cag cat cag gct gaa gtc gcc aag atg gag cca tta<br>Leu Ala Phe Ala Gln His Gln Ala Glu Val Ala Lys Met Glu Pro Leu<br>            220                      225                      230 | | 831 |
| aac aat gtg tgt gcc aaa aag atg gac tgg act gga agt atc tgg gaa<br>Asn Asn Val Cys Ala Lys Lys Met Asp Trp Thr Gly Ser Ile Trp Glu<br>                235                      240                      245 | | 879 |
| tgg ttt aga agt tca tgg acc tat aag gat gac cca tgc caa aaa tac<br>Trp Phe Arg Ser Ser Trp Thr Tyr Lys Asp Asp Pro Cys Gln Lys Tyr<br>250                      255                      260 | | 927 |
| tat gag ctc tta cta gtc aac cct att tgg ttg gtc cca cca aca aag<br>Tyr Glu Leu Leu Leu Val Asn Pro Ile Trp Leu Val Pro Pro Thr Lys<br>265                      270                      275                      280 | | 975 |
| gca ctt gca gtt aca ttc acc aca ttt gta acg gag cca ttg aag cat<br>Ala Leu Ala Val Thr Phe Thr Thr Phe Val Thr Glu Pro Leu Lys His<br>                      285                      290                      295 | | 1023 |
| att gga aaa gga act ggg gaa ttt att aaa gca ctc atg aag gaa att<br>Ile Gly Lys Gly Thr Gly Glu Phe Ile Lys Ala Leu Met Lys Glu Ile<br>                300                      305                      310 | | 1071 |
| cca gcg ctg ctt cat ctt cca gtg ctg ata att atg gca tta gcc atc<br>Pro Ala Leu Leu His Leu Pro Val Leu Ile Ile Met Ala Leu Ala Ile<br>                315                      320                      325 | | 1119 |
| ctg agt ttc tgc tat ggt gct gga aaa tca gtt cat gtg ctg aga cat<br>Leu Ser Phe Cys Tyr Gly Ala Gly Lys Ser Val His Val Leu Arg His<br>330                      335                      340 | | 1167 |
| ata ggc ggt cct gag agc gaa cct ccc cag gca ctt cgg cca cgg gat<br>Ile Gly Gly Pro Glu Ser Glu Pro Pro Gln Ala Leu Arg Pro Arg Asp | | 1215 |

|  |  |  |  |  |  |  |  |  |  |  |  |  |  |  |  |
|---|---|---|---|---|---|---|---|---|---|---|---|---|---|---|---|
| aga | aga | cgg | cag | gag | gaa | att | gat | tat | aga | cct | gat | ggt | gga | gca | ggt | 1263 |
| Arg | Arg | Arg | Gln | Glu | Glu | Ile | Asp | Tyr | Arg | Pro | Asp | Gly | Gly | Ala | Gly |
|  |  |  | 365 |  |  |  |  | 370 |  |  |  |  | 375 |  |  |
| gat | gcc | gat | ttc | cat | tat | agg | ggc | caa | atg | ggc | ccc | act | gag | caa | ggc | 1311 |
| Asp | Ala | Asp | Phe | His | Tyr | Arg | Gly | Gln | Met | Gly | Pro | Thr | Glu | Gln | Gly |
|  |  | 380 |  |  |  |  | 385 |  |  |  |  | 390 |  |  |  |
| cct | tat | gcc | aaa | acg | tat | gag | ggt | aga | aga | gag | att | ttg | aga | gag | aga | 1359 |
| Pro | Tyr | Ala | Lys | Thr | Tyr | Glu | Gly | Arg | Arg | Glu | Ile | Leu | Arg | Glu | Arg |
|  | 395 |  |  |  |  | 400 |  |  |  |  | 405 |  |  |  |  |
| gat | gtt | gac | ttg | aga | ttt | cag | act | ggc | aac | aag | agc | cct | gaa | gtg | ctc | 1407 |
| Asp | Val | Asp | Leu | Arg | Phe | Gln | Thr | Gly | Asn | Lys | Ser | Pro | Glu | Val | Leu |
| 410 |  |  |  |  | 415 |  |  |  |  | 420 |  |  |  |  |  |
| cgg | gca | ttt | gat | gta | cca | gac | gca | gag | gca | cga | gag | cat | ccc | acg | gtg | 1455 |
| Arg | Ala | Phe | Asp | Val | Pro | Asp | Ala | Glu | Ala | Arg | Glu | His | Pro | Thr | Val |
| 425 |  |  |  | 430 |  |  |  |  | 435 |  |  |  |  | 440 |  |
| gta | ccc | agt | cat | aaa | tca | cct | gtt | ttg | gat | aca | aag | ccc | aag | gag | aca | 1503 |
| Val | Pro | Ser | His | Lys | Ser | Pro | Val | Leu | Asp | Thr | Lys | Pro | Lys | Glu | Thr |
|  |  |  |  | 445 |  |  |  |  | 450 |  |  |  |  | 455 |  |
| ggt | gga | atc | ctg | ggg | gaa | ggc | aca | ccg | aaa | gaa | agc | agt | act | gaa | agc | 1551 |
| Gly | Gly | Ile | Leu | Gly | Glu | Gly | Thr | Pro | Lys | Glu | Ser | Ser | Thr | Glu | Ser |
|  |  | 460 |  |  |  |  | 465 |  |  |  |  | 470 |  |  |  |
| agc | cag | tcg | gcc | aag | cct | gtc | tct | ggc | caa | gac | aca | tca | ggg | aat | aca | 1599 |
| Ser | Gln | Ser | Ala | Lys | Pro | Val | Ser | Gly | Gln | Asp | Thr | Ser | Gly | Asn | Thr |
|  | 475 |  |  |  |  | 480 |  |  |  |  | 485 |  |  |  |  |
| gaa | ggt | tca | ccc | gca | gcg | gaa | aag | gcc | cag | ctc | aag | tct | gaa | gcc | gca | 1647 |
| Glu | Gly | Ser | Pro | Ala | Ala | Glu | Lys | Ala | Gln | Leu | Lys | Ser | Glu | Ala | Ala |
| 490 |  |  |  |  | 495 |  |  |  |  | 500 |  |  |  |  |  |
| ggc | agc | cca | gac | caa | ggc | agc | aca | tac | agc | ccc | gca | aga | ggt | gtg | gct | 1695 |
| Gly | Ser | Pro | Asp | Gln | Gly | Ser | Thr | Tyr | Ser | Pro | Ala | Arg | Gly | Val | Ala |
| 505 |  |  |  | 510 |  |  |  |  | 515 |  |  |  |  | 520 |  |
| gga | cca | cgt | gga | cag | gat | ccg | gtc | agc | agc | ccc | tgt | ggc | tagaggaaca |  |  | 1744 |
| Gly | Pro | Arg | Gly | Gln | Asp | Pro | Val | Ser | Ser | Pro | Cys | Gly |  |  |  |
|  |  |  | 525 |  |  |  |  | 530 |  |  |  |  |  |  |  |

```
ccagcacaaa cgacagcctc aagtctcctt cgagctttat atccatttgg ggatgaagtc   1804
tactttgaca gctagcaagg cgacatgcaa ctgttgttga atgatgacag caattcagga   1864
aagacttaaa tatgaaagca aattgaacac atcgggtgtt tgttatcaga aaagagatga   1924
gatgagataa gacttgttta ttgactagcc aatatgtcat taaaattaag gtttaaaaaa   1984
aaaaaaaaaa aaaaa                                                    2000

<210> SEQ ID NO 82
<211> LENGTH: 35
<212> TYPE: DNA
<213> ORGANISM: Artificial Sequence
<220> FEATURE:
<223> OTHER INFORMATION: Description of Artificial Sequence: XhoI-randam
      9mer to synthesize doble strands cDNA
<220> FEATURE:
<221> NAME/KEY: modified_base
<222> LOCATION: (1)..(35)
<223> OTHER INFORMATION: "n" represents a, t, c, or g

<400> SEQUENCE: 82
cgattgaatt ctagacctgc ctcgagnnnn nnnnn                                35

<210> SEQ ID NO 83
<211> LENGTH: 27
<212> TYPE: DNA
<213> ORGANISM: Artificial Sequence
<220> FEATURE:
```

-continued

<223> OTHER INFORMATION: Description of Artificial Sequence:
      biotin-conjugated ON056-F1 primer

<400> SEQUENCE: 83
aacatgaatc tttcgctcgt cctggct                                               27

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence:
      biotin-conjugated ON034-F1 primer

<400> SEQUENCE: 84
tgaagcccat cactacatcg ccattacg                                              28

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: OX003-F1
      primer

<400> SEQUENCE: 85
caaaacccac aagaaattca ccaaggc                                               27

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: OX003-F2
      primer

<400> SEQUENCE: 86
tcaccaaggc taacatggtg gcc                                                   23

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: OA052-F1
      primer

<400> SEQUENCE: 87
atgcctagaa gaggactgat tcttcac                                               27

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: OC004-F1
      primer

<400> SEQUENCE: 88
atgaggaaag ggaaccttct gctgagc                                               27

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: OC004-F2

```
                             primer

<400> SEQUENCE: 89
tgagcttcca gagctgtc                                                  18

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: OM017-F3
      primer

<400> SEQUENCE: 90
gggaaatgaa acatttctgt aacctgc                                        27

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: OM017-F1
      primer

<400> SEQUENCE: 91
atgaaacatt tctgtaacct gctttgt                                        27

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: OM101-F3
      primer

<400> SEQUENCE: 92
tgaagttgca gataatgagg acttacc                                        27

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: OM101-F1
      primer

<400> SEQUENCE: 93
atgaggactt accattatat accatta                                        27

<210> SEQ ID NO 94
<211> LENGTH: 27
<212> TYPE: DNA
<213> ORGANISM: Artificial Sequence
<220> FEATURE:
<223> OTHER INFORMATION: Description of Artificial Sequence: OM126-F3
      primer

<400> SEQUENCE: 94
aggaaggatg aggaagacca ggctctg                                        27

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence:
      biotin-conjugated OM160-F1 primer
```

```
<400> SEQUENCE: 95
atgcttcagt ggaggagaag acactgc                                              27

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: OMA016-F1
      primer

<400> SEQUENCE: 96
agaaatggtg aatgcctgct ggtgtgg                                              27

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence: OMB130-F1
      primer

<400> SEQUENCE: 97
tcctctgact tttcttctgc aagctcc                                              27

<210> SEQ ID NO 98
<211> LENGTH: 27
<212> TYPE: DNA
<213> ORGANISM: Artificial Sequence
<220> FEATURE:
<223> OTHER INFORMATION: Description of Artificial Sequence: OMB142-F2
      primer

<400> SEQUENCE: 98
gcccaaggtc aaggagatgg tacggat                                              27

<210> SEQ ID NO 99
<211> LENGTH: 28
<212> TYPE: DNA
<213> ORGANISM: Artificial Sequence
<220> FEATURE:
<223> OTHER INFORMATION: Description of Artificial Sequence: OMB142-F1
      primer

<400> SEQUENCE: 99
ggagatggta cggatcttaa ggactgtg                                             28

<210> SEQ ID NO 100
<211> LENGTH: 27
<212> TYPE: DNA
<213> ORGANISM: Artificial Sequence
<220> FEATURE:
<223> OTHER INFORMATION: Description of Artificial Sequence: OTB033-F1
      primer

<400> SEQUENCE: 100
tgcactatcc aaaagctcca tgtacac                                              27

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: OTB003-F2
      primer
```

```
<400> SEQUENCE: 101
ccatgtacac agtgggggc                                                    19

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: OVB100-F1
      primer

<400> SEQUENCE: 102
cacttggtgt ttgatttacc taagcac                                           27

<210> SEQ ID NO 103
<211> LENGTH: 27
<212> TYPE: DNA
<213> ORGANISM: Artificial Sequence
<220> FEATURE:
<223> OTHER INFORMATION: Description of Artificial Sequence: OAF062-F2
      primer

<400> SEQUENCE: 103
gagtttcgta agcaaaatag aggacag                                           27

<210> SEQ ID NO 104
<211> LENGTH: 27
<212> TYPE: DNA
<213> ORGANISM: Artificial Sequence
<220> FEATURE:
<223> OTHER INFORMATION: Description of Artificial Sequence: OAF062-F3
      primer

<400> SEQUENCE: 104
tagaggacag aaatgcagtt catgaac                                           27

<210> SEQ ID NO 105
<211> LENGTH: 28
<212> TYPE: DNA
<213> ORGANISM: Artificial Sequence
<220> FEATURE:
<223> OTHER INFORMATION: Description of Artificial Sequence: OAF075-F1
      primer

<400> SEQUENCE: 105
gacatgaggt ggatactgtt cattgggg                                          28

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: OAG119-F1
      primer

<400> SEQUENCE: 106
tggcgtgtaa ctatgctcat cattgttc                                          28

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: OAH040-F1
      primer

<400> SEQUENCE: 107
```
ttagcccacc catgttgata gaacaccc                                          28

<210> SEQ ID NO 108
<211> LENGTH: 28
<212> TYPE: DNA
<213> ORGANISM: Artificial Sequence
<220> FEATURE:
<223> OTHER INFORMATION: Description of Artificial Sequence: OAH058-F1
      primer

<400> SEQUENCE: 108
acaatgttgg cctgtctgca agcttgtg                                          28

<210> SEQ ID NO 109
<211> LENGTH: 27
<212> TYPE: DNA
<213> ORGANISM: Artificial Sequence
<220> FEATURE:
<223> OTHER INFORMATION: Description of Artificial Sequence:
      biotin-conjugated OM011-F1 primer

<400> SEQUENCE: 109
gaagtgactc ttcctctagt ttgccac                                           27

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence:
      biotin-conjugated OM028-F1 primer

<400> SEQUENCE: 110
atgaaggaca tgccactccg aattcat                                           27

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: OMB092-F1
      primer

<400> SEQUENCE: 111
actcacctgg atccctaagg gcacagc                                           27

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: OMB092-F2
      primer

<400> SEQUENCE: 112
agaatgagct attacggcag cagctatc                                          28

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: OMB108-F1
      primer

<400> SEQUENCE: 113

-continued

```
ctctctccat ctgctgtggt tatggcc                                              27

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: OMB108-F2
      primer

<400> SEQUENCE: 114
tggttatggc ctgtcgctgg ag                                                   22

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence:
      biotin-conjugated OT007-F1 primer

<400> SEQUENCE: 115
aaaatgactc cccagtcgct gctgcag                                              27

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: OAG051-F1
      primer

<400> SEQUENCE: 116
ggaaatgttt acatttttgt tgacgtg                                              27

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence:
      biotin-conjugated OUB068-F1 primer

<400> SEQUENCE: 117
cactcatgaa ggaaattcca gcgctgc                                              27
```